(12) United States Patent
Rogers et al.

(10) Patent No.: US 11,517,238 B2
(45) Date of Patent: Dec. 6, 2022

(54) ENCAPSULATED FLEXIBLE ELECTRONICS FOR LONG-TERM IMPLANTATION

(71) Applicants: Northwestern University, Evanston, IL (US); The Board of Trustees of the University of Illinois, Urbana, IL (US)

(72) Inventors: John A. Rogers, Wilmette, IL (US); Hui Fang, Urbana, IL (US); Jianing Zhao, Urbana, IL (US); Enming Song, Urbana, IL (US); Yoon Kyeung Lee, Urbana, IL (US)

(73) Assignees: NORTHWESTERN UNIVERSITY, Evanston, IL (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 340 days.

(21) Appl. No.: 16/162,613

(22) Filed: Oct. 17, 2018

(65) Prior Publication Data
US 2020/0022601 A1 Jan. 23, 2020

Related U.S. Application Data

(60) Provisional application No. 62/738,608, filed on Sep. 28, 2018, provisional application No. 62/573,533, filed on Oct. 17, 2017.

(51) Int. Cl.
*A61B 5/283* (2021.01)
*H01L 21/02* (2006.01)
(Continued)

(52) U.S. Cl.
CPC .............. *A61B 5/283* (2021.01); *A61B 5/031* (2013.01); *A61B 5/361* (2021.01); *A61N 1/0587* (2013.01);
(Continued)

(58) Field of Classification Search
CPC ........... H01L 23/3121; H01L 21/02115; H01L 21/02118; H01L 21/02164;
(Continued)

(56) References Cited

U.S. PATENT DOCUMENTS

| | | | |
|---|---|---|---|
| 8,561,292 B2* | 10/2013 | Seymour | H01L 23/293 29/847 |
| 2014/0163390 A1* | 6/2014 | Rogers | A61B 5/6867 600/476 |

(Continued)

OTHER PUBLICATIONS

Jiang, G. Design challenges of implantable pressure monitoring system. Frontiers in Neuroscience 4 (2010).
(Continued)

*Primary Examiner* — Minh N Trinh
(74) *Attorney, Agent, or Firm* — Locke Lord LLP; Tim Tingkang Xia, Esq.

(57) ABSTRACT

Provided are methods of making a long-term implantable electronic device, and related implantable devices, including by providing a substrate having a first encapsulation layer that covers at least a portion of the substrate, the first encapsulation layer having a receiving surface; providing one or more electronic devices on the first encapsulation layer receiving surface; and removing at least a portion of the substrate from the first encapsulation layer; thereby making the long-term implantable electronic device. Further desirable properties, including device lifetime increases during use in environments that are challenging for sensitive electronic device components, are achieved through the use of additional layers such as longevity-extending layers and/or ion-barrier layers in combination with an encapsulation layer.

44 Claims, 66 Drawing Sheets

(51) Int. Cl.
| | |
|---|---|
| *A61N 1/05* | (2006.01) |
| *A61B 5/03* | (2006.01) |
| *A61B 5/361* | (2021.01) |
| *G01N 27/414* | (2006.01) |

(52) U.S. Cl.
CPC .. *H01L 21/02115* (2013.01); *H01L 21/02118* (2013.01); *H01L 21/02164* (2013.01); *H01L 21/02167* (2013.01); *H01L 21/02178* (2013.01); *H01L 21/02181* (2013.01); *H01L 21/02258* (2013.01); *H01L 21/02271* (2013.01); *H01L 21/02282* (2013.01); *G01N 27/414* (2013.01)

(58) Field of Classification Search
CPC . H01L 21/02167; A61N 1/3758; A61B 5/031; A61B 5/283; A61B 5/333; A61B 5/361
See application file for complete search history.

(56) References Cited

U.S. PATENT DOCUMENTS

| | | | | |
|---|---|---|---|---|
| 2014/0305900 | A1* | 10/2014 | Rogers | H01L 23/49894 216/13 |
| 2015/0314129 | A1* | 11/2015 | Perraud | A61N 1/375 607/116 |
| 2020/0022601 | A1* | 1/2020 | Rogers | H01L 21/02118 |

OTHER PUBLICATIONS

Yu, L., Kim, B. & Meng, E. Chronically Implanted Pressure Sensors: Challenges and State of the Field. Sensors 14, 20620 (2014).
Sit, A. J. Continuous Monitoring of Intraocular Pressure: Rationale and Progress Toward a Clinical Device. Journal of Glaucoma 18, 272-279 (2009).
Boutry, C. M. et al. Towards biodegradable wireless implants. Philosophical Transactions of the Royal Society A: Mathematical, Physical and Engineering Sciences 370, 2418-2432 (2012).
Chamis, A. L. et al. *Staphylococcus aureus* Bacteremia in Patients With Permanent Pacemakers or Implantable Cardioverter-Defibrillators. Circulation 104, 1029-1033 (2001).
Hall-Stoodley, L., Costerton, J. W. & Stoodley, P. Bacterial biofilms: from the Natural environment to infectious diseases. Nature Reviews Microbiology 2, 95 (2004).
Polikov, V. S., Tresco, P. A. & Reichert, W. M. Response of brain tissue to chronically implanted neural electrodes. Journal of Neuroscience Methods 148, 1-18 (2005).
Kang, S.-K. et al. Bioresorbable silicon electronic sensors for the brain. Nature 530, 71 (2016).
Luo, M., Martinez, A. W., Song, C., Herrault, F. & Allen, M. G. A Microfabricated Wireless RF Pressure Sensor Made Completely of Biodegradable Materials. Journal of Microelectromechanical Systems 23, 4-13 (2014).
Hwang, S.-W. et al. Biodegradable Elastomers and Silicon Nanomembranes/Nanoribbons for Stretchable, Transient Electronics, and Biosensors. Nano Letters 15, 2801-2808 (2015).
Yu, K. J. et al. Bioresorbable silicon electronics for transient spatiotemporal mapping of electrical activity from the cerebral cortex. Nature Materials 15, 782 (2016).
Lee, G. et al. Fully Biodegradable Microsupercapacitor for Power Storage in Transient Electronics. Advanced Energy Materials 7, 1700157 (2017).
Lee, C. H. et al. Wireless Microfluidic Systems for Programmed, Functional Transformation of Transient Electronic Devices. Advanced Functional Materials 25, 5100-5106 (2015).
Tao, H. et al. Silk-based resorbable electronic devices for remotely controlled therapy and in vivo infection abatement. Proceedings of the National Academy of Sciences 111, 17385-17389 (2014).
Hwang, S.-W. et al. A Physically Transient Form of Silicon Electronics. Science 337, 1640-1644 (2012).
Hwang, S.-W. et al. High-Performance Biodegradable/Transient Electronics on Biodegradable Polymers. Advanced Materials 26, 3905-3911, doi:10.1002/adma.201306050 (2014).
Kang, S.-K. et al. Dissolution Behaviors and Applications of Silicon Oxides and Nitrides in Transient Electronics. Advanced Functional Materials 24, 4427-4434 (2014).
Kang, S.-K. et al. Biodegradable Thin Metal Foils and Spin-On Glass Materials for Transient Electronics. Advanced Functional Materials 25, 1789-1797 (2015).
Fang, H. et al. Ultrathin, transferred layers of thermally grown silicon dioxide as biofluid barriers for biointegrated flexible electronic systems. Proceedings of the National Academy of Sciences 113, 11682-11687 (2016).
Lee, Y. K. et al. Kinetics and Chemistry of Hydrolysis of Ultrathin, Thermally Grown Layers of Silicon Oxide as Biofluid Barriers in Flexible Electronic Systems. ACS Applied Materials & Interfaces 9, 42633-42638 (2017).
Haddad, S. H. & Arabi, Y. M. Critical care management of severe traumatic brain injury in adults. Scandinavian Journal of Trauma, Resuscitation and Emergency Medicine 20, 12 (2012).
Nang, Q., Ding, J. & Wang, W. Fabrication and temperature coefficient compensation technology of low cost high temperature pressure sensor. Sensors and Actuators A: Physical 120, 468-473 (2005).
Camino, G., Lomakin, S. M. & Lazzari, M. Polydimethylsiloxane thermal degradation Part 1. Kinetic aspects. Polymer 42, 2395-2402 (2001).
Kanda, Y. A graphical representation of the piezoresistance coefficients in silicon. IEEE Transactions on Electron Devices 29, 64-70 (1982).
Lund, E. & Finstad, T. G. Temperature and Doping Dependency of Piezoresistivity in p-type Silicon. MRS Proceedings 657 (2000).
Norton, P. & Brandt, J. Temperature coefficient of resistance for p- and n-type silicon. Solid-State Electronics 21, 969-974 (1978).
Brain Trauma, F. et al. Guidelines for the management of severe traumatic brain injury. VI. Indications for intracranial pressure monitoring. J Neurotrauma 24 Suppl 1, S37-44 (2007).
Post craniotomy subdural pressure monitoring kit. Model 110-4G, in San Diego, CA: Integra NeuroSciences (2010).
Johanson, C. E et al. Multiplicity of cerebrospinal fluid functions: New challenges in health and disease. Cerebrospinal Fluid Research 5, 10 (2008).
Moghimi, S. M. & Patel, H. M. Serum-mediated recognition of liposomes by phagocytic cells of the reticuloendothelial system— The concept of tissue specificity. Advanced Drug Delivery Reviews 32, 45-60 (1998).
Gelabert-Gonzalez, M. et al. The Camino intracranial pressure device in clinical practice. Assessment in a 1000 cases. Acta Neurochirurgica 148, 435-441 (2006).
Martinez-Mañas, R. M., Santamarta, D., de Campos, J. M. & Ferrer, E. Camino® intracranial pressure monitor: prospective study of accuracy and complications. Journal of Neurology, Neurosurgery & amp;amp; Psychiatry 69, 82 (2000).
Zacchetti, L., Magnoni, S., Di Corte, F., Zanier, E. R. & Stocchetti, N. Accuracy of intracranial pressure monitoring: systematic review and meta-analysis. Critical Care 19, 420 (2015).
Dunn, J. F. et al. Functional mapping at 9.4T using a new MRI compatible electrode chronically implanted in rats. Magnetic resonance in medicine 61, 222-228 (2009).
M., S. G. A. & G., S. F. Pre-MRI Procedure Screening: Recommendations and Safety Considerations for Biomedical Implants and Devices. Journal of Magnetic Resonance Imaging 12, 92-106 (2000).
Insanally M et al. A low-cost, multiplexed μECoG system for high-density recordings in freely moving rodents. J. Neural Eng. 2016; 13(2): 026030.
Polley DB, Read HL, Storace DA, Merzenich MM. Multiparametric auditory receptive field organization across five cortical fields in the albino rat. J. Neurophys. 2007; 97(5):3621-38.
X. Dai, W. Zhou, T. Gao, J. Liu, C. M. Lieber, Nat. Nanotechnol., 2016, 11, 776-782.

(56) References Cited

OTHER PUBLICATIONS

R. Nawrocki, N. Matsuhisa, T. Yokota, T. Someya, Adv. Electron. Mater., 2016, 2(1500452), 1-4.
D.-H. Kim, N. Lu, R. Ma, Y.-S. Kim, R.-H. Kim, S. Wang, J. Wu, S. M. Won, H. Tao, A. Islam, 1 K. J. Yu, T.-i. Kim, R. Chowdhury, M. Ying, L. Xu, M. Li, H.-J. Chung, H. Keum, M. McCormick, P. Liu, Y.-W. Zhang, F. G. Omenetto, Y. Huang, T. Coleman, J. A. Rogers, Science, 2011, 333(6044), 838-43.
D.J. Lipomi, M. Vosgueritchian, B. C. Tee, S. L. Hellstrom, J. A. Lee, C. H. Fox, Z. Bao, Nature Nanotechnology, 2011, 6(12), 788-792.
M. C. McAlpine, H. Ahmad, D. Wang, J. R. Heath, Nature Materials, 2007, 6(5), 379-384.
W. Gao, S. Emaminejad, H. Y. Nyein, S. Challa, K. Chen, A. Peck, H. M. Fahad, H. Ota, H. Shiraki, D. Kiriya, D. H. Lien, G. A. Brooks, R. W. Davis, A. Javey, Nature, 2016, 529(7587), 509-514.
W. Wu, L. Wang, Y. Li, F. Zhang, L. Lin, S. Niu, D. Chenet, X. Zhang, Y. Hao, T. F. Heinz, J. Hone, Z. L. Wang, Nature, 2014, 514(7523), 470-474.
S. Xu, Y. Zhang, L. Jia, K. E. Mathewson, K. I. Jang, J. Kim, H. Fu, X. Huang, P. Chava, R. Wang, S. Bhole, L. Wang, Y. J. Na, Y. Guan, M. Flavin, Z. Han, Y. Huang, J. A. Rogers, Science, 2014, 344(6179), 70-74.
M. Kaltenbrunner, T. Sekitani, J. Reeder, T. Yokota, K. Kuribara,T. Tokuhara, M. Drack, R. Schwödiauer, I. Graz, S. Bauer-Gogonea, S. Bauer, T. Someya, Nature, 2013, 499(7459), 458-463.
Thejo Kalyani N, Dhoble SJ, Renewable and Sustainable Energy Reviews, 2015, 44, 319-347.
J.-S. Park, H. Chae, H. K. Chung, S. I. Lee, Semiconductor Science and Technology, 2011, 26(3), 034001.
H. Fang, K. J. Yu, C. Gloschat, Z. Yang, E. Song, C.-H. Chiang, J. Zhao, S. M. Won, S. Xu, M. Trumpis, Y. Zhong, S. W. Han, Y. Xue, D. Xu, S.W. Choi, G. Cauwenberghs, M. Kay, Y. Huang, J. Viventi, I. R. Efimov and J. A. Rogers, Nature Biomedical Engineering, 2017, 1(3), 0038.
R. Li, H. Cheng, Y. Su, S.-W. Hwang, L. Yin, H. Tao, M. A. Brenckle, D.-H. Kim, F. G. Omenetto, J. A. Rogers, Y. Huang, Advanced Functional Materials, 2013, 23, 3106.
P. V. Danckwerts, Transactions of the Faraday Society, 1950, 46, 300.
K. M. Davis, M. Tomozawa, Journal of Non-Crystalline Solids, 1995, 185, 203.
M. Tomozawa, K. M. Davis, Materials Science and Engineering, 1999, A272, 114.
J. D. Rimstidt, Geochim. Cosmochim. Acta , 2015, 167, 195.
P. M. Dove & D. A. Crerar, Geochim. Cosmochim. Acta, 1990, 54, 955.
P. V. Brady, J. V. Walther, Chem. Geol., 1990, 82, 253.
M. Karlsson, C. Craven, P. M. Dove, W. H. Casey, Aquat. Geochemistry, 2001, 7, 13.
O. Majérus, T. Gérardin, G. Manolescu, P. Barboux, D. Caurant, Phys. and Chem. of Glasses—European Journal of Glass Science and Technology B, 2014, 13, 261.
K. C. Jena, P. A. Covert, D. K. Hore, J. Phys. Chem. Lett., 2011, 2, 1056.
P. M. Dove, P. M., C. J. Nix, Geochim. Cosmochim. Acta, 1997, 61, 3329.
Kim D-H, et al. (2011) Epidermal electronics. Science 333(6044):838-843.
Lipomi DJ, et al. (2011) Skin-like pressure and strain sensors based on transparent elastic films of carbon nanotubes. Nat Nanotechnol 6(12):788-792.
Xu S, et al. (2014) Soft microfluidic assemblies of sensors, circuits, and radios for the skin. Science 344(6179):70-74.
Gao W, et al. (2016) Fully integrated wearable sensor arrays for multiplexed in situ perspiration analysis. Nature 529(7587):509-514.
Wu W, et al. (2014) Piezoelectricity of single-atomic-layer MoS2 for energy conversion and piezotronics. Nature 51(7523):470-474.
McAlpine MC, Ahmad H, Wang D, Heath JR (2007) Highly ordered nanowire arrays on plastic substrates for ultrasensitive flexible chemical sensors. Nat Mater 6(5):379-384.
Kaltenbrunner M, et al. (2013) An ultra-lightweight design for imperceptible plastic electronics. Nature 499(7459):458-463.
Lochner CM, Khan Y, Pierre A, Arias AC (2014) All-organic optoelectronic sensor for pulse oximetry. Nat Commun 5:5745.
Son D, et al. (2014) Multifunctional wearable devices for diagnosis and therapy of movement disorders. Nat Nanotechnol 9(5):397-404.
Montgomery KL, et al. (2015) Wirelessly powered, fully internal optogenetics for brain, spinal and peripheral circuits in mice. Nat Methods 12(10):969-974.
Kim TI, et al. (2013) Injectable, cellular-scale optoelectronics with applications for wireless optogenetics. Science 340(6129):211-216.
Canales A, et al. (2015) Multifunctional fibers for simultaneous optical, electrical and chemical interrogation of neural circuits in vivo. Nat Biotechnol 33(3):277-284.
Viventi J, et al. (2010) A conformal, bio-interfaced class of silicon electronics for mapping cardiac electrophysiology. Sci Transl Med 2(24):24ra22.
Kim D-H, et al. (2011) Materials for multifunctional balloon catheters with capabilities in cardiac electrophysiologicalmapping and ablation therapy. Nat Mater 10(4):316-323.
Xu L, et al. (2014) 3D multifunctional integumentary membranes for spatiotemporal cardiac measurements and stimulation across the entire epicardium. Nat Commun 5:3329.
Kim D-H, et al. (2012) Electronic sensor and actuator webs for large-area complex geometry cardiac mapping and therapy. Proc Natl Acad Sci USA 109(49):19910-19915.
Sekitani T, Zschieschang U, Klauk H, Someya T (2010) Flexible organic transistors and circuits with extreme bending stability. Nat Mater 9(12):1015-1022.
Schwartz G, et al. (2013) Flexible polymer transistors with high pressure sensitivity for application in electronic skin and health monitoring. Nat Commun 4:1859.
Tian B, et al. (2010) Three-dimensional, flexible nanoscale field-effect transistors as localized bioprobes. Science 329(5993):830-834.
Wu W, Wen X, Wang ZL (2013) Taxel-addressable matrix of vertical-nanowire piezotronic transistors for active and adaptive tactile imaging. Science 340(6135): 952-957.
Rogers JA, Someya T, Huang Y (2010) Materials and mechanics for stretchable electronics. Science 327(5973):1603-1607.
Wilson BS, et al. (1991) Better speech recognition with cochlear implants. Nature 352(6332):236-238.
Hochberg LR, et al. (2006) Neuronal ensemble control of prosthetic devices by a human with tetraplegia. Nature 442(7099):164-171.
Bowman L, Meindl JD (1986) The packaging of implantable integrated sensors. IEEE Trans Biomed Eng 33(2):248-255.
Sanders RS, Lee MT (1996) Implantable pacemakers. Proc IEEE 84(3):480-486.
Mayberg HS, et al. (2005) Deep brain stimulation for treatment-resistant depression. Neuron 45(5):651-660.
Rousche PJ, Normann RA (1998) Chronic recording capability of the Utah Intracortical Electrode Array in cat sensory cortex. J Neurosci Methods 82(1):1-15.
Harrison RR, et al. (2007) A low-power integrated circuit for a wireless 100-electrode neural recording system. IEEE J Solid-State Circuits 42(1):123-133.
Hoogerwerf AC, Wise KD (1994) A three-dimensional microelectrode array for chronic neural recording. IEEE Trans Biomed Eng 41(12):1136-1146.
Wise KD, Anderson DJ, Hetke JF, Kipke DR, Najafi K (2004) Wireless implantable microsystems: High-density electronic interfaces to the nervous system. Proc IEEE 92(1):76-97.
Tyler DJ, Durand DM (2002) Functionally selective peripheral nerve stimulation with a flat interface nerve electrode. IEEE Trans Neural Syst Rehabil Eng 10(4):294-303.
Viventi J, et al. (2011) Flexible, foldable, actively multiplexed, high-density electrode array for mapping brain activity in vivo. Nat Neurosci 14(12):1599-1605.
Khodagholy D, et al. (2013) In vivo recordings of brain activity using organic transistors. Nat Commun 4:1575.

(56) References Cited

OTHER PUBLICATIONS

Bellin DL, et al. (2014) Integrated circuit-based electrochemical sensor for spatially resolved detection of redox-active metabolites in biofilms. Nat Commun 5:3256.
Thejo Kalyani N, Dhoble SJ (2015) Novel materials for fabrication and encapsulation of OLEDs. Renew Sustain Energy Rev 44:319-347.
Park J-S, et al. (2011) Thin film encapsulation for flexible AM-OLED: A review. Semicond Sci Technol 26(3):034001.
Ahmad J, Bazaka K, Anderson LJ, White RD, Jacob MV (2013) Materials and methods for encapsulation of OPV: A review. Renew Sustain Energy Rev 27:104-117.
Xie X, Rieth L, Merugu S, Tathireddy P, Solzbacher F (2012) Plasma-assisted atomic layer deposition of Al2O3 and parylene C bi-layer encapsulation for chronic implantable electronics. Appl Phys Lett 101(9):93702.
Andringa A-M, et al. (2015) Low-temperature plasma-assisted atomic layer deposition of silicon nitride moisture permeation barrier layers. ACS Appl Mater Interfaces 7(40): 22525-22532.
Huang Y, et al. (2008) Evaluation of the corrosion resistance of anodized aluminum 6061 using electrochemical impedance spectroscopy (EIS). Corros Sci 50(12): 3569-3575.
Yong-Qiang Y, et al. (2014) High barrier properties of transparent thin-film encapsulations for top emission organic light-emitting diodes. Org Electron 15(6):1120-1125.
Worley WG (1994) Dissolution kinetics and mechanisms in quartz- and grainite-water systems. PhD dissertation (Massachusetts Institute of Technology, Cambridge, MA).
Knauss KG, Wolery TJ (1988) The dissolution kinetics of quartz as a function of pH and time at 70° C. Geochim Cosmochim Acta 52(1):43-53.
Icenhower JP, Dove PM (2000) The dissolution kinetics of amorphous silica into sodium chloride solutions: Effects of temperature and ionic strength. Geochim Cosmochim Acta 64(24):4193-4203.
Dove PM, Han N, De Yoreo JJ (2005) Mechanisms of classical crystal growth theory explain quartz and silicate dissolution behavior. Proc Natl Acad Sci USA 102(43): 15357-15362.
Gibson JM, Dong DW (1980) Direct evidence for 1 nm pores in "dry" thermal SiO2 from high resolution transmission electron microscopy. J Electrochem Soc 127(12):2722.
Hasegawa M, et al. (2000) Positron and positronium studies of irradiation-induced defects and microvoids in vitreous metamict silica. Nucl Instrum Methods Phys Res B 166:431-439.
Yin L, et al. (2015) Mechanisms for hydrolysis of silicon nanomembranes as used in bioresorbable electronics. Adv Mater 27(11):1857-1864.
Ito T, et al. (1982) Advantages of thermal nitride and nitroxide gate films in VLSI process. IEEE J Solid-State Circuits 17(2):128-132.
Thomas, C., Springer, P., Loeb, G., Berwald-Netter, Y. & Okun, L. A miniature microelectrode array to monitor the bioelectric activity of cultured cells. Exp. Cell Res. 74, 61-66 (1972).
Pertsov, A. M., Davidenko, J. M., Salomonsz, R., Baxter, W. T. & Jalife, J. Spiral waves of excitation underlie reentrant activity in isolated cardiac muscle. Circ. Res. 72, 631-650 (1993).
Sprössler, C., Denyer, M., Britland, S., Knoll, W. & Offenhäusser, A. Electrical recordings from rat cardiac muscle cells using field-effect transistors. Phys. Rev. E 60, 2171-2176 (1999).
Camelliti, P. et al. Adult human heart slices are a multicellular system suitable for electrophysiological and pharmacological studies. J Mol. Cell. Cardiol. 51, 390-398 (2011).
Huys, R. et al. Single-cell recording and stimulation with a 16k micro-nail electrode array integrated on a 0.18 µm CMOS chip. Lab Chip 12, 1274-1280 (2012).
Zhang, X., Tai, J., Park, J. & Tai, Y.-C. Flexible MEA for adult zebrafish ECG recording covering both ventricle and atrium. In Proc. IEEE 27th Int. Conf. Micro Electro Mechanical Systems (MEMS) 841-844 (IEEE, 2014).
Friedman, P. A. Novel mapping techniques for cardiac electrophysiology. Heart 87, 575-582 (2002).

Laks, M. M., Arzbaecher, R., Bailey, J. J., Geselowitz, D. B. & Berson, A. S. Recommendations for safe current limits for electrocardiographs a statement for healthcare professionals from the Committee on Electrocardiography, American Heart Association. Circulation 93, 837-839 (1996).
Swerdlow, C. D. et al. Cardiovascular collapse caused by electrocardiographically silent 60-Hz intracardiac leakage current implications for electrical safety. Circulation 99, 2559-2564 (1999).
Beech, I. B. & Sunner, J. Biocorrosion: towards understanding interactions between biofilms and metals. Curr. Opin. Biotechnol. 15, 181-186 (2004).
Liu, X. et al. Stability of the interface between neural tissue and chronically implanted intracortical microelectrodes. IEEE Trans. Rehab. Eng. 7, 315-326 (1999).
Bazaka, K. & Jacob, M. V. Implantable devices: issues and challenges. Electronics 2, 1-34 (2012).
Someya, T. et al. Conformable, flexible, large-area networks of pressure and thermal sensors with organic transistor active matrixes. Proc. Natl Acad. Sci. USA 102, 12321-12325 (2005).
Lacour, S. P., Jones, J., Wagner, S., Li, T. & Suo, Z. Stretchable interconnects for elastic electronic surfaces. Proc. IEEE 93, 1459-1467 (2005).
Takei, K. et al. Nanowire active-matrix circuitry for low-voltage macroscale artificial skin. Nat. Mater. 9, 821-826 (2010).
Khodagholy, D. et al. NeuroGrid: recording action potentials from the surface of the brain. Nat. Neurosci. 18, 310-315 (2015).
Fromherz, P., Offenhausser, A., Vetter, T. & Weis, J. A neuron-silicon junction: a Retzius cell of the leech on an insulated-gate field-effect transistor. Science 252, 1290-1293 (1991).
Zeck, G. & Fromherz, P. Noninvasive neuroelectronic interfacing with synaptically connected snail neurons immobilized on a semiconductor chip. Proc. Natl Acad. Sci. USA 98, 10457-10462 (2001).
Chi, Y. M., Jung, T.-P. & Cauwenberghs, G. Dry-contact and noncontact biopotential electrodes: methodological review. IEEE Rev. Biomed. Eng. 3, 106-119 (2010).
Spira, M. E. & Hai, A. Multi-electrode array technologies for neuroscience and cardiology. Nat. Nanotech. 8, 83-94 (2013).
Berdondini, L. et al. Active pixel sensor array for high spatio-temporal resolution electrophysiological recordings from single cell to large scale neuronal networks. Lab Chip 9, 2644-2651 (2009).
Eversmann, B. et al. A 128× 128 CMOS biosensor array for extracellular recording of neural activity. IEEE J. Solid-State Circ. 38, 2306-2317 (2003).
Bakkum, D. J. et al. Tracking axonal action potential propagation on a high-density microelectrode array across hundreds of sites. Nat. Commun. 4, 21821 (2013).
Byers, C. L., Beazell, J. W., Schulman, J. H. & Rostami, A. Hermetically sealed ceramic and metal package for electronic devices implantable in living bodies. U.S. Pat. No. 4,991,582 A (1991).
Zeng, F.-G., Rebscher, S., Harrison, W., Sun, X. & Feng, H. Cochlear implants: system design, integration, and evaluation. IEEE Rev. Biomed. Eng. 1, 115-142 (2008).
Sillay, K. A., Larson, P. S. & Starr, P. A. Deep brain stimulator hardware-related infections: incidence and management in a large series. Neurosurgery 62, 360-367 (2008).
Jeong, J. W. et al. Capacitive epidermal electronics for electrically safe, long-term electrophysiological measurements. Adv. Health. Mater. 3, 642-648 (2014).
Duan, X. et al. Quantification of the affinities and kinetics of protein interactions using silicon nanowire biosensors. Nat. Nanotech. 7, 401-407 (2012).
Fattahi, P., Yang, G., Kim, G. & Abidjan, M. R. A review of organic and inorganic biomaterials for neural interfaces. Adv. Mater. 26, 1846-1885 (2014).
Langendorff, O. Untersuchungen am übedebenden Säugethierherzen. Pflügers Archiv Eur. J. Physiol. 61, 291-332 (1895).
Efimov, I. R., Nikolski, V. P. & Salama, G. Optical imaging of the heart. Circ. Res. 95, 21-33 (2004).
Bossaert, L. Fibrillation and defibrillation of the head. Br. J. Anaesth. 79, 203-213 (1997).

(56) References Cited

OTHER PUBLICATIONS

Efimov, I. R., Cheng, Y., Van Wagoner, D. R., Mazgalev, T. & Tchou, P. J. Virtual electrode-induced phase singularity a basic mechanism of defibrillation failure. Circ. Res. 82, 918-925 (1998).
Rogers, J. M. Combined phase singularity and wavefront analysis for optical maps of ventricular fibrillation. IEEE Trans. Biomed. Eng. 51, 56-65 (2004).
Narayan, S. M. et al. Treatment of atrial fibrillation by the ablation of localized sources: CONFIRM (conventional ablation for atrial fibrillation with or without focal impulse and rotor modulation) trial. J. Am. Coll. Cardiol. 60, 628-636 (2012).
Lim, H. S. et al. Noninvasive mapping to guide atrial fibrillation ablation. Cardiac Electrophysiol. Clinics 7, 89-98 (2015).
Bray, M. A., Lin, S. F., Aliev, R. R., Roth, B. J. & Wikswo, J. P. Experimental and theoretical analysis of phase singularity dynamics in cardiac tissue. J.Cardiovasc. Electrophysiol. 12, 716-722 (2001).
Onuki, Y., Bhardwaj, U., Papadimitrakopoulos, F. & Burgess, D. J. A review of the biocompatibility of implantable devices: current challenges to overcome foreign body response. J Diabetes Sci. Technol. 2, 1003-1015 (2008).
Ward, W. K. A review of the foreign-body response to subcutaneously-implanted devices: the role of macrophages and cytokines in biofouling and fibrosis. J Diabetes Sci. Technol. 2, 768-777 (2008).
Morais, J. M., Papadimitrakopoulos, F. & Burgess, D. J. Biomaterials/tissue interactions: possible solutions to overcome foreign body response. AAPS J. 12, 188-196 (2010).
Vegas, A. J. et al. Combinatorial hydrogel library enables identification of materials that mitigate the foreign body response in primates. Nat. Biotechnol. 34, 345-352 (2016).
Hibbitt, H., Karisson, B. & Sorensen, P. Abaqus analysis user's manual v.6.10 (Dassault Systemes Simulia Corp, 2011).
Shi, Y., Rogers, J. A., Gao, C. & Huang, Y. Multiple neutral axes in bending of a multiple-layer beam with extremely different elastic properties. J. Appl. Mech. 81, 114501 (2014).
Li, L. et al. Integrated flexible chalcogenide glass photonic devices. Nat. Photon. 8, 643-649 (2014).
Su, Y., Li, S., Li, R. & Dagdeviren, C. Splitting of neutral mechanical plane of conformal, multilayer piezoelectric mechanical energy harvester. Appl. Phys. Lett. 107, 041905 (2015).
Balk P, Eldridge JM (1969) Phosphosilicate glass stabilization of FET devices. Proc IEEE 57(9):1558-1563.
Min Yan M, et al. (2005) A transparent, high barrier, and high heat substrate for organic electronics. Proc IEEE 93(8):1468-1477.
Miller JR, Outlaw RA, Holloway BC (2010) Graphene double-layer capacitor with ac line-filtering performance. Science 329(5999):1637-9.
Van Duin AC, Dasgupta S, Lorant F, A. GW (2001) ReaxFF: A Reactive Force Field for Hydrocarbonds. Journal of Physical Chemistry A 105(41):9396-9409.
Plimpton S (1995) Fast Parallel Algorithms for Short-Range Molecular Dynamics. Journal of Computational Physics 117(1):1-19.
Fogarty JC, Aktulga HM, Grama AY, Van Duin AC, Pandit SA (2010) A reactive molecular dynamics simulation of the silica-water interface. The Journal of Chemical Physics 132(17):174704.
Van Duin AC, et al. (2003) ReaxFFSiO reactive force field for silicon and silicon oxide systems. The Journal of Physical Chemistry A 107(19):3803-3811.
Evans DJ, Holian BL (1985) The Nose—Hoover thermostat. The Journal of Chemical Physics 83(8):4069.
Dove PM, Han N, Wallace AF, De Yoreo JJ (2008) Kinetics of amorphous silica dissolution and the paradox of the silica polymorphs. Proceedings of the National Academy of Sciences 105(29):9903-9908.
Kang S-K, et al. (2014) Dissolution Behaviors and Applications of Silicon Oxides and Nitrides in Transient Electronics. Advanced Functional Materials 24(28):4427-4434.
Mecha J & Steinmann J (1979) Mobility of Sodium Ions in Silica Glass of Different OH Content. Journal of the American Ceramic Society 62(7-8):343-346.
Sze SM (2008) Semiconductor devices: physics and technology (2nd edition). John Wiley & Sons, p. 183.
Y. Sun, J. A. Rogers, Adv. Mater. 2007, 19, 1897-1916.
H. Fang, J. Zhao, K. J. Yu, E. Song, A. B. Farimani, C.-H. Chiange, X. Jin, Y. Xue, D. Xu, W. Dui, K. J. Seo, Y. Zhong, Z. Yang, S. M. Won, G. Fang, S. W. Choi, S. Chaudhuri, Y. Huang, M. A. Alam, J. Viventi, N. R. Aluru, J. A. Rogers, Proceedings of the National Academy of Sciences, 2016, 113(42), 11682-11687.
E. Yon, W. Ko, A. Kuper, IEEE Transactions on Electron Devices, 1966, Ed13, 276-280.
V. Korol, Physica status solidi (a), 1988, 110, 9-34.
T. Burges, J. C. Baum, F. M. Fowkes, R. Holmstrom, G. A. Shim, J. Electrochem. Soc., 1969, 116(7), 1005-1008.
K. J. Yu, D. Kuzum, S.-W. Hwang, B.H. Kim, H. Juul, N.H. Kim, S.M. Won, K. Chiang, M. Trumpis, A.G. Richardson, H. Cheng, H. Fang, M. Thompson, H. Bink, D. Talos, K.J. Seo, H.N. Lee, S.-K. Kang, J.-H. Kim, J.Y. Lee, Y. Huang, F.E. Jensen, M.A. Dichter, T.H. Lucas, J. Viventi, B. Litt and J.A. Rogers, Nature Materials, 2016, 15, 782.
P. Dak, M. A. Alam, IEEE Transactions on Electron Devices, 2016, 63(6), 2524-2530.
Y. Taur, T. H. Ning, Fundamentals of Modern VLSI Devices. Cambridge University Press, USA 2009.
S.-K. Kang, S.-W. Hwang, H. Cheng, S. Yu, B. H. Kim, J.-H. Kim, Y. Huang, J. A. Rogers, Adv. Funct. Mater., 2014, 24, 4427-4434.
J. Osenbach, S. Voris, Journal of applied physics, 1988, 63, 4494-4500.
P. R. Gray, P. J. Hurst, S. H. Lewis, R. G. Meyer, Analysis and Design of Analog Integrated Circuits (5th edition). John Wiley & Sons, USA 2009.

\* cited by examiner

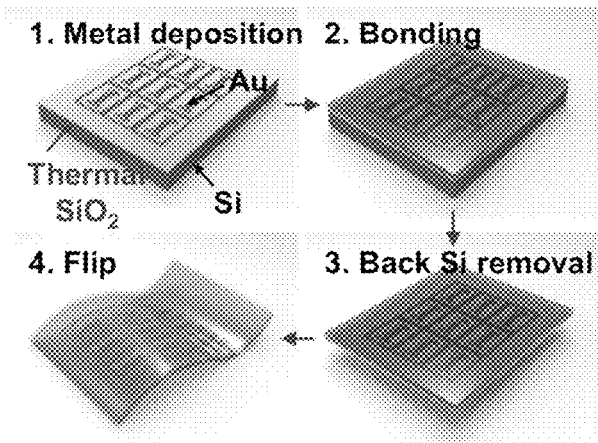
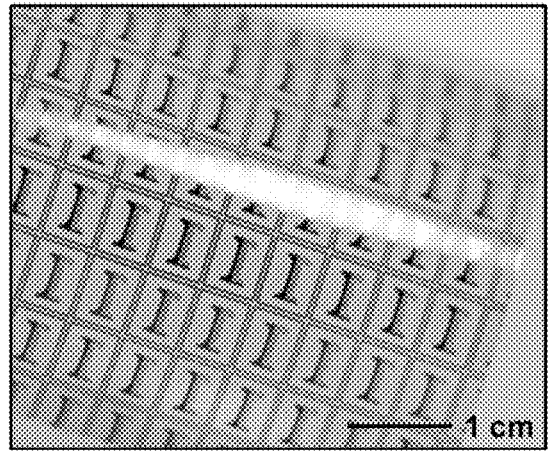
FIG. 1A  FIG. 1B
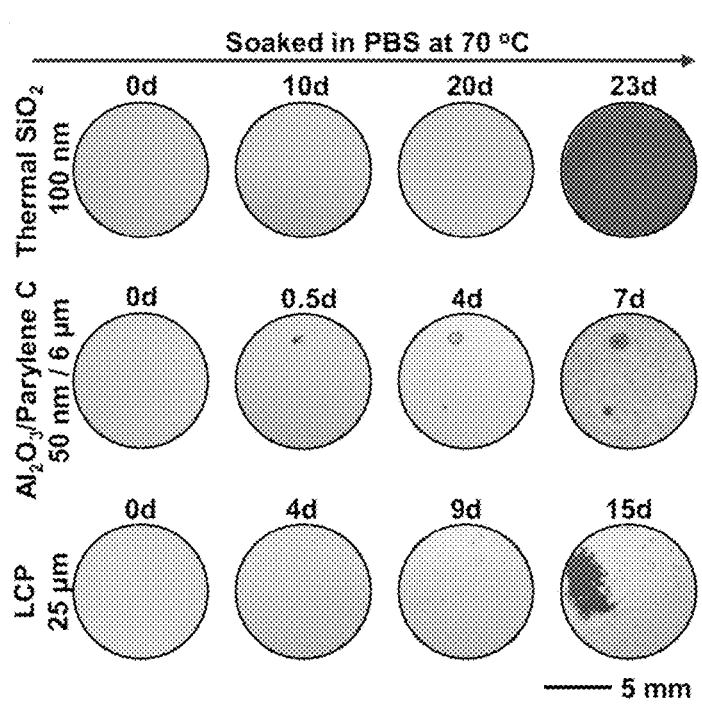
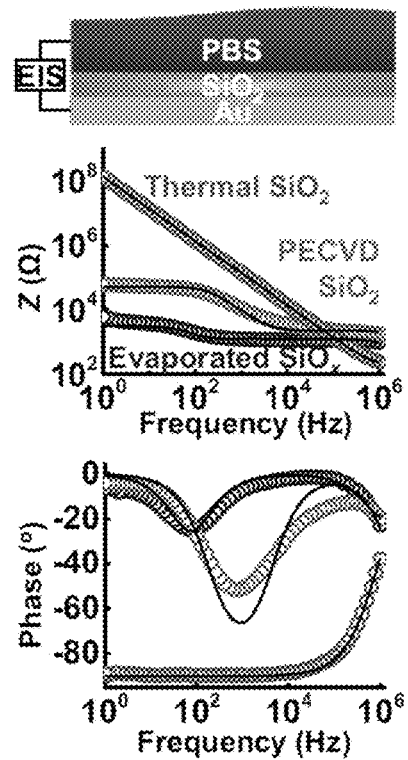
FIG. 1C  FIG. 1D

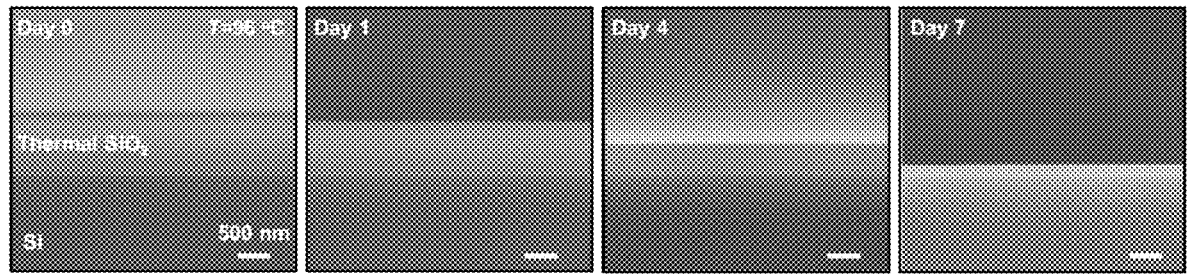
FIG. 2A
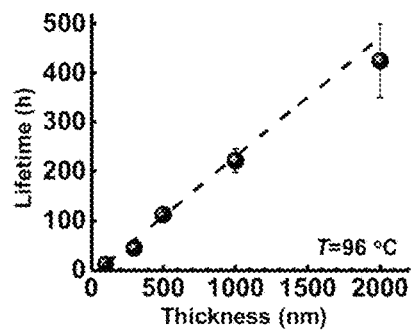
FIG. 2B
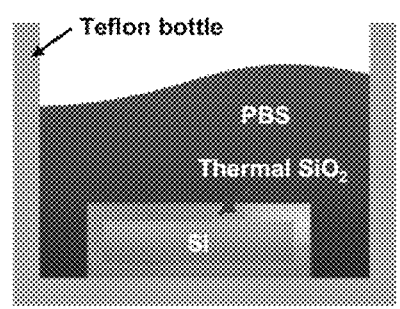
FIG. 2D
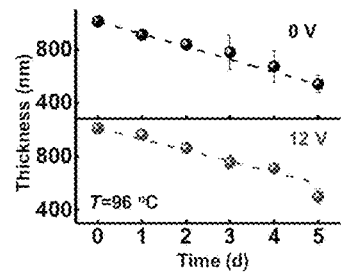
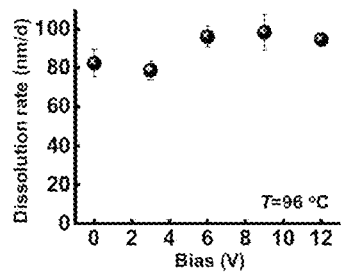
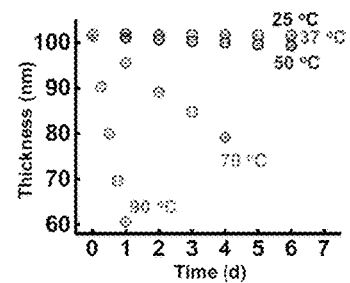
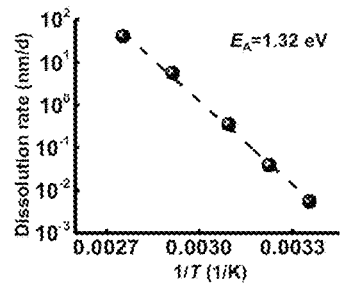
FIG. 2C

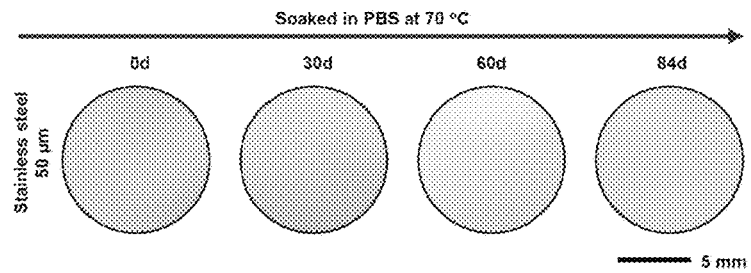
FIG. 7
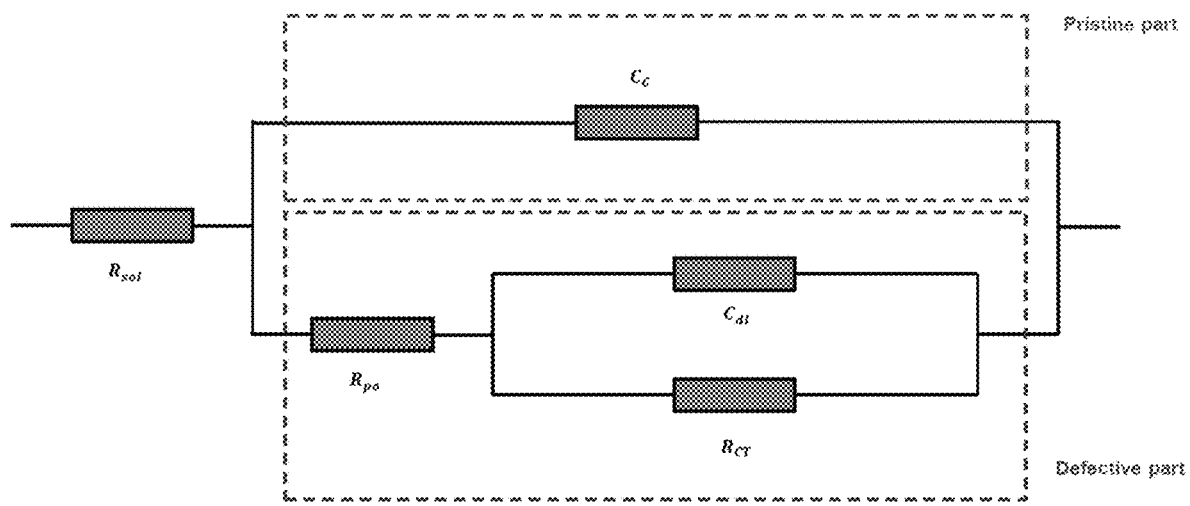
FIG. 8A
| Circuit element | Physical Meaning | Expression of impedance | Evaporated SiO$_x$ | PECVD SiO$_2$ | Thermal SiO$_2$ |
|---|---|---|---|---|---|
| $R_{sol}$ /Ω | Solution resistance | $R_{sol}$ | 600 | 200 | 180 |
| $R_{po}$ /Ω | Pore resistance | $R_{po}$ | 600 | 2000 | N/A |
| $R_{CT}$ /Ω | Charge transfer resistance | $R_{CT}$ | 1800 | 48000 | N/A |
| $C_{dl}$ /µF | Double layer capacitance | $\frac{1}{j\omega C_{dl}}$ | 1.9 | 0.018 | N/A |
| $C_C$ /nF | Coating capacitance | $\frac{1}{j\omega C_C}$ | 0.3 | 0.86 | 1.17 |
FIG. 8B

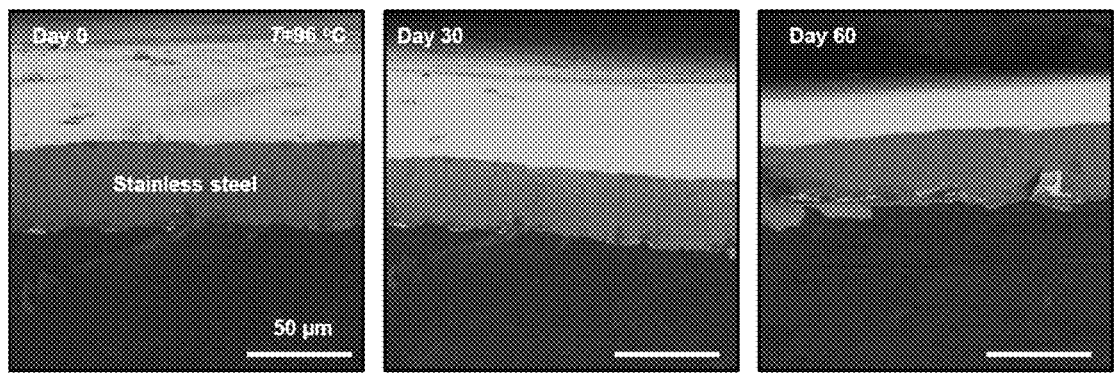
FIG. 12
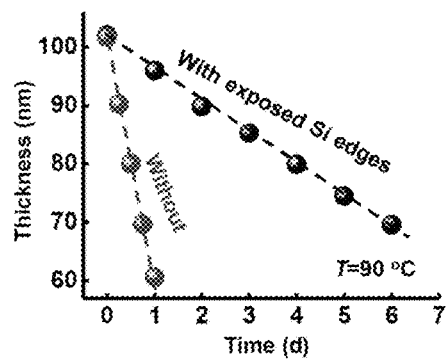
FIG. 13
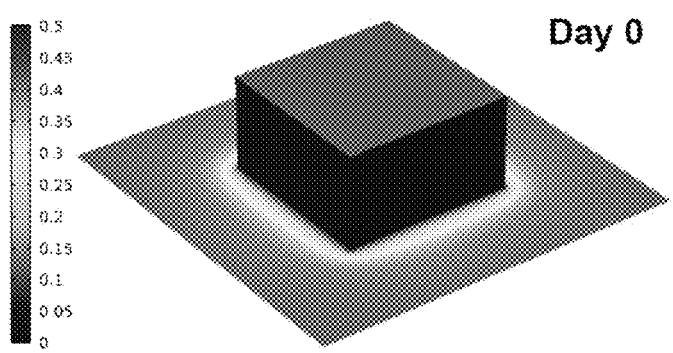
Day 0
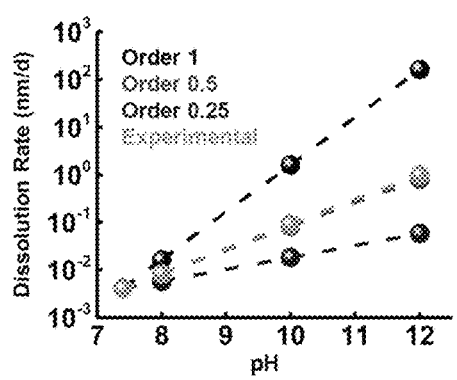
FIG. 14A
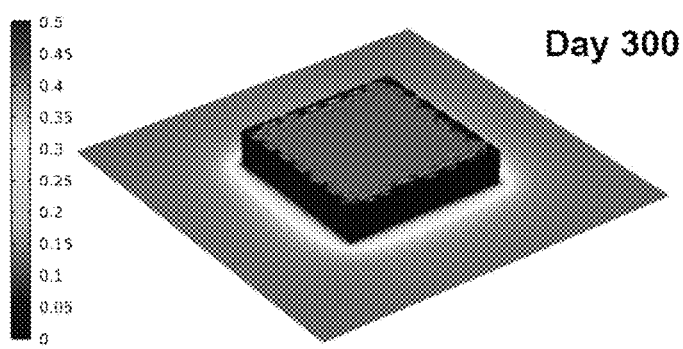
Day 300
FIG. 14B

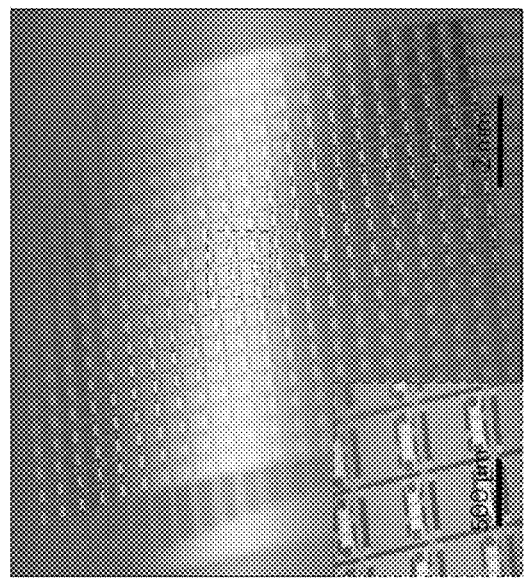
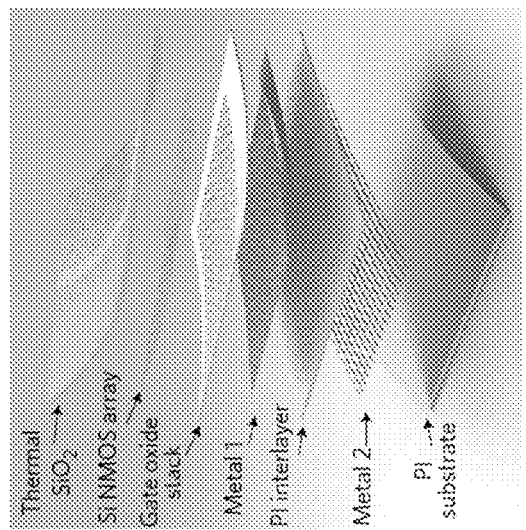
FIG. 31A
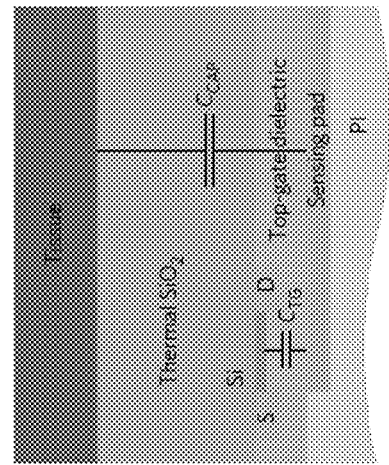
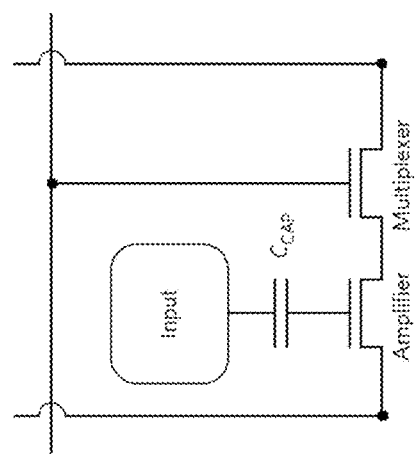
FIG. 31B

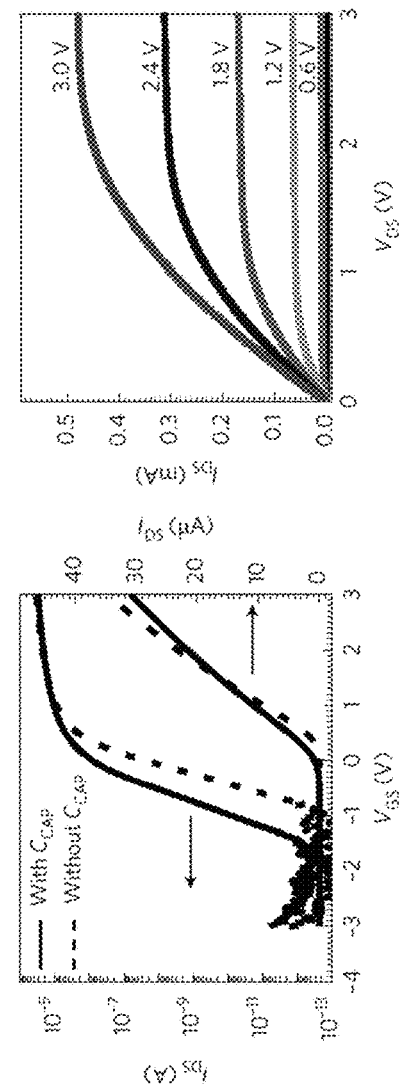
FIG. 31C
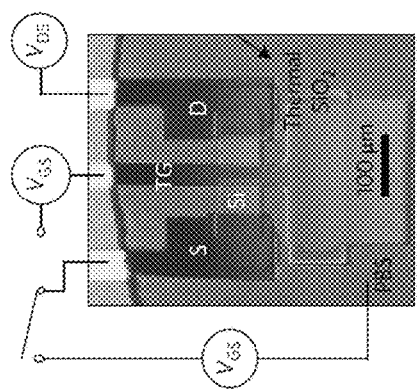
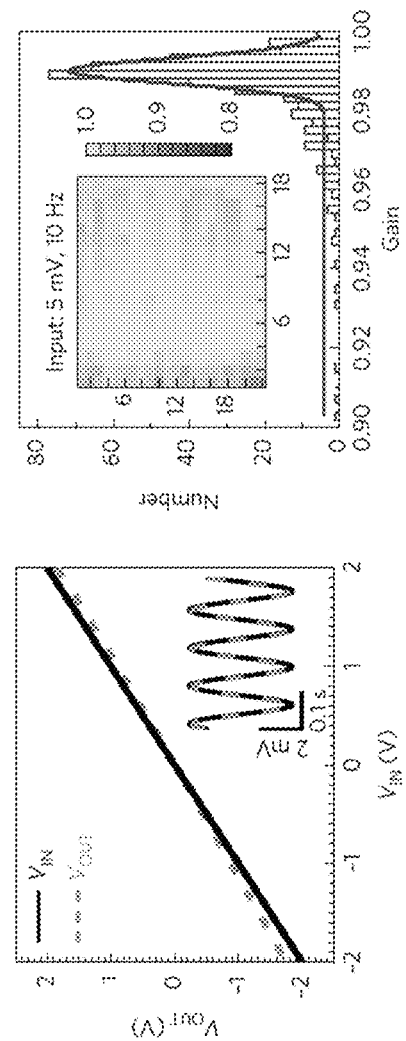
FIG. 31E
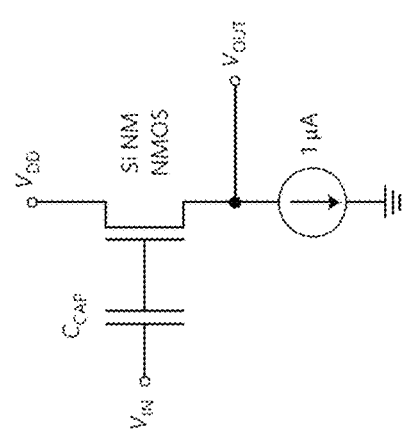
FIG. 31D

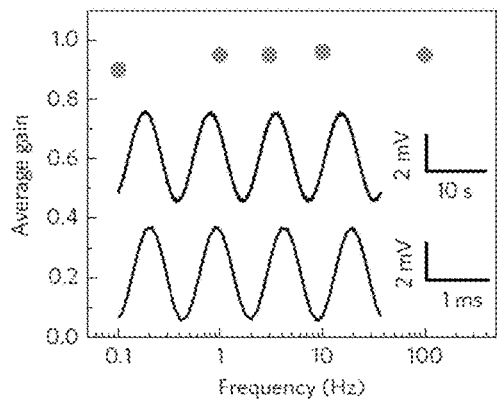
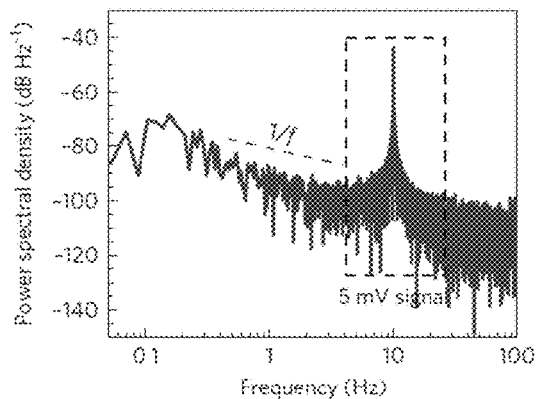
FIG. 32A  FIG. 32B
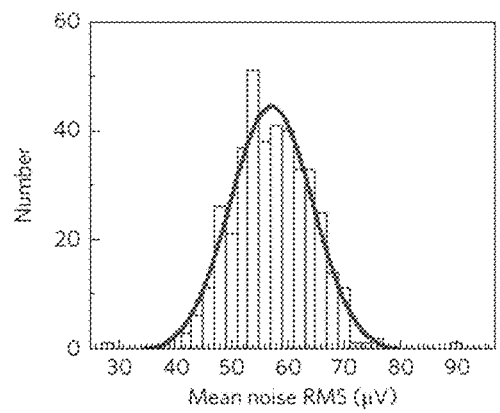
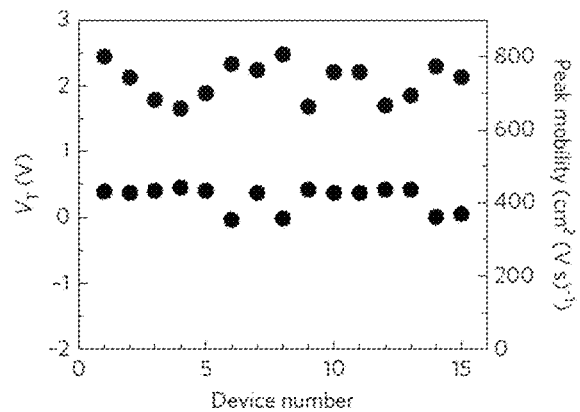
FIG. 32C  FIG. 32D
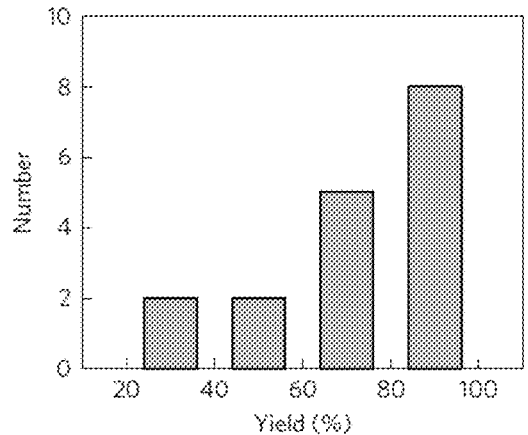
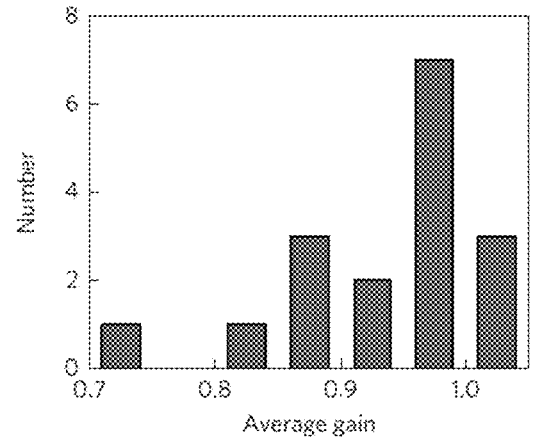
FIG. 32E

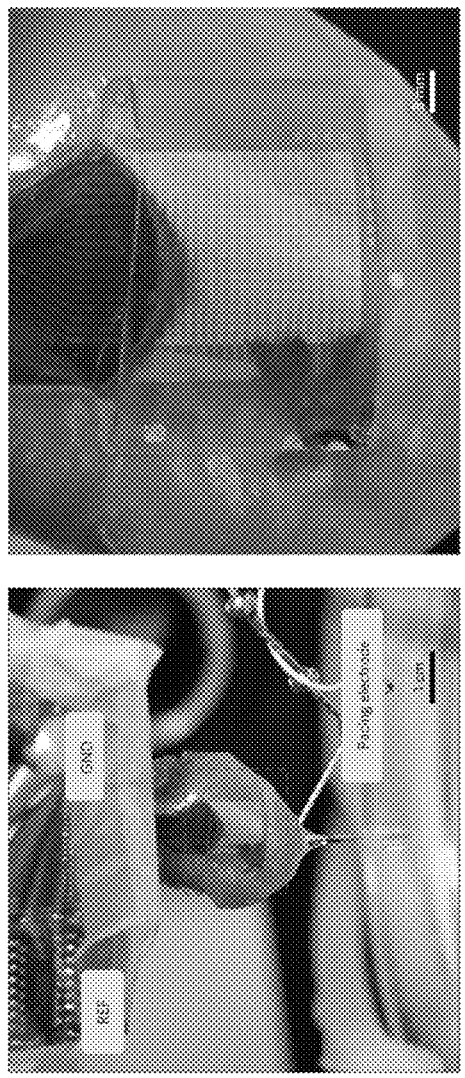
FIG. 33A
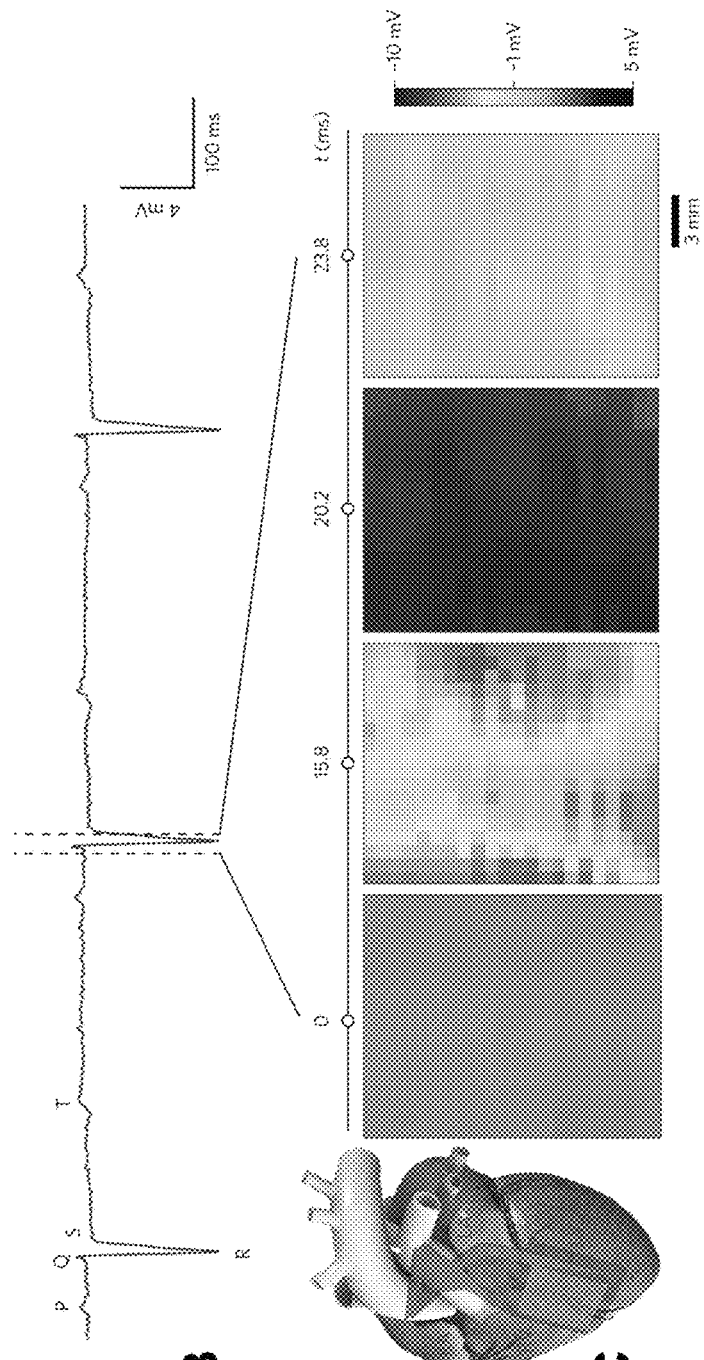
FIG. 33B
FIG. 33C

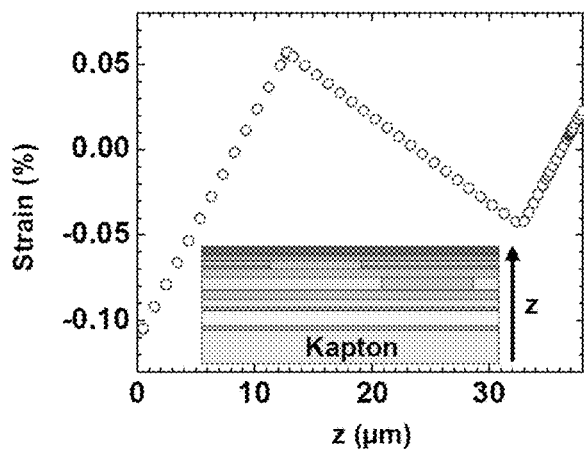
FIG. 44A
| Material | Young's Modulus | Poisson's ratio |
|---|---|---|
| $SiO_2$ | 70 GPa | 0.17 |
| Si | 130 GPa | 0.27 |
| Au | 78 GPa | 0.44 |
| PI | 2.5 GPa | 0.34 |
| Kwik Sil | 1 MPa | 0.49 |
| Kapton | 2.5 GPa | 0.34 |
FIG. 44B
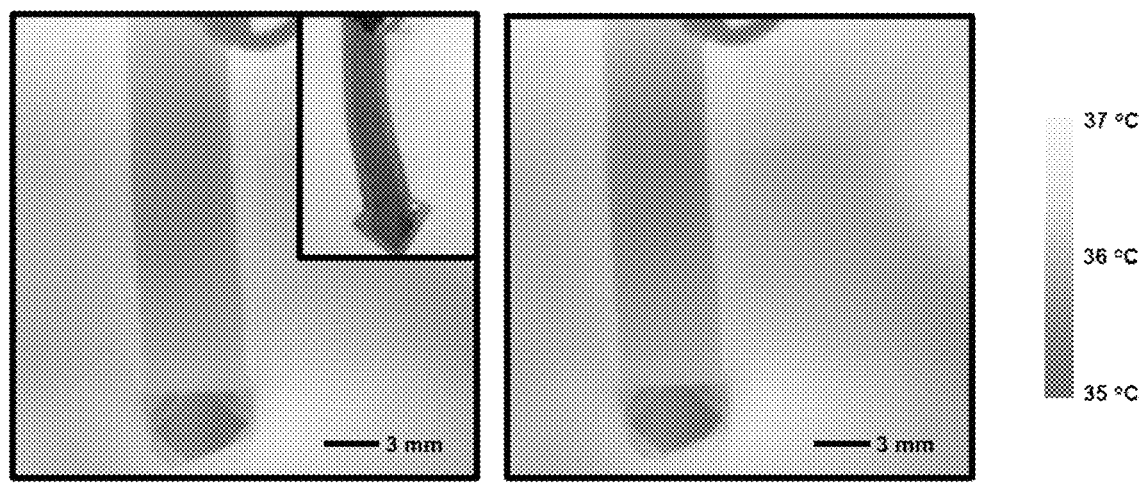
FIG. 45

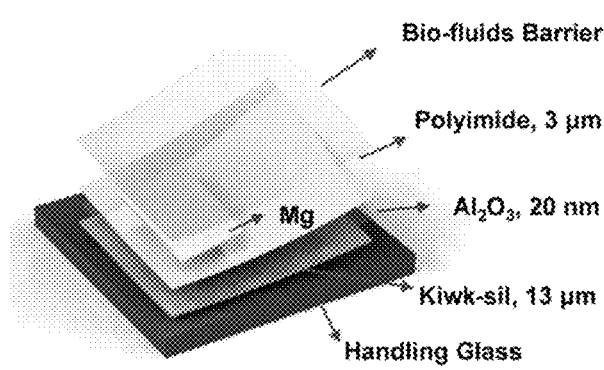 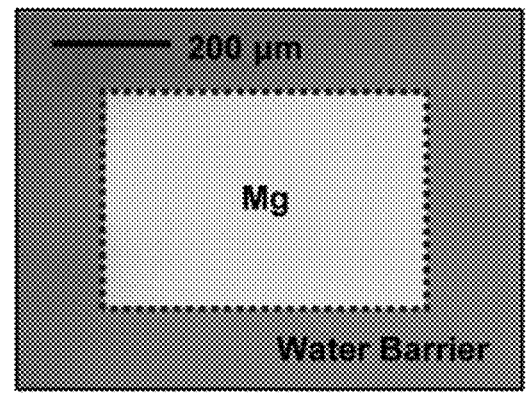
FIG. 62A  FIG. 62B
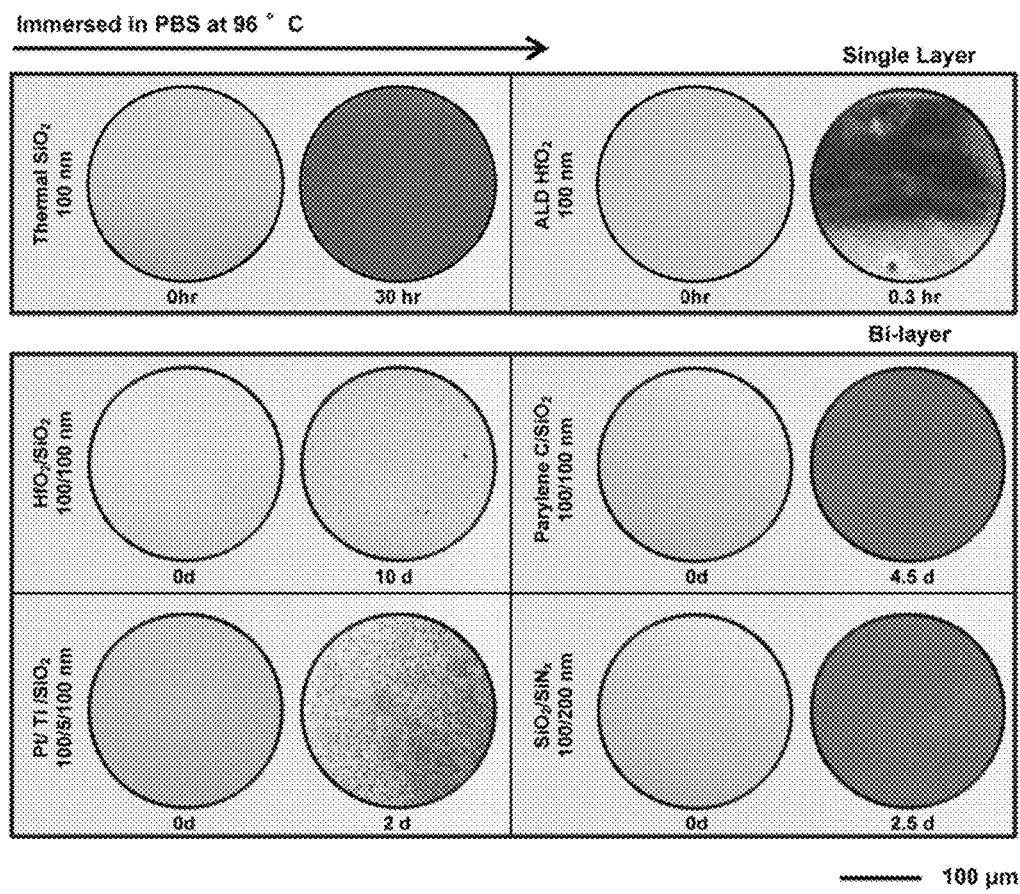
FIG. 62C

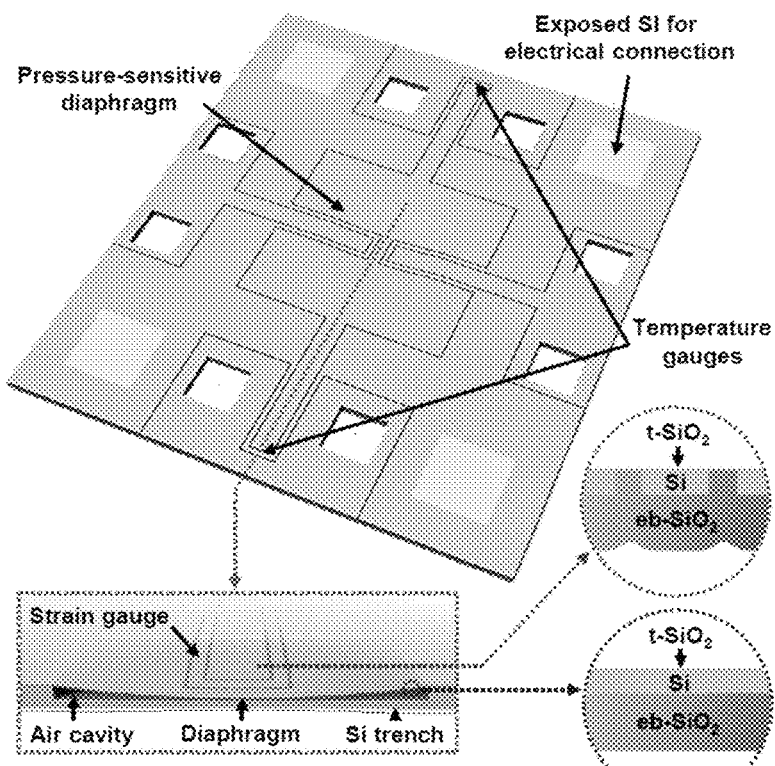
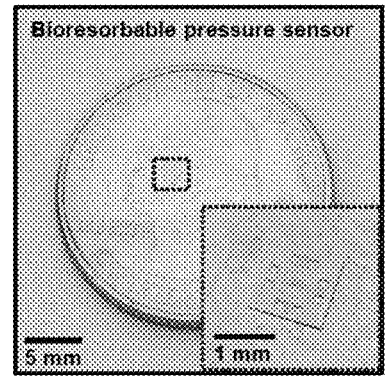
FIG. 79B
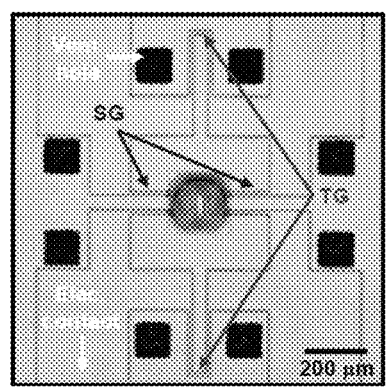
FIG. 79C
FIG. 79A
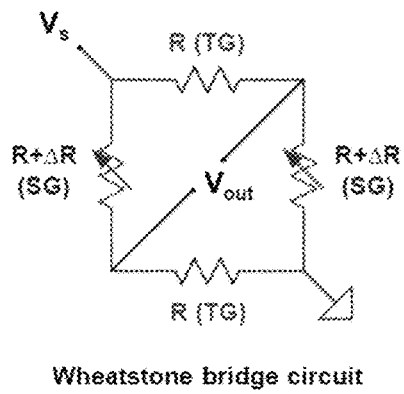
Wheatstone bridge circuit
FIG. 79D
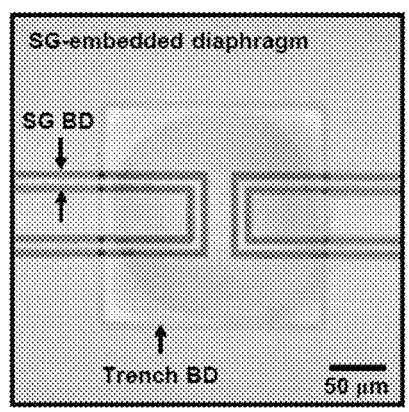
FIG. 79E

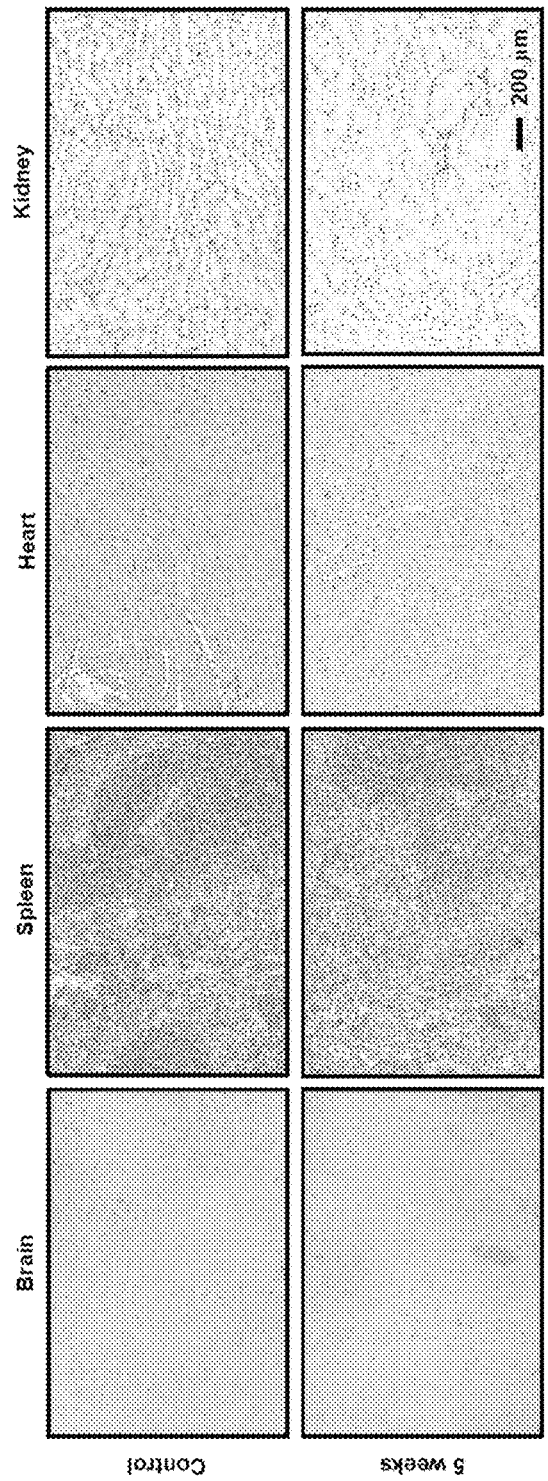
FIG. 81E
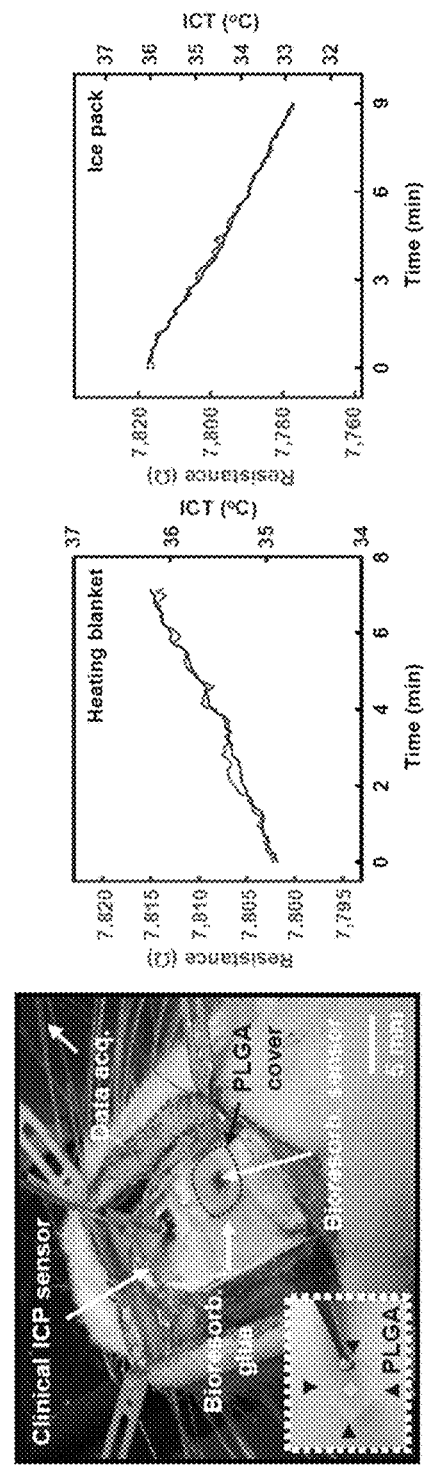
FIG. 82B
FIG. 82A

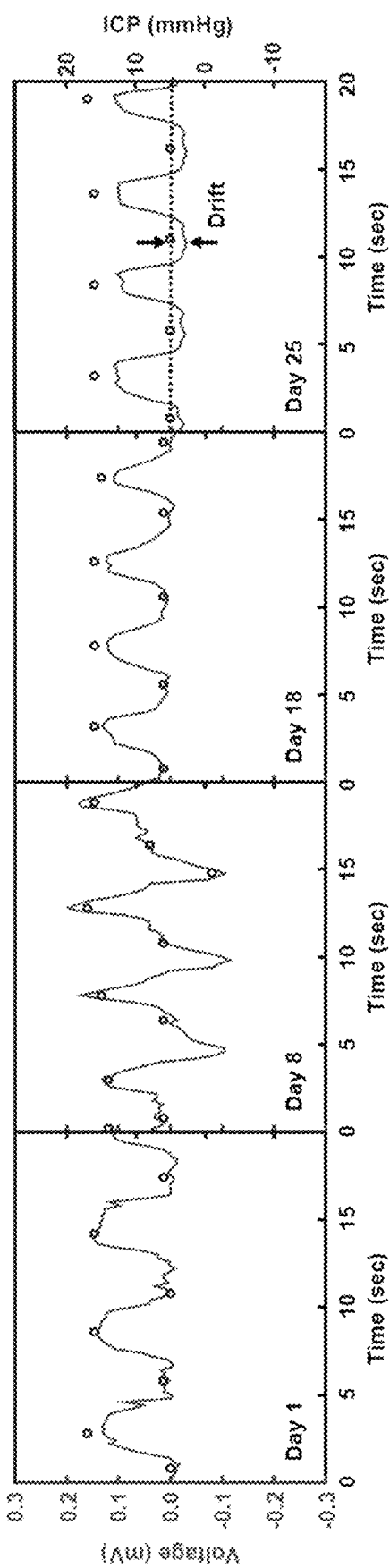
FIG. 82F
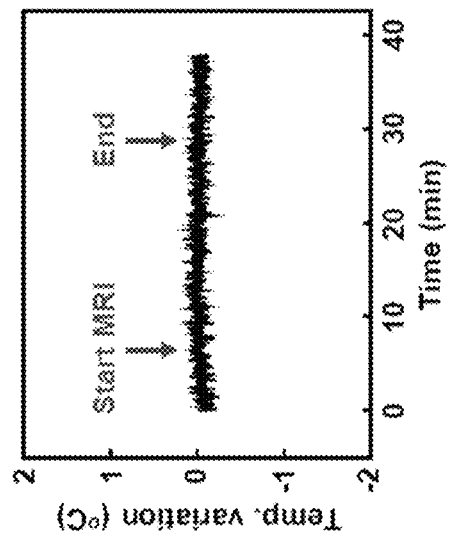
FIG. 83B
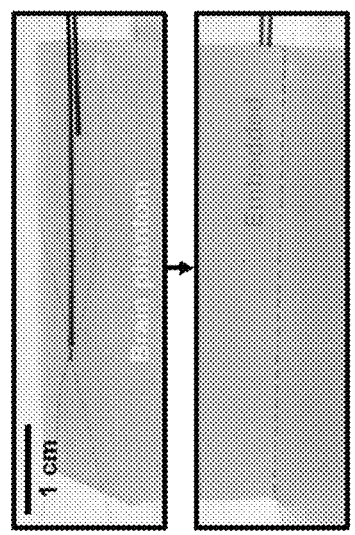
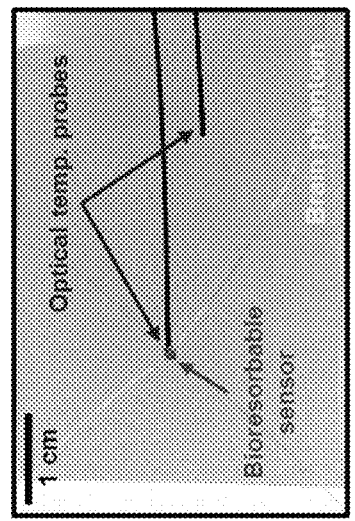
FIG. 83A

ENCAPSULATED FLEXIBLE ELECTRONICS FOR LONG-TERM IMPLANTATION

CROSS-REFERENCE TO RELATED APPLICATIONS

This application claims the benefit of U.S. Provisional Patent Application Nos. 62/573,533 filed Oct. 17, 2017 and 62/738,608 filed Sep. 28, 2018, each of which is specifically incorporated by reference to the extent not inconsistent herewith.

STATEMENT REGARDING FEDERALLY SPONSORED RESEARCH OR DEVELOPMENT

This invention was made with government support under HR0011-14-C-0102 awarded by the Defense Advanced Research Projects Agency (DARPA). The government has certain rights in the invention.

BACKGROUND OF INVENTION

A fundamental problem encountered by use of flexible electronics for chronic implantation in biological systems is the need for thin-film barriers to biofluids with multi-decade lifetimes. Various materials proposed as biofluid barriers in the art are unsuitable for a range of reasons. First, to achieve reliable long-term water impermeability, conventional materials must be relatively thick, thereby impacting the ability for the implantable device to have desired mechanical properties to match surrounding environment, including flexibility, stretchability and bendability. Mechanical mismatch between an implant and adjacent biological tissue and organs, result in a range of adverse physiological outcomes. Making the material of suitable thickness, however, brings into play fundamental limitations around: tendency of localized defects adversely impacting water impermeability and/or the intrinsic property of the material composition having too high baseline water permeability. Those challenges are addressed herein by providing an initial barrier layer having desired physical properties that is compatible for subsequent processing, including support of relevant electronic devices and electronic device processing. The resultant implants are then suitable for long-term or chronic implantation and have broad relevance to diverse biointegrated electronics and optoelectronics.

Conventional encapsulation schemes for implants such as pacemakers, cochlear implants, and deep-brain stimulators, rely on thick (millimeter-scale), rigid enclosures constructed using bulk metal or ceramic parts. Those systems are fundamentally incompatible with systems where flexible platforms are desired. Strategies based on thin flexible films are suitable for passive arrays of sensing/actuating electrodes or related devices, but they are not immediately applicable to active, semiconductor-based electronic platforms where continuous, or nearly continuous, applied voltages and induced currents are essential for operation. Organic/inorganic multilayer encapsulation schemes designed to protect flexible electronic devices from oxygen and moisture have some promise, but known adaptations of them cannot address the extremely demanding conditions encountered in the body, where full immersion in warm, circulating biofluids on multi-decade timescales is required. The methods and devices provided herein address these problems and provide a platform for biofluid barriers that can provide device operability in a biological environment for up to multi-decade timescales.

SUMMARY OF THE INVENTION

Provided herein are platform-level processes for making electronic devices, including bendable, flexible and/or stretchable devices, having high quality encapsulation layers useful in a range of applications. The methods, and related devices, first define an encapsulation layer and the relevant electronic devices are provided on a receiving surface of the encapsulation layer. In this manner, the encapsulation layer can be processed separately from the electronics and is advantageous, particularly for encapsulation layer processes that are incompatible with electronic devices. For example, processing of the encapsulation layer may involve high temperatures that electronic devices cannot reliably withstand without damage and corresponding functional degradation. Similarly, exposure to chemicals that would typically damage electronics is compatible with the methods and devices provided herein that separate the encapsulation layer processing from the electronic device processing and transfer.

The methods provided herein can provide electronic devices having a high quality encapsulation layer with desired physical properties, depending on the application of interest. For example, for applications requiring a long-term resistance to water permeation, the encapsulation layer may effectively reduce or avoid unwanted liquid or liquid vapor passage into the encapsulated electronic device. In particular, the improvement in the encapsulation layer characteristics can be achieved without any undue sacrifice in encapsulated device characteristics, including flexibility, bendability and/or stretchability. The methods and devices are compatible with a range of applications, including for long-term biological implants. As desired, the device characteristics are adjustable to have useful implant life ranging from the order of hours to multiple decades. As discussed, the long-term biological implant application is particularly suited given the functional benefit of the instant methods and devices to encapsulation layer quality and mechanical properties, to ensure the implanted device is conformal to tissue or organ of interest, including tissue or organ having a shape that changes with time. This is achieved herein by ensuring the implanted device maintains a good impermeable characteristic without sacrificing device flexibility, bendability and/or stretchability.

Provided herein are various methods of making a long-term implantable electronic device, including by any of the claims appended herein, which are specifically incorporated by reference herein. For example, the method may comprise the steps of providing a substrate having a first encapsulation layer that covers at least a portion of the substrate, the first encapsulation layer having a receiving surface. One or more electronic devices are provided on the first encapsulation layer receiving surface and at least a portion of the substrate from the first encapsulation layer is removed, thereby making the long-term implantable electronic device.

In this manner, conceptually the first encapsulation layer can be considered functionally as an initial step in the overall processing sequence. This decoupling of encapsulation layer from electronic device processing onto the first encapsulation layer provides a number of functional benefits. First, maximum quality of the encapsulation layer (e.g., defect density less than $1/mm^2$, leakage less than 1%, 0.1% or 0.01% relative to total, including electrical current, or desired flux such as flux of water vapor across the encapsulation layer that is less than $1\times10^{-7}$ $g/m^2/day$) can be obtained even for harsh processing conditions such as high temperature, that is fundamentally incompatible with typical electronic device materials and composition. Second, the encapsulation layer having low defect number may be relatively thin, while being able to withstand processing, including deposition, etching, transfer printing by virtue of the support of the underlying substrate. Third, the substrate may be later removed, thereby leaving relatively thin layers in the device, including encapsulation layer(s) and electronic devices, so as to achieve good mechanical properties, including stretchability, bendability, foldability, compliance, conformability and the like.

The substrate removal may be relevant so as to achieve a desired mechanical property of the substrate/encapsulation layer, while accommodating the ability of the substrate to act as a handle substrate that protects desired components or constituents during processing. For example, the initial substrate may have a relatively high stiffness, rigidity and strength to facilitate handling during the relevant processing steps, including related to electronic device manufacture or addition onto the encapsulation layer. Once electronic devices are provided on the encapsulation layer, the substrate may be at least partially removed to ensure there is minimal impact on the overall device mechanical parameters. One example is that a relatively thick substrate supporting the encapsulation layer may result in an overly stiff, non-compliant device not suited for implantation into a biological environment. Desired mechanical matching between the device and relevant adjacent biological environment is desirable for a number of reasons. For example, mechanical mismatch may result in unwanted immune response, tissue degradation and general irritation. All those unwanted results will adversely impact the lifetime of the implanted device, as well as the health of the tissue and animal in which the implant is implanted. For these reasons, any of the methods and devices described herein, may be characterized as having a bulk mechanical property, such as one or more of a modulus, including Young's modulus, bending stiffness moment, compliance modulus, shear modulus, bulk modulus, Poisson's ratio, that is within 30%, within 20%, within 10% or within 5% of adjacent tissue or organ.

Particularly useful substrates include pristine Si wafers. Particularly useful encapsulation layers include oxides of the substrate, such as silicon oxide of a Si wafer, including by thermal oxidation of the substrate.

Also provided is a method of making a liquid and liquid vapor-proof material, the method comprising the steps of: providing a first substrate having a first-side encapsulating layer supported by at least a portion of the first substrate; providing a material onto the first-side encapsulating layer; providing a second substrate having a second-side encapsulating layer supported by at least a portion of the second substrate; covering an exposed surface of the material provided onto the first-side encapsulation layer with the second-side encapsulating layer; and wherein the encapsulating layers are substantially defect free so that liquid or liquid vapor is prevented from passing through each of the encapsulating layers.

Also provided are devices made by any of the methods described herein, including the appended method claims.

The device may comprise a first thermally oxidized layer from a first substrate, wherein the thermally oxidized layer forms a first encapsulation layer; an electronic device supported by the first encapsulation layer, wherein the electronic device and first encapsulation layer have an exposed surface relative to the encapsulation layer; a barrier layer that covers the first encapsulation layer and electronic device exposed surfaces; a second thermally oxidized layer from a second substrate, wherein the second thermally oxidized layer forms a second encapsulation layer and the second encapsulation layer is in contact with the barrier layer; adhering to the barrier layer a top substrate having a thermally oxidized second encapsulation layer, wherein the second encapsulation layer faces the barrier layer; wherein each of the encapsulation layers, barrier layer, and electronic device are flexible or bendable, so that the long-term implantable electronic device is capable of conformal contact with a curved biological surface Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIGS. 1A-1D. Materials and integration strategies for use of ultrathin layers of $SiO_2$ thermally grown on device-grade silicon wafers, as water barriers in flexible electronics. FIG. 1A. Schematic illustration of schemes for exploiting layers of thermal $SiO_2$ for encapsulation in test structures: (1) electron beam evaporation, photolithography, and etching of Mg to form "I"-shape patterns as test structures on $SiO_2$ thermally grown on a silicon wafer; (2) pressure bonding the top surface to a glass substrate that supports a thin film of polyimide (Kapton; 25 µm); (3) removal of the silicon wafer from back side by dry etching; (4) release of the final flexible test structure from the glass substrate. FIG. 1B. Optical image of a sample produced in this manner, with a ~100-nm-thick layer of thermal $SiO_2$ on its top surface. FIG. 1C. Sequential images of Mg encapsulated by layers of thermal $SiO_2$ and $Al_2O_3$/Parylene C and a bulk film of liquid crystal polymer (LCP) soaked in PBS solution at 70° C. FIG. 1D. EIS and modeling results for layers of $SiO_2$ grown by thermal oxidation and deposited by PECVD and electron beam evaporation.

FIGS. 2A-2D. Failure mechanisms associated with thermal $SiO_2$ encapsulation layers. FIG. 2A. SEM images showing decreases in the thickness of a 1,000-nm-thick layer of thermal $SiO_2$ as a result of soaking in PBS at 96° C. FIG. 2B. Time before the leakage current reaches more than 100 nA, for thermal $SiO_2$ measured in an electrical leakage test (described in FIG. 9A-9B). FIG. 2C. Thickness changes associated with a 1,000-nm-thick layer of thermal $SiO_2$ without DC bias and with 12-V bias (Left), and extracted dissolution rate for voltages of 0, 3, 6, 9, and 12 V (Right). FIG. 2D. Thermal $SiO_2$ on the surfaces and edges of a piece of Si in PBS solution (Left) allowed measurements of changes in thickness at different temperatures (Center). The results indicate a linear relationship between the dissolution rate and 1/T (Right).

FIG. 3A. Perspective snapshot of the $SiO_2$ slab in water. FIG. 3B. Top-view representation of four different oxide densities of the $SiO_2$ slab in water. FIG. 3C. Simulation snapshots of hydrolysis reactions that lead to the dissociation of one molecule of $SiO_2$ from the structure.

FIGS. 4A-4D. Results of soak tests of resistors, capacitors, diodes, and n-type metal-oxide-semiconductor transistors with optical images (Insets). Tests in PBS solutions at 96° C.

indicate that failure occurs at day 12 for all devices. FIG. 4E. A photograph of a platform of active multiplexed flexible electronics with double-sided thermal $SiO_2$ encapsulation in a slightly bent configuration. The Inset presents a magnified view of the sensing sites, each of which consists of one sensing transistor and one multiplex transistor connected in series. FIGS. 4F-4H. Accelerating soak test with in vitro measurement of electrical performance including yield ($Y/Y_0$, defined as the number of working sensing sites divided by the total number of sites), gain (the ideal gain is 1), and mean noise rms. The results indicate device stability throughout 9 d in 70° C. PBS. The Inset in FIG. 4F presents a photograph of an active multiplex device fully immersed in PBS.

FIG. 7. Mg soak test of a 50-μm-thick stainless steel foil in 70° C. PBS solution throughout 84 days.

FIGS. 8A-8B. Theoretical modeling of EIS measurement of different $SiO_2$. FIG. 8A. Equivalent circuit consists of both pristine and defective parts. FIG. 8B. Parameters used for $SiO_2$ produced by evaporation, PECVD and thermally grown.

FIG. 12. A sequence of SEM images in a 45° view illustrate dissolution of the 50-μm-thick stainless steel foil in accelerating PBS soak test at 96° C. throughout 60 days.

FIG. 13. The edge effect in thermal $SiO_2$ dissolution rate test.

FIGS. 14A-14B. Multiphysics simulations of thermal $SiO_2$ dissolution. FIG. 14A. Dissolution rate dependence on pH (Order 1: $k_0=3.85\times10^9$ $m^4$ $mol^{-1}$ $s^{-1}$, Order 0.5: $k_0=6.11\times10^7$ $m^{2.5}$ $mol^{-0.5}$ $s^{-1}$, Order 0.25: $k_0=7.68\times10^6$ $m^{1.75}$ $mol^{-0.25}$ $s^{-1}$). FIG. 14B. Visualization of layer after 0 and 300 days separately (pH=7.4, T=50° C.).

FIG. 16A. Number of Si dissolved in different temperatures and for different oxide densities. FIG. 16B. Number of Si dissolved for different oxides at temperatures 80° C. and 100° C.

FIG. 29A. Optical microscope image of a test transistor layout. FIG. 29B. Transfer characteristics in both linear and semilog scale, with supply voltage $V_{DS}$=0.1 V. FIG. 29C. Output characteristics, $V_{GS}$ ranging from −1 V to 4 V with a step of 1 V.

FIGS. 31A-31E. Capacitively coupled silicon nanomembrane transistors (covered by a thermal $SiO_2$ layer) as amplified sensing nodes in an actively multiplexed flexible electronic system for high-resolution electrophysiological mapping. FIG. 31A. An exploded-view schematic (left, highlighting the key functional layers) and a photograph (right) of a completed capacitively coupled flexible sensing system with 396 nodes in a slightly bent state. The inset shows a magnified view of a few nodes. FIG. 31B. A circuit diagram for a node in this capacitively coupled array, with annotations for each component (left), and an optical microscope image of the cell (middle). A schematic of the circuit cross-section (right) illustrates the mechanism for capacitively coupled sensing through a thermal $SiO_2$ layer to an underlying transistor. FIG. 31C. Demonstration of capacitively coupled sensing using a test transistor (left), and its transfer (middle) and output (right) characteristics. S, source; D, drain; TG, top gate. The supply voltage ($V_{DS}$) was set to 3 V for in vitro bench testing, and fed back from the output signal during ex vivo measurements (FIG. 54). The transfer characteristics ($I_{DS}$-$V_{GS}$) correspond to cases with and without capacitive coupling (channel width W=80 μm, effective channel length $L_{eff}$=13.8 μm, $V_{DS}$=0.1 V), in both semi-log and linear scale. Dashed curves depict characteristics measured by directly biasing the gate metal; the solid curves follow the results from biasing a droplet of saline solution (red, left) in contact with the thermal $SiO_2$ layer above the transistor and the gate metal pad. FIG. 31D. Validation of capacitively coupled sensing from a single-transistor source-following amplifier, with a schematic of the circuit (left), and its output characteristics (right). The inset in the right panel shows the output characteristics with an a.c. input of 5 mV at 10 Hz. FIG. 31E. Histogram (with Gaussian lineshape fitting) of gain values from all 396 nodes of a typical system. The results indicate 100% yield and near-unity average gain. The inset shows a spatial map of the gain values.

FIGS. 32A-32J. In vitro assessment of electrical performance. FIG. 32A. Average gain of a representative capacitively coupled transistor as a function of the input frequency from 0.1 to 100 Hz. The inset shows the responses from this sensor node at 0.1 Hz (top) and 100 Hz (bottom), after band-pass filtering (0.05-568 Hz). FIG. 32B. Power spectral density of a 5 mV a.c. signal at 10 Hz measured at a representative node, showing a typical 1/f relationship at low frequency. The input was a sine wave of 5 mV at 10 Hz. FIG. 32C. Histograms of noise (with Gaussian fitting) measured from all 396 nodes of the device in FIG. 31C. FIG. 32D. Statistics of the threshold voltage ($V_T$) and peak effective mobility ($\mu_{eff}$) of test transistors from 15 different arrays. FIG. 32E. Statistics of yield (left) and gain (right) of 17 capacitively coupled, active sensing 18×22 electrode arrays. FIG. 32F. An image of a device during a mechanical bending test. FIG. 32G. An image of a device completely immersed in a saline solution, during a soak test. PBS, phosphate-buffered solution. FIG. 32H. Yield (Y, defined as the number of working nodes divided by the total number of nodes) as a function of cycles of bending to a 5 mm bend radius, showing minimal changes up to 10,000 cycles. FIG. 32I. Electrical leakage current of 2 devices during soak testing. Minimal leakage appears over a period of 120 days at 37° C. FIG. 32J. The response of a representative node to a sine-wave input (at 10 Hz) before, after 10,000 cycles of bending and after saline immersion for 120 days.

FIGS. 33A-33C. High-density cardiac electrophysiological mapping on ex vivo rabbit heart models. FIG. 33A. A photograph of a flexible capacitively coupled sensing electronic system on a Langendorff-perfused rabbit heart (left). REF and GND represent the reference and ground electrodes, respectively. The magnified view (right) shows conformal contact of the device to the cardiac tissue, through the action of surface tension. FIG. 33B. Representative single-voltage trace from the electrode array without external pacing. Signatures related to the P, Q, R, S and T waves in ECG traces can be identified from the recordings. FIG. 33C. Representative voltage data for all electrodes at four time points (indicated in FIG. 33B), showing normal cardiac wave-front propagation. The progress of the cardiac wave is consistent with the physical location of the array on heart, as illustrated in the diagram on the left (RA, LA, RV and LV: right atrium, left atrium, right ventricle and left ventricle, respectively).

FIG. 34A. Representative electrical (e) and optical (o) signals captured simultaneously on a Langendorff-perfused rabbit heart at multiple cycle lengths (300, 250 and 200 ms). FIG. 34B. Interpolated spatial activation maps derived from these data. The top row shows activation as measured during sinus rhythm. The bottom row corresponds to 300 ms ventricular pacing. The activation maps from left to right are optical signals from the whole heart, optical signals from the device area, and electrical signals, respectively. The dashed boxes in the left images depict the device area. FIG. 34C. Comparison of activation and repolarization measurements in single simultaneously measured electrical and optical signals. The left panel highlights a quantitative comparison of electrical and optical signals during one depolarization/repolarization cycle. The middle panel shows the comparison of activation times measured across all electronic nodes and the corresponding optical fields of view. The right panel shows the comparison of optical and electrical restitution curves measured at various cycle lengths (300, 250, 225, 200 and 175 ms).

FIG. 35A. Three representative electronic node signals taken from a heart during ventricular fibrillation (VF). The dashed box specifies the window of time corresponding to two reentrant cycles of VF. The labels −π, 0 and +π indicate the initial phase values of the respective signals at the beginning of the reentrant cycle. I to VI correspond to the panels in FIG. 35B. FIG. 35B. Voltage, phase and phase-singularity maps at six time points corresponding to the dash lines specified in FIG. 35A. Numbers 1, 2 and 3 on the maps mark the locations where the signals in FIG. 35A were taken. Voltage and phase data indicate a reentrant cycle of VF. A phase singularity commonly refers to a point on a phase map around which all values of phase (−π to +π) are represented. The phase singularities are identified as the ±1 values associated with regions of the phase map where this occurs. Optical signals from the sensing electronics area also match well with electrical recordings (FIG. 52).

(FIG. 41A) Impedance and (FIG. 41B) phase as a function of frequency for a 900-nm $SiO_2$ layer with 0.25 cm² area. The electrode input impedance for each capacitively coupled sensing electrode (270 μm×460 μm) is calculated to be 2.6×10⁹Ω at 10 Hz. Inset in FIG. 41A: a schematic illustration of the cross-section of the EIS sample.

FIG. 44A-44B. Strain distribution in the flexible electrode array. FIG. 44A. Axial strain distribution along the thickness direction. Inset: schematic illustration of the array cross-section. FIG. 44B. Material parameters in FEA simulations.

FIG. 45. Infrared imaging of a capacitively coupled array of 252 nodes before (left) and after (right) 5 min recording, while resting on a hot plate at 37° C. The results indicate no apparent increase in temperature associated with operation of the device.

FIG. 46A. Display of all 396 recordings. FIG. 46B. Box plot showing the signal-to-noise ratio (SNR) range for the 396 recordings. FIG. 46C. Display of the recordings with the highest, median, and lowest SNR.

FIG. 49A. A photograph of a device laminated onto the left ventricle of a beating heart in an open chest experiment on a canine model. FIG. 49B. Representative single voltage trace from the device (top), with representative voltage data map at four time points, showing normal cardiac wave-front propagation (bottom).

FIG. 50A. Exploded-view schematic illustration (left) and a photograph (right) of a completed system in a slightly bend state. FIG. 50B. Photograph of a device on the rat auditory cortex. FIG. 50C. Leakage current measured from the array as a function of time, up to 20 days. FIG. 50D. Map of best frequency revealed the dorsorostral-ventrocaudal gradient of representation in rat primary auditory cortex on day 0 (left) and day 20 (right), indicating stable sensing capabilities throughout the study.

FIG. 61A. Scheme for fabricating test structures that include silicon transistors: 1. Fabrication of transistors on an SOI wafer; 2. Pressure bonding the top surface of this wafer, face down, onto to a glass substrate that is laminated with a thin film of polyimide (Kapton, 13 μm); 3. Removal of the silicon handle wafer by dry etching; 4. Surface cleaning and ALD of $HfO_2$; Release of the flexible device from the substrate. FIG. 61B. Transfer characteristics collected during immersion in PBS solution at pH 7.4 and 96° C. for 10 days, at a supply voltage $V_{DS}$=0.1 V. The upper insets show optical images of a sample produced in this manner with a 100/100 nm thick bilayer of $HfO_2/SiO_2$ as a barrier on its top surface and a single transistor structure after bonding. The lower inset shows a schematic illustration of the NMOS transistor stack. FIG. 61C. Transfer characteristics at Day 0 plotted in both linear and semi-log scales, at a supply voltage $V_{DS}$=0.1 V. The inset shows transfer characteristics collected at the time of failure on Day 11. FIG. 61D. Schematic illustration of the material stack at the location of an NMOS transistor.

FIGS. 62A-62C. Effects of the capping layer thickness and materials type on the rate of dissolution of $SiO_2$. FIG. 62A. Illustration of the layer configuration for tests that use thin films of Mg as indicators of water penetration. FIG. 62B. Top view optical image of a Mg pad encapsulated by a barrier layer. FIG. 62C. Results of accelerated immersion tests that involve immersion in PBS solution at 96° C. The single-layer row displays findings for 100 nm thick layers of $SiO_2$ and $HfO_2$ as barriers, respectively. The double-layer rows show sequential images of Mg encapsulated by various capping layers on $SiO_2$, including $HfO_2$, Parylene C, Ti/Pt and LPCVD $SiN_x$.

FIG. 63A. Schematic illustration of the single-layer model. FIG. 63B. Simulated (lines) and measured (symbols) changes in thickness of a single layer of thermal $SiO_2$ with initial thicknesses of 30, 50, and 75 nm in PBS solution at 96° C. FIG. 63C. Schematic illustration of the bilayer model. FIG. 63D. Simulated (line) and measured (symbols) lifetime of a $HfO_2/SiO_2$ bilayer barrier with a 100 nm thick layer of $HfO_2$ and different thicknesses of thermal $SiO_2$. FIG. 63E. Distribution of water concentration at the interface and at the top surface of a 100 nm/100 nm thick bilayer of $HfO_2/SiO_2$ barrier. FIG. 63F. Changes in thickness of thermal $SiO_2$ in a $HfO_2/SiO_2$ bilayer barrier with a 100 nm thick layer of $SiO_2$ and $HfO_2$ with initial thicknesses of 0, 10, 50, and 100 nm. The inset presents the simulated (line) and measured (symbols) lifetime of a $HfO_2/SiO_2$ bilayer barrier with a 100 nm thick layer of $SiO_2$ and different thicknesses of $HfO_2$ (0, 10, 50, and 100 nm).

FIG. 64A. Optical properties of a 320 nm thick layer of thermal $SiO_2$ after soaking in solutions with various [$Na^+$]. Optical images (left) and reflectance (right) of the $SiO_2$. FIG. 64B. Optical properties of the same $SiO_2$ layer after soaking in solutions with various [$Ca^{2+}$]. FIG. 64C. Dissolution rates for a single layer of $SiO_2$ in solutions containing $Na^+$ and $Ca^{2+}$. FIG. 64D. Lifetime of barrier layer of $SiO_2$ (100 nm thick) with and without a capping layer of $HfO_2$ (100 nm thick) in solutions with various [$Na^+$] and [$Ca^{2+}$]. FIG. 64E. Relative lifetime of a bilayer of $HfO_2/SiO_2$ with respect to a single layer of $SiO_2$ in solutions containing $Na^+$ and $Ca^{2+}$. Here the ratios of the lifetimes between bilayer barriers and single-layer barriers are presented.

FIG. 65A. Cross-sectional illustration of the embedded MOSFET device with sodium in the channel region. FIGS. 65B-65C. Results of tests for (FIG. 65B) a 200 nm thick layer of $SiO_2$ and (FIG. 65C) a 100/100 nm thick bilayer of $HfO_2/SiO_2$ in PBS soak tests at 96° C. and with an applied bias, $V_{app}$=3V. Schematic illustrations of the samples and bias configurations appear in the upper insets. FIG. 65D. Shift in the threshold voltage as a function of time with $V_{app}$=3V bias for a 200 nm thick layer of $SiO_2$ at 96° C. The solid dots are experimental data and the lines are simulations. Inset indicates shifts in threshold voltage for a 100/100 nm bilayer of $HfO_2/SiO_2$ as a function of time with $V_{app}$=3 V bias at 96° C. FIG. 65E. Acceleration factors for both ion diffusion and dissolution as a function of temperature for a 200 nm thick layer of $SiO_2$ and a 100/100 nm bilayers of $HfO_2/SiO_2$, respectively. The inset offers a schematic illustration of the geometry.

FIG. 67A shows encapsulation of a single 100-nm-thick layer of thermal $SiO_2$ and FIG. 67B is $HfO_2$ with thickness of 100 nm. Equivalent circuits are shown in both of upper insets. Lower insets are $I_{DS}$-$V_{GS}$ curves right before failure within each lifetime.

FIG. 72A. Scheme for fabricating test structures that include silicon transistors: 1. Fabrication of transistors on an SOI wafer; 2. Bonding of this wafer, face down, onto to a glass substrate that is coated with a thin film of polyimide (Kapton, 12 μm); 3. Removal of the silicon handle wafer by dry etching; 4. Release of the final flexible test structure from the substrate. FIG. 72B. Schematic illustration of the material stack layout and various thickness of the different layers at the location of an NMOS transistor. FIG. 72C. Optical image of a sample produced in this manner with a 1 μm thick layer of thermal $SiO_2$ on its top surface. FIG. 72D. Colorized SEM images of a transistor structure before bonding. FIG. 72E. Transfer characteristics in both linear and semi-log scale, at a supply voltage $V_{DS}$=0.1 V. The inset shows the gate leakage current.

FIGS. 73A-73F. Results of tests during different electrical bias conditions (AC |3 V|, DC −3 V, DC 0 V, DC+1.5 V, DC+3 V, DC+4.5 V). Schematic illustrations of the samples and bias configurations appear in the upper insets. Lower insets in frames FIGS. 73C-73F correspond to $I_{DS}$-$V_{GS}$ curves collected just before failure. FIG. 73G. Computed Na+ concentration profiles and potential distributions within a layer of thermal $SiO_2$ after 10 days of immersion in PBS at T=96° C. The applied bias is 0, 1.5 V, 3 V and 4.5 V, respectively. FIG. 73H. Shift in the threshold voltage as a function of time with different bias voltages at T=96° C. The solid dots are experimental data and the lines are simulations.

FIG. 74A. Schematic illustration of a material stack that uses a bilayer of thermal $SiO_2$/LPCVD $SiN_x$ as an ion and water barrier for underlying silicon transistors. FIG. 74B. Thickness of a layer of LPCVD $SiN_x$ as a function of time of immersion in PBS at pH 7.4 and at various temperatures. The inset shows the geometry of the test structure. FIG. 74C. Data that indicate a linear relationship between dissolution rate and 1/T. FIG. 74D. Electrical characteristics of NMOS transistors encapsulated by $SiO_2$/$SiN_x$ (200/200 nm) in PBS soak tests at 96° C. and an applied bias, $V_{app}$=3 V. The upper inset shows an optical image of a typical device. The bottom inset shows transfer characteristics collected at the failure time of 5 days. FIG. 74E. Threshold voltage shift as a function of time with $V_{app}$=3 V bias at T=96° C., for three different bilayer thicknesses of $SiO_2/SiN_x$ indicated in the legend. The solid dots are experimental data and the dotted line is a simulation. The bottom inset provides a schematic illustration.

FIG. 75A. $Na^+$ concentration profiles through a bilayer of $h_1$=100 nm thermal $SiO_2$ and $h_2$=200 nm LPCVD $SiN_x$ at the end of 1 day, 30 days, 1 year, 5 years and 10 years at T=37° C. FIG. 75B. Simulations of ion diffusion for an Equivalent Oxide thickness of $SiO_2$ that corresponds to $SiO_2/SiN_x$ (100/200 nm). $Na^+$ concentration within h=211 nm thermal $SiO_2$ layer at the end of 1 hour, 3 hours, 5 hours, 1 day and 2 days at T=37° C. FIG. 75C. Simulated failure times for an encapsulation of thermal $SiO_2$ associated with ion diffusion at $V_{app}$ 1.5 V, 3 V and 4.5 V. The inset provides a schematic illustration of the geometry. FIG. 75D. Accelerated factors for both ion diffusion and dissolution as a function of temperature in $SiO_2$ and $SiO_2/SiN_x$ at thicknesses of 1 μm and 100/200 nm, respectively. The inset provides a schematic illustration of the geometry.

FIG. 78A shows encapsulation of single 200 nm thick layer of LPCVD $SiN_x$ and FIG. 78B is bilayer of upper thermal $SiO_2$/lower LPCVD $SiN_x$ with thickness of 100/200 nm. Equivalent circuits are shown in both of upper insets. Lower insets are $I_{DS}$-$V_{GS}$ curves right before failure within each lifetime.

FIGS. 79A-79H. Materials and designs for long-lived, inorganic Bioresorbable pressure sensors. FIG. 79A. Schematic illustration of a bioresorbable pressure sensor comprised of layers of monocrystalline silicon and silicon dioxides, formed by thermal oxidation (t-$SiO_2$) or electron-beam evaporation (eb-$SiO_2$). Silicon nanomembrane (Si NM) strain gauges (SGs) on a pressure-sensitive diaphragm capture variations in pressure via piezoresistive response of silicon, while temperature gauges (TGs) react to changes in surrounding temperature via temperature-dependent resistance. Cross-sectional illustration along mid-line of the diaphragm reveals air cavity and silicon trench underneath (inset, green). Schematics of cross-section across SG (inset, red) and non-SG (blue) regions show tri-layer composition of the diaphragm. FIG. 79B. Photograph of a device placed on a quarter. The inset presents a magnified view of the sensor. FIG. 79C. Optical micrograph of the sensor. Two pairs of SGs and TGs combine to form a Wheatstone bridge circuit. FIG. 79D. Circuit diagram of a Wheatstone bridge, consisting of SGs, TGs, voltage source and meter, that compensates temperature-induced variations in the piezoresistivity of the SGs. FIG. 79E. Optical micrograph of SGs embedded in a diaphragm. Two boundary lines (grey area, no silicon) isolate the SGs (pink area, silicon) from the surrounding Si NM. FIG. 79F. Steps for fabricating bioresorbable pressure sensors. Formation of silicon sensors on the Si NM (pink) of a silicon-on-insulator (SOI) wafer, SOI-A (1). Fabrication of a silicon trench (top white) on a separate SOI wafer, SOI-B (2). Aligned bonding of SOI-A and SOI-B using a thin film of PDMS (beige) as an adhesion interlayer, followed by calcination of the PDMS to yield amorphous silica by heating in a furnace (3). Reactive ion etching and patterned wet etching to eliminate silicon wafers, thin buried oxide layers, and expose regions of Si NM for electrical contacts (4). Thicknesses are not to scale. FIG. 79G. Three-dimensional finite element analysis (3D-FEA) results for distribution of principal strains (left) and vertical displacements (right) of the diaphragm for an external pressure of 40 mmHg above atmospheric. FIG. 79H. Responses of a bioresorbable pressure sensor (red, $V_s$=2.5V) and a commercial sensor (blue) to time-varying pressures over a range relevant to variations in intracranial pressure (ICP).

FIG. 80A. Measured changes in thickness as a function of time of immersion of t-$SiO_2$ (left), eb-$SiO_2$ (middle), and amorphous silica (obtained from calcination of PDMS, right) in artificial cerebrospinal fluid (ACSF, pH 7.4) at 37° C. The dissolution rates are 0.11±0.01, 13.6±1.6, and 129±9 nm/day, respectively. Circles and error bars indicate the mean and S.E. for ten measurements, respectively. FIG. 80B. Schematic illustration of the in vitro dissolution experiment set-up. The blue arrow indicates the angle for optical microscope imaging. FIG. 80C. Optical micrographs at various stages of accelerated dissolution of a bioresorbable pressure sensor due to immersion in phosphate buffered saline (PBS, pH 7.4) at 95° C. FIG. 80D. Voltage response of a sensor with t-$SiO_2$ encapsulation (~10 nm) and comparison to a commercial device at various times after immersion in PBS at 95° C. (left), with corresponding responsitivities as a function of time (right). The data indicate two-stage kinetics in function, involving stable operation for several hours, defined by dissolution of thermal $SiO_2$ encapsulation layer, followed by rapid degradation due to formation of hole/crack in the diaphragm due to dissolution of the functional layers. FIG. 80E. Optical micrograph of a cracked diaphragm.

FIGS. 81A-81E. In vivo measurements of elemental biodistribution and biocompatibility of Bioresorbable devices throughout their functional lifetimes and beyond. FIG. 81A. Biodistribution of products of dissolution of bioresorbable pressure sensors (size: 750 μm×750 μm×10 μm; weight ~12 μg; no t-SiO2 encapsulation) implanted within the intracranial spaces of mice (2 for each time point), with comparisons to 2 control mice. Concentrations of silicon in organs explanted at 1, 3, and 5 weeks post implantation, determined by inductively coupled plasma optical emission spectrometry (ICP-OES). High silicon concentrations in spleen, heart, and lung tissues in the first week after implantation decrease gradually to normal levels. Circles, bars, and error bars indicate individual data points, the mean, and S.E. for six spectrometric measurements, three each from 2 sets of organs, respectively. FIG. 81B. Computed tomography (CT) scans of a mouse brain after 5 weeks. Cartoon illustrations and CT images 5 weeks post implant of the sagittal (left), coronal (middle), and axial (right) planes show the locations of the craniectomy and a sensor near the surface of the brain. FIG. 81C-81D. Results of FIG. 81C complete blood count test and FIG. 81D blood chemistry test for the mice in FIG. 81A. No significant differences from control animals can be found for both tests. Control data provided by the mouse supplier (Charles River, gray) or collected from 22-24 mice acquired from two batches within 2 months' span (cyan). Circles, bars, and error bars indicate individual data points, the mean, and 95% confidence intervals. Abbreviations include, WBC: white blood cell, RBC: red blood cell, HGB: blood hemoglobin level, HCT: hematocrit level, PLT: platelet count in blood, ALT: alanine aminotransferase, CHOL: cholesterol, TRIG: triglycerides, PHOS: phosphorus, BUN:

urea nitrogen, GLU: glucose, CAL: calcium, TP: total protein, ALB: albumin. FIG. 81E. Representative histology of brain, spleen, heart, and kidney tissues of a control mouse and a mouse implanted with a bioresorbable sensor 5 weeks post implantation (3 independent experiments).

FIGS. 82A-82F. Acute and chronic monitoring of intracranial temperature and pressure in rats using Bioresorbable sensors. FIG. 82A. Photograph of a bioresorbable ICP sensor, mounted on a thin film of poly(lactide-co-glycolide) (PLGA, ~10 um thick; inset), implanted device-side down in an intracranial cavity of a rat. Bioresorbable glue bonds the edges of the film to the surrounding skull and seals the cavity. Wired connection to a digital multimeter allows data acquisition from the sensor. A clinical ICP monitor probe inserted in the same hemisphere of the brain serves as reference. FIG. 82B. In vivo recordings of intracranial temperature (ICT) of a rat as a function of time. Both bioresorbable (red) and commercial (blue) devices capture gradual increase (left) and decrease (right) in ICT caused by application of heating blanket/ice pack. FIGS. 82C-82E. In vivo monitoring of variations in ICP due to FIG. 82C contracting and releasing rat's flank, FIG. 82D laying in Trendelenburg (30° head-down) and reverse Trendelenburg (30° head-up) positions, FIG. 82E and infusing Mannitol in the saphenous vein, as a function of time by both bioresorbable (red) and commercial (blue) sensors. FIG. 82F. In vivo recordings of ICP as a function of time on days 1, 8, 18, and 25 post implantation. Contracting and releasing the flank induce variations in ICP. Recordings on day 25 show ~3 mmHg negative drift for the bioresorbable device.

FIGS. 83A-83C. MRI compatibility of Bioresorbable sensors. FIG. 83A. Photograph of a bioresorbable sensor and two fiber-optic temperature probes placed in between two slabs of brain phantom, designed to imitate the conductivity and dielectric constant of brain tissue. FIG. 83B. Recordings of the difference in temperatures measured by the two probes throughout a 20-minute scan, indicating no significant heating of the device. FIG. 83C. Representative MRI images of a rat brain implanted with bioresorbable sensor along axial, coronal, and sagittal planes. Five images in each plane are collected at locations parallel to one another with 0.5 mm separation (slice thickness). Images show no sign of magnetic-susceptibility-related artifacts. Arrows indicate positions of the sensor.

DETAILED DESCRIPTION OF THE INVENTION

Figure 3B:
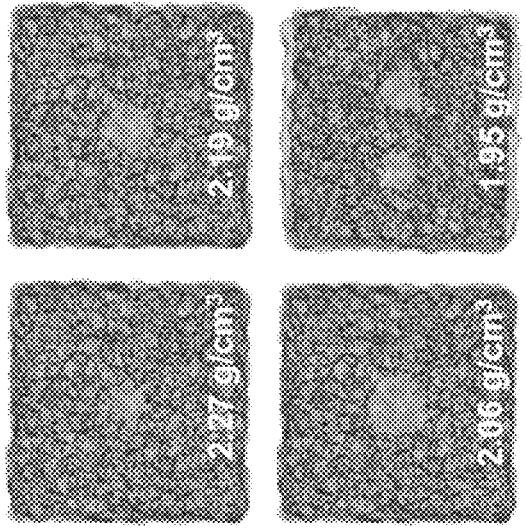
FIGS. 3A-3C. Reactive molecular dynamics (RMD) simulations of hydrolysis of defective layers of $SiO_2$.

In general, the terms and phrases used herein have their art-recognized meaning, which can be found by reference to standard texts, journal references and contexts known to those skilled in the art. The following definitions are provided to clarify their specific use in the context of the invention.

"Long-term implantable" refers to chronically implantable electronic devices where in vivo sensing, actuating, or both sensing and actuating, is required. The devices and methods provided herein are capable of achieving device functionality during use over the time scale of multiple decades, including a lifetime that is at least as long as the lifetime of the person or animal in which the device is implanted. Of course, the devices provided herein are certainly compatible with shorter durations, including on the range of hours.

"Substrate" refers to a material having a surface that is capable of supporting a structure, including an electronic device or an encapsulation layer that separates the substrate from the electronic device. A substrate can be configured to support, at least temporarily, any other portions of the device, including assisting with processing steps. Specific examples are substrates that support an encapsulation layer. As discussed, the encapsulation layer is desirably relatively thin, which can make handling challenging, including for subsequent deposition steps of electronic components and devices, as well as deposition of other layers. A substrate may assist with further processing. Upon completion of processing, any portion or all of the substrate may be removed.

"Encapsulation layer" is used to refer to a layer that provides at least in part desired water barrier characteristics and upon which electronic devices are provided. Accordingly, conceptually the encapsulation layer is at least an early precursor in the method, and is a platform upon which subsequent device deposition or printing occurs. A functionally similar encapsulation layer may be provided on the opposite surface of the electronic device that faces away from the first initial encapsulation layer that initially supports the electronic devices. In this manner, both the front and back-side of the electronic device may be encapsulated.

"Barrier layer" is used broadly herein to refer to other layers distinct from the encapsulation layer, either in function and/or location. For example, a barrier layer that is functionally equivalent to a planarizing layer may be used to coat a relatively uneven electronic device on a first encapsulation layer, so that a second encapsulation layer may be reliably bonded to provide good water barrier characteristics on both the top and bottom side of the electronic device. Planarizing may refer to a top surface of barrier layer that is smooth, with less than 1 μm, 500 nm, 100 nm, 10 nm or 1 nm spatial variation. The barrier layer may be a pre-polymer or adhesive, that is applied to the electronic device, and subsequently polymerized or hardened and solidified, in contact with another layer. Barrier layer may also refer to "Cover" is used broadly with respect to the relative position of the encapsulation layer and the substrate and functionally refers to the ability of the substrate and encapsulation layer that, at least temporarily, supports an electronic device. In this manner, the encapsulation layer may be a distinct layer that is provided over the substrate. Alternatively, the encapsulation layer may be formed from a part of the substrate, such as by a chemical process, a physical process or a chemical and physical process. This includes oxidation of a material, including thermal oxidation, such as thermal oxidation of a silicon wafer, including a device-grade silicon wafer or pristine silicon wafer having an inherently low defect density.

"Electronic devices" is used to broadly include an electrical, optical, mechanical, thermal sensor and/or actuator, and relevant components thereof. Components include, but are not limited to, a photodiode, LED, TFT, electrode, semiconductor, other light-collecting/detecting components, transistor, integrated circuit, contact pad capable of receiving a device component, thin film devices, circuit elements, control elements, microprocessors, transducers and combinations thereof. A device component can be connected to one or more contact pads as known in the art, such as metal evaporation, wire bonding, application of solids or conductive pastes, for example. Electronic device generally refers to a device incorporating a plurality of device components, and includes large area electronics, printed wire boards, integrated circuits, device components arrays, biological and/or chemical sensors, physical sensors (e.g., temperature, light, radiation, etc.), solar cell or photovoltaic arrays, display arrays, optical collectors, systems and displays. The electronic device may be formed from a plurality of layers. Preferably, the electronic device is relatively thin, so that the end device may be conformable to a surface, such as a biological surface corresponding to tissue or an organ. The electronic device may be flexible and stretchable, so as to accommodate time-varying shape changes.

"Sensor" refers to an electronic device useful for detecting the presence, absence, amount, magnitude or intensity of a physical property, object, radiation and/or chemical. Sensors in some embodiments function to transduce a biological signal into an electrical signal, optical signal, wireless signal, acoustic signal, etc. Useful sensing elements include, but are not limited to electrode elements, chemical or biological sensor elements, pH sensors, optical sensors, photodiodes, temperature sensors, capacitive sensors strain sensors, acceleration sensors, movement sensors, displacement sensors, pressure sensors, acoustic sensors or combinations of these.

"Actuator" refers to an electronic device component useful for interacting with, stimulating, controlling, or otherwise affecting an external structure, material or fluid, for example a biological tissue. Useful actuating elements include, but are not limited to, electrode elements, electromagnetic radiation emitting elements, light emitting diodes, lasers and heating elements. Actuating elements include electrodes for providing a voltage or current to a tissue. Actuating elements include sources of electromagnetic radiation for providing electromagnetic radiation to a tissue. Actuating elements include ablation sources for ablating tissue. Actuating elements include thermal sources for heating tissue. Actuating elements include displacement sources for displacing or otherwise moving a tissue.

"Active circuit" and "active circuitry" refers to one or more device components configured for performing a specific function. Useful active circuits include, but are not limited to, amplifier circuits, multiplexing circuits, logic circuits, CMOS circuits, processors, and current limiting circuits. Useful active circuit elements include, but are not limited to, transistor elements and diode elements.

"Semiconductor" refers to any material that is an insulator at a low temperature, but which has an appreciable electrical conductivity at temperatures of about 300 Kelvin. In the present description, use of the term semiconductor is intended to be consistent with use of this term in the art of microelectronics and electronic devices. Useful semiconductors include those comprising element semiconductors, such as silicon, germanium and diamond, and compound semiconductors, such as group IV compound semiconductors such as SiC and SiGe, group III-V semiconductors such as AlSb, AlAs, Aln, AlP, BN, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors CuCl, group IV-VI semiconductors such as PbS, PbTe and SnS, layer semiconductors such as $PbI_2$, $MoS_2$ and GaSe, oxide semiconductors such as CuO and $Cu_2O$. The term semiconductor includes intrinsic semiconductors and extrinsic semiconductors that are doped with one or more selected materials, including semiconductor having p-type doping materials and n-type doping materials, to provide beneficial electronic properties useful for a given application or device. The term semiconductor includes composite materials comprising a mixture of semiconductors and/or dopants. Specific semiconductor materials useful for in some embodiments include, but are not limited to, Si, Ge, SiC, AlP, AlAs, AlSb, GaN, GaP, GaAs, GaSb, InP, InAs, GaSb, InP, InAs, InSb, ZnO, ZnSe, ZnTe, CdS, CdSe, ZnSe, ZnTe, CdS, CdSe, CdTe, HgS, PbS, PbSe, PbTe, AlGaAs, AlInAs, AlInP, GaAsP, GaInAs, GaInP, AlGaAsSb, AlGaInP, and GaInAsP. Porous silicon semiconductor materials are useful for applications of aspects described herein in the field of sensors and light emitting materials, such as light emitting diodes (LEDs) and solid state lasers. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

"Dielectric" refers to a non-conducting or insulating material. In an embodiment, an inorganic dielectric comprises a dielectric material substantially free of carbon. Specific examples of inorganic dielectric materials include, but are not limited to, silicon nitride and silicon dioxide.

"Conformal contact" refers to contact established between a device and a receiving surface, which may for example be a target tissue in a biological environment. In one aspect, conformal contact involves a macroscopic adaptation of one or more surfaces (e.g., contact surfaces) of an implantable device to the overall shape of a tissue surface. In another aspect, conformal contact involves a microscopic adaptation of one or more surfaces (e.g., contact surfaces) of an implantable device to a tissue surface resulting in an intimate contact substantially free of voids. In an embodiment, conformal contact involves adaptation of a contact surface(s) of the implantable device to a receiving surface(s) of a tissue such that intimate contact is achieved, for example, wherein less than 20% of the surface area of a contact surface of the implantable device does not physically contact the receiving surface, or optionally less than 10% of a contact surface of the implantable device does not physically contact the receiving surface, or optionally less than 5% of a contact surface of the implantable device does not physically contact the receiving surface. Conformal contact includes large area conformal contact, for example, wherein conformal contact between a tissue and device component is over an area greater than or equal to 1000 $mm^2$, and optionally greater than or equal to 10,000 $mm^2$.

"Conformable" refers to a device, material or substrate which has a bending stiffness sufficiently low to allow the device, material or substrate to adopt a desired contour profile, for example a contour profile allowing for conformal contact with a surface having a pattern of relief or recessed features. In certain embodiments, a desired contour profile is that of a tissue in a biological environment, for example heart tissue.

"Low modulus" refers to materials having a Young's modulus less than or equal to 10 MPa, less than or equal to 5 MPa, or optionally less than or equal to 1 MPa and optionally for some applications less than or equal to 0.1 MPa.

"Young's modulus" and "modulus" are, unless indicated otherwise, used interchangeably and refer to a mechanical property of a material, device or layer which refers to the ratio of stress to strain for a given substance. Young's modulus may be provided by the expression;

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably 10 times larger for some applications, more preferably 100 times larger for other applications and even more preferably 1000 times larger for yet other applications. "Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire layer of material.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. For example, a flexible material, structure, device or device component may be deformed into a curved shape without introducing strain larger than or equal to 5%, for some applications larger than or equal to 1%, and for yet other applications larger than or equal to 0.5% in strain-sensitive regions. As used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 100 microns, optionally less than 10 microns and optionally less than 1 micron) and device geometries such as thin film and mesh geometries.

"Biocompatible" refers to a material that does not elicit an immunological rejection or detrimental effect when it is disposed within an in-vivo biological environment. For example, a biological marker indicative of an immune response changes less than 10%, or less than 20%, or less than 25%, or less than 40%, or less than 50% from a baseline value when a biocompatible material is implanted into a human or animal.

"Bioinert" refers to a material that does not elicit an immune response from a human or animal when it is disposed within an in-vivo biological environment. For example, a biological marker indicative of an immune response remains substantially constant (plus or minus 5% of a baseline value) when a bioinert material is implanted into a human or animal.

Example 1: Ultrathin, Transferred Layers of Thermally Grown Silicon Dioxide as Biofluid Barriers for Biointegrated Flexible Electronic Systems Materials that can serve as long-lived barriers to biofluids are essential to the development of any type of chronic electronic implant. Devices such as cardiac pacemakers and cochlear implants use bulk metal or ceramic packages as hermetic enclosures for the electronics. Emerging classes of flexible, biointegrated electronic systems demand similar levels of isolation from biofluids but with thin, compliant films that can simultaneously serve as biointerfaces for sensing and/or actuation while in contact with the soft, curved, and moving surfaces of target organs. This example introduces a solution to this materials challenge that combines (i) ultrathin, pristine layers of silicon dioxide ($SiO_2$) thermally grown on device-grade silicon wafers, and (ii) processing schemes that allow integration of these materials onto flexible electronic platforms. Accelerated lifetime tests suggest robust barrier characteristics on timescales that approach 70 y, in layers that are sufficiently thin (less than 1 μm) to avoid significant compromises in mechanical flexibility or in electrical interface fidelity. Detailed studies of temperature- and thickness-dependent electrical and physical properties reveal the key characteristics. Molecular simulations highlight essential aspects of the chemistry that governs interactions between the $SiO_2$ and surrounding water. Examples of use with passive and active components in high-performance flexible electronic devices suggest broad utility in advanced chronic implants.

A critical obstacle of flexible electronics for chronic implants is the absence of thin-film barriers to biofluids with multidecade lifetimes. Previously explored materials are unsuitable due to limitations of (i) extrinsic factors, such as the practical inability to avoid localized defects, and/or (ii) intrinsic properties, such as finite water permeability. Those challenges are addressed by combining pristine thermal $SiO_2$ layers with processing steps for their integration onto flexible electronics. Experimental and theoretical studies reveal the key aspects of this material system. Accelerated immersion tests and cyclic bending measurements suggest robust, defect-free operation with various electronic components and an integrated system for multiplexed mapping of electrophysiological signals. The findings have broad relevance to diverse biointegrated electronics and optoelectronics.

Advanced concepts in materials science and engineering form the foundations for emerging classes of high-performance, flexible electronic/optoelectronic devices, with levels of functionality that far exceed those of passive components and arrays. These systems are of interest because they can conform to the surfaces of biological systems in ways that enable important capabilities of relevance to both biomedical research and clinical practice. Examples include devices for continuous monitoring of health status through the skin (1-9), optical stimulation of targeted neural circuits in the brain (10-13), and electrophysiological mapping on the epicardial surface (14-17). These platforms are unique because their lightweight construction, thin geometry, and low bending stiffness allow high-quality, minimally invasive interfaces to soft, dynamic biological tissues, in a manner that cannot be replicated with conventional wafer-based forms of electronics. Such physical properties and mechanical attributes follow from the successful codevelopment of organic, inorganic, and hybrid inorganic/organic semiconductor materials together with mechanical designs and manufacturing schemes that enable their deployment in systems that can bend to small radii of curvature and, in some cases, stretch to high levels of elongation (2, 18-22). Skin-mounted devices, sometimes referred to as "epidermal" electronics (1), represent one of the most successful forms of this technology, where commercial embodiments are just now becoming widely available. Extensions of these types of systems for use as chronic implants have the potential to improve capabilities in human health care across broad categories of disease states and disorders (23, 24). A daunting challenge is in the development of materials that can serve as long-lived, perfect barriers to biofluids at thicknesses that allow high-quality sensing/actuating interfaces to the surrounding biology without adversely affecting the compliant mechanics.

Ideal systems have a material that would encapsulate the entire front and back surfaces of the electronics, to prevent biofluid penetration across any exposed interfaces, with the following additional characteristics: (i) biocompatible molecular composition; (ii) high electrical capacitance (for electrical interfaces); (iii) low thermal conductivity and thermal mass (for thermal interfaces); (iv) good optical transparency (for optical interfaces); (v) low areal mass density (for minimized inertial load); (vi) low flexural rigidity (for conformal integration onto curved surfaces); (vii) defect-free, material perfection over large areas (several or many square centimeters); (viii) thermal and chemical compatibility with polymer substrates (for device fabrication) and (ix) lifetimes of multiple decades in electrolyte solutions at physiological pH and temperature, under cyclic bending conditions (for robust operation throughout the life of the patient). Despite extensive research on this topic in academic and industrial groups around the world, there is currently no proven material system that offers these properties.

Established encapsulation schemes for conventional electronic implants such as pacemakers, cochlear implants, and deep-brain stimulators, rely on thick (millimeter-scale), rigid enclosures constructed using bulk metal or ceramic parts, incompatible with the types of flexible platforms discussed here (23, 25-27). Strategies based on thin flexible films are suitable for passive arrays of sensing/actuating electrodes or related devices (28-32), but they are not immediately applicable to active, semiconductor-based electronic platforms where continuous, or nearly continuous, applied voltages and induced currents are essential for operation (14, 18, 33-35). Organic/inorganic multilayer encapsulation schemes designed to protect flexible consumer electronic devices from oxygen and moisture have some promise (36-38), but known adaptations of them cannot address the extremely demanding conditions encountered in the body, where full immersion in warm, circulating biofluids on multidecade timescales is required.

Here, we report a different approach, based on an unusual materials solution that offers all of the nine attributes listed above. The scheme combines (i) defect-free, ultrathin encapsulation layers, such as $SiO_2$ grown at high temperatures on pristine, single crystalline surfaces of device-grade silicon wafers, with (ii) procedures for integrating these layers as uniform, front-side biofluid barriers and biointerfaces on flexible electronic platforms, and as backside barriers on their thin polymer supports. Detailed studies and comparative measurements against many of the most widely explored thin-film encapsulation strategies illustrate the exceptional characteristics that are possible. Thicknesses can range between tens and thousands of nanometers, in robust flexible geometries that are compatible with all important classes of materials and devices for flexible electronics. A combination of temperature-dependent measurements, microscopy investigations, electrical leakage and permeation tests, electrochemical impedance spectroscopic characteristics, and molecular dynamics simulations reveal the essential materials properties. Experiments with basic components, ranging from passive elements such as resistors, capacitors, and diodes to active, metal-oxide semiconductor transistors and multiplexed arrays, demonstrate compatibility with the highest performance types of flexible electronic devices.

Figure 5:
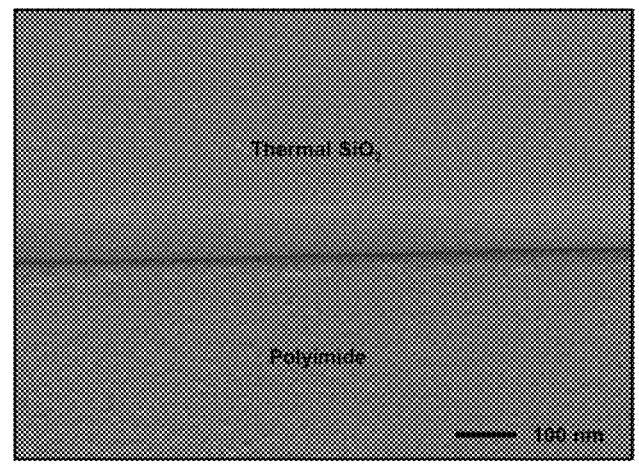
FIG. 5. The SEM image in a 45° view of a ~100-nm-thick thermal $SiO_2$ above the polyimide layer, of the test vehicle shown in FIG. 1B.

Thermal Growth of Ultrathin Layers of $SiO_2$ and Their Integration onto Flexible Plastic Substrates: FIG. 1A shows the four main steps for thermally growing, transferring, and integrating ultrathin layers of $SiO_2$ onto flexible electronic platforms. The process begins with thermal oxidation of a silicon wafer at ~1,100° C. Standard semiconductor processing techniques and/or more recent methods in growth and transfer printing, enable fabrication of high-quality electronics on this layer of oxide, which for the illustrative example here consists simply of a pattern of gold (Au). The transfer consists of bonding the top surface of this substrate onto a thin polymer film (polyimide, 25 µm thick) on a glass substrate as a temporary, rigid support to facilitate manual manipulation. A combination of dry etching steps removes the silicon in a way that terminates at the bottom surface of the $SiO_2$ (Materials and Methods). Peeling the device from the temporary support completes the process, to yield a piece of flexible electronics encapsulated across its entire front surface with a layer of thermal $SiO_2$ as a defect-free barrier to biofluids, with chronic stability. Unlike traditional processing flows in which deposition of barrier occurs last (also referred herein generally as an "encapsulating" or "encapsulation" layer), the scheme reported here starts with a planar, fully formed barrier (encapsulating) layer and then builds device functionality directly on top. Similar growth and transfer processes can deliver an encapsulation layer, including a layer of $SiO_2$ to the bottom of the flexible substrate, to similarly prevent biofluid penetration from the back side. FIG. 1B displays an image of a test vehicle that incorporates a front-side layer of $SiO_2$ with thickness of 100 nm (FIG. 5). These steps can be easily scaled to the largest silicon wafers available (currently 450-mm diameter), but is compatible to larger substrates, thereby allowing for systems with overall sizes that can provide nearly full area coverage across any internal organ of the human body. As in semiconductor manufacturing, the cost per unit area decreases with increasing wafer sizes. In matured manufacturing processes, the costs for implementing these barrier coatings on biomedical implants have the potential to approach costs that are only incrementally larger than those of the wafers themselves.

Figure 6:
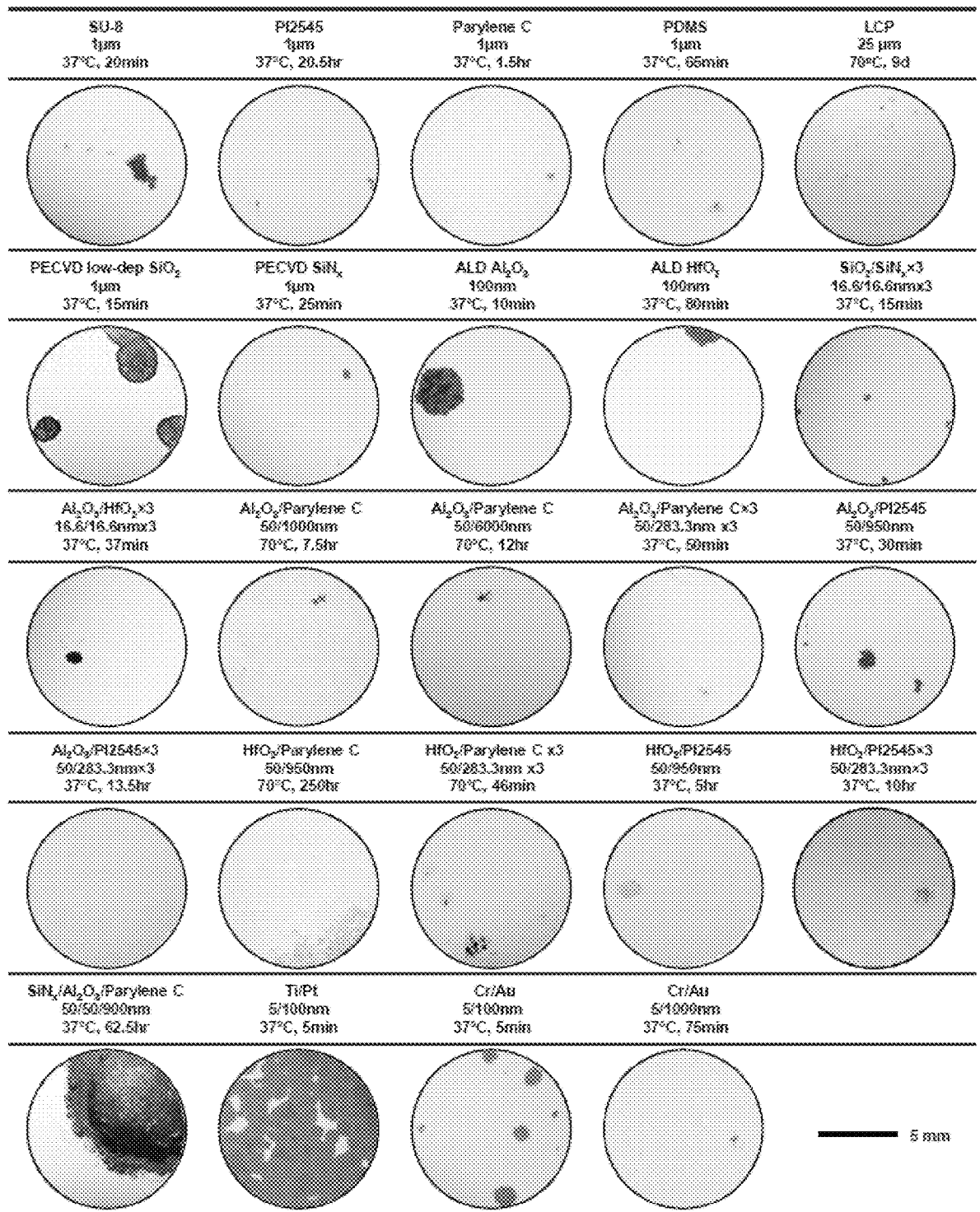
FIG. 6. Summary of Mg soak tests for different candidate barrier materials.

A thin, uniform layer of magnesium (Mg) (200 nm thick, ~1-cm$^2$ area) formed by electron beam evaporation serves as a convenient test vehicle for examining the water barrier properties of thin layers of $SiO_2$ grown and processed in this manner. Here, the strong reactivity of Mg with water [Mg+ $2H_2O\rightarrow Mg(OH)_2+H_2$] quickly produces defects that can be visualized easily by standard microscopy techniques. As shown in FIG. 1C and FIG. 6 and Table 1, a 100-nm-thick layer of thermal $SiO_2$ survives for 22 d of complete, continuous immersion in phosphate-buffered saline (PBS) solution at pH of 7.4 and a temperature of 70° C. After this period, the Mg layer dissolves at once, in a spatially uniform fashion across the entire area of the sample. Experiments performed in the same manner but with other barrier materials, including various chemistries, deposition methods, thicknesses, and single/multilayer configurations, provide points of comparison. The results for all cases examined here indicate rapid degradation of the Mg in modes that involve either permeation directly through the barrier materials themselves (e.g., polymers deposited by spin coating), or through isolated, "pinhole" defects in the layers [e.g., silicon nitrides formed by plasma-enhanced chemical vapor deposition (PECVD)]. Specific examples of these intrinsic (former case) and extrinsic (latter case) effects appear in FIG. 1C. The only system, other than thermal $SiO_2$, that shows stable operation is a stainless-steel foil with thickness of 50 μm (FIG. 7). This option is, however, not suitable for capacitive, biosensing applications, and it has only limited value in other possible biointerface measurements, such as those based on thermal or optical interfaces. Barrier layers formed by other deposition techniques, such as plasma-assisted atomic layer deposition (ALD), $O_3$-assisted ALD, and anodization show pinhole-like defects as well (39-42). For example, although plasma-assisted ALD-deposited $SiN_x$ has a low intrinsic water vapor transmission rate, pinholes lead to extrinsic effects that limit the encapsulation performance of the entire barrier (40). The extent and nature of these types of extrinsic effects are expected to vary depending on the deposition methods, the deposition tools, and the detailed conditions for deposition and post-processing, but may generally have challenges with respect to consistently achieving a high defect-free levels needed for the uses envisioned herein.

Of course, the systems and methods provided herein are compatible with a range of materials as the encapsulating layer, so long as desired defect-free levels are achieved for the application of interest, with some applications requiring lower defect-free levels than others that may tolerate relatively higher defect-free levels. Such defect-free levels may be described functionally or quantitatively, such as less than 1 defect/mm$^2$ of the layer for relatively stringent applications (e.g., long-term implant), to less than 10 defect/mm$^2$ for less stringent applications (e.g., shorter-term implant or non-biological applications), or a water flux less than that required to ensure the implanted device has a functional operational lifetime greater than a user-defined lifetime, that depends on the application of interest, which could range from between one year or multiple decades for long-term implants.

Additional areas of potential application of the encapsulation layers and related processing platforms provided herein, including thermal $SiO_2$ barriers, are in aseptic packaging, food containers, and others. Here, the performance of thermal $SiO_2$ thin-film barriers surpasses that of polymer-based antimicrobial food packaging layers by many orders of magnitude. Compared with some of the most advanced multilayer systems, such as the Barix barrier (developed by Vitex Systems, Inc.), thermal $SiO_2$ offers much lower water vapor transmission rates, even at thicknesses that are orders of magnitude smaller (37).

Electrochemical impedance spectroscopy (EIS) analysis of layers of $SiO_2$ formed by thermal growth and comparisons to those formed by other methods yield additional insights. One can interpret the EIS measurement by the equivalent circuit shown in FIG. 8A. A pinhole-free ideal oxide in contact with the PBS solution can be represented by the solution resistance ($R_{sol}$) in series with the oxide capacitance ($C_{ox}$). In practice, the presence of pinholes provides a parasitic branch that contains the resistance of the solution within the pore ($R_{po}$), in series with a parallel combination of charge transfer resistance ($R_{CT}$) and double-layer capacitance ($C_{dl}$).

FIG. 1D presents results obtained in PBS solution. In direct contrast to electron beam evaporated $SiO_x$ and PECVD $SiO_2$, thermal $SiO_2$ exhibits a nearly perfect capacitive response: in the log-log impedance vs. frequency figure (FIG. 1D, Middle), a plot of the impedance (Z) as a function of the frequency (f) exhibits a slope of −1. The results indicate that the oxide defines the total impedance, and that the signal is not corrupted by resistive leakage through pinholes/pores or by direct permeation. The plot in the bottom part of FIG. 1D, Bottom, shows that the phase remains fixed at −90° for frequencies up to $10^4$ Hz (capacitive response of a R-C series circuits), as further support of this conclusion. The phase rises to −40° at $10^6$ Hz as the solution resistance begins to contribute to the response. The oxide capacitance extracted from the plot (~1 nF) is consistent with the known thickness and dielectric constant. Because $C_{dl} \gg C_{ox}$, this parameter does not affect the measurements of thermal $SiO_2$ (FIGS. 8A-8B).

Figure 9A:
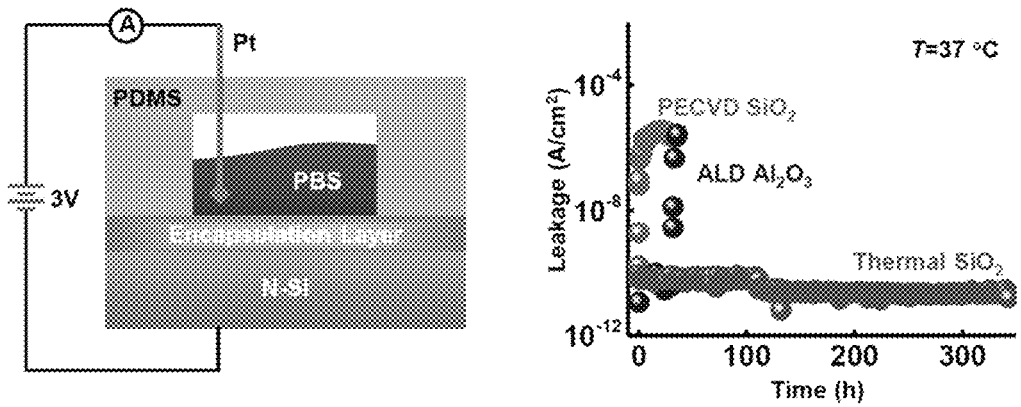
FIG. 9A. Schematic illustration of the two-terminal potentiostat system (left) used to measure leakage current through 100-nm-thick layers of PECVD $SiO_2$, ALD $Al_2O_3$ and thermal $SiO_2$ at 37° C. Measurements involved a 3V DC bias continuously applied between a Pt electrode immersed in the PBS solution and a highly doped n-type silicon substrate using a two-electrode configuration. The results (right) highlight that thermal $SiO_2$ maintained leakage current below 100 nA throughout 360 hours while both PECVD $SiO_2$ and ALD $Al_2O_3$ failed within 50 hours.
Figure 9B:
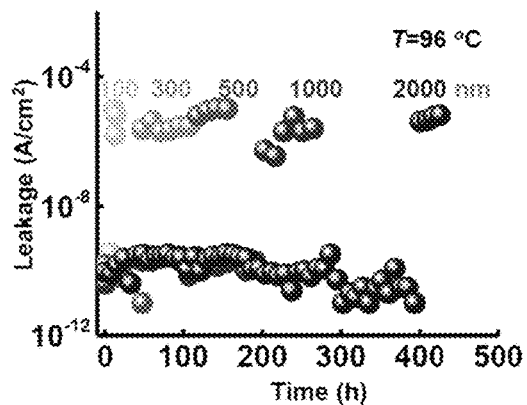
FIG. 9B. Leakage currents associated with thermal $SiO_2$ encapsulation layers with different thickness at 96° C.
Figure 10:
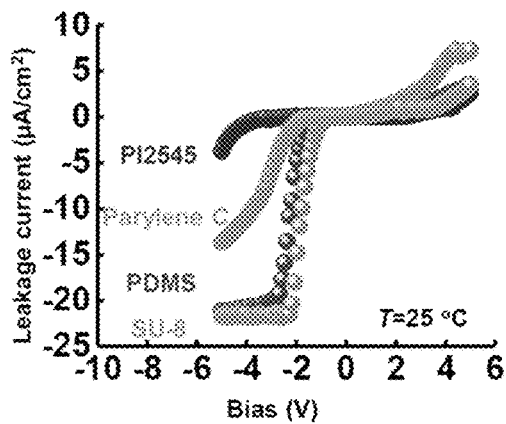
FIG. 10. Leakage current as a function of applied voltage for different organic layers with a thickness of 1 μm, tested at room temperature.
Figure 11:
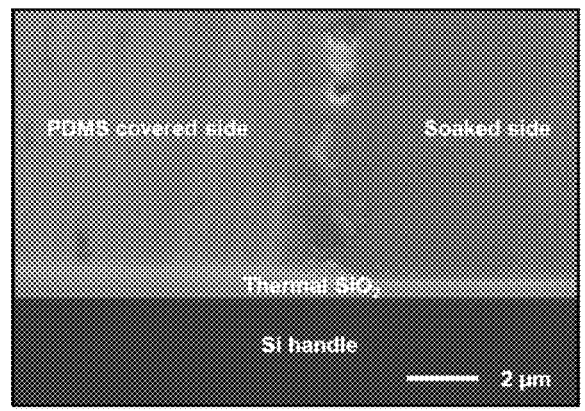
FIG. 11. The SEM image in a 45° view of a 1000 nm thermal $SiO_2$ dissolved after accelerating PBS soak test at 96° C., compared with unchanged thickness in the area of PDMS covered side.

Chemical and Physical Effects in Electrical Leakage Through Layers of $SiO_2$: Results of electrical leakage tests conducted using thermal $SiO_2$ at thicknesses of 100, 300, 500, 1,000, and 2,000 nm at 96° C. to accelerate failure-related chemical/physical processes appear in FIG. 2A and FIGS. 9A-9B, with comparison with conventional inorganic and organic materials (FIGS. 9A-9B and FIG. 10). The results show abrupt transitions to high leakage currents at time durations that depend linearly on the thickness. FIG. 2A displays colorized cross-sectional scanning electron microscope (SEM) images of a 1,000-nm-thick layer at various times after immersion. The results indicate a systematic reduction in the thickness, likely due to dissolution by hydrolysis, $SiO_2+2H_2O\rightarrow Si(OH)_4$ (FIG. 11; dissolution occurs also for stainless steel as summarized in FIG. 12). The timescale for complete dissolution is consistent with that for the appearance of large leakage currents, as shown in FIG. 2B, which illustrates the linear dependence of lifetime (i.e., time to large leakage current) on thickness. This linear form, and its zero intercept, also suggests that hydrolysis proceeds exclusively by surface reactions without a significant role of reactive diffusion into the bulk of the $SiO_2$ or of permeation through defect sites. Additional studies show that the dissolution rate for thermal $SiO_2$ does not depend on electrical bias for values relevant to biointegrated electronics (FIG. 2C). Similar characterization is available for other encapsulation layer materials, thereby facilitating selection of appropriate encapsulation layer materials depending on required defect tolerances that may vary with the application of interest.

Temperature-dependent studies of the rate of hydrolysis of thermal $SiO_2$ in PBS reveal additional details. These experiments use thermal $SiO_2$ grown on all surfaces of the silicon wafer, including its edges (FIG. 2D), to avoid any exposed Si, which itself will dissolve according to $Si+4H_2O \rightarrow Si(OH)_4+2H_2$ (FIG. 13). The dissolution rates depend exponentially on 1/T, consistent with Arrhenius scaling and an apparent activation energy $E_A=1.32$ eV (FIG. 2D). This energy is higher than that inferred from previous studies of natural quartz mineral and fused amorphous silica (0.48-1.11 eV) in deionized water or various aqueous solutions (such as NaCl solution), possibly due to the formation of activated complexes on the surfaces of $SiO_2$ in PBS (43, 44). For comparison, measurement of the dissolution rate at a pH of 7.4 and 70° C. yields a value of 5.6 nm/d ($2.9 \times 10^{-13}$ mol/cm²·s), which is roughly one order of magnitude higher than that of quartz or amorphous silica in deionized water at the same temperature (44, 45). This increase is likely due to an expected "salt effect" that leads to enhanced reaction rates in PBS (46). From these measurements, a multiphysics computational model for the temperature and pH dependence of the dissolution rate has been developed and validated (Materials and Methods). The dissolution rate is found to have a half-order dependence on hydroxide concentration (FIGS. 14A-14B). Simulations can yield estimates of the lifetime of thermal $SiO_2$ layers for pH values ranging from 7 to 12, and temperatures from 25 to 90° C. At a pH of 7.4 and 37° C., the dissolution rate for thermal $SiO_2$ is $\sim 4 \times 10^{-2}$ nm/d, corresponding to a lifetime of nearly 70 y. This timescale exceeds the lifetime of most patients who might benefit from chronic flexible electronic implants, for a layer with thickness of 1,000 nm, sufficiently thin to meet the key requirements outlined previously. Any of the processes, methods and systems provided herein may have an encapsulation layer that covers both a support surface and exposed edges of a substrate, thereby providing good barrier characteristics over any remaining substrate remnants remaining after processing.

Figure 3A:
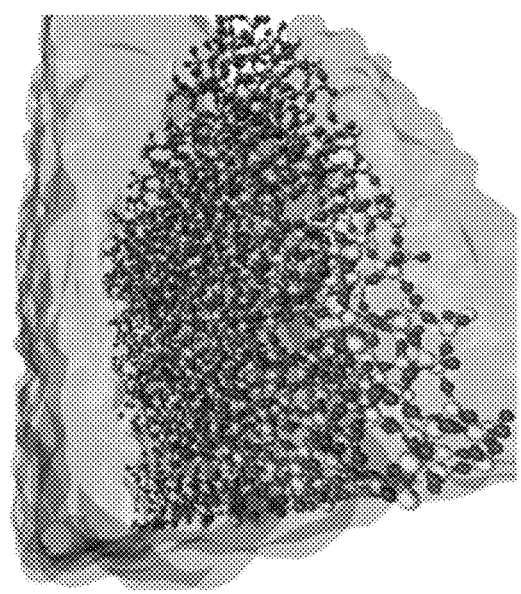
Figure 3C:
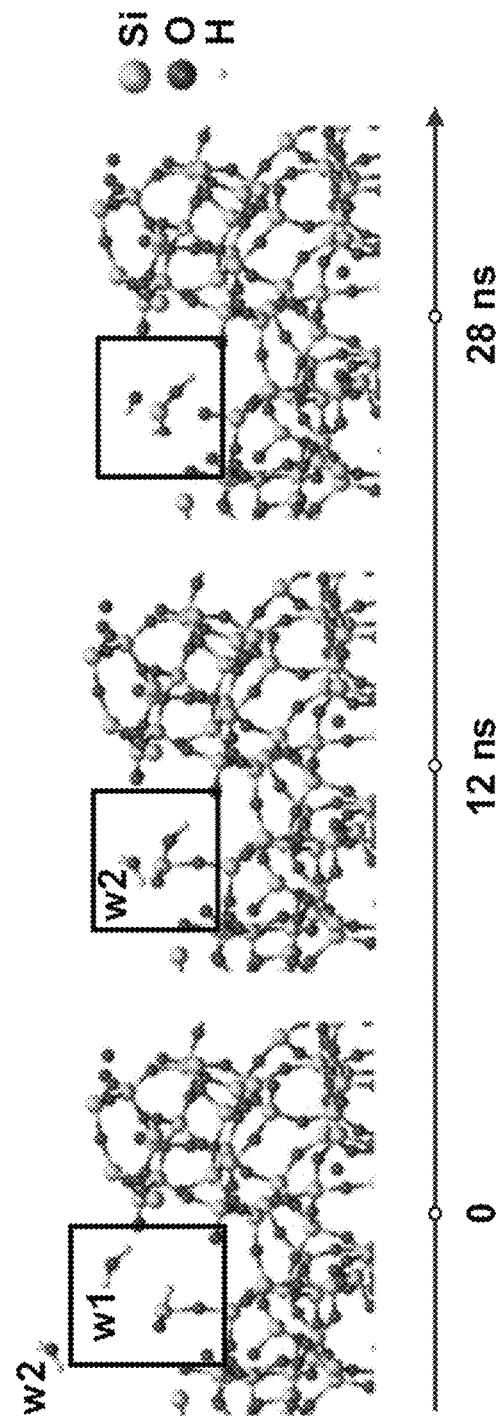
Figure 15:
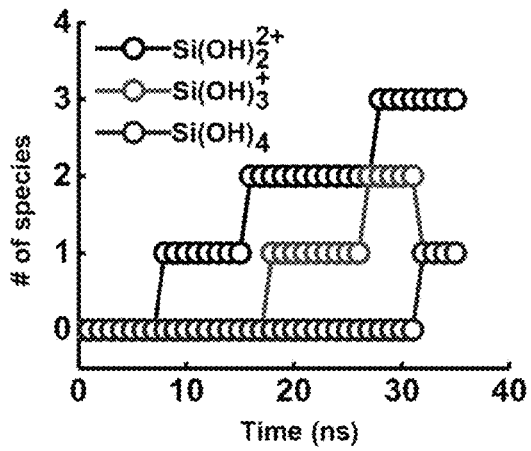
FIG. 15. Number of reaction products during simulation of Si dissolution at 100° C.

Theoretical Modeling: Reactive molecular dynamics (RMD) simulations (FIGS. 3A and 3B) provide some additional insights into the dissolution chemistry. FIG. 3A presents schematic illustrations of the simulation box explained in detail in Materials and Methods. Adding/removing protons from the system provides a means to adjust the pH of the surrounding bath that is free of ions. As shown in FIG. 3B, adding void-like defects in a perfect material serves as a route to reduce the effective density, motivated partly by previous work that shows that voids and defects larger than 1 nm can exist in $SiO_2$ structures (47, 48). FIG. 3C depicts snapshots of sequential reactions that lead to the dissociation of Si from a surface defective site, with a dangling Si—OH, or Si—H bond. On average, ~80% of the Si in the oxide layer are OH terminated and ~20% are H terminated. Analysis therefore focuses on the dissolution chemistry of the former. The frame on the left (t=0 ns) shows two water molecules (labeled w1 and w2) that approach a Si atom at the location of a Si—OH bond. At t=12 ns, the hydrogen of molecule w1 dissociates and forms a bond with the H from the —OH— terminated Si and yields $H_2$. This reaction increases the length of the bond between the Si and the O on the bottom side from 2.3 to 2.95 Å, with a corresponding reduction in its strength. At t=28 ns, molecule w2 approaches the Si and one of its hydrogen atoms dissociates in the vicinity of the dissolution site (FIG. 3C). This hydrogen chemically bonds with the dangling O of the Si. Cleavage of the previously weakened Si—O bond releases the ionic species $Si(OH)_2^{2+}$. The w2 remains as $OH^-$ for an additional 3 ns and forms a water molecule by bonding with another $H^+$ at t=31 ns. The conversion of $Si(OH)_2^{2+} \rightarrow Si(OH)_4$ finishes at 80-90 ns at T=37° C., such that the final product of dissolution is silicic acid, similar to findings from previous studies of dissolution of bulk Si using comparable models (49). These reaction products appear within the 35-ns timescale of the simulations presented here under accelerated conditions, that is, at 100° C., $Si(OH)_2^{2+} \rightarrow Si(OH)_3^+ \rightarrow Si(OH)_4$ occurs in ~32 ns (FIG. 15). Simulation results of different mass density, influence of defects, and temperature dependence on intermediate products during Si hydrolysis are detailed in FIGS. 16A-16B and 17A-17C.

Figure 4A:
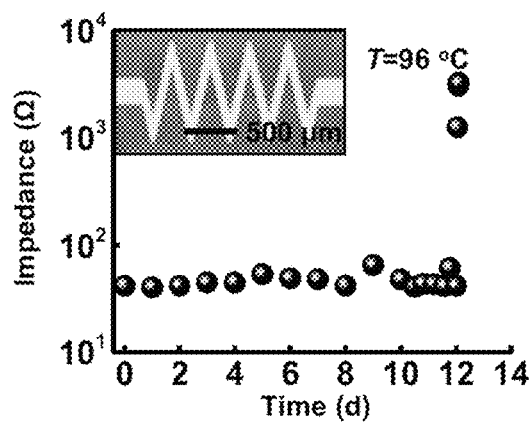
FIGS. 4A-4H. Demonstration of electronic devices and flexible electronic systems encapsulated with thermal $SiO_2$.
Figure 4B:
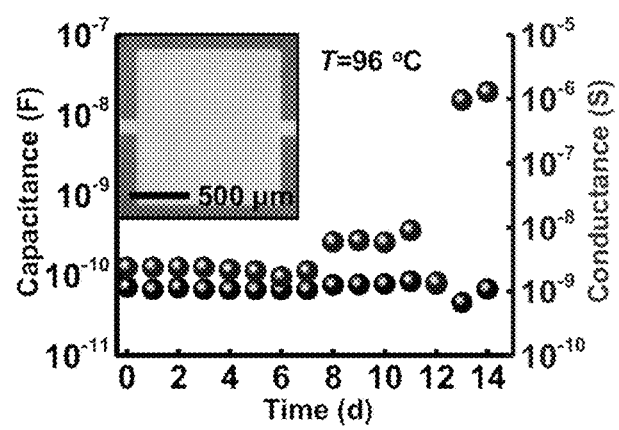
Figure 4C:
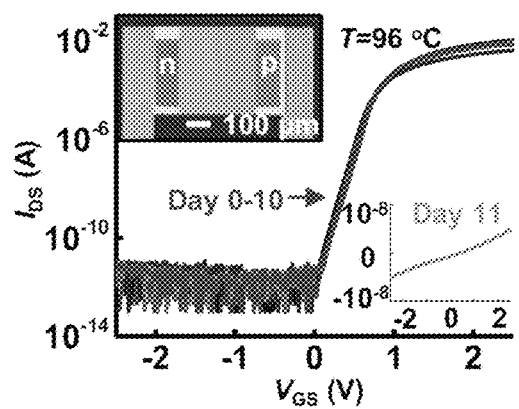
Figure 4D:
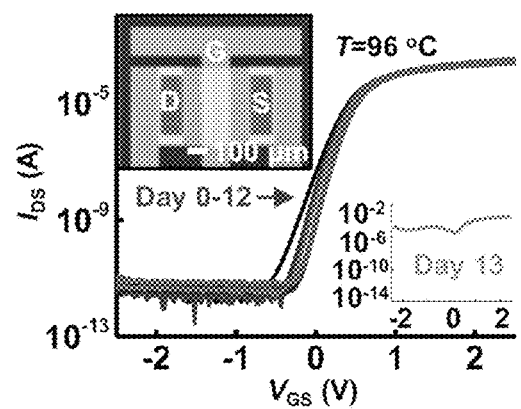
Figure 21A:
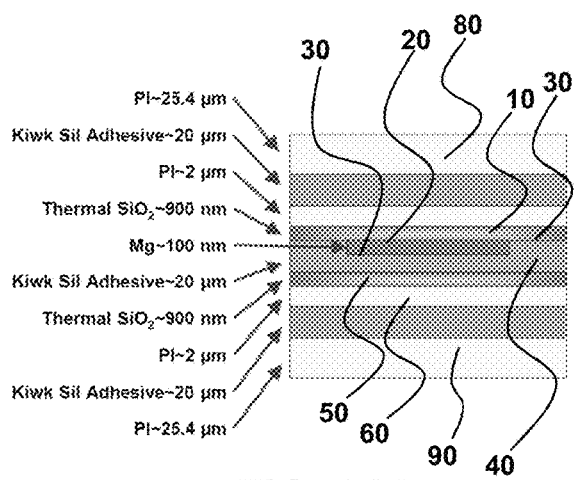
FIGS. 21A-21B. Cross-section illustrations of Mg device with double-sided thermal $SiO_2$ encapsulation layers (FIG. 21A), and control device (FIG. 21B).
Figure 21B:
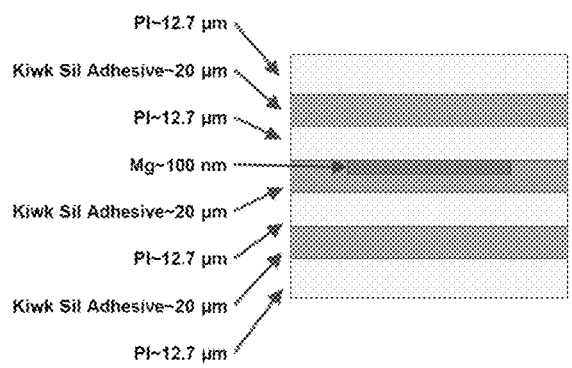
Figure 22A:
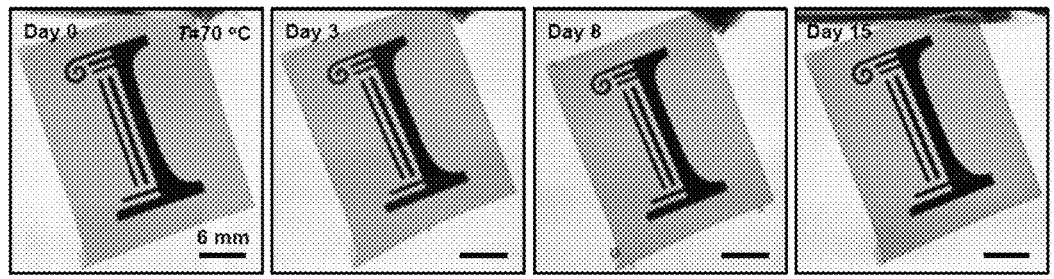
FIGS. 22A-22B. 70° C. PBS soak test of Mg device with double-sided thermal $SiO_2$ encapsulations (FIG. 22A), and control device (FIG. 22B).
Figure 22B:
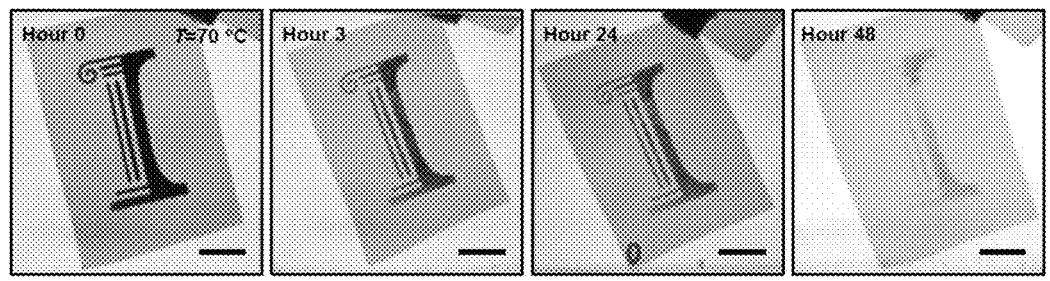
Figure 23:
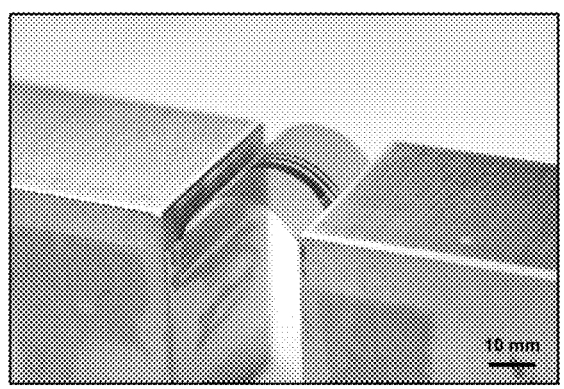
FIG. 23. Bending the Mg device with double-sided thermal $SiO_2$ encapsulations to a radius of 5 mm exhibits high flexibility.

Water Barriers Demonstrated in Key Electronic Devices: The overall process outlined in FIG. 1A provides versatility for application with nearly any class of silicon or silicon-compatible electronic systems, and with other forms of flexible electronics. Resistors, capacitors, p-n diodes, and metal-oxide-semiconductor field effect transistors (MOSFETs) based on silicon nanomembranes (SiNM) serve as examples, each constructed with a 1-µm-thick layer of thermal $SiO_2$ (FIG. 4A-4D, FIGS. 18A-18D, and tested in the manner illustrated in FIG. 9A). All devices retain functionality, without measurable change from their initial state, during complete immersion in PBS at 96° C. (FIGS. 19A-19C and 20A-20C). The $SiO_2$ fully dissolves in 12±1 d, consistent with data presented previously. At this time, all devices fail suddenly and catastrophically. For example, the resistor behaves as an open circuit (FIG. 4A). For the capacitor, ions penetrate into the polyimide dielectric, which significantly increases the capacitance and contributes to leakage current across this layer (FIG. 4B). The characteristics of the diode and the n-channel MOSFET change to resemble those of a resistor, as illustrated in FIGS. 4C and 4D. As described previously, an additional transfer step can integrate a layer of thermal $SiO_2$ on the back side of the polyimide substrate, to prevent water penetration through this surface. FIG. 21A shows a sample with this type of design, in which a patterned layer of Mg persists unchanged for up to 15 d during complete immersion (without well structure) in PBS at 70° C. Under similar conditions, samples without the thermal $SiO_2$ layer on the back side of the polyimide fail within a few hours due to water permeation directly through the polyimide (FIGS. 21A-21B and 22A-22B). FIG. 23 demonstrates applicable flexibility of this design with 5 mm of bending radius. Accordingly, any of the processes and devices provided herein may include both a "top-side" and a "back-side" encapsulation layer.

Figure 24:
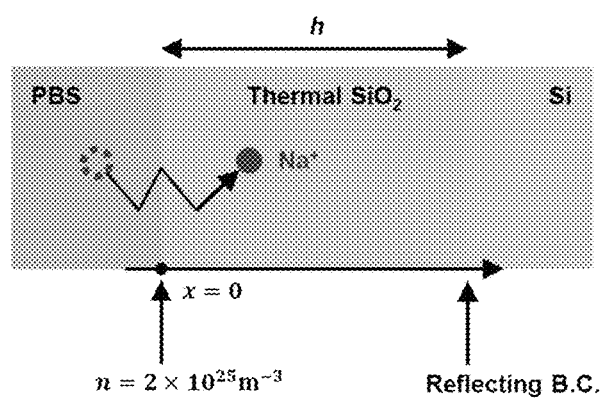
FIG. 24. Set up of sodium ion transport simulation with constant boundary condition at x=0 and reflective boundary condition at x=h.
Figure 25:
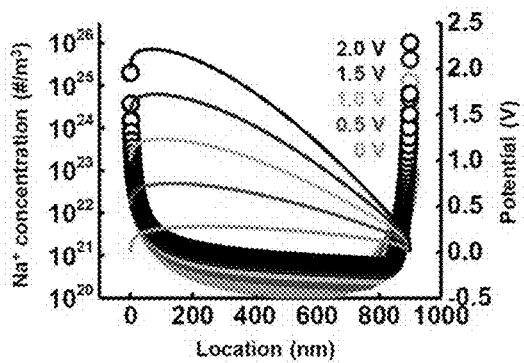
FIG. 25. $Na^+$ concentration and potential distribution within thermal $SiO_2$ (h=900 nm) layer at the end of 2-years simulation at T=37° C.
Figure 26A:
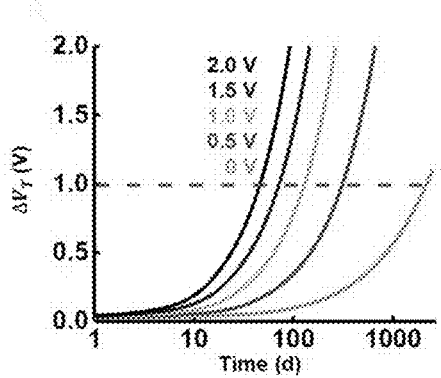
FIGS. 26A-26B. $\Delta V_T$ threshold voltage shift as a function of time (FIG. 26A) and normalized time (FIG. 26B) with different $SiO_2$ bias voltage at T=37° C.
Figure 26B:
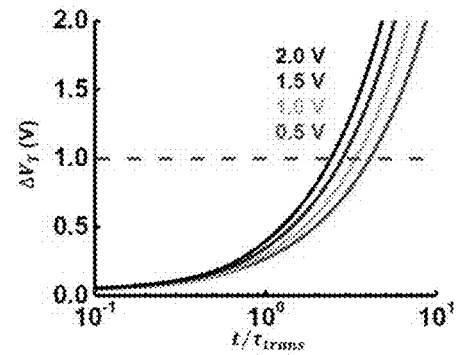

In addition to water, ions present in biofluids such as $Na^+$ and $K^+$ can also degrade/alter performance, particularly in active semiconductor devices. For example, proximity of $Na^+$ to the conducting channel of a MOSFET causes its threshold voltage to shift. The challenge is that these and other ions have a nonnegligible mobility inside the bulk of the thermal $SiO_2$ material. The transport is, in general, dependent on electric field, such that operation of the device can enhance this drift. When the ion transport is drift dominated, the failure time is proportional to the ion transition time $T_{trans}=h/\mu\xi=h^2/\mu V=kTh^2/DqV$, where h is the thickness of thermal $SiO_2$, $\mu$ is the mobility of the ion, $\xi$ is the internal electric field, V is the voltage across the $SiO_2$, k is the Boltzmann constant, T is temperature, D is the diffusivity of the ion, and q is the charge. In practice, the lifetime increases significantly with reductions in voltages (for a fixed thickness) and/or increases in thickness (at fixed voltage). Self-consistent simulations described herein show that ions accumulate inside the thermal $SiO_2$ where they can change the potential distribution in a manner that alters the transport (FIGS. 24 and 25). Solutions to the coupled drift-diffusion and Poisson's equation for $Na^+$ indicate that devices last several times longer than expected based on purely drift-dominated transport (which provides the lower bound for device lifetime; FIGS. 26A-26B). Penetration of ions can be further retarded by the incorporation of high-quality silicon nitride or phosphosilicate glass, as adopted by the semiconductor industry since the 1980s (50, 51). An ideal barrier for both water and ions may come from thin layers of thermal nitride, oxide/nitride bilayers, or even oxynitrides. Exploration of these configurations is further described in Examples 3 and 4.

Figure 4E:
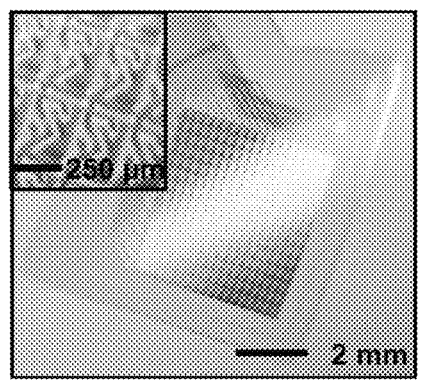
Figure 4F:
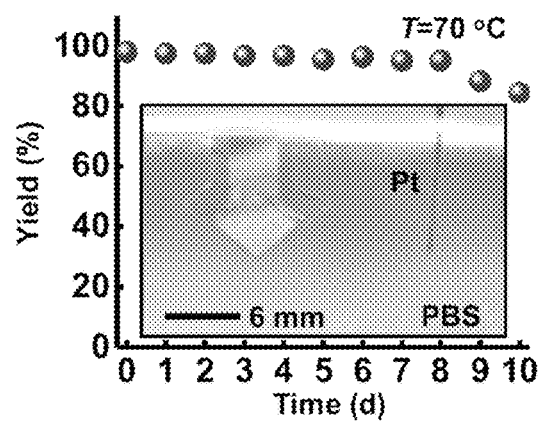
Figure 4G:
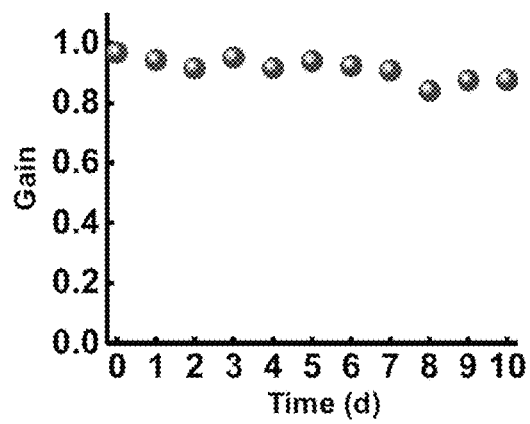
Figure 4H:
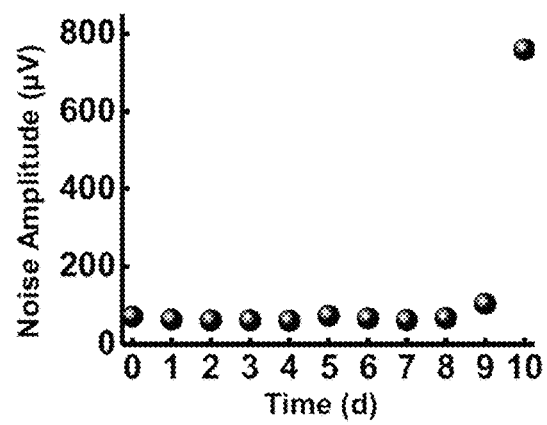
Figure 27:
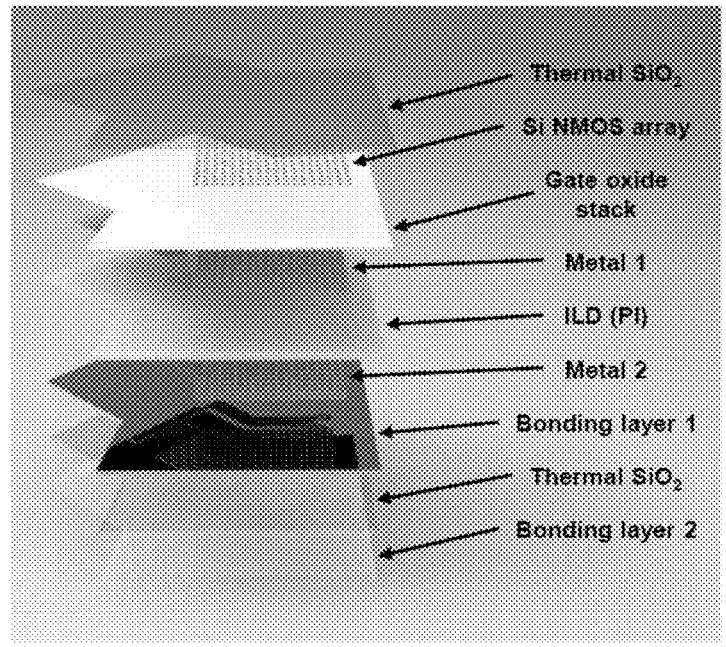
FIG. 27. Exploded-view schematic illustration of sensing system with top and bottom side thermal $SiO_2$.
Figure 28:
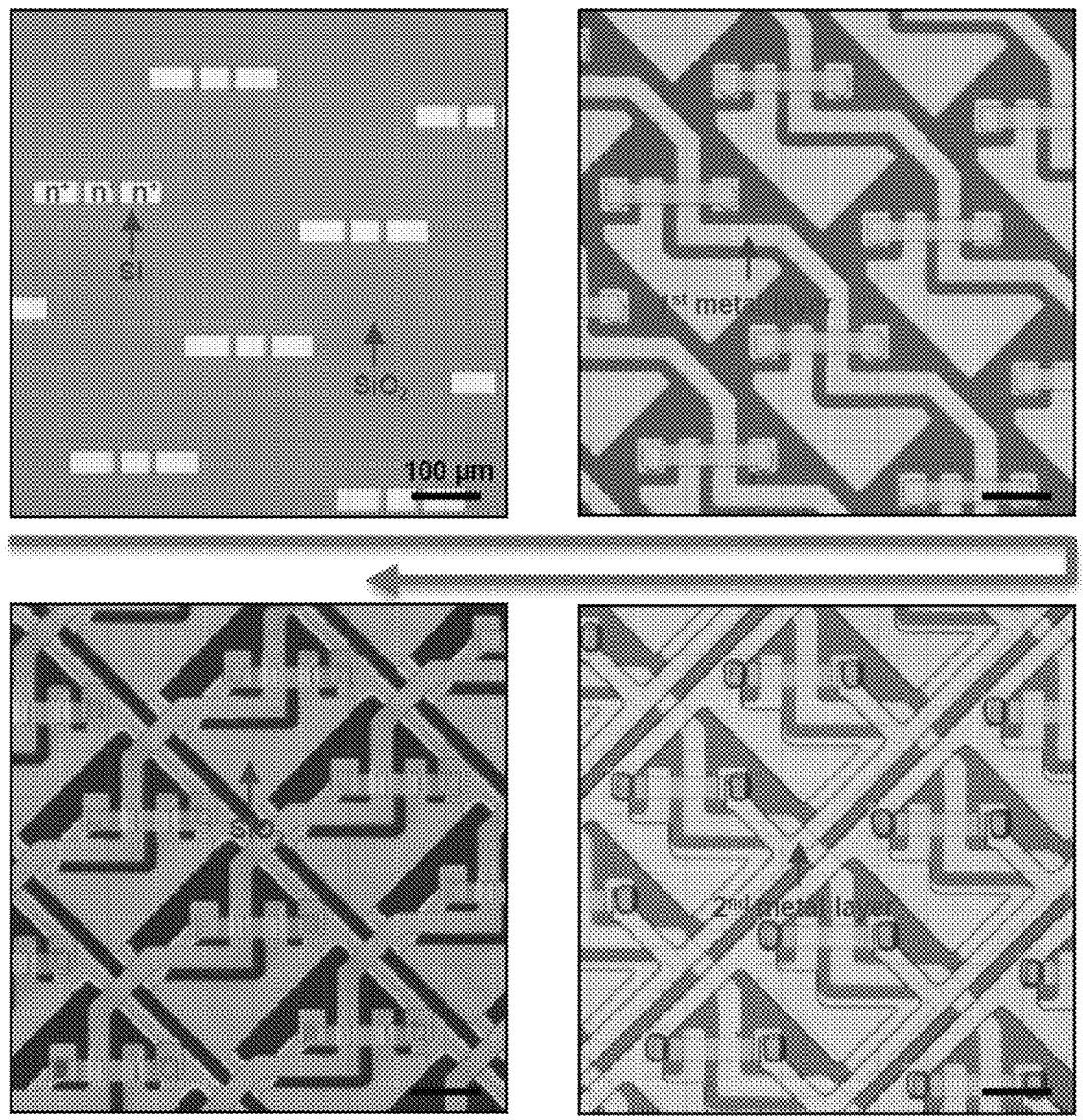
FIG. 28. Images of active multiplexed electronics in four key fabrication steps: 1. isolated Si transistors above thermal $SiO_2$; 2. photolithographic patterning of 1st metallization for source, drain, gate (connected to sensing electrode pad) and row wires for multiplexing; 3. $2^{nd}$ metallization of the column wires for signal output; 4. final device layout after removing Si substrate with exposed thermal $SiO_2$ as frontside encapsulation.
Figure 29A:
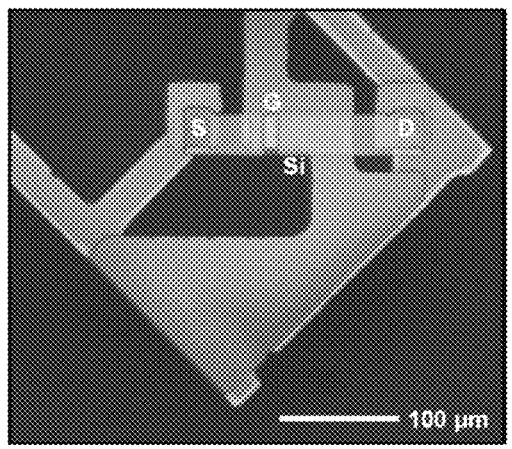
FIGS. 29A-29C. Si transistor performances of the active multiplexed electronics.
Figure 30A:
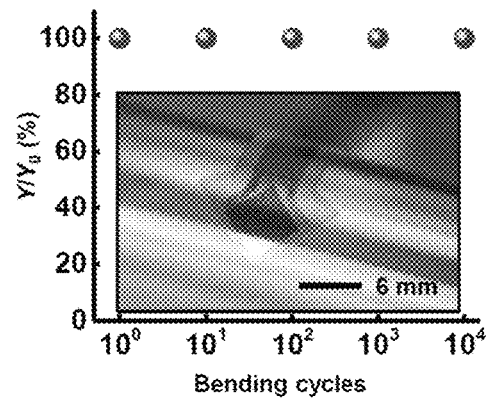
FIGS. 30A-30C. Yield, gain and mean noise RMS remain unchanged after $10^4$ bending cycles. Inset in the left figure shows a photograph of a device bent to a radius of ~5 mm on a glass tube.
Figure 29B:
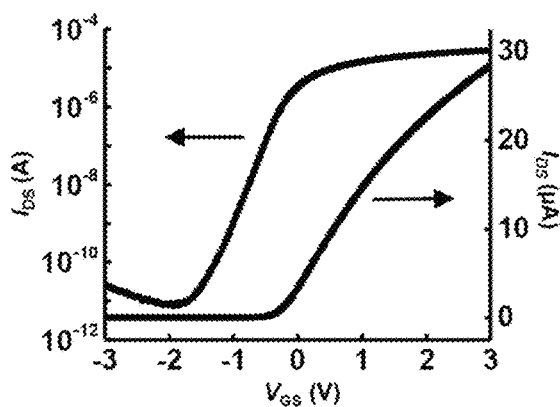
Figure 30B:
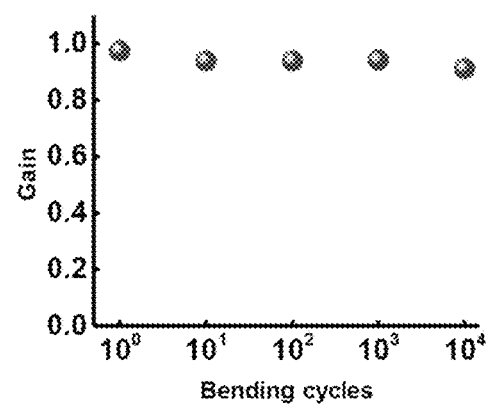
Figure 29C:
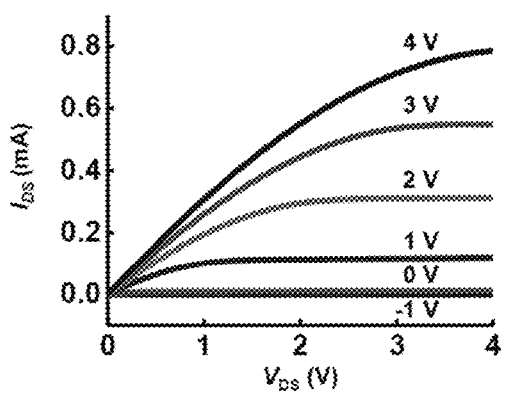
Figure 30C:
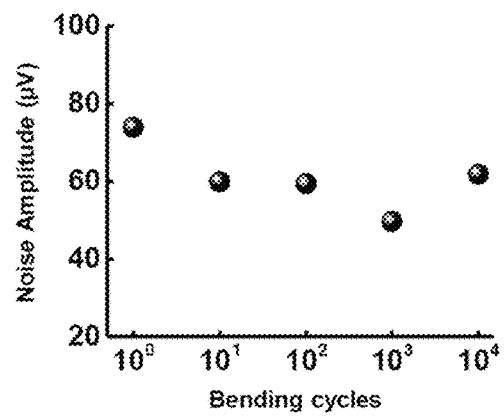

Integration of 900-nm thermal $SiO_2$ as encapsulation layers for actively multiplexed electronics designed to allow high-speed spatiotemporal mapping of biopotentials highlights the compatibility of the materials and concepts provided herein with the most sophisticated classes of flexible electronics. FIG. 4E and FIG. 27, present exploded view schematic illustrations of the system and an image of a completed device with top- and bottom-side encapsulation layers made of thermal $SiO_2$ material, respectively. This platform provides 252 sensing sites (18 rows by 14 columns) with silicon transistors at each site for actively multiplexed addressing, over an area of 4.5 mm×4.6 mm. The multiplexing is realized by connecting a pair of transistors in series, one of which functions for capacitive sensing of biopotentials through thermal $SiO_2$ by connecting its gate terminal to an electrode pad. The other transistor serves as a switch to allow multiplexed readout from the sensing site (FIGS. 28 and 29A-29C). In addition to its barrier role, the front-side $SiO_2$ layer acts as the dielectric layer for capacitive coupling. FIGS. 4F-4H show excellent yield, stable high average gain values with low noise operation during complete immersion in PBS solution at 70° C. for 10 d. FIGS. 30A-30C illustrate robust performances in bending test. Accordingly, any of the methods and devices presented herein may have at least one of the encapsulation layers that functions as a desired barrier to reliably increase device lifetime while also functioning as an interface with surrounding environment, capacitivly coupling the device with adjacent environment, including biological environment.

Although the approaches presented here do not encapsulate the exposed edges at the periphery of the overall device platforms, this constraint seems to have little practical effect on the lifetimes for the cases examined. One potential limitation is that $SiO_2$/polymer interface might suffer from delamination, especially under external stimuli such as thermal cycles (52). Edge effects may be addressed by use of slightly oversized layers of thermal $SiO_2$ together with $SiO_2/SiO_2$ bonding chemistries, including as adapted from the semiconductor industry.

In summary, the results from this example establish materials strategies and integration schemes for use of ultrathin layers of an encapsulation layer, including a layer of $SiO_2$ thermally grown on device-grade Si wafers, provide long-lived water barriers for active, flexible electronic systems. Comparisons against conventional encapsulation strategies highlight the advantages. Detailed experimental and theoretical investigations reveal that a slow hydrolysis process defines the ultimate lifetimes, consistent with the exceptionally high quality of $SiO_2$ films formed and manipulated in the schemes introduced here. In regimes of thicknesses compatible with mechanically flexible form factors, and in layouts that can support high-quality electrical interfaces, accelerated testing and modeling at both atomistic and continuum length scales suggest robust operation over many decades at physiological temperatures. Results presented here use PBS as the test solution. Lifetimes in biofluids may be somewhat different, due to differences in composition. Demonstrations at wafer-level sizes and in dual-sided encapsulation geometries illustrate the scalability of these approaches to devices of relevance for nearly all envisioned applications in biointegrated electronics. Schemes may be provided to address additional applications, including advanced embodiments that can inhibit both water and ion permeation, and further providing electronic and optoelectronic devices for neural and cardiac applications.

Example 1 References

1. Kim D-H, et al. (2011) Epidermal electronics. Science 333(6044):838-843.
2. Lipomi D J, et al. (2011) Skin-like pressure and strain sensors based on transparent elastic films of carbon nanotubes. Nat Nanotechnol 6(12):788-792.
3. Xu S, et al. (2014) Soft microfluidic assemblies of sensors, circuits, and radios for the skin. Science 344 (6179):70-74.
4. Gao W, et al. (2016) Fully integrated wearable sensor arrays for multiplexed in situ perspiration analysis. Nature 529(7587):509-514.
5. Wu W, et al. (2014) Piezoelectricity of single-atomic-layer $MoS_2$ for energy conversion and piezotronics. Nature 514(7523):470-474.
6. McAlpine M C, Ahmad H, Wang D, Heath J R (2007) Highly ordered nanowire arrays on plastic substrates for ultrasensitive flexible chemical sensors. Nat Mater 6(5): 379-384.
7. Kaltenbrunner M, et al. (2013) An ultra-lightweight design for imperceptible plastic electronics. Nature 499 (7459):458-463.
8. Lochner C M, Khan Y, Pierre A, Arias A C (2014) All-organic optoelectronic sensor for pulse oximetry. Nat Commun 5:5745.
9. Son D, et al. (2014) Multifunctional wearable devices for diagnosis and therapy of movement disorders. Nat Nanotechnol 9(5):397-404.
10. Jeong J-W, et al. (2015) Wireless optofluidic systems for programmable in vivo pharmacology and optogenetics. Cell 162(3):662-674.
11. Montgomery K L, et al. (2015) Wirelessly powered, fully internal optogenetics for brain, spinal and peripheral circuits in mice. Nat Methods 12(10):969-974.
12. Kim T I, et al. (2013) Injectable, cellular-scale optoelectronics with applications for wireless optogenetics. Science 340(6129):211-216.
13. Canales A, et al. (2015) Multifunctional fibers for simultaneous optical, electrical and chemical interrogation of neural circuits in vivo. Nat Biotechnol 33(3):277-284.
14. Viventi J, et al. (2010) A conformal, bio-interfaced class of silicon electronics for mapping cardiac electrophysiology. Sci Transl Med 2(24):24ra22.
15. Kim D-H, et al. (2011) Materials for multifunctional balloon catheters with capabilities in cardiac electrophysiologicalmapping and ablation therapy. Nat Mater 10(4): 316-323.

16. Xu L, et al. (2014) 3D multifunctional integumentary membranes for spatiotemporal cardiac measurements and stimulation across the entire epicardium. Nat Commun 5:3329.
17. Kim D-H, et al. (2012) Electronic sensor and actuator webs for large-area complex geometry cardiac mapping and therapy. Proc Natl Acad Sci USA 109(49):19910-19915.
18. Sekitani T, Zschieschang U, Klauk H, Someya T (2010) Flexible organic transistors and circuits with extreme bending stability. Nat Mater 9(12):1015-1022.
19. Schwartz G, et al. (2013) Flexible polymer transistors with high pressure sensitivity for application in electronic skin and health monitoring. Nat Commun 4:1859.
20. Tian B, et al. (2010) Three-dimensional, flexible nanoscale field-effect transistors as localized bioprobes. Science 329(5993):830-834.
21. Wu W, Wen X, Wang Z L (2013) Taxel-addressable matrix of vertical-nanowire piezotronic transistors for active and adaptive tactile imaging. Science 340(6135): 952-957.
22. Rogers J A, Someya T, Huang Y (2010) Materials and mechanics for stretchable electronics. Science 327(5973): 1603-1607.
23. Wilson B S, et al. (1991) Better speech recognition with cochlear implants. Nature 352(6332):236-238.
24. Hochberg L R, et al. (2006) Neuronal ensemble control of prosthetic devices by a human with tetraplegia. Nature 442(7099):164-171.
25. Bowman L, Meindl J D (1986) The packaging of implantable integrated sensors. IEEE Trans Biomed Eng 33(2):248-255.
26. Sanders R S, Lee M T (1996) Implantable pacemakers. Proc IEEE 84(3):480-486.
27. Mayberg H S, et al. (2005) Deep brain stimulation for treatment-resistant depression. Neuron 45(5):651-660.
28. Rousche P J, Normann R A (1998) Chronic recording capability of the Utah Intracortical Electrode Array in cat sensory cortex. J Neurosci Methods 82(1):1-15.
29. Harrison R R, et al. (2007) A low-power integrated circuit for a wireless 100-electrode neural recording system. IEEE J Solid-State Circuits 42(1):123-133.
30. Hoogerwerf A C, Wise K D (1994) A three-dimensional microelectrode array for chronic neural recording. IEEE Trans Biomed Eng 41(12):1136-1146.
31. Wise K D, Anderson D J, Hetke J F, Kipke D R, Najafi K (2004) Wireless implantable microsystems: High-density electronic interfaces to the nervous system. Proc IEEE 92(1):76-97.
32. Tyler D J, Durand D M (2002) Functionally selective peripheral nerve stimulation with a flat interface nerve electrode. IEEE Trans Neural Syst Rehabil Eng 10(4): 294-303.
33. Viventi J, et al. (2011) Flexible, foldable, actively multiplexed, high-density electrode array for mapping brain activity in vivo. Nat Neurosci 14(12):1599-1605.
34. Khodagholy D, et al. (2013) In vivo recordings of brain activity using organic transistors. Nat Commun 4:1575.
35. Bellin D L, et al. (2014) Integrated circuit-based electrochemical sensor for spatially resolved detection of redox-active metabolites in biofilms. Nat Commun 5:3256.
36. Thejo Kalyani N, Dhoble S J (2015) Novel materials for fabrication and encapsulation of OLEDs. Renew Sustain Energy Rev 44:319-347.
37. Park J-S, et al. (2011) Thin film encapsulation for flexible AM-OLED: A review. Semicond Sci Technol 26(3):034001.
38. Ahmad J, Bazaka K, Anderson L J, White R D, Jacob M V (2013) Materials and methods for encapsulation of OPV: A review. Renew Sustain Energy Rev 27:104-117.
39. Xie X, Rieth L, Merugu S, Tathireddy P, Solzbacher F (2012) Plasma-assisted atomic layer deposition of $Al_2O_3$ and parylene C bi-layer encapsulation for chronic implantable electronics. Appl Phys Lett 101(9):93702.
40. Andringa A-M, et al. (2015) Low-temperature plasma-assisted atomic layer deposition of silicon nitride moisture permeation barrier layers. ACS Appl Mater Interfaces 7(40): 22525-22532.
41. Huang Y, et al. (2008) Evaluation of the corrosion resistance of anodized aluminum 6061 using electrochemical impedance spectroscopy (EIS). Corros Sci 50(12): 3569-3575.
42. Yong-Qiang Y, et al. (2014) High barrier properties of transparent thin-film encapsulations for top emission organic light-emitting diodes. Org Electron 15(6):1120-1125.
43. Worley W G (1994) Dissolution kinetics and mechanisms in quartz- and grainite-water systems. PhD dissertation (Massachusetts Institute of Technology, Cambridge, Mass.).
44. Knauss K G, Wolery T J (1988) The dissolution kinetics of quartz as a function of pH and time at 70° C. Geochim Cosmochim Acta 52(1):43-53.
45. Icenhower J P, Dove P M (2000) The dissolution kinetics of amorphous silica into sodium chloride solutions: Effects of temperature and ionic strength. Geochim Cosmochim Acta 64(24):4193-4203.
46. Dove P M, Han N, De Yoreo J J (2005) Mechanisms of classical crystal growth theory explain quartz and silicate dissolution behavior. Proc Natl Acad Sci USA 102(43): 15357-15362.
47. Gibson J M, Dong D W (1980) Direct evidence for 1 nm pores in "dry" thermal $SiO_2$ from high resolution transmission electron microscopy. J Electrochem Soc 127(12): 2722.
48. Hasegawa M, et al. (2000) Positron and positronium studies of irradiation-induced defects and microvoids in vitreous metamict silica. Nucl Instrum Methods Phys Res B 166:431-439.
49. Yin L, et al. (2015) Mechanisms for hydrolysis of silicon nanomembranes as used in bioresorbable electronics. Adv Mater 27(11):1857-1864.
50. Ito T, et al. (1982) Advantages of thermal nitride and nitroxide gate films in VLSI process. IEEE J Solid-State Circuits 17(2):128-132.
51. Balk P, Eldridge J M (1969) Phosphosilicate glass stabilization of FET devices. Proc IEEE 57(9):1558-1563.
52. Min Yan M, et al. (2005) A transparent, high barrier, and high heat substrate for organic electronics. Proc IEEE 93(8):1468-1477.

Figure 18A:
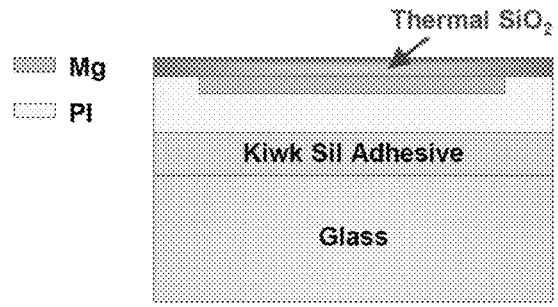
FIGS. 18A-18O. Cross-sectional sketch of resistors, capacitors, diodes and NMOS transistors.
Figure 18B:
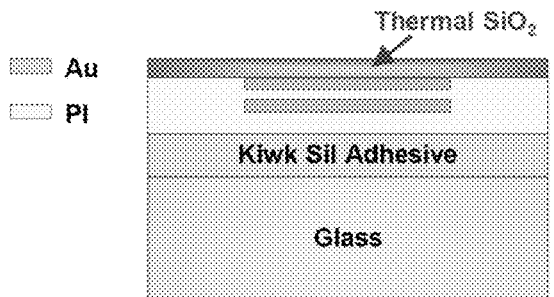
Figure 18C:
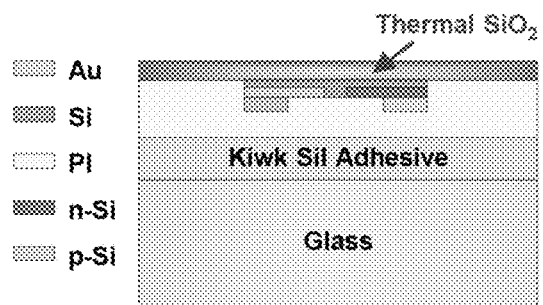
Figure 18D:
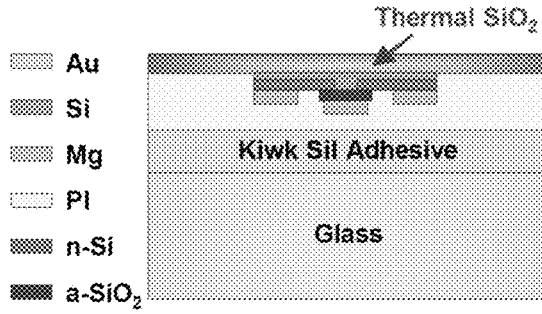
Figure 19A:
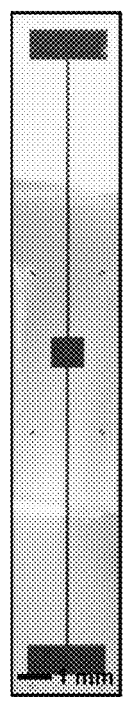
FIGS. 19A-19C. Optical microscope images of capacitor (FIG. 19A), p-n diode (FIG. 19B) and MOSFET (FIG. 19C) encapsulated with 1,000-nm-thick thermal $SiO_2$ for accelerating soak test. Device part sealed in PDMS well, with gold metal wire extended to contact pad.
Figure 19B:
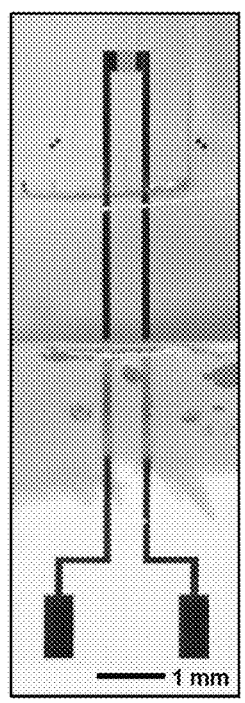
Figure 19C:
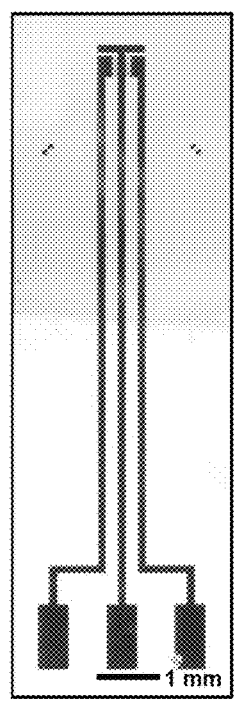
Figure 20A:
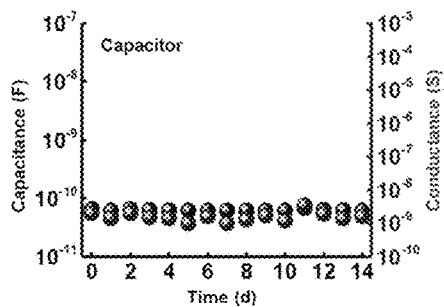
FIGS. 20A-20C. Electrical characteristics of control devices including capacitor (FIG. 20A), p-n diode (FIG. 20B) and MOSFET (FIG. 20C) in PBS soak test at 96° C.
Figure 20B:
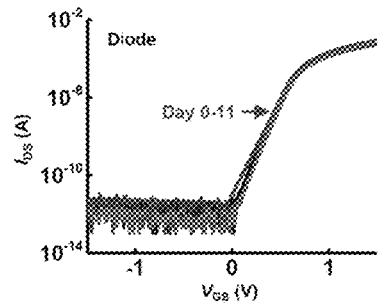
Figure 20C:
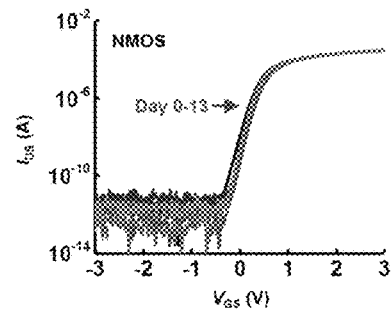

Materials and methods: Details of fabrication steps, device structures of Mg tests, impedance measurement, and electrical leakage tests are provided below. Theoretical analysis including EIS modeling, multiphysics simulations of thermal $SiO_2$ dissolution, molecular simulations, and sodium ion transport simulations are also provided Fabrication of samples with layers of thermal $SiO_2$ as encapsulation begins with wet oxidation (in $O_2/H_2O$) at high temperatures (typically at ~1150° C.) on the surfaces of standard silicon wafers (100-1000 nm thermal $SiO_2$, 500 µm Si substrate, 100 mm diameter, University Wafer). A mechanical grinding process (with an initial coarse grind and a final fine grind to achieve mirror like finish with thickness variance under 5 μm) reduced the thickness to 200 μm (Sygarus Systems). Photolithography and wet etching patterned layers of Ti/Mg (5 nm/100 nm) deposited by electron-beam evaporation into targeted resistor shapes (FIG. 18A). For the capacitors (FIG. 18B), sequential deposition and photolithography patterning of two layers of Cr/Au (5 nm/100 nm) between a dielectric layer of polyimide (1.5 μm, PI-2545, HD MicroSystems) yielded simple, parallel-plate designs (1 mm×1 mm capacitor plate). For the diodes and NMOS devices (FIGS. 18C and 18D), transfer printing delivered devices prefabricated on an SOI substrates using previously reported recipes onto the SiO$_2$/Si substrate, forming the Si nanomembrane diode and transistor (channel length L=600 μm, width W=20 μm, thickness t=100 nm). A layer of Cr/Au (5 nm/100 nm) served as metal interconnects to reach probe pads outside the PDMS well (FIGS. 19A-19C). For each type of device, spin-coating, soft-baking and curing formed an overcoat of polyimide (PI-2545, HD MicroSystems) with a thickness of 3.5 μm. ALD produced a layer of Al$_2$O$_3$ on the polyimide, to facilitate bonding to a thick layer of polyimide (25.4 μm, Kapton, DuPont) coated with a bilayer of Ti/SiO$_2$ (5 nm/100 nm) deposited by electron-beam evaporation and laminated on a glass slide with a layer of PDMS. The bonding involved application of a commercial adhesive (Kwik-Sil, World Precision Instruments) applied at a pressure of ~50 kPa and cured at room temperature. Reactive ion etching (RIE) with SF$_6$/O$_2$ (Plasma Therm) followed by Inductively Coupled Plasma RIE (ICP-RIE, Surface Technology System) with SF$_6$ removed the Si substrate to leave a largely unaltered, pristine surface of the SiO$_2$ as a biofluid barrier and biointerface.

Mg Test Structures for Evaluation of Water Barrier Performance of Conventional Materials: Photolithography with a positive photoresist (AZ nLOF 2070, MicroChemicals) formed 1 cm$^2$ square area on a clean glass substrate. Subsequent electron-beam evaporation and lift-off yielded a layer of Ti/Mg (5 nm/300 nm) in the pre-defined area. Various deposition techniques yielded different types of encapsulation layers for soak testing in PBS (FIG. 6 and Table 1). Spin coating then prepared a photodefinable epoxy (SU-8 2000, MicroChem), polyimide (PI-2545, HD MicroSystems) and PDMS. PECVD formed SiO$_2$ and SiN$_x$ both with deposition frequencies of 13.56 MHz. Al$_2$O$_3$ and HfO$_2$ were grown by ALD at 150° C.

FIG. 6 and Table 1 summarize all of the Mg test results. Popular organic passivation materials, for instance, SU-8 and PDMS, failed within 1 day at body temperature, indicating poor water barrier quality. Inorganic/organic multilayers can be more effective than simple bilayers with the same overall thickness due to the tortuous paths for water permeation through defects and interfaces in multiple layers. In certain cases, however, such as with Parylene C, the multilayer yields poor results, possibly due to non-trivial thickness dependent effects for permeation through Parylene C.

Impedance Measurements and Modeling: Impedance measurements used a Gamry Reference 600 potentiostat system (Gamery Instrument). The SiO$_2$ coated Au electrodes individually connected as the working electrode, with the Ag/AgCl as the reference electrode and a Pt wire as the counter electrode. The experiments used an AC potential of 10 mV with a frequency range of 1 Hz to 1 MHz, and a DC bias of 1 V. PBS solution served as the electrolyte at room temperature. Analysis used an equivalent circuit model shown in FIGS. 8A-8B, where $R_s$ is the solution resistance, Cc represents the capacitance of pristine material, and $R_{po}$ is the cumulative resistance of all pores, pinholes, microcracks and other defects. Additional liquid/metal interfaces form as the solution penetrates the coating. $R_{CT}$ corresponds to the charge transfer resistance and $C_{dl}$ is the double-layer capacitance associated with these interfaces. In all three types of SiO$_2$ materials:

$$C_c = \frac{\varepsilon_r \varepsilon_0 A}{t} \approx 0.86 \text{ nF}$$

where the coating area A=0.25 cm$^2$, thickness t=1 μm, relative permittivity $\varepsilon_r$=3.9 and vacuum permittivity $\varepsilon_r$=8.854×10$^{-12}$ F·m$^{-1}$. Non-linear least squares fitting yielded values for the various parameters.

Results for SiO$_2$ formed by electron beam evaporation and PECVD interpreted using similar methods suggest pore resistances and charge transfer resistances that originate from defect sites (FIGS. 8A-8B). Moreover, in these material systems, $C_{dl}$ cannot be ignored. As expected from the EIS model, the phase response is characterized by two valleys both for these cases. The lower valley (~10$^2$ Hz for evaporated and ~10$^3$ Hz for PECVD materials) can be attributed to $R_{po}$ and $R_{CT}$ in parallel with $C_{dl}$. The valley at 10$^6$ Hz arises from the oxide capacitance and the solution resistance. Discrepancies between theory and experiment likely reflect limitations of the assumption that the pore/pinhole regions and the rest of the otherwise undamaged regions can be treated as parallel branches for charge transfer. In practice, the flow may be two-dimensional. In addition, the complexity of the electrode surface may require a modified representation for $C_{dl}$ (ref. 1). Nonetheless, the simple compact model captures the general trends of the experimental findings, and it is sufficiently sophisticated to identify qualitative differences between thermally grown and deposited forms of SiO$_2$, and their critical role in barrier performance.

Electrical Leakage Tests: Measurements of electrical leakage for different thicknesses of thermal SiO$_2$ and other conventional oxides as an additional comparison involved application of a voltage, comparable to that relevant for operation of standard electronics, between a surrounding bath of PBS and an underlying doped silicon wafer, as in FIG. 9A and FIG. 10. These studies involved PECVD or ALD to form thin layers of SiO$_2$ or Al$_2$O$_3$ on n-type Si wafers (1-10 Ω·cm), and SiO$_2$ grown thermally. In these tests, the wafer connects to the cathode to prevent the possibility of anodizing the silicon; the anode is a wire of platinum in the PBS solution. A well structure made of poly(dimethylsiloxane) (PDMS) confines the PBS to the central regions of the layers (~1 cm$^2$), thereby eliminating any effects of the edges of the samples. Ultraviolet ozone (UVO) treatment of the surfaces of these materials and the bottom surfaces of PDMS well (~1 cm in depth) structures enabled strong bonding upon physical contact, thereby yielding a waterproof seal around an exposed area of 1 cm$^2$. The well formed in this way confined the PBS solution during the course of the testing. A Platinum (Pt) electrode dipped into the PBS served as an anode and the n-type Si substrate served as the cathode for measurements with the potentiostat system with two-terminal configuration under a constant 3 V DC bias.

As shown in FIGS. 9A-9B, at a pH of 7.4 and a temperature of 37° C., leakage currents quickly (within 60 hours)

reach levels that significantly exceed $10^{-6}$ A/cm$^2$ for 100 nm thick layers of PECVD SiO$_2$, and ALD Al$_2$O$_3$. Most polymers, including photocurable epoxies (SU-8) and elastomers such as PDMS exhibit leakage almost instantaneously after immersion in PBS solution (FIG. 10). At the same thickness, thermal SiO$_2$ exhibits zero leakage, to within measurement uncertainties, throughout the 350-hour duration of the experiment. Leakage current here is a function of applied voltage for different organic layers at room temperature.

Measurement and Modeling of Rates of Dissolution of Thermal SiO$_2$: These measurements used pieces of Si wafers (1 cm×2 cm dies) with thermal SiO$_2$ layers (100 nm thickness) grown across the top and bottom surfaces and the edges. Soaking occurred in plastic bottles containing PBS solution (25-30 ml) at room temperature, 37° C., 50° C., 70° C. and 90° C. separately. Ellipsometry defined the thickness of the SiO$_2$ as a function of soaking time.

Measurement results were also utilized to validate multiphysics models of the dissolution process coupling of all relevant continuum-scale physics: chemical species transport (using the Nernst-Planck equations), chemical reaction kinetics, electrostatics, and moving boundaries. Reaction kinetics were modeled using the Arrhenius form, with rate constant and activation energy for the primary SiO$_2$ dissolution reaction calculated from measurements and those of other reactions (forward and backward ionization of salts, PBS and water self-ionization) estimated to proceed much more quickly than SiO$_2$ dissolution. As seen in FIG. 14A, the dissolution rate is dominated by a half-order dependence on hydroxide concentration. The moving boundary velocity was calculated based on a mass balance at the boundary interface based on the local dissolution rate and assuming a baseline density of 2.19 g/cm$^3$. This model allows the time-dependent evolution of a SiO$_2$ layer with arbitrary initial thickness to be directly calculated and visualized for arbitrary pH and temperature, and the lifetime to be predicted (FIG. 14B). Simulations were performed on both 2-D and 3-D geometries using COMSOL Multiphysics®.

Reactive Molecular Dynamics (RMD) Simulations: Reactive Molecular Dynamics (RMD) simulations provided molecular insights into the effects of temperature and defects/oxide density on the dissolution process. The RMD used the Reaxff potential, integrated in a Large-scale Atomic/Molecular Massively Parallel Simulator (LAMMPS) package (2, 3). Previous work establishes the accuracy of this potential for interactions between SiO$_2$ and H$_2$O, through comparison to the macroscale experimental properties of these interfaces (4). The calculations involved initially pristine slabs of SiO$_2$ (density of 2.33 g/cm$^3$ and thickness of 2 nm, in lateral dimensions of 5 nm×5 nm) solvated in water (FIG. 3A). Removing a few SiO$_2$ molecules from the center of the slab yielded effective oxide densities of 2.27, 2.19, 2.06 and 1.95 g/cm$^3$, each of which was then solvated again in water (FIG. 3B). The pH of the solution was fixed at 7.4 by balancing the number of protons in the system. Periodic boundary conditions were applied in all the directions. Energy minimization of the system was performed for 1,000,000 steps. The time step was 0.1 fs (ref. 5). The Nose-Hoover thermostat (6) held the temperature constant. Simulations included 10 runs at temperatures between 10° C.-100° C. at intervals of 10° C., for each oxide density. To generate statistical data, five replicas were performed for each set. The presented data correspond to the average of five simulation runs, each for a total of 35 ns with data collection a 0.1 ps intervals.

The root mean square displacement (RMSD) of each Si atom in each simulation step defined the dissociation events. In particular, the RMSD of bound Si atoms is 1.56 Å. Upon dissociation, this value sharply increased to >10 Å. The molecular species associated with the dissociated Si was defined by the atoms that exist within a distance of 3.2 Å from the center of the Si.

Figure 16A:
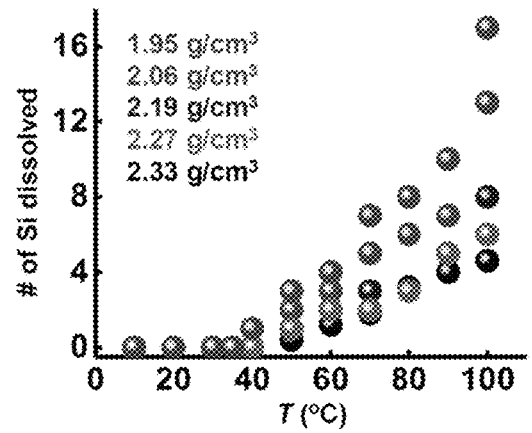
FIGS. 16A-16B. Theoretical analysis of density and temperature effect on Si dissolution.
Figure 16B:
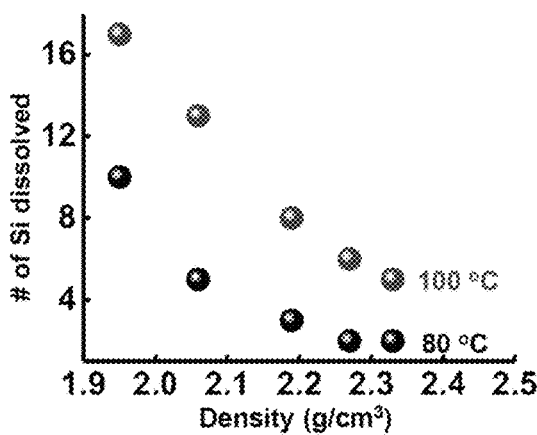
Figure 17A:
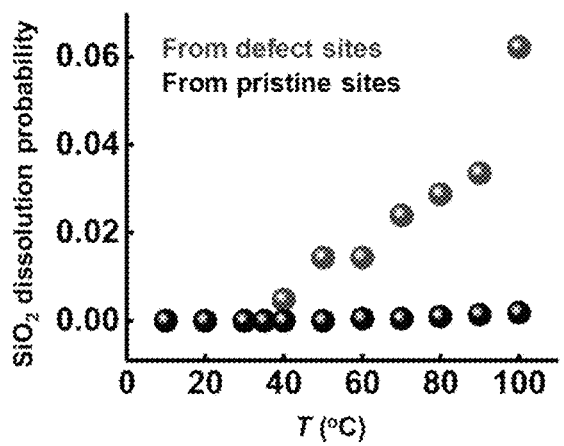
FIG. 17A. The probability of $SiO_2$ dissolved from defective sites versus pristine regions.

Similar simulations can yield results on the influence of mass density and the density of pinhole defects (FIG. 3B and FIGS. 16A-16B). As might be expected, the number of Si dissolution events is highest for the lowest density (1.95 g/cm$^3$) and the highest temperature (100° C.) (FIG. 16A). Specifically, the dissolution process increases exponentially with temperature (for temperatures between 10° C. and 100° C.) and density (for densities between 1.95 and 2.33 g/cm$^3$, at 80° C. and 100° C.), respectively (FIGS. 16A-16B). The rate of dissociation from defective sites greatly exceeds that from pristine sites, thereby suggesting that most dissolution occurs at defective/low density regions (FIG. 17A). This phenomenon is consistent with the defect-assisted dissolution mechanisms presented elsewhere (7, 8). Although the modeling involves many simplifying assumptions, both of these trends are qualitatively consistent with experimental results. The dissolution rates, for all densities, increase with temperature in an Arrhenius manner, consistent with the previous studies (9, 10, 11).

Figure 17B:
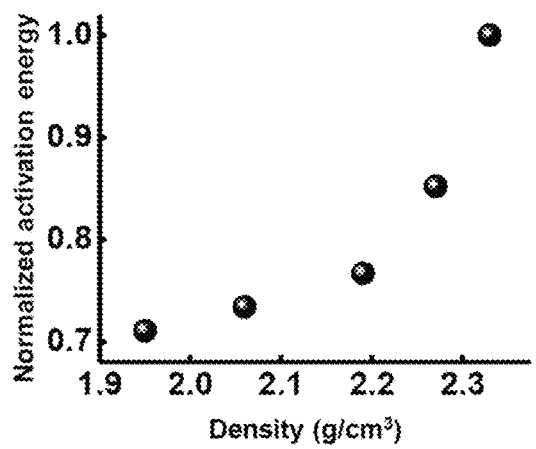
FIG. 17B. Weighted activation energy associated with reaction of $SiO_2$ dissolution as a function of oxide density.

In addition to these qualitative insights, the results allow quantitative extraction of weighted activation energies of dissolution for different densities, based on the ratio of the population of dissolution events (P and P$_0$) at corresponding temperatures (T and T$_0$) according to the Boltzmann distribution law, $$E = -Kln\left(\frac{P}{P0}\right)/\left(\frac{1}{T} - \frac{1}{T0}\right),$$

where K is a constant. FIG. 17B summarizes the results normalized by the maximum E. The findings suggest that the energy needed to dissociate Si atoms from oxide layers with densities of 1.95 g/cm$^3$ is 70% of that for layers with densities 2.33 g/cm$^3$. The energy for dissociation increases with the density. This trend is consistent with previous experimental observations on deposited/grown oxides (11). Previously mentioned multiphysics models coupling reactive diffusion kinetics with electrostatics and moving boundaries can capture certain aspects based on continuum, non-atomistic effects (11). The results presented here complement the continuum modeling work by suggesting that low-density oxides present additional Si—OH dangling sites and therefore accelerated chemical reaction rates.

Figure 17C:
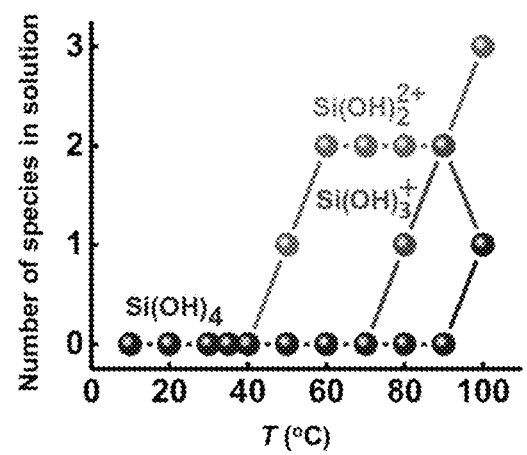
FIG. 17C. Number of Si compounds that exist in the solution at different temperatures.

In order to see the intermediates and final products of Si in the solution, the simulation tracked the molecular identity of each Si which is dissolved in different temperatures. Simulations show that Si first forms Si(OH)$_2^{2+}$ and dissolves into solution. In the solution Si(OH)$_2^{2+}$ forms bonds with two more OH− groups to yield Si(OH)$_4$ (ref. 12). The timescale for the reaction Si(OH)$_2^{2+}$→Si(OH)$_4$ is 60-70 ns at 37° C. (ref. 12). Results did not indicate any Si(OH)$_2^{2+}$ conversions for temperatures below 80° C. within the simulation time i.e. 35 ns while at 80° C. and 90° C., the simulation observed the Si(OH)$_2^{2+}$→Si(OH)$_3^+$ (FIGS. 17A-17C). For 100° C., we the reaction Si(OH)$_2^{2+}$→Si(OH)$_3^+$→Si(OH)$_4$ occurs in 32 ns. The hypothesis is that high temperatures boost the conversion of intermediates and the formation of Si(OH)$_4$.

Cyclic Bending of Active Electronics with Thermal Oxide Encapsulation As shown in FIGS. 30A-30C, cyclic bending test was applied to the flexible electronic system with dual-side thermal oxide encapsulation by bending the device to a radius of 5 mm for 10,000 cycles. Yield, gain and mean noise RMS remain nearly unchanged after 10,000 bending cycles.

Sodium Ion Transport Simulations: Modeling of sodium ion transport processes used the drift-diffusion equation and Poisson's equation. These equations were solved on a one-dimensional domain shown in FIG. 24 using COMSOL Multiphysics®. A value of the diffusivity (D) of $Na^+$ in wet thermal $SiO_2$ from previous reports allowed calculation of the corresponding ion migration mobility (p) using the Nernst-Einstein relation (13). Physically, x=0 and x=h correspond to the $PBS/SiO_2$ and $SiO_2/Si$ interfaces, respectively, where h is the thickness of thermal $SiO_2$. The boundary condition for the drift-diffusion equation is $[Na^+]= 2 \times 10^{25}$ $m^{-3}$ at x=0. This value corresponds to the solid solubility limit of $Na^+$ in wet thermal $SiO_2$ because the concentration of $Na^+$ in PBS solution is a very large [$8.24 \times 10^{25}$ $m^{-3}$ (137 mmol/L)]. At x=h, the simulation used a reflective boundary condition based on the assumption that $Na^+$ diffusivity inside the underlying Si is so low that most $Na^+$ ions are reflected at the $SiO_2/Si$ interface. The boundary conditions for the electrostatic potential are $V=V_{app}$ at x=0 and V=0 at x=h. The assumption is that the resistance of $SiO_2$ is much larger than the PBS solution. The voltage drops primarily across the oxide layer.

FIG. 25 shows the $Na^+$ concentration and potential distribution within a thick (h=900 nm) $SiO_2$ layer at 37° C. after 2 years of operation. The potential bias $V_{app}$ swept from 0 V to 2 V with an increment of 0.5 V. The $Na^+$ concentration decreases significantly near x=0 and $Na^+$ accumulates at the other side, namely, at x=900 nm. A time-dependent rise in the potential barrier retards the $Na^+$ transport process. In this simulation, failure corresponds to the point at which the shift in the threshold voltage $\Delta V_T$ for an 100 nm equivalent oxide thickness (EOT) reaches 1 V. $\Delta V_T$ can be expressed as a function of spatially distributed $Na^+$ density (14):

$$\Delta V_T(t) = \frac{1}{C_0}\left[\frac{1}{h}\int_0^h x \cdot \rho_{Na^+}(x,t)dx\right]$$

where CO is the gate capacitance.

FIG. 26A shows $\Delta V_T$ as a function of time with different bias voltages. The red dashed horizontal lines correspond to the failure criteria of threshold voltage shift. In FIG. 26B, a normalization of the time to $$\tau_{trans} = \frac{h}{\mu \xi} = \frac{h^2}{\mu V} = \frac{kTh^2}{DqV}$$

corresponds to the drift-dominated ion transport with time-independent linear potential drop. In other words, this transport time does not account for charge accumulation self-consistently. If self-consistent were unimportant, the lines would be scaled to a universal curve which cross the horizontal threshold voltage line at $t/\tau_{trans}=1$. However, the curves in FIG. 26B all shift to the right, i.e. a longer failure time. This non-linear electric field dependency arises from changes in the potential associated with spatially distributed $Na^+$.

Also incorporated by reference herein, is Fang et al. "Ultrathin, transferred layers of thermally grown silicon dioxide as biofluid barriers for biointegrated flexible electronic systems" PNAS 113(42): 11682-11687 (Oct. 18, 2016).

REFERENCES

1. Miller J R, Outlaw R A, Holloway B C (2010) Graphene double-layer capacitor with ac line-filtering performance. *Science* 329(5999):1637-9.
2. Van Duin A C, Dasgupta S, Lorant F, A. G W (2001) ReaxFF: A Reactive Force Field for Hydrocarbons. *Journal of Physical Chemistry A* 105(41):9396-9409.
3. Plimpton S (1995) Fast Parallel Algorithms for Short-Range Molecular Dynamics. *Journal of Computational Physics* 117(1):1-19.
4. Fogarty J C, Aktulga H M, Grama A Y, Van Duin A C, Pandit S A (2010) A reactive molecular dynamics simulation of the silica-water interface. *The Journal of Chemical Physics* 132(17):174704.
5. Van Duin A C, et al. (2003) ReaxFFSiO reactive force field for silicon and silicon oxide systems. *The Journal of Physical Chemistry A* 107(19):3803-3811.
6. Evans D J, Holian B L (1985) The Nose-Hoover thermostat. *The Journal of Chemical Physics* 83(8):4069.
7. Dove P M, Han N, De Yoreo J J (2005) Mechanisms of classical crystal growth theory explain quartz and silicate dissolution behavior. Proceedings of the National Academy of Sciences 102(43):15357-15362.
8. Dove P M, Han N, Wallace A F, De Yoreo J J (2008) Kinetics of amorphous silica dissolution and the paradox of the silica polymorphs. Proceedings of the National Academy of Sciences 105(29):9903-9908.
9. Worley W G (1994) Dissolution kinetics and mechanisms in quartz- and grainite-water systems. Doctoral Dissertation, Massachusetts Institute of Technology
10. Icenhower J P, Dove P M (2000) The dissolution kinetics of amorphous silica into sodium chloride solutions: effects of temperature and ionic strength. *Geochimica et Cosmochimica Acta* 64(24):4193-4203.
11. Kang S-K, et al. (2014) Dissolution Behaviors and Applications of Silicon Oxides and Nitrides in Transient Electronics. *Advanced Functional Materials* 24(28):4427-4434.
12. Yin L, et al. (2015) Mechanisms for Hydrolysis of Silicon Nanomembranes as Used in Bioresorbable Electronics. *Advanced Materials* 27(11):1857-1864.
13. Mecha J & Steinmann J (1979) Mobility of Sodium Ions in Silica Glass of Different OH Content. *Journal of the American Ceramic Society* 62(7-8):343-346.
14. Sze S M (2008) Semiconductor devices: physics and technology (2nd edition). John Wiley & Sons, p. 183.

Example 2: Capacitively Coupled Arrays of Multiplexed Flexible Silicon Transistors for Long-Term Cardiac Electrophysiology Advanced capabilities in electrical recording are essential for the treatment of heart-rhythm diseases. The most advanced technologies use flexible integrated electronics; however, the penetration of biological fluids into the underlying electronics and any ensuing electrochemical reactions pose significant safety risks. Here, we show that an ultrathin, leakage-free, biocompatible dielectric layer can completely seal an underlying array of flexible electronics while allowing for electrophysiological measurements through capacitive coupling between tissue and the electronics, without the need for direct metal contact. The resulting current-leakage levels and operational lifetimes are, respectively, four orders of magnitude smaller and between two and three orders of magnitude longer than those of other flexible-electronics technologies. Systematic electro physiological studies with normal, paced and arrhythmic conditions in Langendorff hearts highlight the capabilities of the capacitive-coupling approach. These advances provide realistic pathways towards the broad applicability of biocompatible, flexible electronic implants.

Tools for spatially mapping electrical activity on the surface of the heart are critically important to experimental cardiac electrophysiology and clinical therapy. The earliest reported systems involved microelectrode arrays on flat, rigid substrates, with a focus on recording cardiac excitation in cultured cardiomyocytes and on mapping signal propagation across planar cardiac slices[1-5]. More recent technologies exploit flexible arrays, in formats ranging from sheets to baskets, balloons, 'socks' and integumentary membranes, with the ability to integrate directly across large areas of the epicardium and endocardium in beating hearts[6-10]. The most sophisticated platforms of this type include an underlying back-plane of thin, flexible active electronics for local signal amplification and multiplexed addressing[11,12]. This latter feature is critically important because it enables scaling to high-density, high-speed measurements, in regimes that lie far beyond those accessible with simple, passively addressed systems without integrated electronics. The measurement interface associated with all such cases relies on thin electrode pads in direct physical contact with the tissue, where electrical signals transport through via openings to the underlying electronics. Although this approach has some important modes of use, bio-fluids can readily penetrate through the types of polycrystalline metal films used for the electrodes. Resultant leakage currents from the electronics can cause potentially lethal events such as ventricular fibrillation and cardiovascular collapse[13,14]; they also lead to degradation of the Si electronics and catastrophic failure of the measurement hardware. Moreover, electrochemical reactions with the electrolyte at the metal/tissue interface lead to bio-corrosion of the metal[15]. Consequently, devices with such designs are inherently unsuitable for human use, even in surgical contexts or other acute applications. Similar considerations prevent their application in any class of implant[16-18].

The results presented here provide a robust and scalable solution to these challenges by eliminating all direct metal interfaces and replacing them with capacitive sensing nodes integrated on high-performance, flexible, silicon electronic platforms for multiplexed addressing. Specifically, an ultrathin, thermally grown layer of silicon dioxide covers the entire surface of the system, to serve both as a dielectric to enable direct capacitive coupling to the semi-conducting channels in arrays of silicon nanomembrane (Si NM) transistors and as a robust, biocompatible barrier layer to prevent the penetration of bio-fluids. The co-integration of active electronic circuits affords built-in signal conditioning and processing capabilities, as well as scalability via multiplexed addressing[19-25]. Although capacitive methods for sensing[26-28] and rigid platforms of large-scale active microelectrodes[29-32] are known, our work combines two features that, viewed either individually or collectively, are important advances in technology for electrophysiological mapping at the organ level in living biological systems: (1) the use of an ultrathin thermally grown layer of silicon dioxide for capacitive sensing that simultaneously provides high-yield, leakage-free encapsulation layers with long-term stability in bio-fluids; and (2) a combination of high-fidelity capacitive sensing, long-term stability and mechanical flexibility in a fabrication process that yields thin active electronics with robust operation on dynamically evolving curved surfaces of biological tissue, as demonstrated in cardiac mapping on beating hearts. The technology introduced here is the first to incorporate all of the key features needed for use in high-speed, high-resolution cardiac electrophysiology: (1) large area formats with integrated active electronics for multiplexing and signal amplification on a per-channel level; (2) thin, flexible device mechanics for integration and high-fidelity measurement on the curved, moving surfaces of the heart; (3) cumulative levels of leakage current to the surrounding tissue that remain well below 1 $\mu$A (per ISO 14708-1:2014 standards for implantable devices), for safe operation; (4) long-lived, thin, bendable bio-fluid barriers as near-perfect, hermetic sealing of the underlying electronics for stable, reliable function; and (5) biocompatible interfaces for long-term use, without either direct or indirect contact to traditional electronic materials. Detailed studies of the materials and the combined electrical and mechanical aspects of the designs reveal the key features and advantages of this type of system. Application to epicardial mapping of ex vivo Langendorff heart models quantitatively validates the capabilities in various contexts of clinical relevance. The resulting high levels of safety in operation and the long-term, stable measurement capabilities create unique opportunities in both cardiac science and translational engineering.

Capacitively Coupled Silicon Nanomembrane Transistors as Active Sensing Nodes.

Figure 37:
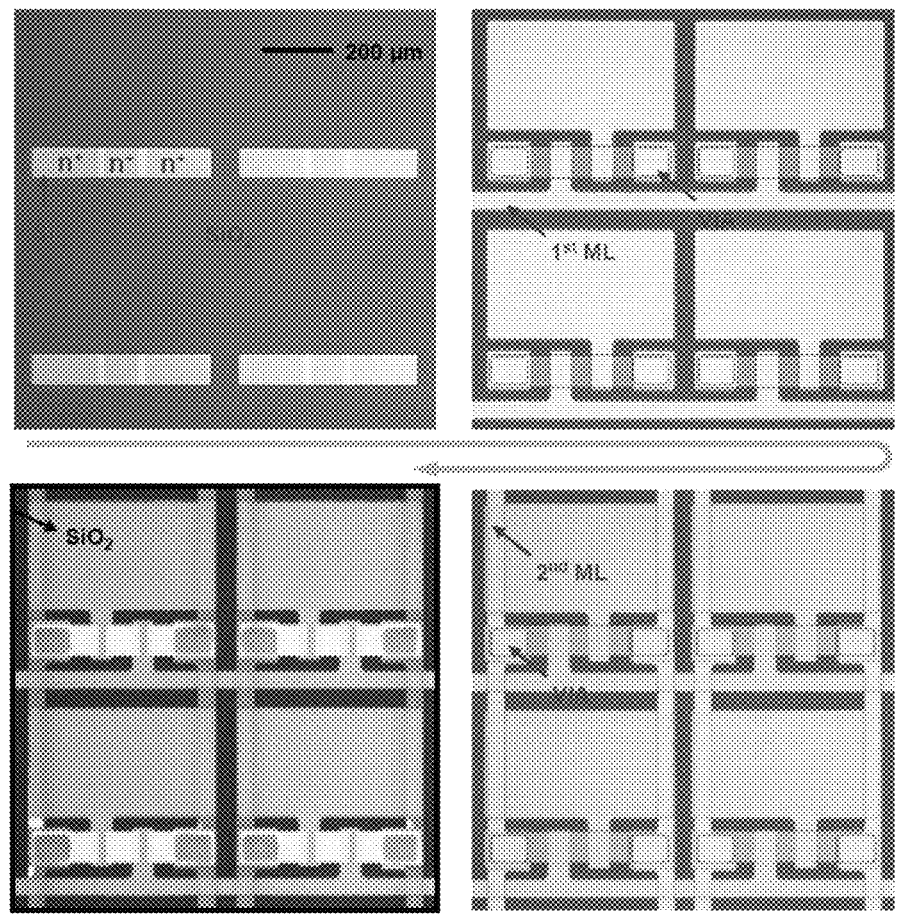
FIG. 37. Images of four pixels within a device at various different key steps during the fabrication. From first to last: configuration after isolation of doped Si nanomembranes (Si NMs) in four unit cells; configuration after fabrication of the source, drain, gate sensing pads, and row electrodes for multiplexed addressing; configuration after second metallization, including the column output electrodes. Final layout of the device after removing the Si-handle-wafer removal, revealing the buried oxide (BOX) layer as the tissue-contacting side.
Figure 38:
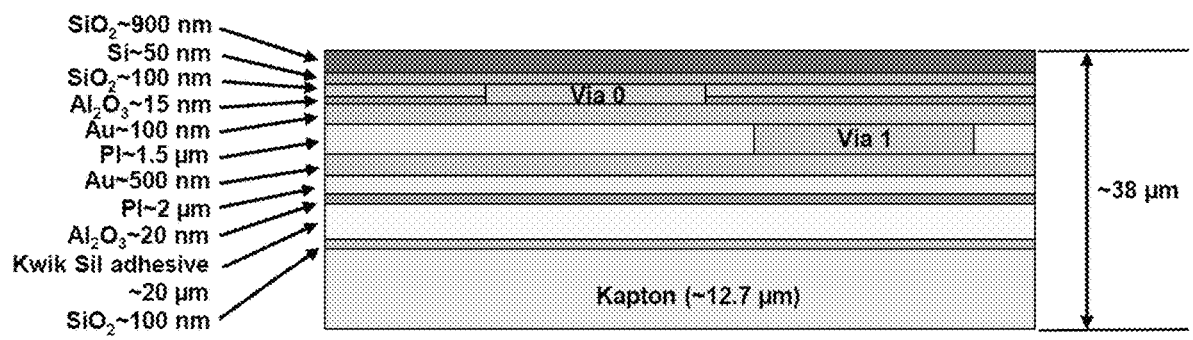
FIG. 38. Illustration of the cross-section of the capacitively coupled, flexible active sensing matrix. The material and thickness for each layer is denoted.
Figure 39:
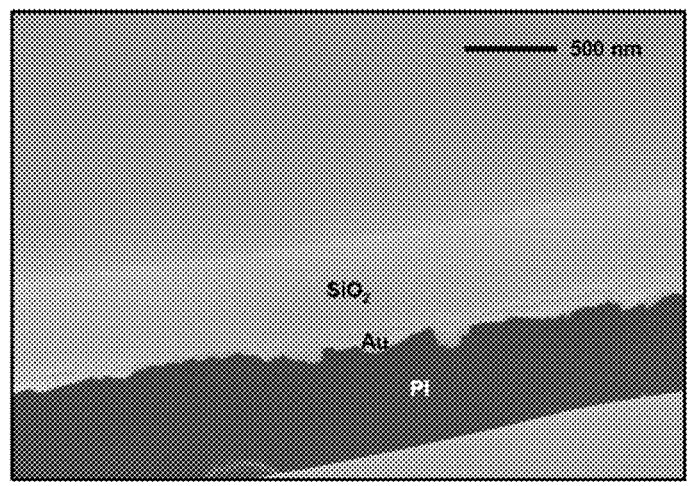
FIG. 39. A 45° tilted-view SEM image depicting the $SiO_2$, Au and PI interface in the final device.

The overall system consists of 396 multiplexed capacitive sensors (18 columns, 22 rows), each with dimensions of 500×500 $\mu$m, as shown in FIG. 31A, distributed uniformly over a total area of 9.5×11.5 mm. Each sensor consists of two underlying Si NM transistors, one of which connects to a metal pad from its gate electrode (FIGS. 31A-31B). A layer of thermally grown silicon dioxide (900 nm, $SiO_2$) covers the entire top surface of the system (FIG. 31A and FIGS. 36-39). This ultrathin (compared to the thickness of the layers used previously for encapsulation[33-35]; also referred herein as a thickness that is less than 1 $\mu$m) thermal $SiO_2$ layer serves not only as the dielectric for capacitive coupling of adjacent tissue to the semiconducting channels of the associated Si NM transistors, but also as a barrier layer that prevents penetration of bio-fluids to the underlying metal electrode and associated active electronics. The fabrication begins with definition of 792 Si n-channel metal-oxide semiconductor (NMOS) transistors on a silicon on insulator (SOI) wafer. A sequence of deposition, etching and photolithographic patterning steps forms the necessary dielectric and metal layers for the interconnects and sensing electrodes. Bonding a layer of polyimide on top of these electronics yields a thin, flexible system upon removal of the silicon wafer. Here, the buried oxide (BOX) layer of the SOI wafer serves as the capacitive interface and encapsulation layer. Detailed information on the device fabrication is provided below and FIG. 36. FIGS. 37 and 38 show optical images at various stages of the fabrication and a corresponding cross-sectional schematic illustration of the final device, respectively. This fabrication process is capable of scaling up to the largest silicon wafers available (currently 450 mm diameter), allowing for systems that provide full area coverage across most of the internal organs of the human body.

As presented in the equivalent circuit, top and cross-sectional views of FIG. 31B, each sensor includes an amplifier and a multiplexer, with capacitive input. The amplifier consists of a Si NM transistor (channel length $L_{eff}$=13.8 $\mu$m, width W=80 $\mu$m, thickness t=50 nm), with a gate that extends to a large metal pad (270×460 μm). The thermal $SiO_2$ layer above the transistor and the metal pad physically contacts adjacent tissue during operation. The tissue/$SiO_2$/gate metal pad forms a large capacitor ($C_{CAP}$) that couples with the gate that drives the transistor channel. This direct coupling to the semiconductor channel of the amplifier, bypasses the effects of capacitance in the wiring to remote electronics, and as such represents an important distinction between the architecture presented here and traditional, passive capacitive sensors[28,38]. Such coupling provides immediate signal amplification and eliminates signal crosstalk along the pathway. Previously reported nanowire biosensors[21,37] rely on similar schemes, although difficulties in scaling prevent their use in the types of large-scale, multiplexed arrays introduced here. The capacitance, $C_{CAP}$, is configured to be over one order of magnitude larger than the top gate capacitance ($C_{TG}$) of the transistor, thereby preventing the formation of a voltage divider and attenuating the signal. This design is important for high-performance signal amplification and low noise levels[28]. Detailed electrical models of the operation can be found in the Methods section. The sensing system also uses an active multiplexing circuitry design similar to that described previously[12], where the electrical signal from the tissue at each given node in the array is selected in a rapid time sequence by the multiplexing transistors (with the same dimensions as the amplifier transistor) for external data acquisition. Additional details are provided below.

FIG. 31C illustrates the principle of the capacitive coupling to a Si NM transistor. Electrically biasing a droplet of phosphate buffered saline (PBS) solution placed in contact with the $SiO_2$ layer causes coupling to the gate pad of the transistor (while the gate pad is not directly biased), thereby allowing measurement of the transfer characteristic in a manner that simulates the effects of electrical potential generated from the contacting tissue (FIG. 31C, left and middle). The resulting transconductances, threshold voltages and subthreshold swings are similar to those measured by directly biasing the gate pad, thereby validating the capacitively coupled sensing design. (The minor discrepancies in the subthreshold swing and transconductance arise from slight differences in the overall capacitance to the channel.) The capacitively coupled transistor exhibits an on/off ratio of ~$10^7$ and a peak effective electron mobility of ~800 cm$^2$ (Vs)$^{-1}$ (FIG. 31C and FIG. 40), as calculated from standard field effect transistor models (see Methods). FIG. 31C (right) shows the output characteristics, consistent with Ohmic source/drain contacts and well-behaved current saturation. This high-performance operation is critically important for high-fidelity amplification and fast, multiplexed addressing.

Figure 41A:
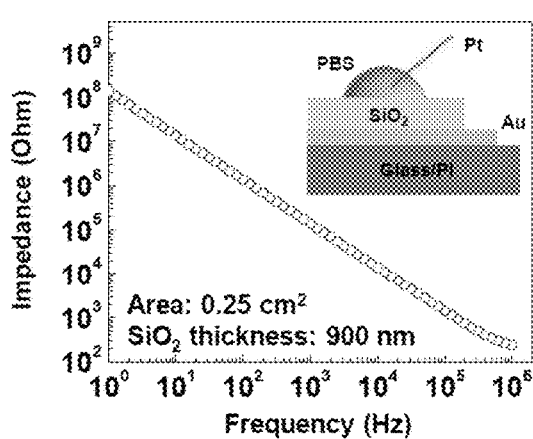
FIGS. 41A-41B. EIS characterization of the top $SiO_2$ layer on the electrode array.
Figure 41B:
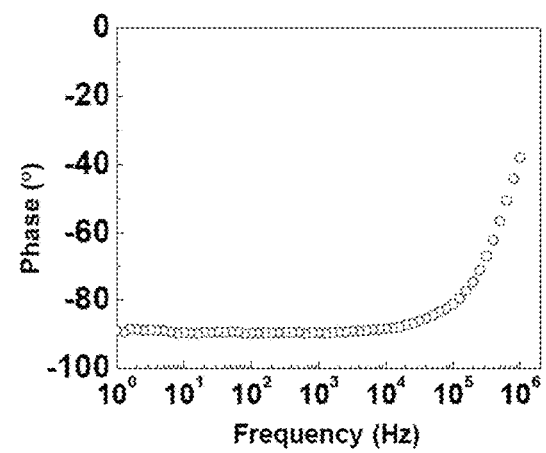

The operation and output characteristics of the amplifier appear in FIG. 31D. Here, a current sink and a single-stage Si NM transistor with capacitively coupled input forms a common drain amplifier (source follower). As a result of the large capacitive coupling, this circuit offers high voltage gain (0.97, where 1 is the ideal value) for both d.c. (−2 to 2 V) and a.c. (5 mV, 10 Hz) inputs (FIG. 31D, right), where the gain corresponds to the ratio between the output and input voltages ($V_{OUT}/V_{IN}$). The presence of the thermal $SiO_2$ layer yields an ultra-high input impedance measurement interface (~2.6 GΩ per sensing node at 10 Hz; FIGS. 41A-41B), and nearly perfect encapsulation of the electronics from the surroundings. This high-input impedance at the $SiO_2$/tissue interface transfers into a low-output impedance (~855Ω per sensing node; detailed calculation in Methods) via the current gain of the source follower. Additional circuit-level improvements such as input capacitance neutralization and circuit reference grounding, with reduced thermal $SiO_2$ thickness, can further enhance the recording quality of bio-potentials[38].

Such sensing systems can be constructed with excellent uniformity in electrical responses across all sensing nodes. FIG. 31E shows a histogram plot of the gain measured on all nodes of a 396-channel sensing matrix; the yield is 100% and the average gain is 0.99 (minimum, 0.9; maximum, 1; with a standard deviation of 1.12×10$^{-4}$). The yield here defines the number of working (with gain above 0.6) sensing nodes divided by the number of total sensing nodes on the array. In testing and ex vivo experiments, the 22 row-select signals cycle at 25 kHz, yielding a sampling rate of 1,136 Hz per node. This rate can be further increased by improving the multiplexing rate in the back-end data acquisition system.

In Vitro Assessment of Electrical Performance.

Figure 32F:
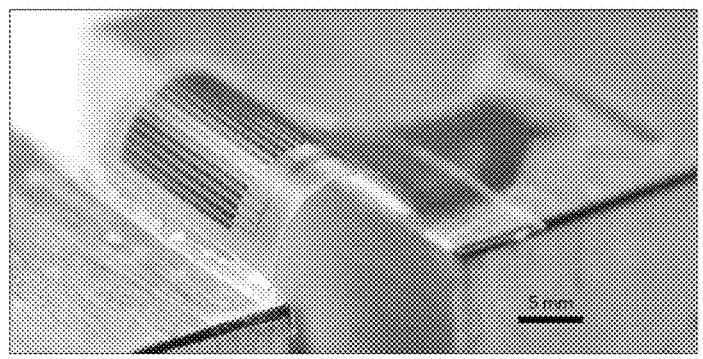
Figure 32G:
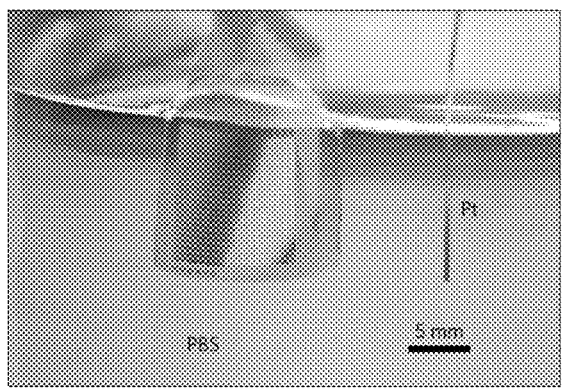
Figure 32H:
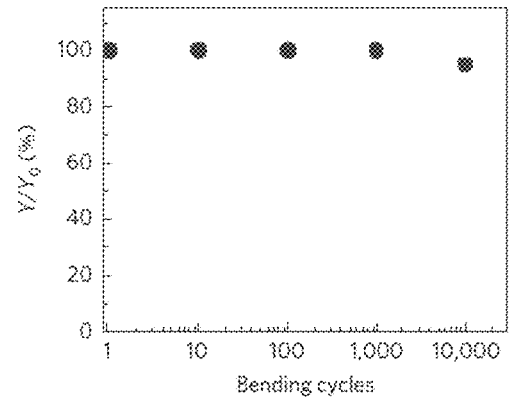
Figure 42:
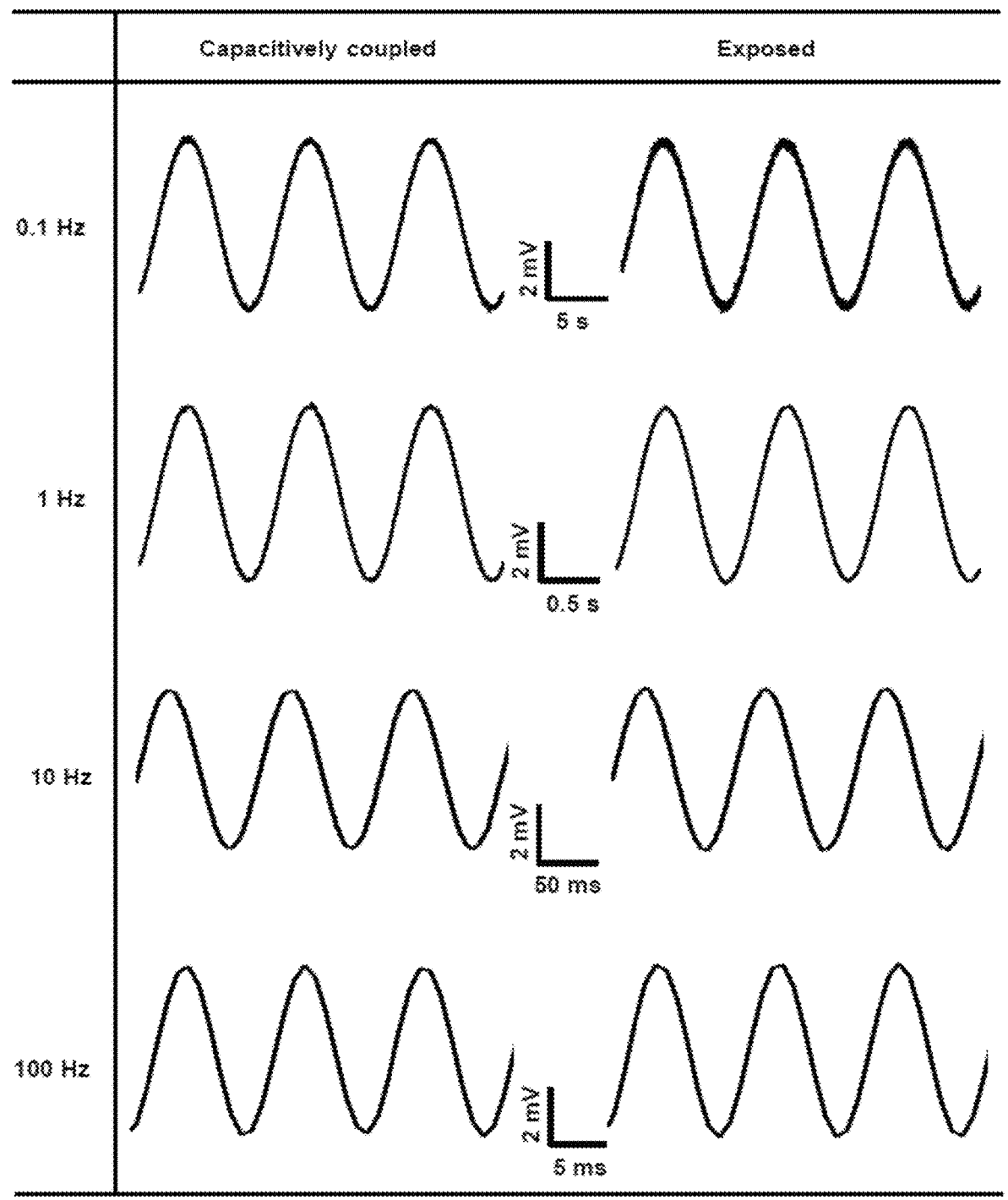
FIG. 42. Comparison of electronic response with and without capacitive coupling from different input frequencies, demonstrating that capacitively coupled sensing electronics performed well over a wide dynamic range, with similar or better performance than exposed-metal electronic interface.
Figure 43A:
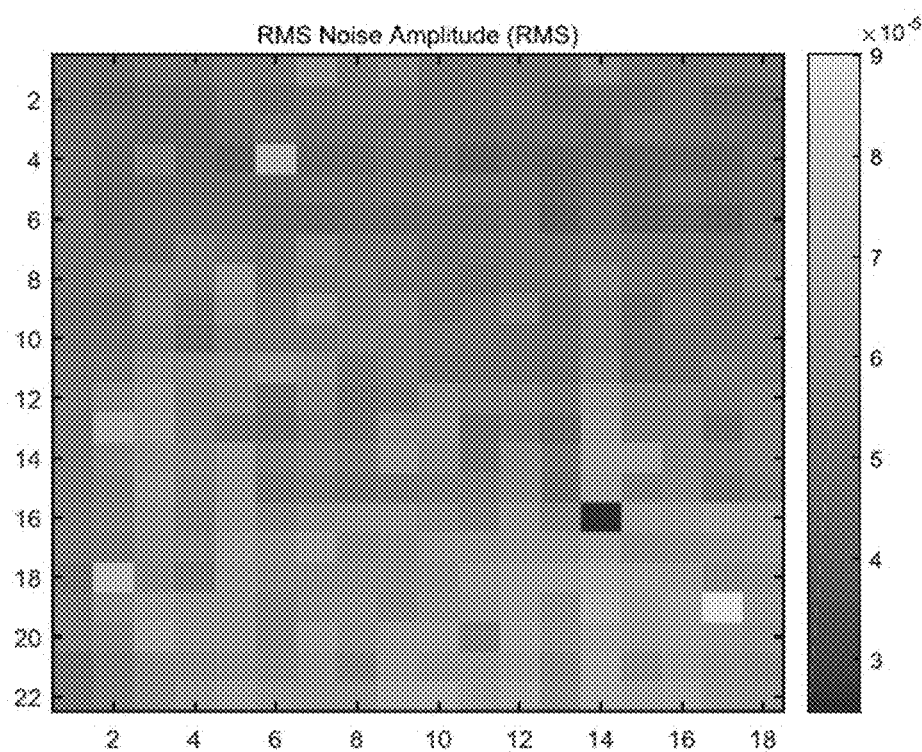
FIGS. 43A-43B. Color map illustrating the spatial distribution of (FIG. 43A) noise and (FIG. 43B) SNR of the electrode array in FIGS. 31A-31E, demonstrating the low noise of the capacitively coupled sensing.
Figure 43B:
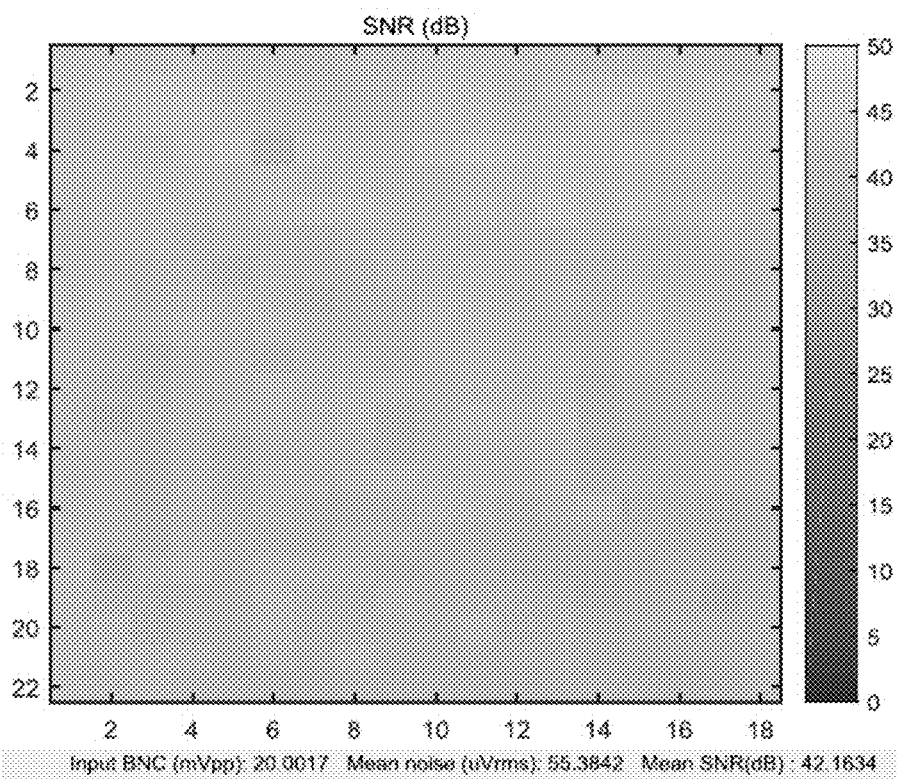

The performance of the capacitively coupled active sensing nodes is stable across a broad time dynamic range. FIG. 32A shows high-gain, low-noise measurements for input signal frequencies between 0.1 and 100 Hz, with similar or better performance than simple, directly coupled metal sensing interfaces (FIG. 42). The power spectral density (PSD) of the output signal, computed from the Fourier transform of the auto-correlation function, describes its frequency behaviour. As an example, the PSD of the noise (FIG. 32B, when measuring with a 5 mV, 10 Hz sine-wave input) indicates expected ~1/f behaviour at low frequencies, consistent with circuit models (see Methods). FIG. 32C displays a 396-channel sensing system with mean noise as low as ~55 μV and a signal-to-noise ratio (SNR) over 42 dB (also see FIGS. 43A-43B), and excellent uniformity across the entire device. The transistor mobility, the sensing node gain and the array yield are also superior, probably due to the better interface from Si and thermal $SiO_2$. Statistics on the test transistor threshold voltage, mobility, array yield and average gain from different devices show very small sample-to-sample and batch-to-batch variations (FIGS. 32D-32E). Mechanical bending tests and in vitro soak tests highlight the flexibility and robustness of the system (FIGS. 32F-32G). For −5 mm bending radii, the finite element analysis (FEA; FIGS. 44A-44B) indicates that the strain induced in the Si and top $SiO_2$ layers are less than 0.025%, far below their fracture limits (~1%). The device performance remains unchanged in the bent state and does not vary after bending to a radius of 5 mm for 1, 10, 100, 1,000 and 10,000 cycles (FIG. 32H). Infrared imaging also reveals that there is no apparent increase in temperature associated with operation of the device (FIG. 45).

Figure 32I:
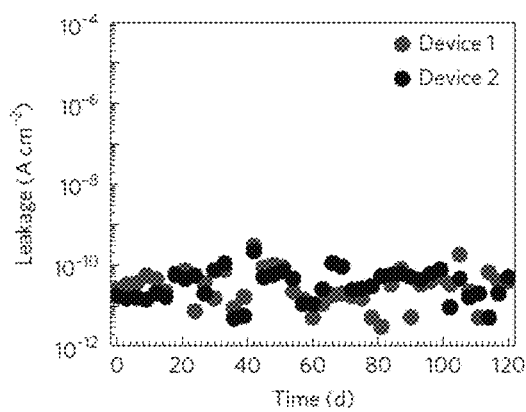
Figure 32J:
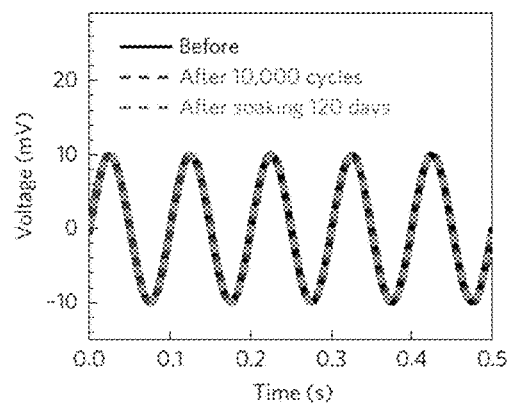

The system also demonstrates outstanding stability of continuous operation when completely immersed in saline solution and bio-fluids, due to the thermal $SiO_2$ encapsulation. FIG. 32G depicts the set-up for the soak test, where PBS solution simulates the cardiac bio-fluid. Evaluations involve application of a 3 V d.c. bias between the sensing system and a Pt reference electrode throughout the test, at a temperature of 37° C. The leakage current remains lower than 10$^{-9}$ Å cm$^{-2}$ for at least 120 days for 2 devices (FIG. 32I). FIG. 32J shows the response to a 10 Hz sine-wave input, before and after the bending and soaking experiments. All indications are consistent with reliable, invariant operation associated with conditions that mimic those for in vivo cardiac applications. The most compelling demonstrations are in leakage levels that are factors of 10,000 smaller than those of previous related cardiac mapping technologies (factors of 1,000 smaller than the safety limit standard for active implantable medical device in ISO 14708-1:2014, 1

μA). Compared to previously reported devices with lifetimes of only a few hours in soak tests[11], the operational lifetimes here are between two and three orders of magnitude longer, with interfaces that consist of a uniform layer of a well-established material (thermal $SiO_2$) in traditional implants. This device longevity highlights the pinhole-free nature and robustness of the thermal $SiO_2$ layer, which is extremely difficult to achieve with films deposited using conventional methods.

Cardiac Mapping in Animal Heart Models.

Figure 46A:
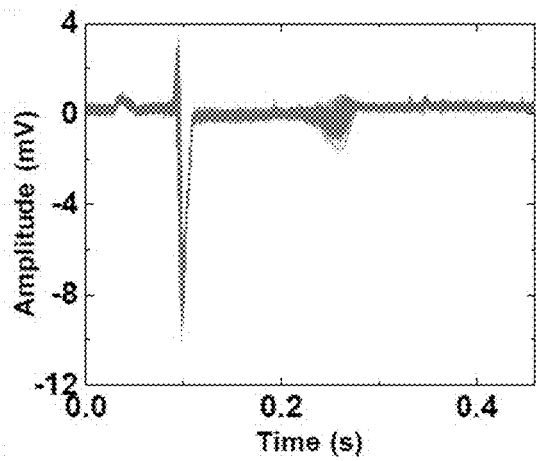
FIGS. 46A-46C. Noise analysis of recordings from all 396 channels from a flexible capacitively coupled sensing electronic system on a Langendorff-perfused rabbit heart.
Figure 46B:
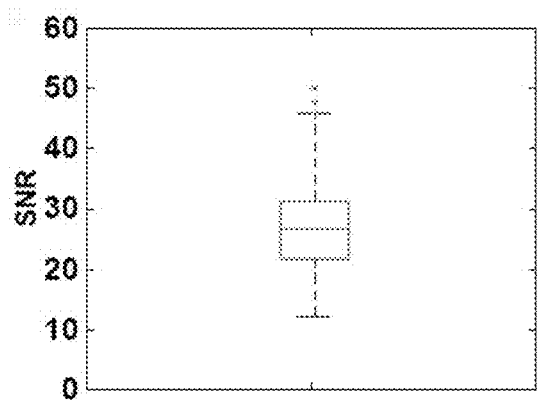
Figure 46C:
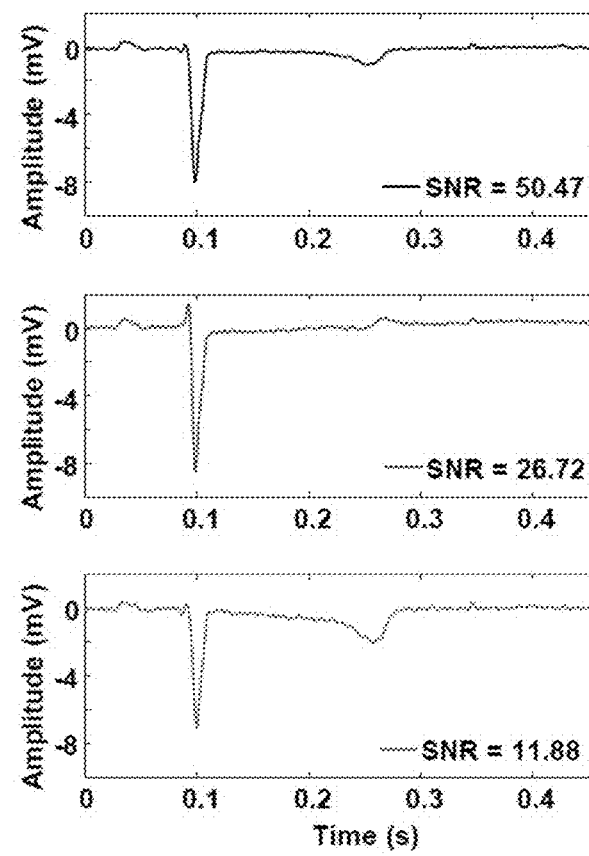
Figure 47:
FIG. 47. Voltage traces from the same channel in the capacitively coupled sensing electronic system at the beginning and end of an ex vivo Langendorff perfused rabbit heart experiment. The amplitude and noise levels of the signal remain the same, demonstrating the stability of capacitive sensing over the entire course of the ex vivo experiment.
Figure 48:
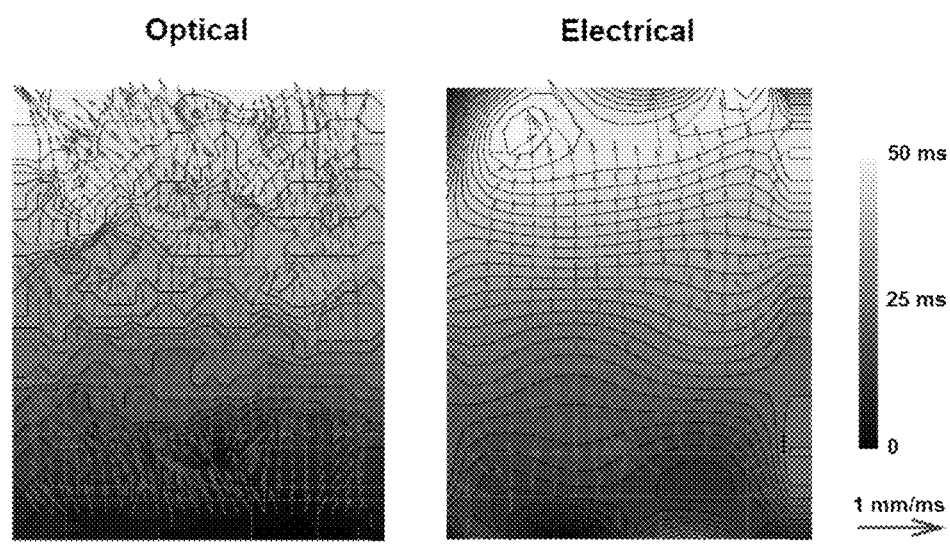
FIG. 48. Calculated conduction velocity vector from optical and electrical maps at pacing of 300 ms cycle length. The magnitude of the red arrows indicates the amplitude of the velocity. The background maps are activation in grayscale.

Experiments that validate the function involve recording of unipolar voltage signals from all 396 nodes on multiple ex vivo Langendorff perfused rabbit hearts[39]. FIG. 33A shows a system placed on the anterior aspect of the heart with equal overlap on the right and left ventricles. The device conformally covers the curvilinear surface of the heart. Although capillary forces associated with the moist cardiac surface can fixate the device in place, the use of a thin polyvinyl chloride (PVC) film wrapped around the heart further enhances the robustness of the mechanical coupling. A representative single-node voltage trace during sinus rhythm is shown in FIG. 33B. Clear components, similar to the P wave, QRS complex and T wave in clinical electrocardiogram (ECG) recordings, are apparent. The low noise levels are consistent with the in vitro results (FIGS. 46A-46C). The average heart rate is ~125 beats per minute. Attaching the device on the heart does not interfere with the heart's rhythm, based on experimental observations (FIG. 47). The slowing of the sinus rhythm rate can be attributed to normal heart deterioration that results from the use of a blood substitute in the ex vivo Langendorff perfused model. High-definition spatiotemporal electrophysiology mapping results from plotting the signals from all 396 nodes as a function of time. Spatial voltage maps of all nodes at four sequential time points appear in FIG. 33C, corresponding to phases 4 to 1 in the cardiac action potential (dashed lines in FIG. 33B illustrate the time window in which FIG. 33C is taken). The wave of cardiac activation approaches the centre of the anterior aspect of the heart from both the left and right sides, which matches well the physical location of the device. The extracted conduction velocities ($0.9506 \pm 0.3340$ mm ms$^{-1}$) are close to values inferred from optical data ($0.8124 \pm 0.3438$ mm ms$^{-1}$) as described in the following paragraph, for the 300 ms cycle length (FIG. 48). This same technology platform is important not only for cardiac applications (both ex vivo and in vivo, as demonstrated below and FIGS. 49A-49B), but also for high-speed mapping of electrophysiology of other organ systems, including those that exhibit much smaller changes in voltage, and for use as implants in live animal models. Successful in vivo recording from rat auditory cortex (described further below and FIGS. 50A-50D) demonstrates these capabilities.

Comparison with Fluorescence Imaging.

Figure 34A:
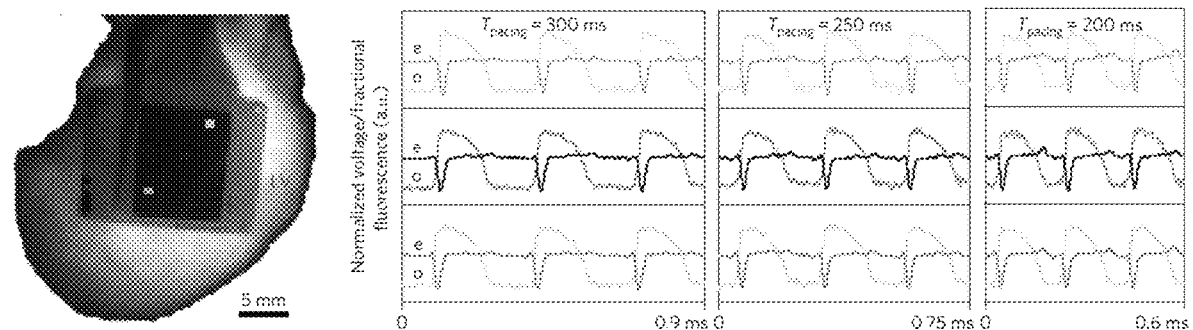
FIGS. 34A-34C. Comparison of electrical mapping with optical fluorescence recording.
Figure 34B:
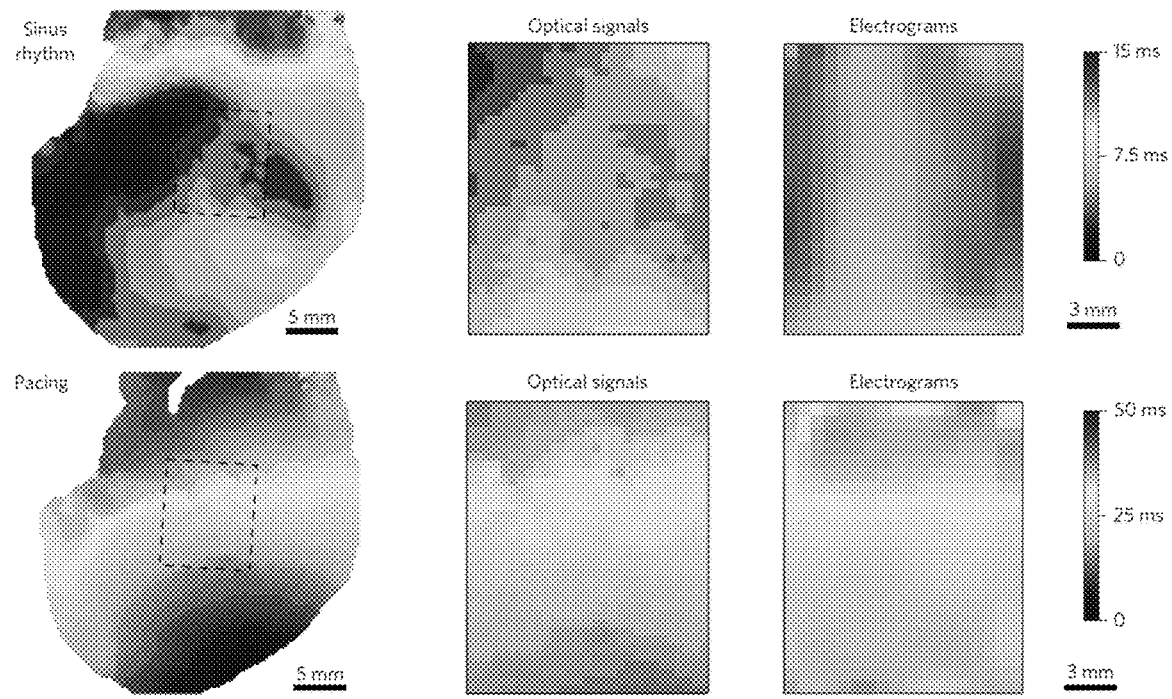
Figure 34C:
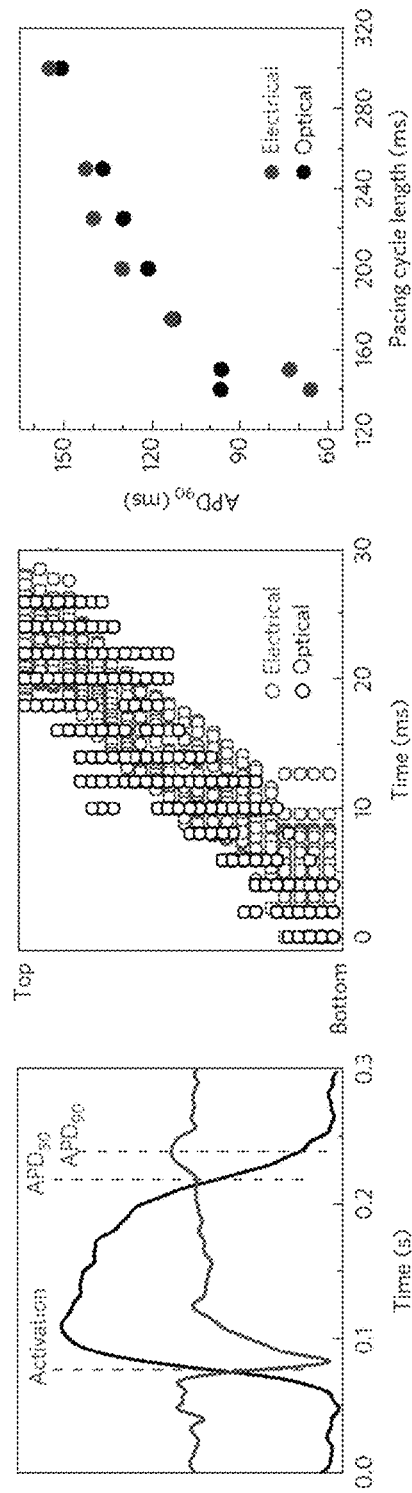
Figure 51A:
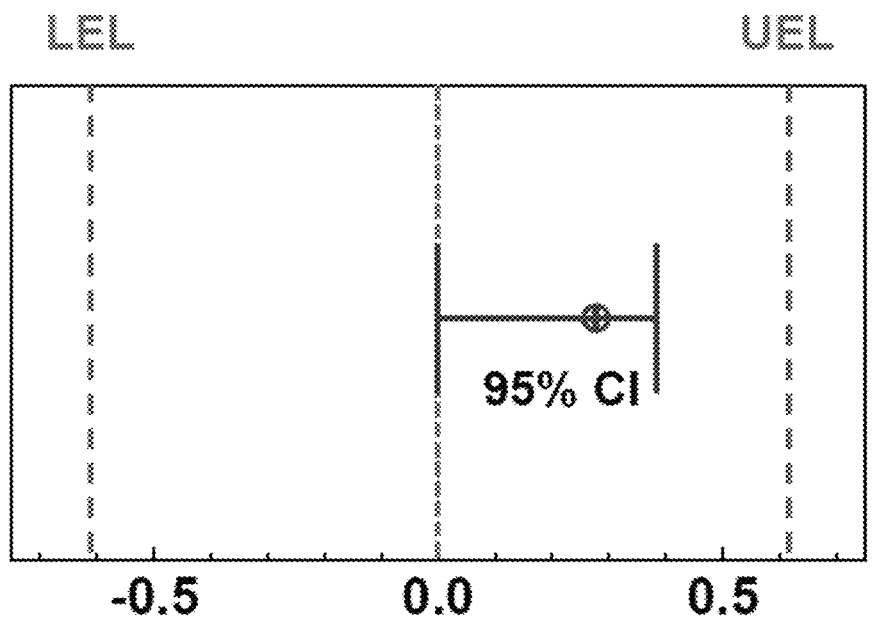
FIGS. 51A-51B. Sample equivalence test between the electrical and optical recordings. In order to demonstrate the accuracy of the bioelectric signals measured by the electrode a two sample equivalency test was performed using the electrode measurements as the test data and the optical measurements as the reference data. In the case of both (FIG. 51A) sinus rhythm (SR) and (FIG. 51B) 300 ms ventricular pacing, the isochronal maps of activation were found to be equivalent (p<0.05) for both upper and lower bounds. Here the CI, LEL, UEL stand for confidence interval, lower equivalence limit and upper equivalence limit respectively.
Figure 51B:
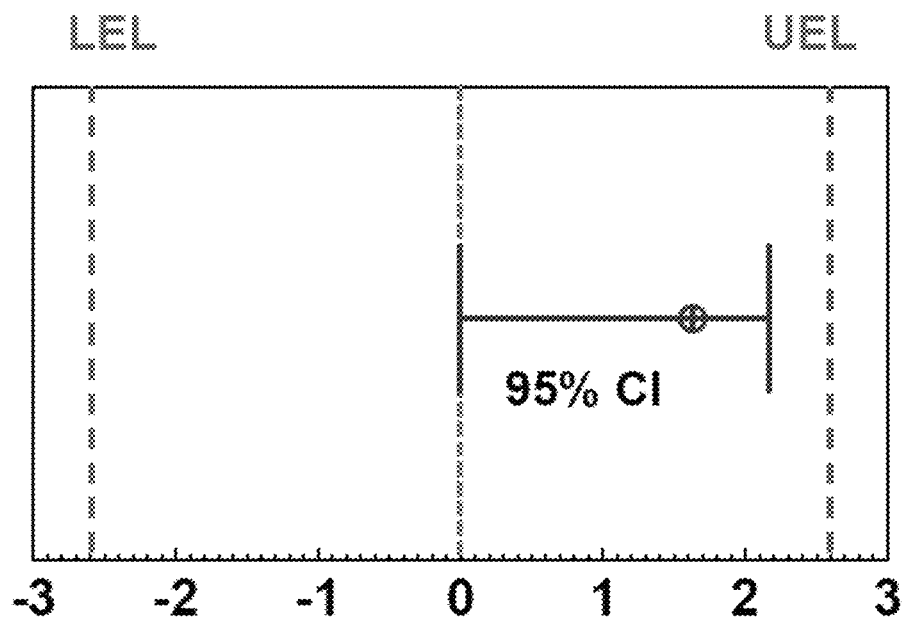
Figure 52:
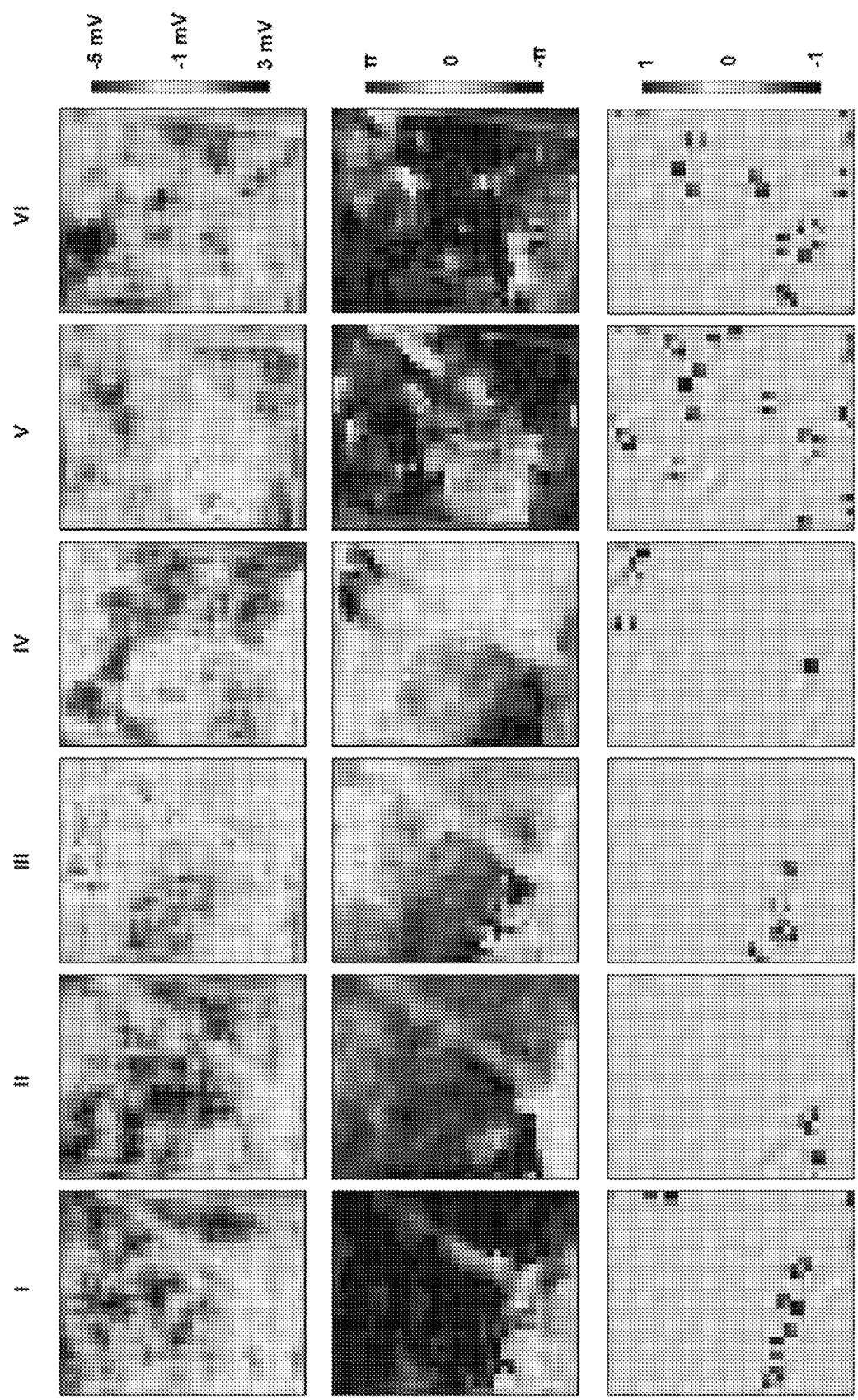
FIG. 52. Optical signal (top row), phase (middle row), and phase singularity (bottom row) for ventricular fibrillation, corresponding to electrical mappings in FIGS. 35A-35B.

The optical transparency of the system in the spaces between the metal electrodes and transistors allows validation of electrical measurements by means of simultaneous optical mapping[40]. In particular, comparison of electrical and optical recordings provides a robust method for establishing morphological criteria for phenomena such as activation and repolarization. FIG. 34A shows a three-beat comparison of optical and electrical signals at three distinct pacing cycle lengths. Representative optical action potentials show an adequate SNR for this comparison despite the dense nature of the sensing circuits. Interpolated activation maps of both data types reveal a strong association during both sinus rhythm (FIG. 34B, top) and pacing (FIG. 34B, bottom). Close inspection (FIG. 34C, left) of the two signal types indicates a close correspondence of key morphologies associated with activation (QRS complex in electrogram versus $(dV/dt)_{max}$ in optical signal, where V is the optical signal and t is the time) and repolarization (T wave in electrogram versus $APD_{50}$ and $APD_{90}$ in optical signal, where $APD_{50}$ and $APD_{90}$ are the action potential durations at 50% and 90% of repolarization, respectively). Strong correlations in activation (FIG. 34C, middle) and repolarization (FIG. 34C, right) are also apparent. The electrical and optical recordings also demonstrate good accuracy from the equivalence test (FIGS. 51A-51B).

Study of Ventricular Fibrillation.

Figure 35A:
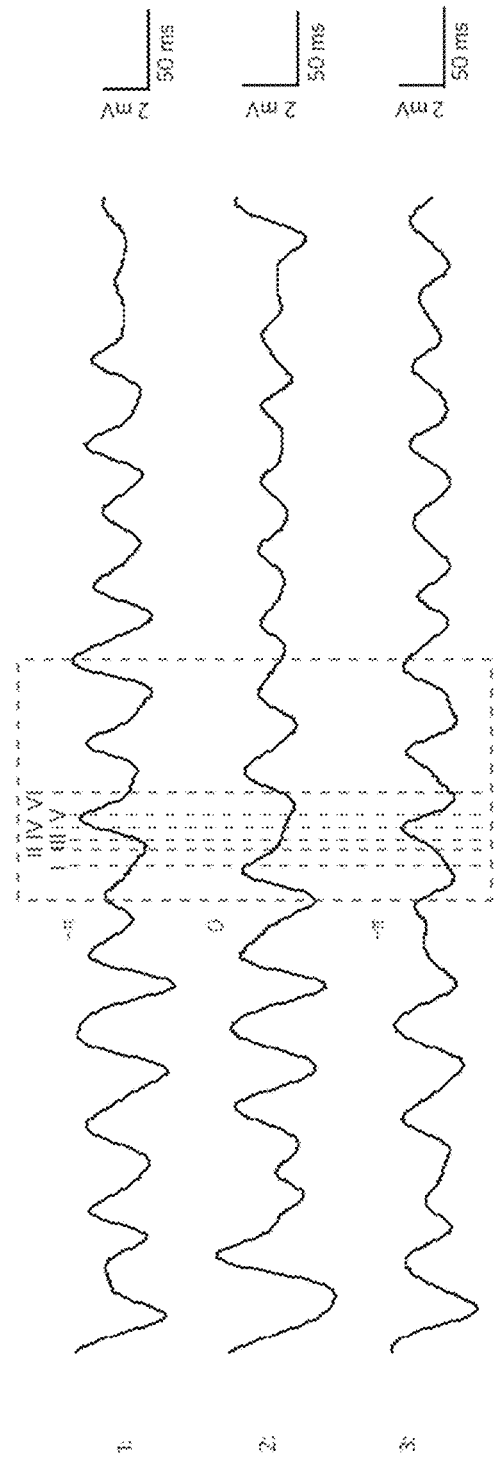
FIGS. 35A-35B. Study of ventricular fibrillation.
Figure 35B:
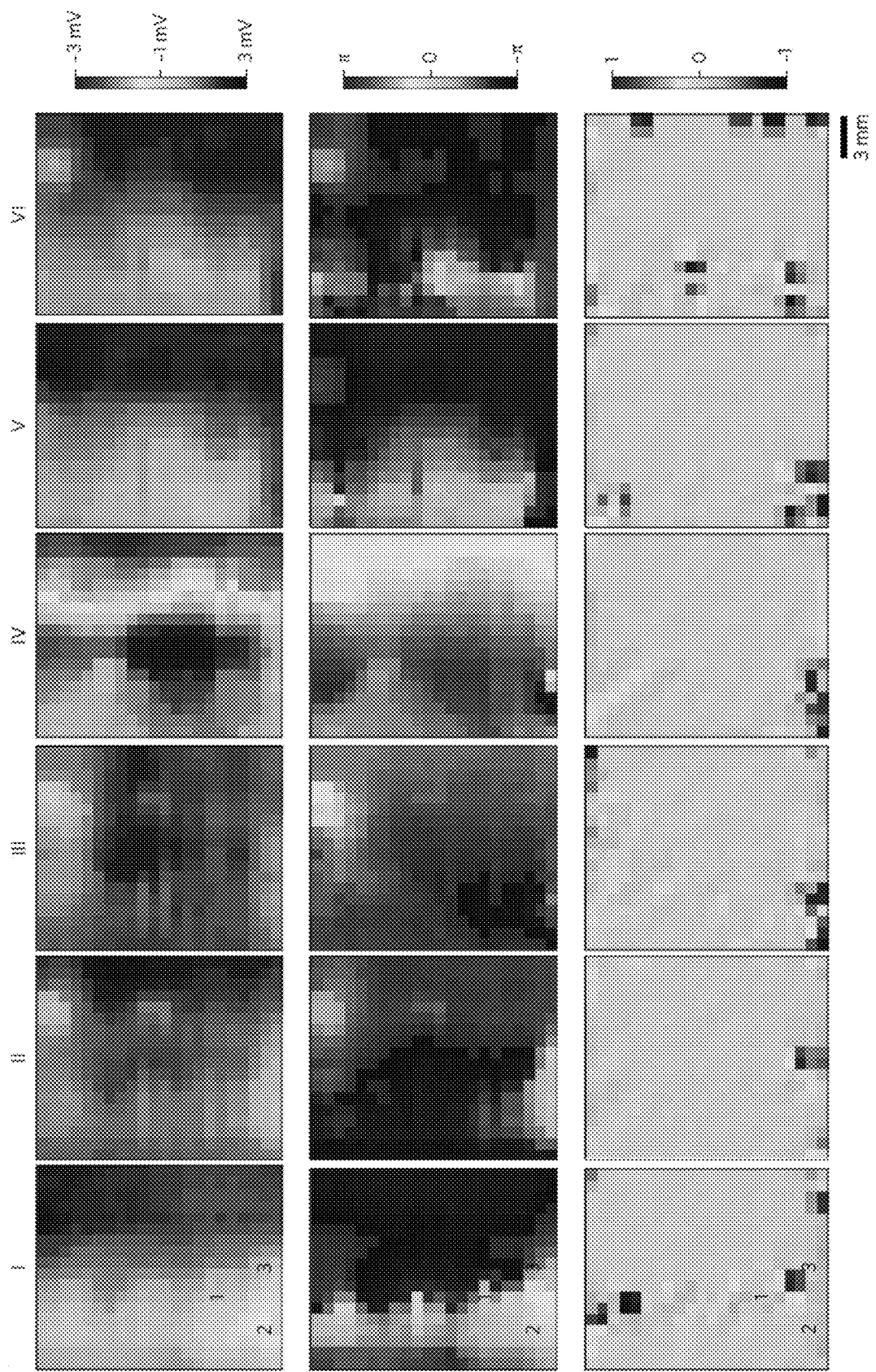

Previously reported flexible passive electrode arrays lacked sufficient spatial density to map and reconstruct patterns of activity associated with ventricular fibrillation (VF)[10]. The capacitive high-density sensing electronics presented here overcome this limitation to allow reliable tracking of reentrant patterns of activation (FIGS. 35A-35B, top). Calculation of the signal phase values (FIG. 35B, bottom), a common clinical method for assessing arrhythmias, corroborates these observations. Detecting a singularity in the phase map can identify a reentrant pattern of activation. This singularity is a location around which all values of phase from $-\pi$ to $\pi$ are represented[41-43] and can be seen in the first frame of the top two rows of FIG. 35B. In clinical practice, the identification of phase singularities is commonly used to guide ablation therapy of arrhythmias[44,45]. The location of the phase singularity in each frame (FIG. 35B, bottom) can be calculated using previously published methodology[46]. The phase singularity is the most positive point on the map that wanders within the bottom left quadrant as the wave of activation passes through a single reentrant pattern. In a single second of recorded data, six such reentrant patterns occur, with an average duration of $8.089 \pm 2.734$ ms. This demonstration has significant implications for use of the device in diagnostic catheters and implantable devices aimed at treating patients with life-threatening atrial and ventricular arrhythmias.

The results presented here demonstrate a promising route towards safe, robust and high-performance flexible electronics for high-density cardiac mapping in both clinical and research settings. Devices with larger area coverages and/or higher densities can be readily achieved through scaling the same basic materials and architectures, in a way that leverages advanced processing techniques from the integrated-circuit and information-display industries. We see no fundamental hurdles, for example, in achieving systems with thousands or even hundreds of thousands of nodes. Auto-correlation methods can be used to identify the node spacing that will maximize acquisition of electrophysiological data while reducing unnecessary redundancy. Future efforts have the potential to yield advanced, stretchable variants of these kinds of systems, to allow coverage across the entire epicardium in a pericardium-like membrane, or across the entire endocardium by integrating the electronics on balloon catheters. Parallel efforts should also focus on mitigating the foreign-body response from these flexible electronic systems. Though minimally invasive, in certain scenarios the devices could potentially induce inflammatory responses that could result in fibrotic tissue and associated impairment of the capacitive measurement interface[47-50]. The addition of triazole-modified hydrogels[50] and/or anti-inflammatory agents[49] could help to minimize such effects.

Although this work focuses on electrical sensing, energy-delivery capabilities could stem from developing high-definition capacitively coupled pace-making stimulators. In distinct contrast with optical mapping, the combination of actuators and sensing electrodes both using a capacitively coupled approach has the potential to enable clinically safe systems capable of diagnosing and treating patients with life-threatening arrhythmias in real time. In addition, many sudden cardiac deaths occur due to abnormal repolarization caused by mutations in various genes encoding ion channels governing repolarization. Lack of adequate technology to map repolarization has been a major obstacle in studies of the so-called long QT and short QT syndromes (which refer to the duration of the QT interval of an electrocardiogram). The device platforms introduced here provide a solution that is key to advancing research, diagnostics and treatment of these lethal cardiac syndromes. Future and ongoing work focuses on the engineering development of power supply, data-processing units and data-transmission interfaces for long-term recording in vivo, achieving systems beyond the realm of what can be envisioned from optical mapping and conventional multi-electrode arrays.

Methods: Capacitively Coupled, Active Sensing Node Design.

Figure 53B:
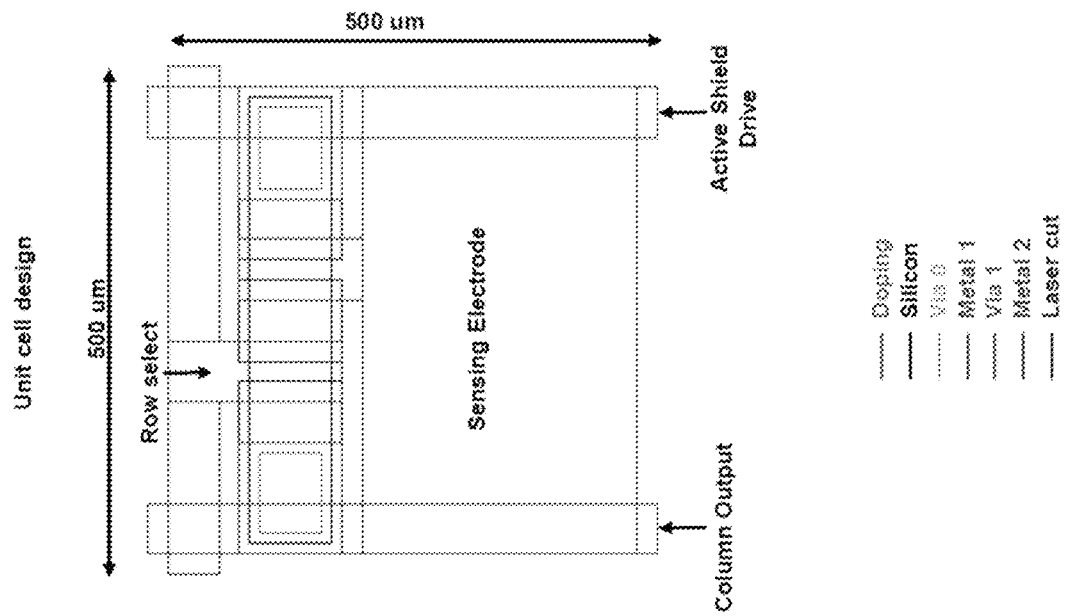
FIGS. 53A-53B. Schematic illustration of a 18×22 array of active multiplexed channels, showing (FIG. 53A) entire device and (FIG. 53B) unit cell design.
Figure 53A:
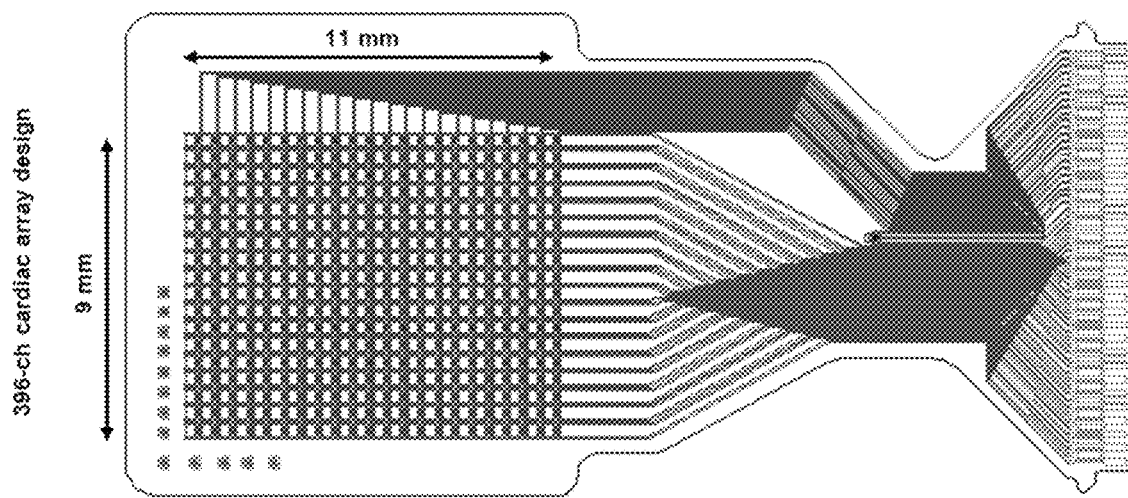

The basic node of the capacitively coupled, active sensing electronics consists of an NMOS source-follower amplifier with a capacitive input and an on-site NMOS multiplexer (FIG. 31B and FIGS. 53A-53B). The area of the sensing pad is sufficiently large such that the capacitance between the sensing pad and the tissue is over one order of magnitude higher than the gate capacitance of the sensing transistor. For the 396-channel flexible Si active sensing electronic system in this study, the area of the sensing pad is 270×460 μm, while the transistor gate area is 13.8×80 μm. From a thin-film capacitor, $C = \varepsilon_r \varepsilon_0 A/t$, where $\varepsilon_r$ is the relative permittivity, $\varepsilon_0$ is the vacuum permittivity, A is the area of the capacitor and t is the thickness of the dielectric, $C_{CAP} = 12.5 C_{TG}$. The total capacitance (CT) driving the Si NM channel in the amplifier transistor yields ~0.93 CTG, from combining $C_{CAP}$ and $C_{TG}$ in series. During sensing, the amplifier transistor operates in saturation (active mode). The transconductance ($g_m$) can be extracted from the standard square-law model with the following equation (1):

$$g_m = \frac{\partial I_{DS}}{\partial V_{GS}} = \sqrt{2 I_{DS} \mu_{eff} C_{OX} \frac{W}{L_{eff}}}$$

where $\mu_{eff}$ is the effective mobility of electrons in the Si nanomembrane transistor and Cox is the specific capacitance of the gate per unit gating area ($C_T/WL_{eff}$). This high-capacitance design can ensure high transconductance, which yields high gain and low-output impedance from the amplifier.

Figure 54:
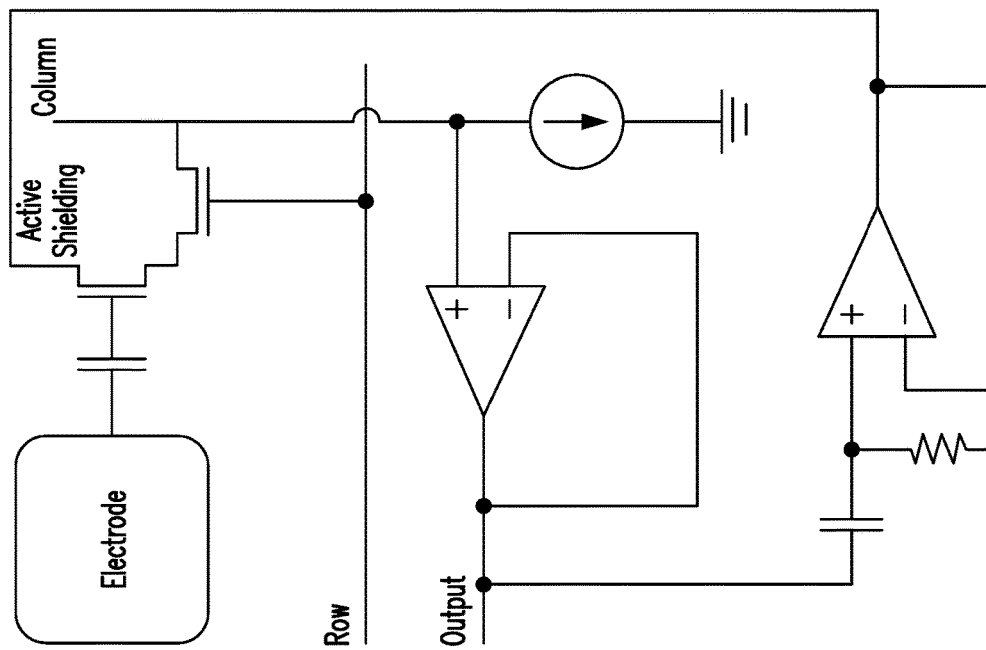
FIG. 54. Schematic circuit diagram for the capacitively coupled, active multiplexed sensing electrode with an active shielding feedback.

The source input referred noise ($v_{n,rms}$, root-mean-squared) of the amplifier circuit can be characterized from the following analytical model[28] (2):

$$v_{n,rms}^2 = \frac{(g_{CAP} + g_i)^2 + \omega^2(C_{CAP} + C_l + C_s)^2}{g_{CAP}^2 + \omega^2 C_{CAP}^2} v_{i,rms}^2 + \frac{1}{g_{CAP}^2 + \omega^2 C_{CAP}^2} i_{i,rms}^2$$

where $v_i(j\omega)$ is the input referred amplifier voltage noise ($\omega = 2\pi f$), $i_i(j\omega)$ is the net current noise at the amplifier input, $g_{CAP} + j\omega C_{CAP}$ is the tissue-electrode coupling admittance, $g_i + j\omega C_i$ is the amplifier input admittance, and Cs is the active shield to electrode capacitance (FIG. 54 depicts the schematic of the active shield circuit). This model clearly shows that high coupling capacitance is beneficial in achieving low-noise circuits. In the low frequency limit, the noise power density can be simplified to $\sim 1/f^\alpha$, where $0 < \alpha < 2$. An active shielding circuit further improves the recording gain and the SNR of the sensing. Here, each column input includes an adjustable active shield drive voltage, an adjustable column bias current and an adjustable compliance voltage to limit the peak voltage on the column lines. The row-select positive and negative voltages are also fully adjustable.

Device Fabrication.

Figure 36:
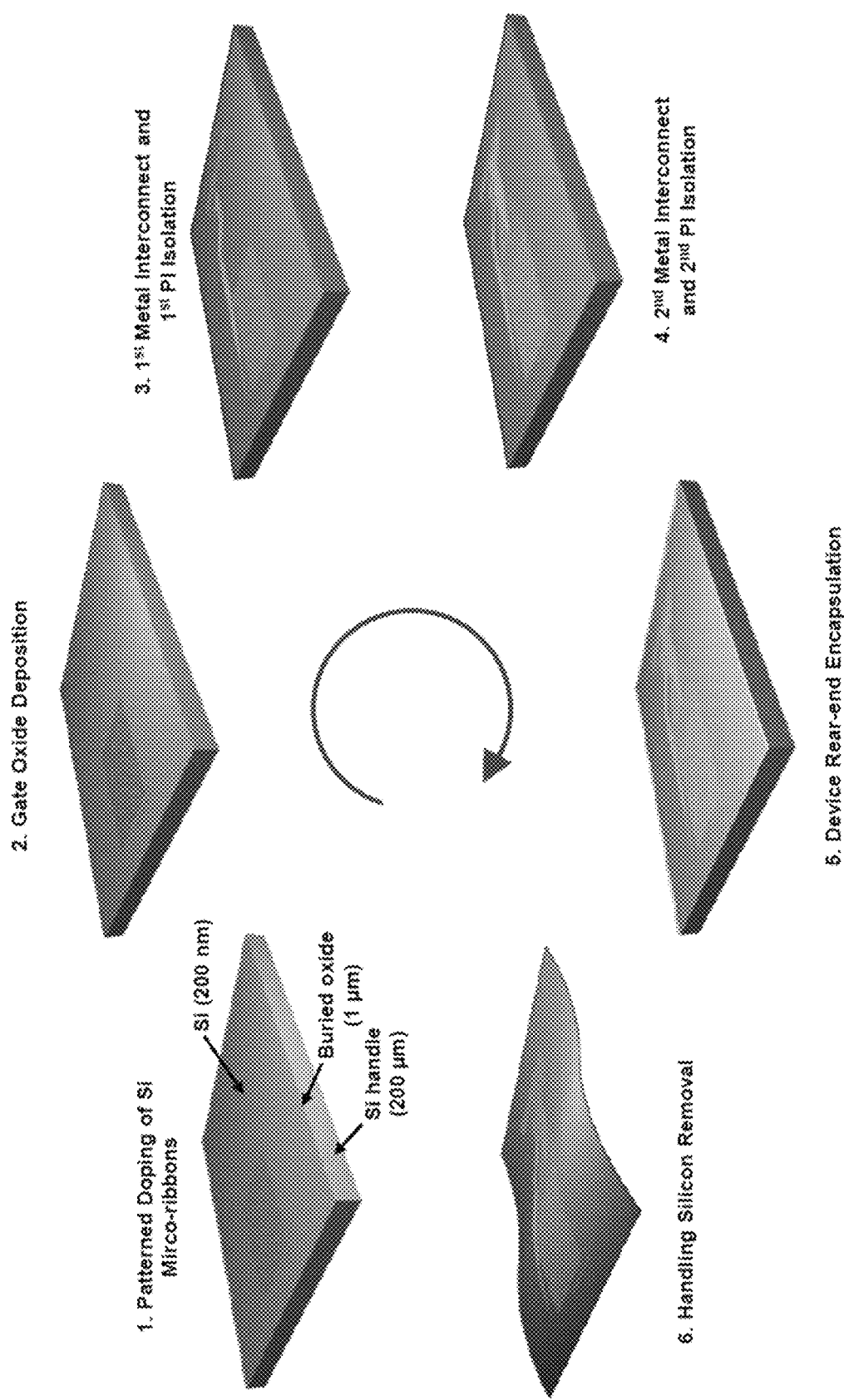
FIG. 36. Procedures for fabricating flexible, capacitively coupled, actively multiplexed sensing matrix. From first to last: (1) Patterned doping of Si micro-ribbons on a SOI wafer; (2) Gate oxide deposition; (3) 1st metal interconnect and 1st Polyimide (PI) isolation; (4) 2nd metal interconnect and 2nd PI isolation; (5) Device rear-end encapsulation; (6) handling silicon removal. The buried oxide (BOX) layer is then revealed on the front end of the device. The original BOX thickness is 1 μm, ~100 nm of which is etched during the Si wafer removal process.

As shown in FIG. 36 and detailed below, the fabrication began with grinding a p-type silicon-on-insulator (SOI) wafer (200-nm-thick Si layer, 1,000-nm-thick BOX layer, and 500-μm-thick Si handle wafer, Soitec) to 200 μm (Syagrus Systems). A 200-nm-thick layer of $SiO_2$ grown at 1,150° C. in a tube furnace served as a diffusion mask. Cleaning the wafer by standard RCA (Radio Corporation of America) procedures preceded high-temperature processing, including oxidation and doping. Conventional photolithography defined doping regions, followed by reactive ion etching (RIE) with $CF_4/O_2$. The diffusion of phosphorus occurred at 1,000° C. in a tube furnace. Photolithography and RIE with $SF_6$ isolated the source, drain and channel regions of the Si. Tube furnace growth (1,150° C. for 37 min) and atomic layer deposition (ALD) yielded a gate oxide stack of $SiO_2$ (100 nm) and $Al_2O_3$ (15 nm). Buffered oxide etchant opened the contact regions for source and drain through photolithographically defined patterns of resist. Electron-beam evaporation yielded a layer of Cr/Au (5 nm/100 nm for the first metal layer; 10 nm/500 nm for the second), patterned by photolithography and wet etching to define the gate electrodes and metal interconnects. An interlayer of polyimide (PI; thickness of 1.6 μm) separated the metal layers. Connections between layers involved through-holes defined by lithographically patterned exposure to RIE with $O_2$. Another coating of PI (thickness of 2 μm) isolated the second layer of metal. A layer of $Al_2O_3$ (20 nm) coated this top PI surface. Separately, a PI film (Kapton; thickness of 13 μm) laminated on a glass substrate with a thin layer of cured poly(dimethylsiloxane) (PDMS) as a soft adhesive served as a handling substrate. Electron-beam evaporation formed a layer of $Ti/SiO_2$ (5 nm/100 nm) on the Kapton film to facilitating bonding with an adhesive (Kwik-Sil, World Precision Instruments) to the devices. Bonding involved placing the device, with PI side facing down, onto the Kapton side, and applying ~50 kPa of pressure. Curing of the adhesive occurred at room temperature within 30 min.

Removal of the Si substrate began with RIE with $SF_6$, followed by inductively coupled plasma reactive ion etching (STS ICP-RIE). The high selectivity of etching of Si over $SiO_2$ in the ICP-RIE prevented any significant removal of the BOX layer during this process. Photolithography then defined areas for forming openings for contact leads via RIE with $CF_4/O_2$ and buffered oxide etching. Finally, a laser-cutting procedure defined the outer perimeter of the device, thereby allowing it to be peeled from the handling substrate. A Kapton stiffener (~150 μm thick) reinforced the reverse side of the contact region, to allow mounting of ZIF (zero insertion force) connectors as interfaces to the external electrical data acquisition (DAQ) system.

Analysis of Transistor Characteristics.

Figure 40:
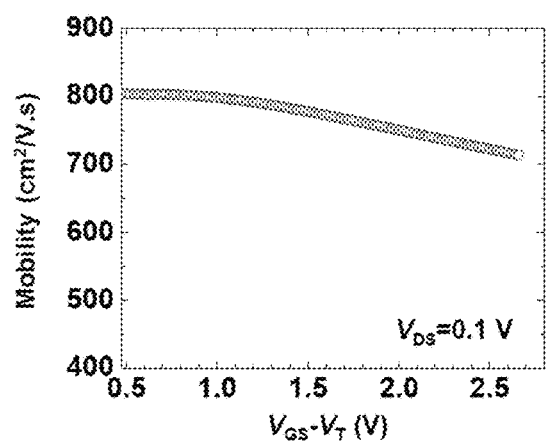
FIG. 40. Effective mobility ($\mu_{eff}$) as a function of gate voltage for the transistor in FIG. 31C, demonstrating the high performance of the Si active circuits. The high mobility leads to low output impedance from the source-following buffer circuit, and high switching speed from the multiplexing transistor.

The effective mobility ($\mu_{eff}$) can be extracted using the following equation (3):

$$\mu_{eff} = \frac{\partial I_{DS}}{\partial V_{DS}} \frac{L}{W C_{OX}(V_{GS} - V_T - 0.5 V_{DS})}$$

where $V_T$ is the threshold voltage. Subtracting the total phosphorus diffusion length ($2x_d$) from the lithography length (L, 20 μm) yields the effective channel length $L_{eff}$. The diffusion length can be determined by the thermal history of phosphorus after doping, dominantly the thermal oxidation step for the gate oxide (1,150° C. for 37 min). Specifically, xd is calculated from the following analytical model for constant source diffusion (4):

$$x_d = 2\sqrt{Dt}\left[\text{erf}^{-1}\left(1 - \frac{N_B}{N_S}\right)\right] = 3.1 \text{ } \mu m$$

where D is the diffusivity of phosphorus in Si at 1,150° C. (9.1×10$^{-13}$ cm$^{-2}$ s$^{-1}$), t is time (37 min), $N_B$ is the background boron doping in Si (1.3×1015 cm$^{-3}$), and Ns is the solid-solubility limit of phosphorus in Si at 1,150° C. (1.5×1021 cm$^{-3}$). Therefore $L_{eff}$=L−$2x_d$ yields 13.8 μm. Note that depending on whether there is capacitive coupling or not, the values of $I_{DS}$, $C_{ox}$ and $V_T$ will be different. FIG. 40 shows the extracted effective mobility values as a function of gate overdrive. The peak mobility is ~800 cm$^2$ (Vs)$^{-1}$. During sensing, $I_{DS}$ was set to 1 μA by the current sink. The peak $g_m$ is 1.17 ms. The approximate output impedance of the source follower circuit is ~855Ω, that is, $1/g_m$.

Device Soak Test.

Figure 55:
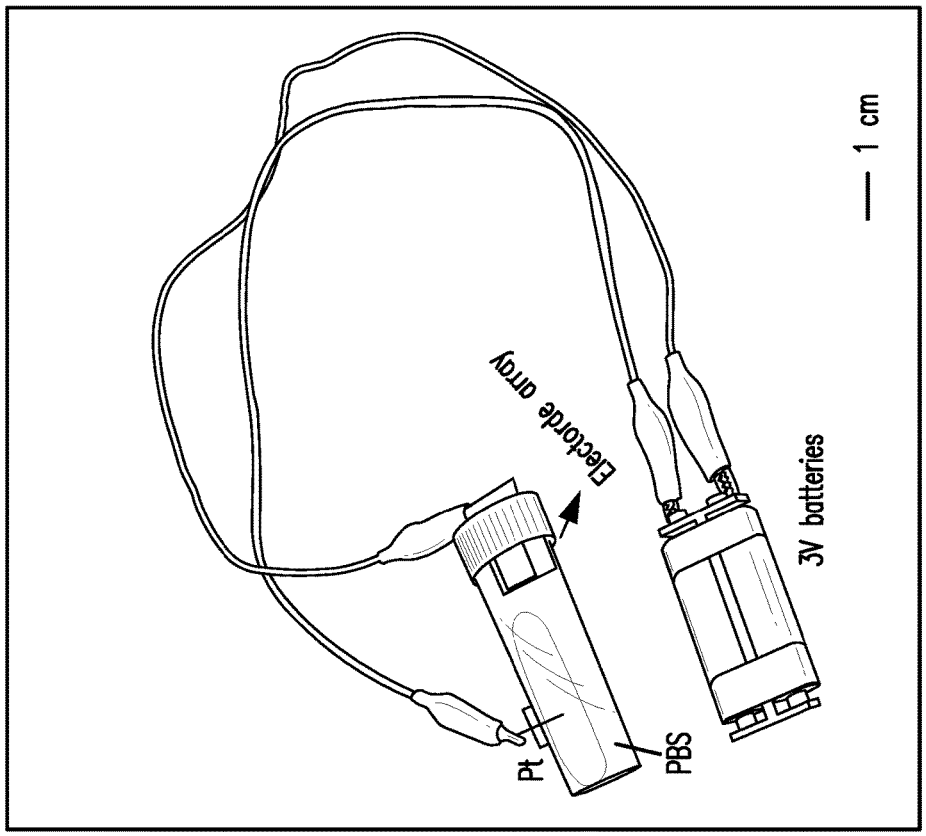
FIG. 55. A photograph of the set-up for soak testing of the electrode array. A sealed HDPE bottle was used to contain the phosphate buffered saline (PBS) solution, the electrode array and a Pt electrode. During the test the set-up was placed in a 37° C. overn and a 3 V DC bias was applied between the array and Pt electrode.

Tests involved soaking the active cardiac sensing electrode arrays in a high-density polyethylene (HDPE) plastic tube, filled with 1×PBS (Sigma-Aldrich) solution (pH=7.4). An oven maintained the temperature at 37° C. Lithium ion batteries biased the device at 3 V relative to a Pt reference electrode inserted into the PBS solution. Detailed experimental settings are in FIG. 55. An adhesive (Underwater Magic) sealed the openings in the tube for the device and the electrode to prevent evaporation.

Data Acquisition.

Figure 56:
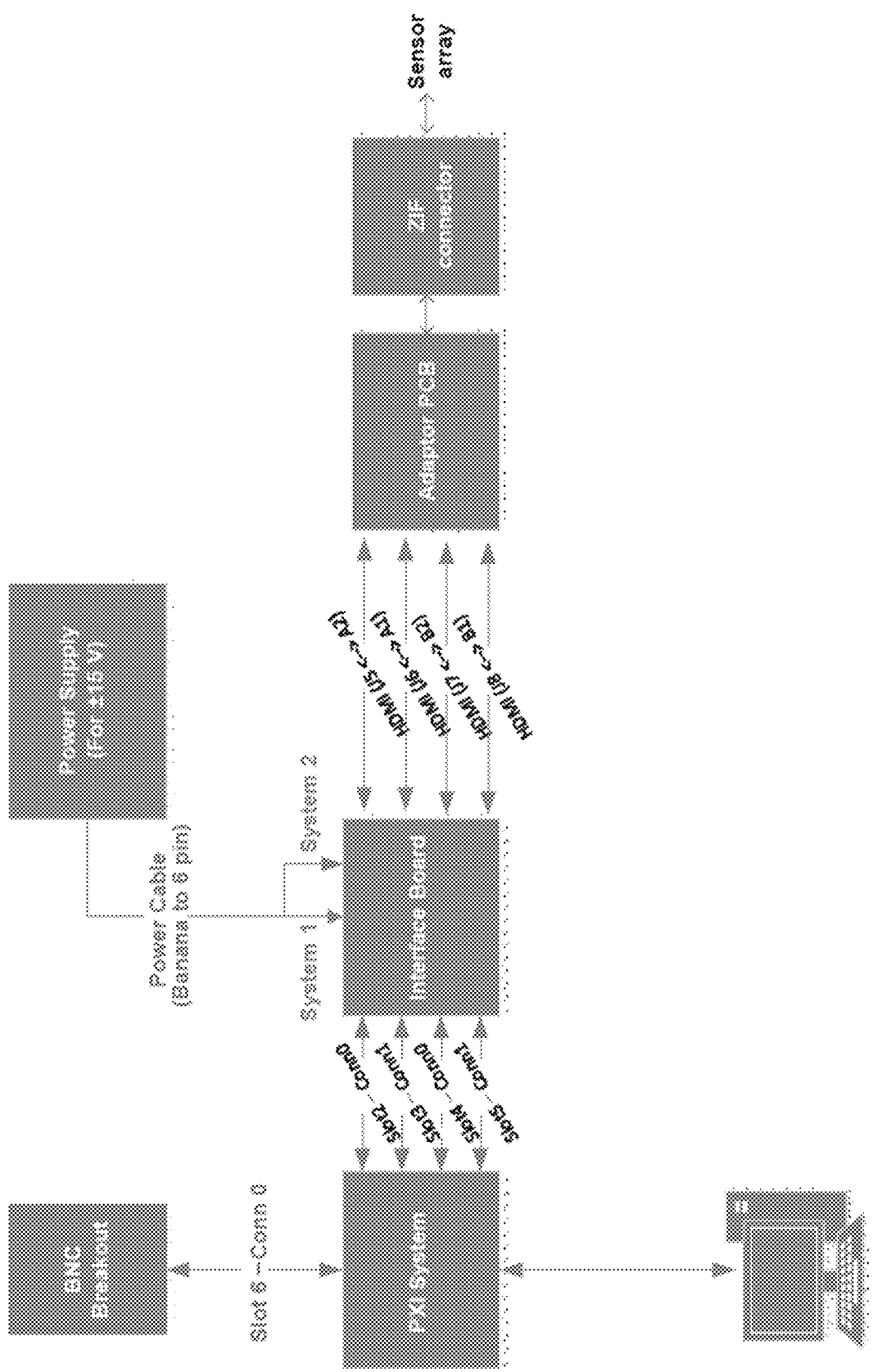
FIG. 56. Schematic wiring diagram for the data acquisition system for sensing.
Figure 58:
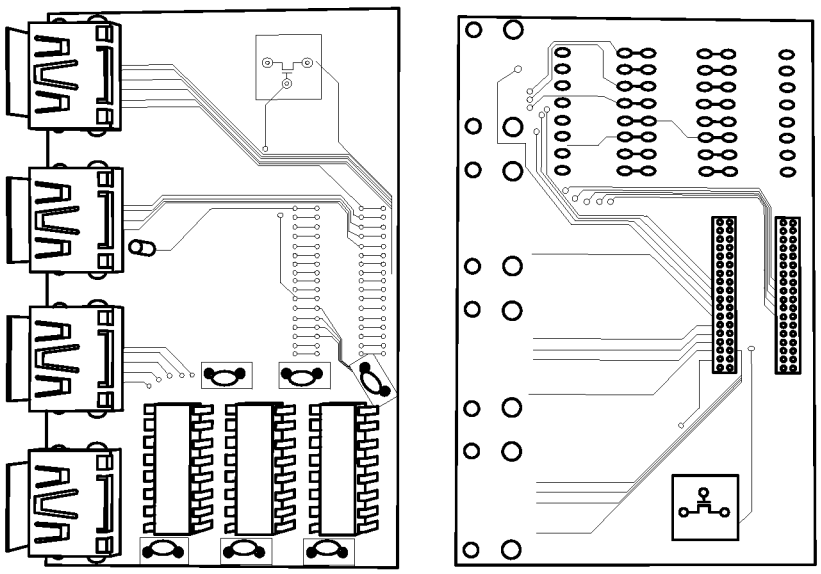
FIG. 58. Photographs of the front (top) and back (bottom) side of the adaptor PCB board used between the electrode array and the DAQ system.
Figure 57:
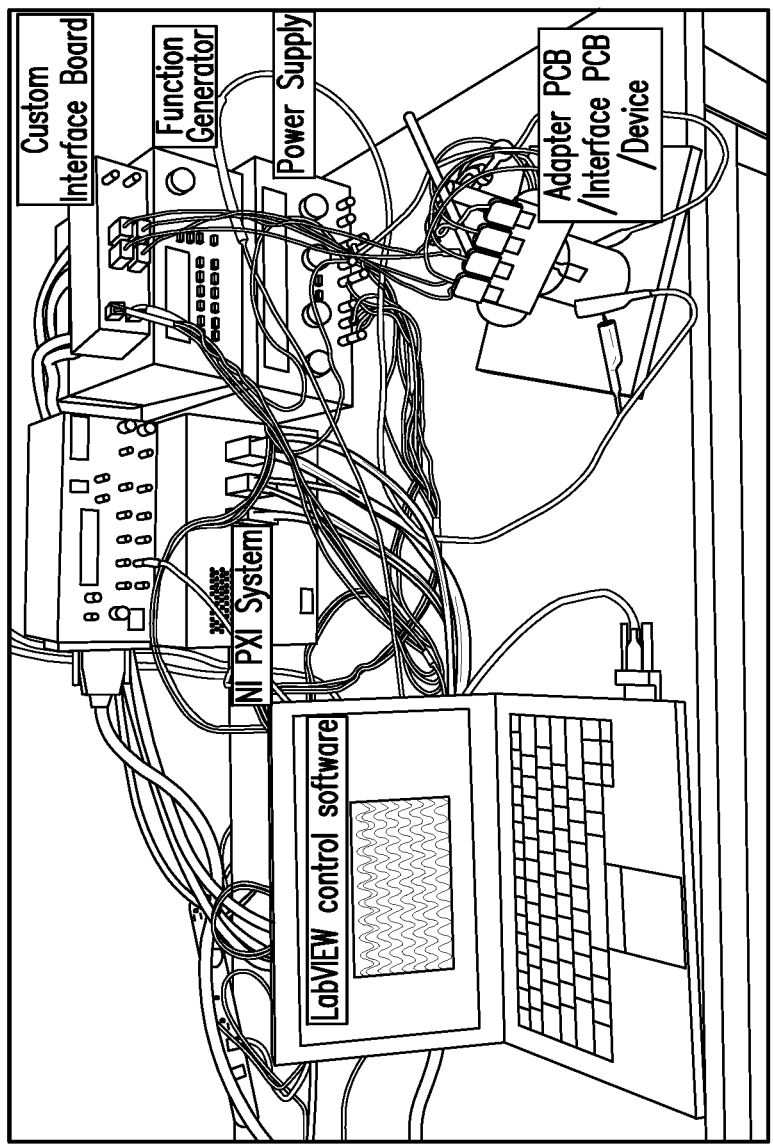
FIG. 57. A photograph of the data acquisition system with the electrode array during in vitro bench testing.
Figure 59:
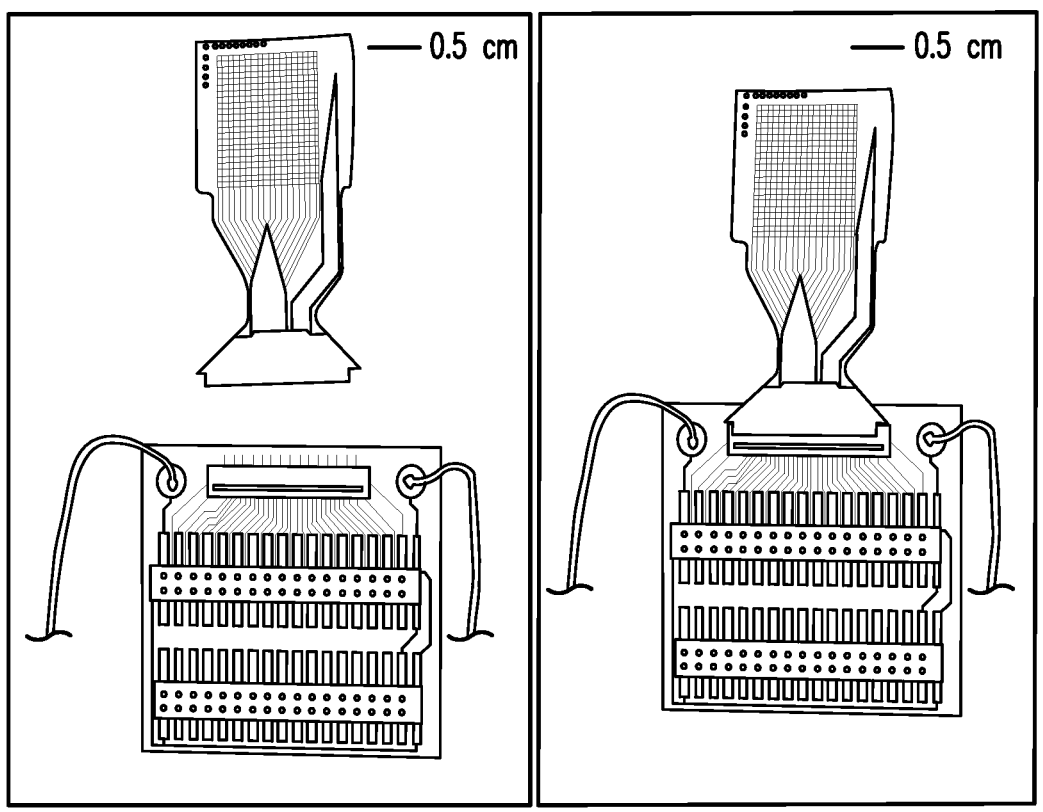
FIG. 59. Photographs of an electrode array before (left) and after (right) being inserted into an interface PCB board through a zero-insertion-force (ZIF) connector.

The DAQ system consists of a set of five PXI-6289 data acquisition cards (National Instruments) and a custom acquisition system interface board (FIGS. 56 and 57). The DAQ connects to the multiplexed arrays using flexible high-definition multimedia interface (HDMI) cables and an adapter printed circuit board (PCB; FIG. 58). The adapter PCB joins to the electrode interface PCB using two 150 μm pitch connectors. The electrode interface PCB adapts from the ZIF connector used on the electrode array to a more durable connector that can be plugged and unplugged without damage (FIG. 59). Custom LabVIEW software (National Instruments) controls the DAQ system. All recordings in this study used an over-sampling ratio of 4 to further reduce the noise. The optical mapping involved a sampling frequency of 1 kHz. A triggered TTL (transistor-transistor logic) pulse aligned the optical signal to electrical data through a direct input of this pulse into the DAQ.

Signal Processing.

MATLAB software (MathWorks) enabled offline filtering and analysis. Unless otherwise specified, electrical data from all channels passed through a notch filter at 60 Hz and a (1 Hz, 150 Hz) band-pass filter. Calculation of the latency of the peak of each channel yielded the minimum latency, for the isochronal maps. Interpolated signals with a 16× enhancement of the sampling mesh allowed accurate location of peaks on a cubic spline. A final channel mask, also applied based on the amplitude of the peak, eliminated spurious delays.

Mechanical Analysis.

Finite element analysis (FEA) simulations yielded the strain distributions in the device under pure bending by imposing rotations at the two ends of the Kapton layer. The multilayer structure modelling deployed the plane-strain element (CPE4R in the ABAQUS finite element software)[51]. FIGS. 44A-44B list the material parameters used for different layers. This simulation neglected the extremely thin $Al_2O_3$ layers. The distribution of axial strain along the thickness direction appears in FIGS. 44A-44B, which also shows the distribution of axial strain in the thickness direction. The extremely soft adhesive layer leads to the split of the neutral axes[52-54], where the axial strain is zero. This split of neutral axes, above and below the soft adhesive layer, reduces the maximum strain in the device, simply because the maximum strain is proportional to the distance to the neutral axis in each stiff layer. For 5 mm bending radius, the maximum strain is: 0.0243% (tensile) in the top $SiO_2$ layer; 0.0111% (tensile) in the top Si layer; 0.0092% (tensile) in the first Au layer; and 0.0185% (compressive) in the second Au layer.

Animal Experiments.

Figure 60:
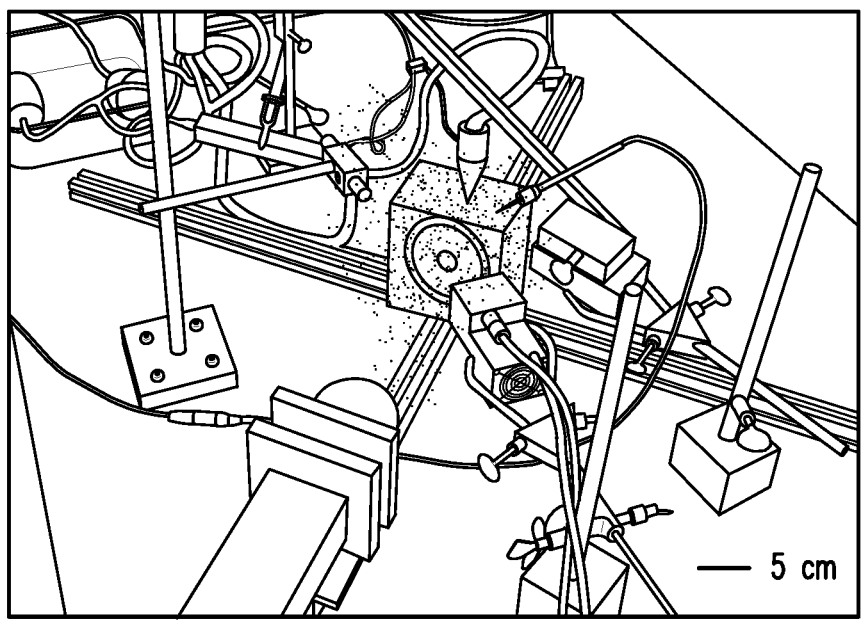
FIG. 60. A photograph of the set-up for ex vivo recording on a Langendorff perfused rabbit heart model.

The experiments were conducted in accordance with the ethical guidelines of the National Institutes of Health and with the approval of the Institutional Animal Care and Use Committee of the George Washington University in Washington, D.C. Six adult male New Zealand White rabbits were used over the course of device validation. No randomization or binding was used since there was only a single group. Representative data from the final two experiments are presented here. Briefly, we injected 400 USP (United States Pharmacopeia) units kg$^{-1}$ of sodium heparin via a lateral ear vein into the rabbit. Afterwards, a progression of 1%-3% isoflurane delivered via facemask anaesthetized the rabbit. Once the animal was unconscious and unresponsive to pain, a midsternal incision removed the heart and the aorta cannulated to facilitate retrograde perfusion of oxygenated Tyrode's solution. The perfusate served a blood substitute for the heart to maintain its electrolyte balance and deliver an energy substrate for continued cardiac function. The solution was at a constant physiologic temperature (37±1° C.) and pH (7.4±0.05) throughout the experiment. The heart was continuously under a constant pressure of 60-80 mm Hg with oxygenated Tyrode's solution. We administered the excitation-contraction uncoupler blebbistatin (Cayman Chemical, Ann Arbor, Mich.) to limit motion artifact in the optical mapping signals. A bolus injection of di-4 ANEPPS (Life Technologies, Grand Island, N.Y.) facilitated fluorescent measurement of membrane potential ($V_m$). A plastic band wrapped the active cardiac sensing array and extended around the heart, facilitating mechanical conformity by capillary force from the moisturized heart surface. The DAQ connected with PCB board to the array and performed data acquisition. For optical mapping, a 520 nm excitation light elicited optical action potentials and a complementary metal-oxide semiconductor (CMOS) camera (SciMedia, Costa Mesa, Calif.) recorded them with a long pass emission filter with a 650 nm cutoff. Finally, to induce VF in a rabbit model, we administered a 20 nM ATP-dependent potassium channel opener pinacidil (Sigma Aldrich, St. Louis, Mo.) to shorten action potential duration and create a substrate for induction of VF. Detailed experimental settings can be found in FIG. 60. Data was analysed using a custom MATLAB software.

REFERENCES

1. Thomas, C., Springer, P., Loeb, G., Berwald-Netter, Y. & Okun, L. A miniature microelectrode array to monitor the bioelectric activity of cultured cells. Exp. Cell Res. 74, 61-66 (1972).

2. Pertsov, A. M., Davidenko, J. M., Salomonsz, R., Baxter, W. T. & Jalife, J. Spiral waves of excitation underlie reentrant activity in isolated cardiac muscle. Circ. Res. 72, 631-650 (1993).
3. Sprössler, C., Denyer, M., Britland, S., Knoll, W. & Offenhäusser, A. Electrical recordings from rat cardiac muscle cells using field-effect transistors. Phys. Rev. E 60, 2171-2176 (1999).
4. Camelliti, P. et al. Adult human heart slices are a multicellular system suitable for electrophysiological and pharmacological studies. J. Mol. Cell. Cardiol. 51, 390-398 (2011).
5. Huys, R. et al. Single-cell recording and stimulation with a 16 k micro-nail electrode array integrated on a 0.18 µm CMOS chip. Lab Chip 12, 1274-1280 (2012).
6. Zhang, X., Tai, J., Park, J. & Tai, Y.-C. Flexible MEA for adult zebrafish ECG recording covering both ventricle and atrium. In Proc. IEEE 27th Int. Conf. Micro Electro Mechanical Systems (MEMS) 841-844 (IEEE, 2014).
7. Friedman, P. A. Novel mapping techniques for cardiac electrophysiology. Heart 87, 575-582 (2002).
8. Kim, D.-H. et al. Materials for multifunctional balloon catheters with capabilities in cardiac electrophysiological mapping and ablation therapy. Nat. Mater. 10, 316-323 (2011).
9. Kim, D.-H. et al. Electronic sensor and actuator webs for large-area complex geometry cardiac mapping and therapy. Proc. Natl Acad. Sci. USA 109, 19910-19915 (2012).
10. Xu, L. et al. 3D multifunctional integumentary membranes for spatiotemporal cardiac measurements and stimulation across the entire epicardium. Nat. Commun. 5, 3329 (2014).
11. Viventi, J. et al. A conformal, bio-interfaced class of silicon electronics for mapping cardiac electrophysiology. Sci. Transl. Med. 2, 24ra22 (2010).
12. Viventi, J. et al. Flexible, foldable, actively multiplexed, high-density electrode array for mapping brain activity in vivo. Nat. Neurosci. 14, 1599-1605 (2011).
13. Laks, M. M., Arzbaecher, R., Bailey, J. J., Geselowitz, D. B. & Berson, A. S. Recommendations for safe current limits for electrocardiographs a statement for healthcare professionals from the Committee on Electrocardiography, American Heart Association. Circulation 93, 837-839 (1996).
14. Swerdlow, C. D. et al. Cardiovascular collapse caused by electrocardiographically silent 60-Hz intracardiac leakage current implications for electrical safety. Circulation 99, 2559-2564 (1999).
15. Beech, I. B. & Sunner, J. Biocorrosion: towards understanding interactions between biofilms and metals. Curr. Opin. Biotechnol. 15, 181-186 (2004).
16. Bowman, L. & Meindl, J. D. The packaging of implantable integrated sensors. IEEE Trans. Biomed. Eng. 33, 248-255 (1986).
17. Liu, X. et al. Stability of the interface between neural tissue and chronically implanted intracortical microelectrodes. IEEE Trans. Rehab. Eng. 7, 315-326 (1999).
18. Bazaka, K. & Jacob, M. V. Implantable devices: issues and challenges. Electronics 2, 1-34 (2012).
19. Someya, T. et al. Conformable, flexible, large-area networks of pressure and thermal sensors with organic transistor active matrixes. Proc. Natl Acad. Sci. USA 102, 12321-12325 (2005).
20. Lacour, S. P., Jones, J., Wagner, S., Li, T. & Suo, Z. Stretchable interconnects for elastic electronic surfaces. Proc. IEEE 93, 1459-1467 (2005).
21. Tian, B. et al. Three-dimensional, flexible nanoscale field-effect transistors as localized bioprobes. Science 329, 830-834 (2010).
22. Takei, K. et al. Nanowire active-matrix circuitry for low-voltage macroscale artificial skin. Nat. Mater. 9, 821-826 (2010).
23. Schwartz, G. et al. Flexible polymer transistors with high pressure sensitivity for application in electronic skin and health monitoring. Nat. Commun. 4, 1859 (2013).
24. Wu, W., Wen, X. & Wang, Z. L. Taxel-addressable matrix of vertical-nanowire piezotronic transistors for active and adaptive tactile imaging. Science 340, 952-957 (2013).
25. Khodagholy, D. et al. NeuroGrid: recording action potentials from the surface of the brain. Nat. Neurosci. 18, 310-315 (2015).
26. Fromherz, P., Offenhäusser, A., Vetter, T. & Weis, J. A neuron-silicon junction: a Retzius cell of the leech on an insulated-gate field-effect transistor. Science 252, 1290-1293 (1991).
27. Zeck, G. & Fromherz, P. Noninvasive neuroelectronic interfacing with synaptically connected snail neurons immobilized on a semiconductor chip. Proc. Natl Acad. Sci. USA 98, 10457-10462 (2001).
28. Chi, Y. M., Jung, T.-P. & Cauwenberghs, G. Dry-contact and noncontact biopotential electrodes: methodological review. IEEE Rev. Biomed. Eng. 3, 106-119 (2010).
29. Spira, M. E. & Hai, A. Multi-electrode array technologies for neuroscience and cardiology. Nat. Nanotech. 8, 83-94 (2013).
30. Berdondini, L. et al. Active pixel sensor array for high spatio-temporal resolution electrophysiological recordings from single cell to large scale neuronal networks. Lab Chip 9, 2644-2651 (2009).
31. Eversmann, B. et al. A 128×128 CMOS biosensor array for extracellular recording of neural activity. IEEE J. Solid-State Circ. 38, 2306-2317 (2003).
32. Bakkum, D. J. et al. Tracking axonal action potential propagation on a high-density microelectrode array across hundreds of sites. Nat. Commun. 4, 21821 (2013).
33. Byers, C. L., Beazell, J. W., Schulman, J. H. & Rostami, A. Hermetically sealed ceramic and metal package for electronic devices implantable in living bodies. U.S. Pat. No. 4,991,582 A (1991).
34. Zeng, F.-G., Rebscher, S., Harrison, W., Sun, X. & Feng, H. Cochlear implants: system design, integration, and evaluation. IEEE Rev. Biomed. Eng. 1, 115-142 (2008).
35. Sillay, K. A., Larson, P. S. & Starr, P. A. Deep brain stimulator hardware-related infections: incidence and management in a large series. Neurosurgery 62, 360-367 (2008).
36. Jeong, J. W. et al. Capacitive epidermal electronics for electrically safe, long-term electrophysiological measurements. Adv. Health. Mater. 3, 642-648 (2014).
37. Duan, X. et al. Quantification of the affinities and kinetics of protein interactions using silicon nanowire biosensors. Nat. Nanotech. 7, 401-407 (2012).
38. Fattahi, P., Yang, G., Kim, G. & Abidian, M. R. A review of organic and inorganic biomaterials for neural interfaces. Adv. Mater. 26, 1846-1885 (2014).
39. Langendorff, O. Untersuchungen am Uberlebenden Saugethierherzen. Pflügers Archiv Eur. J. Physiol. 61, 291-332 (1895).
40. Efimov, I. R., Nikolski, V. P. & Salama, G. Optical imaging of the heart. Circ. Res. 95, 21-33 (2004).
41. Bossaert, L. Fibrillation and defibrillation of the heart. Br. J. Anaesth. 79, 203-213 (1997).

42. Efimov, I. R., Cheng, Y., Van Wagoner, D. R., Mazgalev, T. & Tchou, P. J. Virtual electrode-induced phase singularity a basic mechanism of defibrillation failure. Circ. Res. 82, 918-925 (1998).
43. Rogers, J. M. Combined phase singularity and wavefront analysis for optical maps of ventricular fibrillation. IEEE Trans. Biomed. Eng. 51, 56-65 (2004).
44. Narayan, S. M. et al. Treatment of atrial fibrillation by the ablation of localized sources: CONFIRM (conventional ablation for atrial fibrillation with or without focal impulse and rotor modulation) trial. J. Am. Coll. Cardiol. 60, 628-636 (2012).
45. Lim, H. S. et al. Noninvasive mapping to guide atrial fibrillation ablation. Cardiac Electrophysiol. Clinics 7, 89-98 (2015).
46. Bray, M. A., Lin, S. F., Aliev, R. R., Roth, B. J. & Wikswo, J. P. Experimental and theoretical analysis of phase singularity dynamics in cardiac tissue. J. Cardiovasc. Electrophysiol. 12, 716-722 (2001).
47. Onuki, Y., Bhardwaj, U., Papadimitrakopoulos, F. & Burgess, D. J. A review of the biocompatibility of implantable devices: current challenges to overcome foreign body response. J. Diabetes Sci. Technol. 2, 1003-1015 (2008).
48. Ward, W. K. A review of the foreign-body response to subcutaneously-implanted devices: the role of macrophages and cytokines in biofouling and fibrosis. J. Diabetes Sci. Technol. 2, 768-777 (2008).
49. Morais, J. M., Papadimitrakopoulos, F. & Burgess, D. J. Biomaterials/tissue interactions: possible solutions to overcome foreign body response. AAPS J. 12, 188-196 (2010).
50. Vegas, A. J. et al. Combinatorial hydrogel library enables identification of materials that mitigate the foreign body response in primates. Nat. Biotechnol. 34, 345-352 (2016).
51. Hibbitt, H., Karlsson, B. & Sorensen, P. Abaqus analysis user's manual v.6.10 (Dassault Systemes Simulia Corp, 2011).
52. Shi, Y., Rogers, J. A., Gao, C. & Huang, Y. Multiple neutral axes in bending of a multiple-layer beam with extremely different elastic properties. J. Appl. Mech. 81, 114501 (2014).
53. Li, L. et al. Integrated flexible chalcogenide glass photonic devices. Nat. Photon. 8, 643-649 (2014).
54. Su, Y., Li, S., Li, R. & Dagdeviren, C. Splitting of neutral mechanical plane of conformal, multilayer piezoelectric mechanical energy harvester. Appl. Phys. Lett. 107, 041905 (2015).
55. Fang, H. et al. Dataset for 'Capacitively coupled arrays of multiplexed flexible silicon transistors for long-term cardiac electrophysiology'. figshare https://figshare.com/s/961786fcede5a8703ec5 (2017).

Supplementary Note 1: Step-by-Step Process Flow to Achieve Flexible, Capacitively Coupled, Active Sensing Electrode Array.

Wafer Back Grinding: 1. Start with SOI (Si device layer 200 nm, BOX layer 1 µm, and handling Si 500 µm); 2. Grind the SOI wafer to 200 µm from back side by Syagrus Systems; 3. Cut the wafer into chips of device size.

Doping: 4. RCA cleaning of SOI chips; 5. Dry thermal oxidation to form 200 nm $SiO_2$ at 1150° C.; 6. Photolithography to define S/D doping area using photoresist (PR) (AZ 5214E); 7. RIE to dry etch $SiO_2$, (a) 50 mTorr of $CF_4/O_2$ (40/1.2 sccm), with RF power 100 W for 5 min, (b) gentle $O_2$ plasma, 50 mTorr, 20 sccm of $O_2$, with RF power 100 W for 20 sec; 8.BOE (6:1) wet etch $SiO_2$ for 2 min; 9. PR strip by acetone, IPA and blow dry; 10. RCA cleaning; 11. Dope S/D area with diffusive phosphorus source at 1000° C. for 6 min; 12. Wet etch $SiO_2$ doping mask using 49% HF for 20 sec; and DI rinse.

Isolation: 13. Photolithography to define Si isolation area using PR (AZ 5214E); 14. RIE to dry etch Si (50 mTorr, 40 sccm of $SF_6$, with RF power of 100 W for 1 min); 15. PR stripe by acetone, IPA and blow dry.

Gate Stack Deposition: 16. RCA cleaning; 17. Dry thermal oxidation to form 100 nm $SiO_2$ at 1150° C.; 18. Deposit 15 nm $Al_2O_3$ at 80° C. using an Atomic Layer Deposition (ALD) system.

Via 0: 19. Photolithography to define S/D opening via using PR (AZ 5214E); 20. Gentle $O_2$ plasma using RIE (50 mTorr, 20 sccm of $O_2$, with RF power 100 W for 20 sec); 21. BOE (6:1) to etch gate dielectric for 3 min; 22. PR stripe by acetone soaking, IPA and blow dry.

Metal 1: 23. Deposit Cr/Au, 5/100 nm with an e-beam evaporator; 24. Photolithography to define metal 1 using PR (AZ 5214E); 25. Au, Cr wet etching using Au, Cr etchant respectively; 26. PR stripe by acetone, IPA and blow dry; 27. Measure test transistors.

Interlayer PI 2545: 28. Clean samples using acetone, IPA, DI, and blow dry; 29. Dehydration: bake samples at 110° C. for 5 min; 30. Spin coat PI adhesion promoter (VM 652) using 500 rpm 5 s, hold 20 s, 3000 rpm 30 s; soft bake at 110° C. for 1 min; 31. PI coating: spin coat PI 2545 precursor at 4500 rpm for 30 sec; soft bake at 150° C. for 6 min; cure at 250° C. for 70 min.

Via 1: 32. Photolithography to define via 1 using PR (AZ P4620); 33. RIE to etch Via 1 (200 mTorr, 20 sccm $O_2$, with RF power of 150 W for 15 min); 34. Check microscope and resistance to make sure via is open; 35. PR stripe by acetone, IPA, and blow dry.

Metal 2: 36. Deposit Cr/Au, 10/500 nm with an e-beam evaporator; 37. Photolithography to define metal 2 using PR (AZ 5214E); 38. Au, Cr wet etching using Au, Cr etchant respectively; 39. PR stripe by acetone, IPA and blow dry.

PI Substrate 2545: 40. Clean samples using acetone, IPA, DI, and blow dry; 41. Dehydration: bake samples at 110° C. for 5 min; 42. Spin coat VM 652 using 500 rpm 5 s, hold 20 s, 3000 rpm 30 s; soft bake at 110° C. for 1 min; 43. PI coating: spin coat PI 2545 precursor at 3000 rpm for 30 sec; soft bake at 150° C. for 6 min; cure at 250° C. for 70 min.

Pre-Conditioning Before Bonding: 44. Deposit 20 nm $Al_2O_3$ at 150° C. to the devices' PI side using ALD; 45. Deposit $Ti/SiO_2$ 5/20 nm to the devices' PI side with an e-beam evaporator.

Bonding: 46. Bond devices to 13-µm kapton films (coated with $Ti/SiO_2$ 5/20 nm) using a ~5-µm-thick PDMS layer. Do UV-Ozone treatment on PDMS surface right before bonding. Si—O—Si bonding need to be achieved on both sides of the PDMS layer to ensure good robustness; 47. Bond devices to handling glass substrates using 10:1 PDMS. Use vacuum desiccator to remove bubbles, and cure at 110° C. for 30 min.

Si Wafer Removal: 48. Grind the back Si side briefly until the contamination on the back is gone; 49. Si back RIE etching (50 mTorr of $SF_6/O_2$, 40/3 sccm, with RF power 100 W. Do 6 runs of 30 min; 50. Deep RIE to continue etching back the devices, until all the back Si is etched.

Contact Lead Opening: 51. Spin coat HMDS at 3000 rpm for 30 sec, then bake at 110° C. for 1 min; 52. Photolithography to define zif contact region, using PR (AZ P4620); 53. RIE to dry etch $SiO_2$, (a). 50 mTorr of $CF_4/O_2$ (40/1.2 sccm), with RF power 200 W for 30 min, (b), gentle $O_2$ plasma, 50 mTorr, 20 sccm of $O_2$ with RF power 100 W for 20 sec; 54.

BOE (6:1) to wet etch SiO$_2$ for 4 min; 55. Measure test transistors; 56. Remove PR using acetone, IPA and blow dry.

Laser Cutting: 57. Laser cut to define the device outline profile; 58. Peel off devices gently from handling substrates; 59. Stick the stiffener onto the device zif side under microscope; devices are then ready to be tested with the DAQ.

Figure 49A:
FIGS. 49A-49B. In vivo recording using a capacitively coupled sensing electronic system from a beating heart.
Figure 49B:
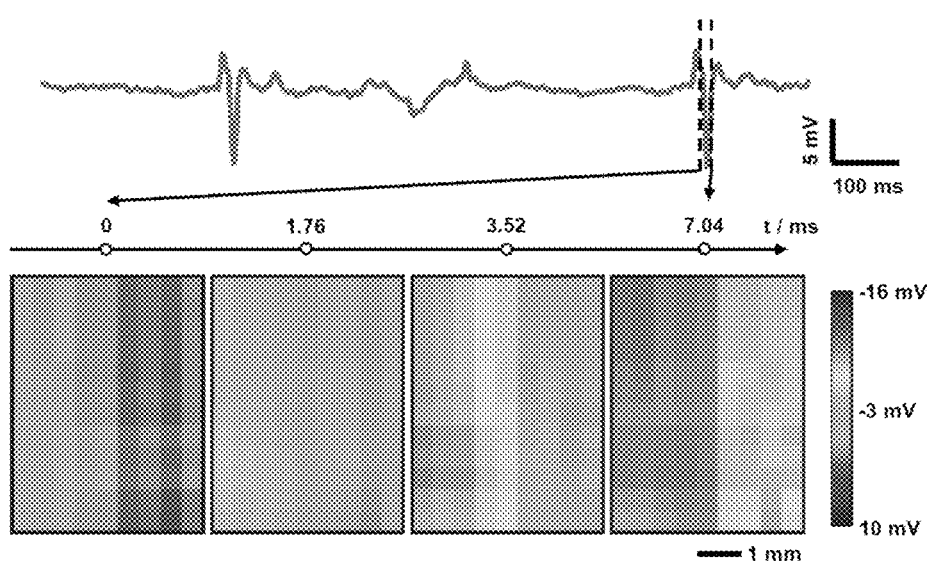
Figure 50A:
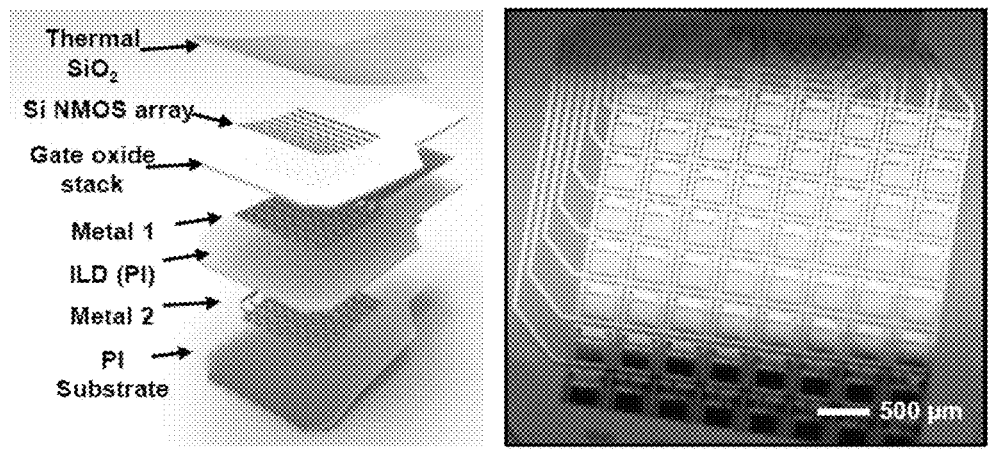
FIGS. 50A-50D. In vivo recording of rat auditory cortex using a flexible, capacitively coupled, actively multiplexed sensing matrix with 64 nodes.
Figure 50B:
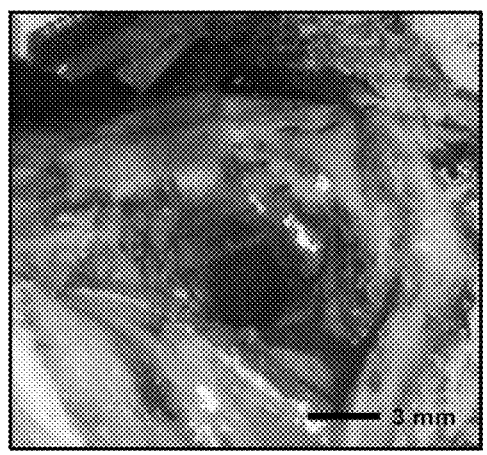
Figure 50C:
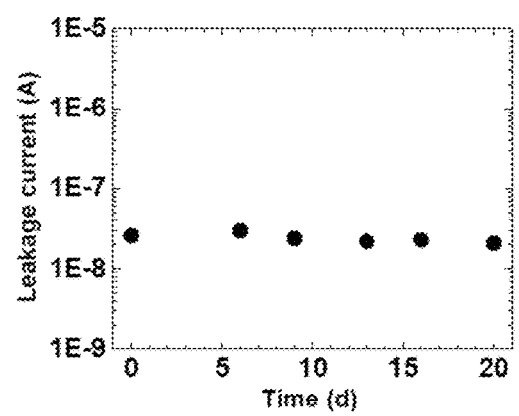
Figure 50D:
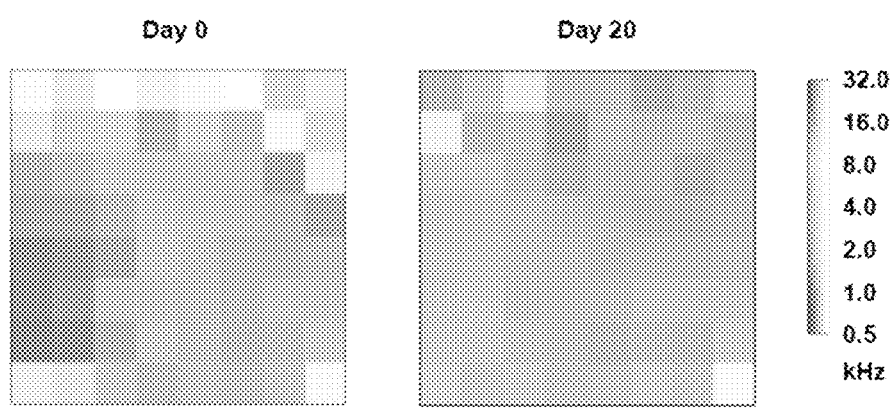

Supplementary Note 2: In Vivo Recording on a Canine Model Using the Flexible, Capacitively Coupled, Active Sensing Electrode Array (Covered by a Thermal SiO2 Layer):

Briefly, we performed in vivo measurements in an open chest canine preparation (FIGS. 49A-49B). A cocktail of midazolam, butorphanol, and ketamine anesthetized the animal. Isoflurane subsequently maintained surgical plane level anesthesia. A sternal thoracotomy opened the ribcage and exposed the thoracic cavity. An incision in the pericardium allowed access to the heart, while maintaining the structural support provided by the remainder of the pericardium. We placed the electrode array on the basal free wall of the left ventricle during sinus rhythm. We acquired data in two-minute intervals and subsequently analyzed.

Supplementary Note 3: In Vivo Recording of Rat Auditory Cortex Using the Flexible, Capacitively Coupled, Active Sensing Electrode Array (Covered by a Thermal SiO$_2$ Layer):

We made an in vivo recording of primary auditory cortex and surrounding areas in an anesthetized rat using the flexible, capacitively coupled, active sensing electrode array with 64 nodes (FIGS. 50A-50D). The array has the same circuit design as the 396-node device used in the ex vivo experiments with just fewer nodes. Auditory evoked potentials (AEPs) were recorded from the epidural surface in response to 13 tone frequencies that ranged between 500 Hz and 32 kHz in half-octave increments. Evoked-response signal-to-noise ratio, which measures variability of the 50 ms post-tone window with respect to baseline windows, was 5.0217±0.2898 (mean±S.E.M.), in good agreement with our previous results from passive electrode arrays[1]. A tonotopic map of the frequency eliciting the highest amplitude response at each site (i.e. best frequency) showed an expected dorsorostral-ventrocaudal oriented gradient of high to low frequencies[1,2]. A best frequency confidence value from 0-1 was computed by a cumulative distribution function evaluated with the sum of-squares of standardized z-scores of each site's tone responses[1]. Confidence, as depicted by the degree of color saturation in the tonotopic map, was higher for strongly responding sites and low for sites with little discernible response. Best frequency confidence (encoded by the color-saturation of the tonotopy heatmap) indicated strong AEPs at the majority of sites. Weakly responding sites were likely a result of non-auditory cortical areas and/or poor electrode contact with the epidural surface.

REFERENCES

1. Insanally M et al. A low-cost, multiplexed μECoG system for high-density recordings in freely moving rodents. J. Neural Eng. 2016; 13(2): 026030.
2. Polley D B, Read H L, Storace D A, Merzenich M M. Multiparametric auditory receptive field organization across five cortical fields in the albino rat. J. Neurophys. 2007; 97(5):3621-38.

We obtain videos of: 1. A flexible capacitively coupled sensing electronic system on a Langendorff-perfused rabbit heart model; 2. Voltage data from all electrodes illustrating the activation pattern of the heart during sinus rhythm; 3. Voltage data from all electrodes illustrating the paced activation pattern moving from the apex to base; 4. Voltage data from all electrodes illustrating the activation pattern of the heart during ventricular fibrillation.

Example 3: Transferred, Ultra-Thin Oxide Bilayers as Biofluid Barriers for Flexible Electronic Implants This example introduces a materials strategy that involves physically transferred, ultra-thin layers of silicon dioxide (SiO$_2$) thermally grown on silicon wafers and then coated with a longetivity-extending layer, including hafnium oxide (HfO$_2$) by atomic layer deposition (ALD), as barriers that satisfy requirements for even the most challenging flexible electronic devices. Materials and physics aspects of hydrolysis and ionic transport associated with such bilayers define their performance and reliability characteristics. Systematic experimental studies and reactive diffusion modeling suggest that the HfO$_2$ film, even with some density of pinholes, slows the dissolution of the underlying SiO$_2$ by orders of magnitude, independent of the concentration ions in the surrounding biofluids. Accelerated immersion tests that involve immersion in phosphate-buffered saline (PBS) solution at a pH of 7.4 and at a constant electrical bias demonstrate that this bilayer barrier can also obstruct the transport of ions that would otherwise cause drifts in the operation of the electronics. Theoretical drift-diffusion modeling defines the coupling of dissolution and ion diffusion, including their effects on device lifetime. Demonstrations of such barriers with passive and active components in thin, flexible electronic test structures highlight the potential advantages for wide applications in chronic bio-integrated devices.

Emerging classes of flexible hybrid electronics/optoelectronic devices offer attractive capabilities as active interfaces to biological systems of relevance to both clinical practice and biomedical research. Associated embodiments range from flexible filaments for optoelectronic stimulation of targeted neural circuits in the brain,[1-4] to conformal sheets for high-resolution multiplexed electrophysiological mapping on the epicardial surfaces.[5-9] Such platforms are of great interest because they can form minimally invasive interfaces to dynamic, soft biological systems, while providing performance characteristics that can approach those of conventional, wafer-based semiconductor devices.[10-20] A critical challenge in this field is in the development of materials that, in flexible, thin film form, can simultaneously serve as perfect barriers to biofluids and as high quality interfaces to the surrounding biology with multi-decade lifetimes.

An ideal material for this purpose must be biocompatible, with both exceptionally low flexural rigidity and water/ion permeability. Conventional encapsulation strategies, ranging from bulk metal/ceramic enclosures in standard implantable devices to organic/inorganic multilayer stacks in organic light emitting diode displays, fail, typically by orders of magnitude, to simultaneously meet both of these latter two critical requirements.[21-27] Even for materials that have minimal permeability, challenges in forming perfect, pinhole free coatings over large areas can be difficult or impossible to overcome, particularly in academic laboratory conditions. Example 1 above is a solution that involves a physically transferred layer of SiO$_2$ thermally grown on a pristine silicon wafer as an encapsulation layer. Results indicate extraordinary water barrier properties at thicknesses that allow both compliant mechanics and a high capacitance electrical measurement interface.[28] Due to its extremely low water permeability and pinhole-free nature, this type of barrier offers key advantages over conventional coatings, as extrapolated from temperature dependent studies of immersion in PBS solution. Additionally, the nature of the growth process and the transfer procedures eliminate the need for particulate-free fabrication environments. System demonstrators exploit 1-μm-thick layers of transferred thermal SiO$_2$ as water barriers and capacitive measurement interfaces in which backplanes of flexible silicon electronics provide amplification and multiplexed addressing for in vivo electrophysiological mapping on the brain and heart (Example 2).[29] An intrinsic limitation of this strategy is that the rates for hydrolysis of thermal SiO$_2$ (0.04 nm/day at 37° C.; ~90 nm/day at 96° C.) limit the ability to exploit ultra-thin film geometries (e.g. 100 nm thick or less) for enhanced capacitive coupling. Also, ions commonly present in bio-fluids, particularly sodium, can diffuse through thermal SiO$_2$ where they can shift and/or degrade the switching properties of the underlying transistors. The addition of silicon nitride can mitigate the diffusion issue, but its rate of hydrolysis exceeds that of SiO$_2$,[30] thereby requiring its use as an underlayer, away from the biofluid interface.

Presented in this example are materials, designs, and integration strategies for an ultra-thin, transferred barrier that combines thermally grown SiO$_2$ with a coating of HfO$_2$ formed by ALD. By comparison to single layer systems of thermal SiO$_2$, systematic experimental studies and reactive diffusion modeling suggest that this bilayer barrier can offer significantly enhanced longevity for underlying flexible electronics, at ultra-thin geometries. Accelerated immersion tests demonstrate that the HfO$_2$ slows the dissolution of the underlying SiO$_2$ in simulated bio-fluids by orders of magnitude, even when present with some density of pinholes. Additional results establish aspects of ionic transport through such materials via measurements of electrostatically induced shifts in the electrical properties of the underlying transistors. A combination of soak tests and temperature dependent simulations provide foundational understanding of the role of two competing failure mechanisms—dissolution and ion diffusion—on device lifetime. The findings indicate that this bilayer barrier offers excellent capabilities of relevance to a diverse range of bio-integrated flexible electronic devices. Accordingly, any of the methods and devices provided herein may comprise an encapsulation with at least one additional layer, such as any of the longevity-extending layers described herein.

Figure 61A:
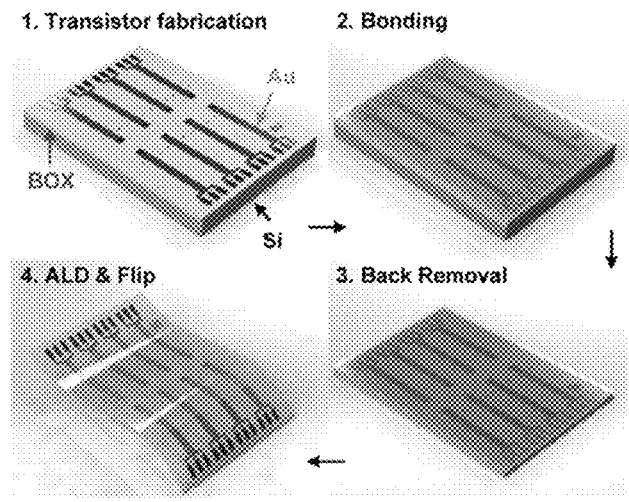
FIGS. 61A-61D. Transferred, ultra-thin bilayer of $SiO_2$ thermally grown on silicon wafers and $HfO_2$ formed by ALD serve as excellent barriers to biofluids and ions in flexible electronic implants.
Figure 66:
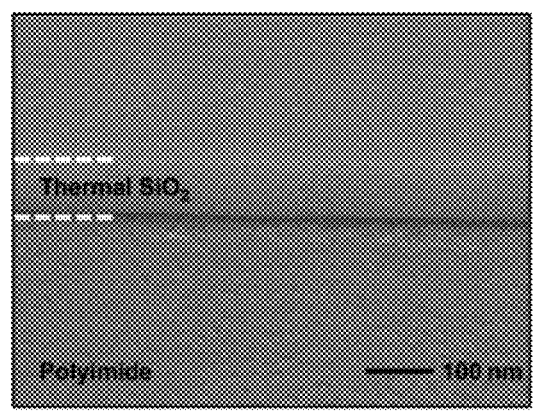
FIG. 66. The SEM image in 45° view of a 100-nm thermal $SiO_2$ above the Polyimide layer, of the test vehicle, as shown in FIG. 61D.

Standard semiconductor processing strategies in growth and transfer printing enable the fabrication of high quality electronics directly on oxide layers as the barriers to bio-fluids (FIG. 61A). The scheme used here combines some aspects of conventional strategies in which deposition of encapsulation material occurs as a last step, with alternatives of Examples 1 and 2, in which device processing occurs in a layer-by-layer fashion on an pre-formed encapsulation or barrier layer. FIG. 61A outlines the four main steps. Briefly, electronic devices formed on an ultra-thin layer of thermal SiO$_2$ on a silicon wafer transfer, with the SiO$_2$, onto a flexible plastic substrate. Subsequently, deposition of HfO$_2$ by ALD forms a capping layer on the top, exposed surface of the SiO$_2$. For the studies reported here, the electronics comprises an array of transistors form on a silicon-on-insulator (SOI) wafer (~100 nm thick device Si and 300 nm thick buried thermal SiO$_2$) with the device Si (silicon nanomembranes, Si NMs) as the active channel material. The transfer process bonds the front side of the wafer to a thin polyimide film laminated on a glass plate as a temporary support. Inductively coupled plasma reactive ion etching removes the silicon wafer and simultaneously reduces the buried thermal SiO$_2$ thickness to 100 nm, as shown in FIG. 66. Peeling the device from the glass after depositing HfO$_2$ (100 nm thick, by a rate of 1.07 Å/cycle in 200° C.) by ALD on the SiO$_2$ yields a piece of flexible electronics encapsulated by an ultra-thin bilayer barrier of HfO$_2$/SiO$_2$ that itself has good bendability by virtue of its small combined thickness.

Figure 61B:
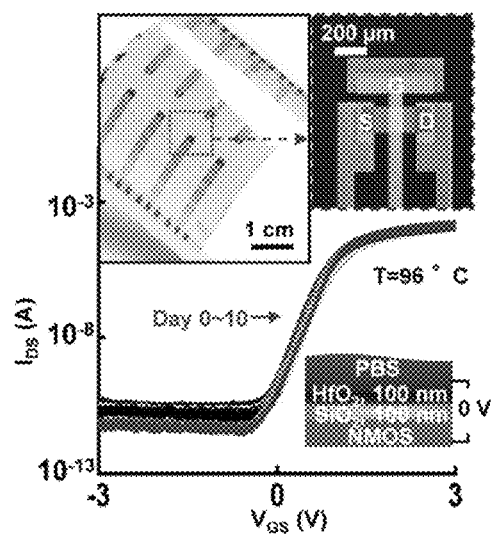
Figure 61C:
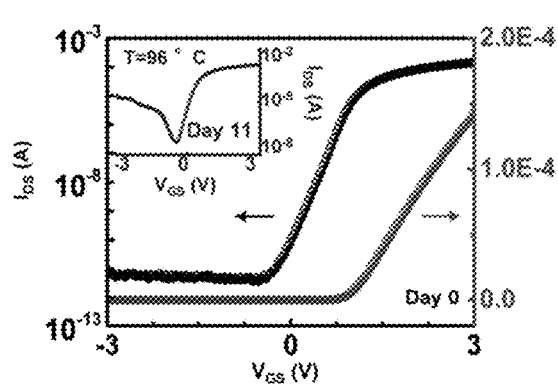

The two upper insets of FIG. 61B are optical images of flexible electronics with a set of NMOS transistors (channel length L=20 μm, width W=200 μm). The bilayer barrier consists of a 100 nm thick capping layer of ALD HfO$_2$ (bio-fluids side) and 100 nm thick underlying layer of thermal SiO$_2$ (device side), as illustrated in the lower inset. Results of accelerated soak tests of NMOS transistors while immersed in PBS solution with a pH of 7.4 at a temperature of 96° C. are in FIG. 61B, in the form of transfer characteristics of a representative transistor at a supply voltage $V_{DS}$=0.1 V. Here, the accelerated tests refer to those performed at elevated temperatures to increase the rate of the hydrolysis reaction. At Day 0, FIG. 61C demonstrates the transfer characteristics in both linear and semi-log scales. The on/off current ratio is ~$10^8$ and the peak effective electron mobility is ~400 cm$^2$/V.s. All transistors exhibit stable performance for 10 days (FIG. 61B) until a sudden failure at Day 11 (inset of FIG. 61C). Previous research indicates that although the water permeability through thermal SiO$_2$ is extremely small, a slow hydrolysis process (SiO$_2$+2H$_2$O→Si(OH)$_4$, corresponding to a dissolution rate of ~90 nm/day in 96° C. PBS solution at a pH of 7.4) consumes the material, thereby leading to eventual failure. By comparison, a 100/100 nm thick bilayer of HfO$_2$/SiO$_2$ barrier has a lifetime ~10 times longer than that of an isolated 100 nm thick layer of thermal SiO$_2$ barrier (~1 day in the same condition, consistent with the dissolution rate of ~90 nm/day in previous report), as displayed in FIG. 67A. A single layer of HfO$_2$ (100 nm thick) fails quickly due to a small, but finite density of pinholes, as in FIG. 67B. As a result, the HfO$_2$/SiO$_2$ bilayer, in which the HfO$_2$ slows the dissolution of the SiO$_2$ and the SiO$_2$ forms a defect-free barrier, can provide an attractive solution to the challenge of chronic encapsulation of thin, flexible electronics. A corresponding schematic illustration of the multilayer configuration is in FIG. 61D, as an exploded-view.

Soak tests using setups that incorporate thin films of magnesium (Mg), as in FIGS. 62A-62C, instead of transistors can facilitate rapid evaluation of various water barriers. The strong reactivity of Mg with water (Mg+2H$_2$O→Mg(OH)$_2$+H$_2$) leads, upon exposure, to defects that are immediately and easily visible by optical microscopy. Here, a 200×400 μm$^2$ pad of 300 nm thick layer of Mg deposited by electron-beam evaporation serves, in this manner, as a water-penetration sensor to test the barrier properties of different layers deposited or transferred on top. FIG. 62A shows a schematic illustration of a test setup (FIG. 62B), for which accelerated testing involves continuous immersion in PBS solution at 96° C. For present purposes, the barrier lifetime corresponds to the period between immersion and the appearance of the first defect observable on the Mg pad by optical microscopy. This criteria has practical value because the lifetimes (days) for systems of interest here are much longer than the time (minutes to hours) for an initial defect in the Mg pad to propagate laterally across its entire spatial extent. As a result, uncertainties in the time to identify the first observable defect are much smaller than the lifetime itself.

As shown in the single-layer row in FIG. 62C, the device encapsulated by a 100 nm thick layer of thermal SiO$_2$ survives for 30 hours, after which time the entire Mg layer dissolves at once, in a 'bulk' mode, by consequence of the spatially uniform dissolution of SiO$_2$, at a consistent rate of ~90 nm/day at 96° C. (0.04 nm/day at 37° C.)[28] and its pinhole free nature. The addition of a layer of HfO$_2$, which itself is insoluble in water (inset of FIG. 68), can dramatically increase the time for failure of the SiO$_2$ layer by hydrolysis. The main limitation of using HfO$_2$ alone is the nearly unavoidable formation of pinholes or other defects across the area of interest during deposition in the type of cleanroom environments available to academic labs. Under our experimental conditions, degradation of Mg with a single layer of HfO$_2$ as a barrier occurs in a very short time in FIG. 62C (see also FIG. 68) due to these defects. Nevertheless, diffusion of water through the HfO$_2$ can be significantly impeded, with consequent reductions on the rate of dissolution of the underlying SiO$_2$.

These observations motivate the use of a bilayer barrier that combines thermal SiO$_2$ (device side) (encapsulation layer) and HfO$_2$ (contact with PBS or surrounding biofluid during implantation) (longevity-extending layer). Here, the SiO$_2$ serves as a water-impermeable barrier without defects, and HfO$_2$ serves as an insoluble, capping layer that slows the dissolution of the SiO$_2$. The HfO$_2$/SiO$_2$ (100/100 nm thick) bilayer, as shown in the second row of FIG. 62C, leads to isolated defects in the Mg pad after 10 days, which then expand to consume the entire layer of Mg in a few hours (consistent with active-transistor results in FIG. 61B). Here isolated defects in the Mg appear at a density of 3~4 per pad (200×400 µm$^2$). Experiments performed in the same manner but with various other capping materials provide points of comparison. Polymers, for example, lead to Mg degradation in a 'bulk' mode, associated with water permeation across the entire area (see Table 2). Others, such as platinum/titanium, display more severe pinhole issues and much shorter lifetimes compared to the bilayer barrier of HfO$_2$/SiO$_2$. Another possibility is SiN$_x$, but its dissolution rate in PBS solution surpasses that of thermal SiO$_2$ by orders of magnitude.[30] As shown in FIG. 62C, the performance of HfO$_2$/SiO$_2$ bilayer barrier is superior to all other combinations explored, due to a combination of low water diffusivities, small pinhole densities and low effective dissolution rates for HfO$_2$.

Figure 61D:
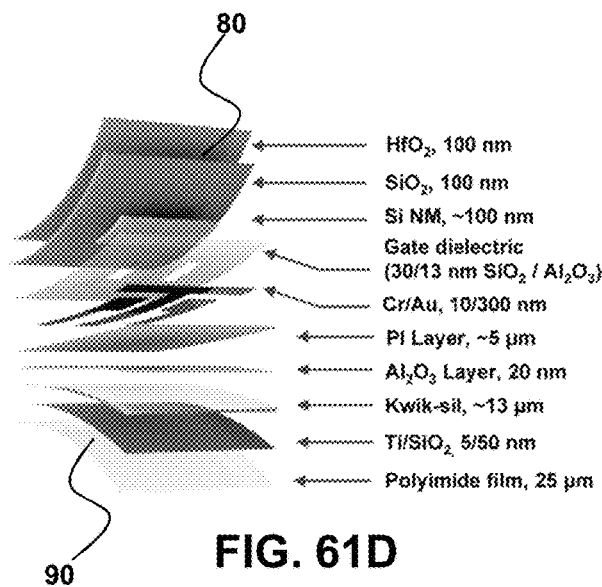
Figure 84:
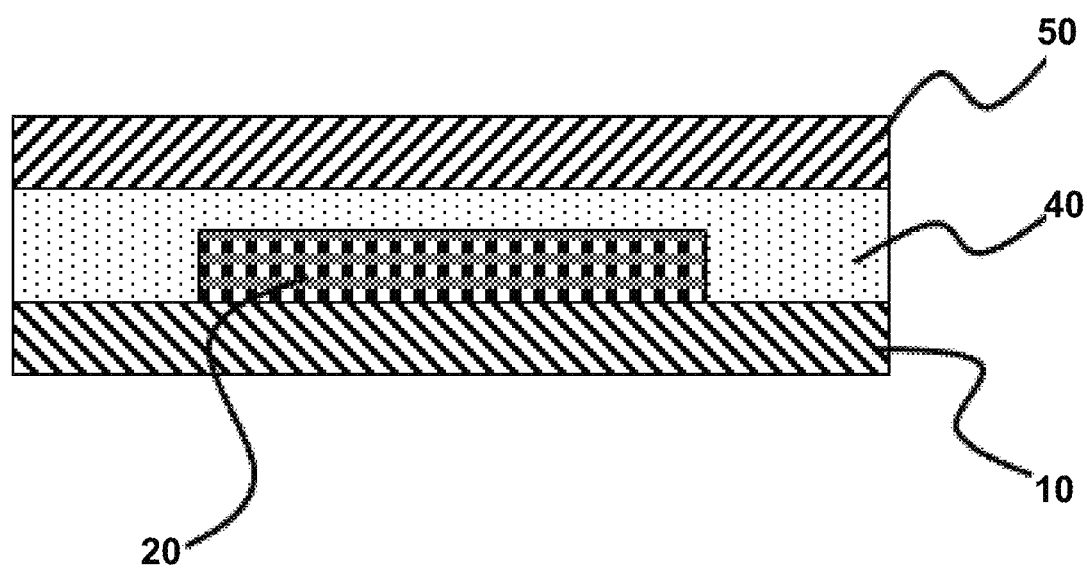
FIG. 84 is a schematic drawing of an electronic device 20 encapsulated with encapsulation layers 40 that are thermally oxidized layers from different substrates 10 and 50, thereby providing beneficial long-term implantation characteristics.
Figure 85:
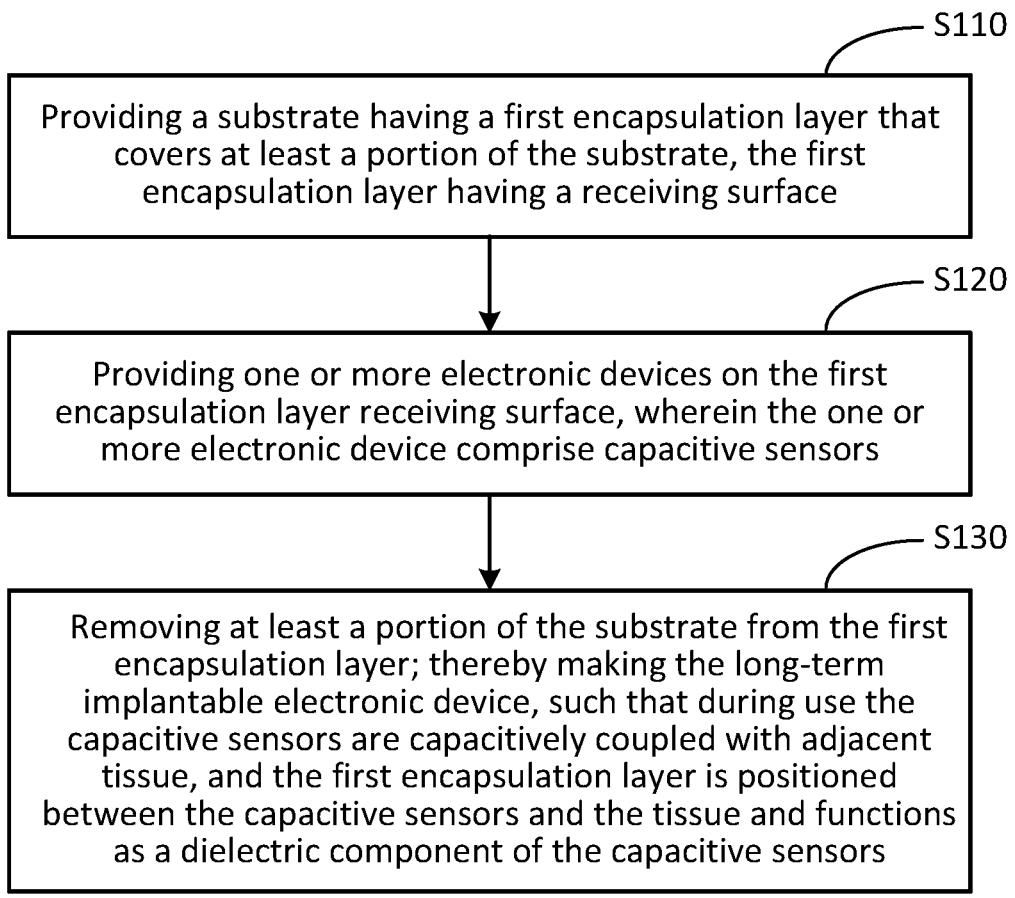
FIG. 85 is a schematic flowchart of a method for making a long-term implantable electronic device according to one embodiment of the invention. The method includes, at step S110, providing a substrate having a first encapsulation layer that covers at least a portion of the substrate, the first encapsulation layer having a receiving surface; at step S120, providing one or more electronic devices on the first encapsulation layer receiving surface, the one or more electronic device comprising capacitive sensors; and at step S130, removing at least a portion of the substrate from the first encapsulation layer, thereby making the long-term implantable electronic device, such that during use the capacitive sensors are capacitively coupled with adjacent tissue, and the first encapsulation layer is positioned between the capacitive sensors and the tissue and functions as a dielectric component of the capacitive sensors.

Referring to the figures, including FIGS. 21A, 61D and 84 first encapsulation layer is formed of a from a first thermally oxidized layer from a first substrate 10, and an electronic device 20 is supported by the first encapsulation layer. Exposed surfaces 30 of the first encapsulation layer and electronic device are covered by a barrier layer 40. Second thermally oxidized layer 55 from a second substrate 50 forms a second encapsulation layer in contact with the barrier layer 40. A top substrate 60 is adhered to the barrier layer, and may have a thermally oxidized encapsulation layer 70. First 80 and second 90 longevity extending layers in contact with first and second encapsulation layers may further extend the implanted device lifetime.

Figure 63A:
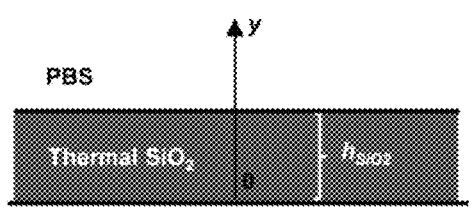
FIGS. 63A-63F. Theoretical modeling of reactive diffusion for the hydrolysis of thermal $SiO_2$ and $HfO_2/SiO_2$ barriers.

FIGS. 63A-63F show results of theoretical modeling of reactive diffusion in thermal SiO$_2$ and HfO$_2$/SiO$_2$ in PBS solution A one-dimensional single-layer model captures dissolution of thermal SiO$_2$, without any capping layer, since the initial thickness h$_0$ is much smaller than the lateral dimensions[31]. FIG. 63A presents a schematic illustration of the model, where y denotes the thickness direction, with y=0 at the bottom of the layer. The governing equation is[32]

$$D_{SiO_2} \frac{\partial^2 w}{\partial y^2} - k_{SiO_2} w = \frac{\partial w}{\partial t}, 0 \leq y \leq h_0, \quad (1)$$

where $D_{SiO_2}$ and $k_{SiO_2}$ are the diffusivity of water and the reaction constant between the SiO$_2$ and water, respectively, w is the water concentration, which depends on position y and time t. The boundary conditions can be written as $w|_{y=h_0}=w_0$ and $\partial w/\partial y|_{y=0}=0$, corresponding to a water concentration that is constant w$_0$ (=1 g cm$^{-3}$) at the water/SiO$_2$ interface and a water flux at the bottom surface of the thermal SiO$_2$ layer that is zero. The initial condition is zero water concentration in the thermal SiO$_2$, i.e., $w|_{t=0}=0$ (0≤y<h$_0$). The water concentration can be analytically solved by applying the method of separation of variables, which gives the thickness $h_{SiO_2}$ of the thermal SiO$_2$ layer as a function of time. For the present study, $$\frac{h_{SiO_2}}{h_0} \approx 1 - \frac{t}{t_{critical}}, \text{ where} \quad (2)$$

$$t_{critical} = \frac{h_0 q \rho_{SiO_2} M_{H_2O}}{w_0 M_{SiO_2} \sqrt{k_{SiO_2} D_{SiO_2}} \tanh \sqrt{\frac{k_{SiO_2} h_0^2}{D_{SiO_2}}}} \quad (3)$$

is the critical time for full dissolution of the thermal SiO$_2$. Here q (=2) is the number of water molecules that react with each atom of SiO$_2$, $\rho_{SiO_2}$ is the mass density of thermal SiO$_2$ (=2.33 g cm$^{-3}$), $M_{SiO_2}$ (=60 g mol$^{-1}$) and $M_{H_2O}$ (=18 g mol$^{-1}$) are the molar masses of SiO$_2$ and water, respectively.

Figure 63B:
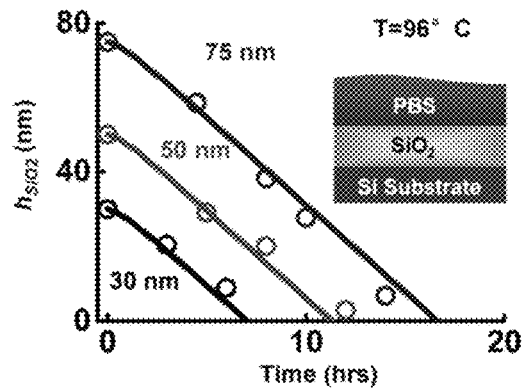

From soak tests of thermal SiO$_2$ in PBS solution, the diffusivity $D_{SiO_2}$ and reaction constant $k_{SiO_2}$ can be extracted using this model as $D_{SiO_2}$=1.5×10$^{-16}$ cm$^2$ s$^{-1}$ and $k_{SiO_2}$=2×10$^{-4}$ s$^{-1}$ at 96° C. These values fall within the range of those inferred from previous studies for PECVD SiO$_2$ (k=5.3×10$^{-5}$~8.1×10$^{-3}$ s$^{-1}$)[31] and silica glass (D=2.1×10$^{-18}$~1.3×10$^{-14}$ cm$^2$ s$^{-1}$).[33, 34] The two constants at the other temperatures can be inferred from those at 96° C. by experimentally measured dissolution rates and the Arrhenius equation, with an apparent activation energy $E_A$=1.32 eV.[28] FIG. 63B shows the change in the thickness of the thermal SiO$_2$ with time in PBS solution at 96° C. The simulated results (lines) agree well with those measured (symbols; Mprobe Station (SemiconSoft, USA) for all three initial thicknesses, i.e., 30, 50, and 75 nm. For a layer of ALD HfO$_2$ submerged in PBS solution, experiments show that the thickness does not change with time (inset of FIG. 68), indicating that the reaction constant between HfO$_2$ and water is zero.

Figure 63C:
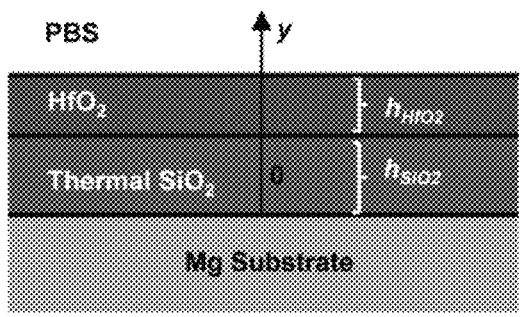

A bilayer model for the case of HfO$_2$/SiO$_2$ is in FIG. 63C. For the thermal SiO$_2$, the reactive diffusion equation (1), as well as the boundary condition $\partial w/\partial y|_{y=0}=0$ and initial condition $w|_{t=0}=0$, still apply. For the HfO$_2$ layer, the diffusion equation is $$D_{HfO_2} \frac{\partial^2 w}{\partial y^2} = \frac{\partial w}{\partial t} \ (h_0 \leq y \leq h_0 + h_{HfO_2}), \quad (4)$$

with the boundary condition $$w|_{y=h_0+h_{HfO_2}} = w_0$$

and initial condition $w|_{t=0}=0$ ($h_0 \leq y \leq h_0+h_{HfO_2}$), where $D_{HfO_2}$ is the diffusivity of water in $HfO_2$. The continuity of concentration and flux of water at the $HfO_2/SiO_2$ interface requires $w|_{y=h_0-0}=w|_{y=h_0+0}$ and $D_{SiO_2} \partial w/\partial y|_{y=h_0-0}=D_{HfO_2}\partial w/\partial y|_{y=h_0+0}$. By applying the method of separation of variables, an analytical solution for the water concentration for this bilayer model can be obtained, which gives the thickness of the thermal $SiO_2$ layer. For the present study, $$\frac{h_{SiO_2}}{h_0} \approx 1 - \frac{t}{t'_{critical}}, \text{ where} \quad (5)$$

$$t'_{critical} = \alpha t_{critical} \quad (6)$$

represents the time when the thermal $SiO_2$ layer completely disappears ($h_{SiO_2}=0$), i.e., the lifetime of the $HfO_2/SiO_2$ bilayer barrier. Here $$\alpha = 1 + \sqrt{D_{SiO_2} k_{SiO_2}} \frac{h_{HfO_2}}{D_{HfO_2}} \tanh \sqrt{\frac{k_{SiO_2} h_0^2}{D_{SiO_2}}}. \quad (7)$$

Figure 63D:
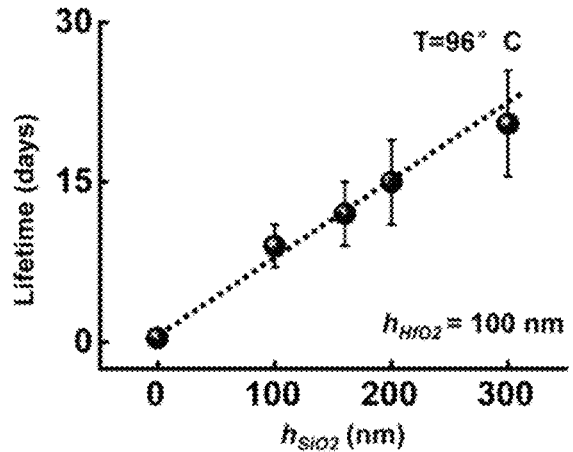
Figure 63E:
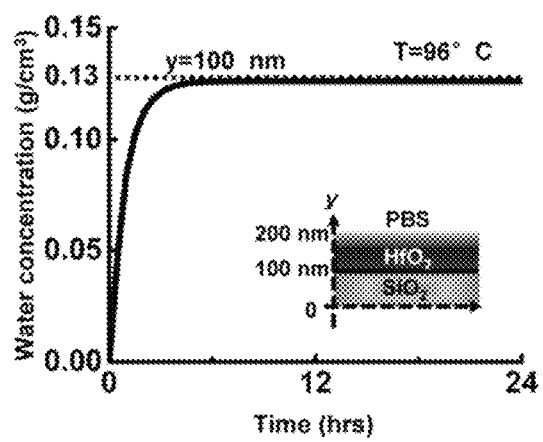
Figure 63F:
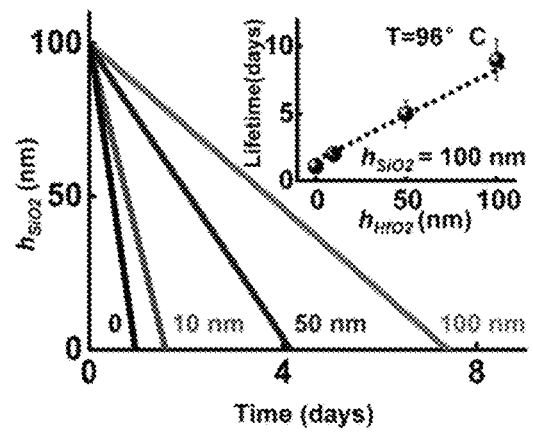

From soak tests, the diffusivity $D_{HfO_2}$ is determined from the bilayer model as $D_{HfO_2}=2.5\times10^{-16}$ cm$^2$ s$^{-1}$ at 96° C. For different polymer capping materials on thermal $SiO_2$, the soak tests in TABLE 2 yield the polymer diffusivities, e.g., $D_{SU-8}=7\times10^{-15}$ cm$^2$ s$^{-1}$, $D_{PI}=5.5\times10^{-15}$ cm$^2$ s$^{-1}$. The detailed simulated results of polymer/$SiO_2$ barriers appear in FIG. 69. The findings clearly indicate that the low water diffusivity of $HfO_2$ makes it superior to all examined polymers. FIG. 63D predicts the bilayer barrier lifetime as a function of the initial thermal $SiO_2$ thickness, for the case of a 100 nm thick $HfO_2$ layer. The simulated results (line) agree well with those measured (symbols). FIG. 63E shows the water concentration as a function of time at the interface (y=100 nm) of a 100/100 nm bilayer of $HfO_2/SiO_2$. The water concentration gradually reaches saturation at ~0.13 g cm$^{-3}$ at the $HfO_2/SiO_2$ interface after ~3 hours, revealing a fast equilibrium between reaction and diffusion. Here, $HfO_2$ serves as a passive layer to effectively mitigate the dissolution of the underlying $SiO_2$. FIG. 63F shows the changes in thickness of the $SiO_2$ in a bilayer barrier of $HfO_2/SiO_2$ with a 100 nm thick layer of $SiO_2$ and $HfO_2$ with initial thicknesses of 0, 10, 50, and 100 nm. The lifetime as a function of the initial $HfO_2$ thickness appears in the inset. The simulated results (line) show good agreement with those measured (symbols). The temperature-dependent lifetimes are also investigated. With $D_{HfO_2}$ at 96° C., the diffusivities at different temperatures can be determined according to the Arrhenius scaling, thus giving the lifetime as a function of temperature (FIG. 70) by Equation (6). Specifically, a bilayer barrier of $HfO_2/SiO_2$ (100/100 nm thick) offers a projected lifetime of over 40 years at 37° C. PBS (pH of 7.4).

Figure 64A:
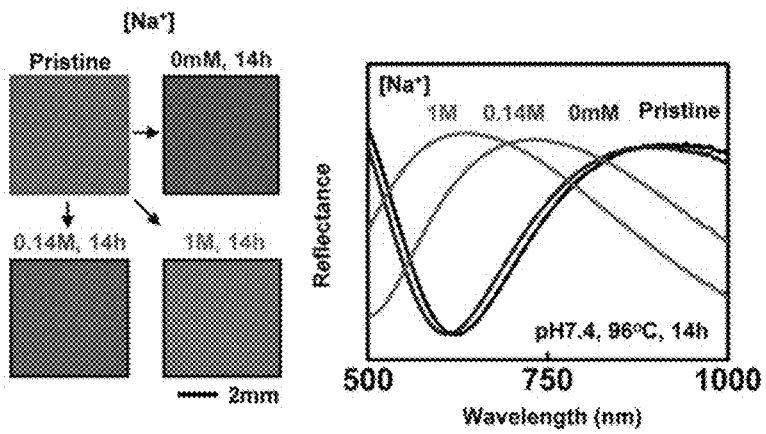
FIGS. 64A-64E. Ion effect on $SiO_2$ dissolution and lifetimes for thermally grown $SiO_2$ with/without a capping layer of $HfO_2$.
Figure 64B:
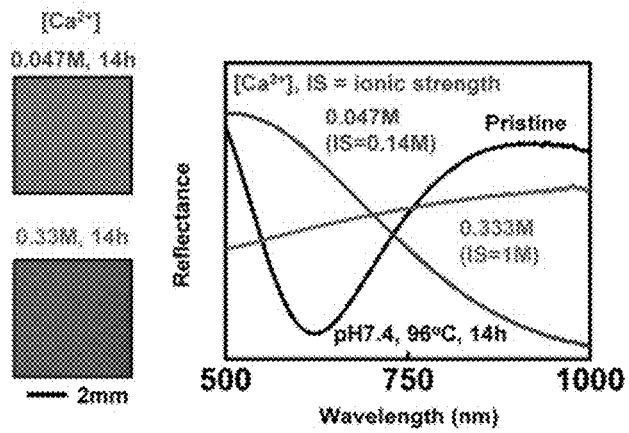
Figure 64C:
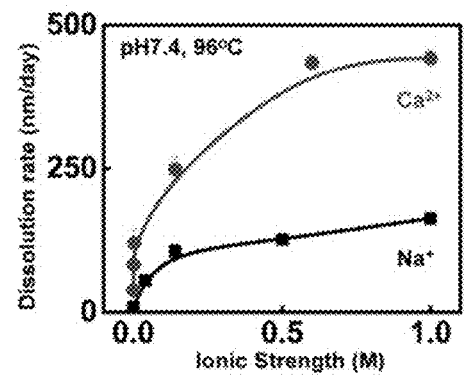

The enhanced lifetime indicates that the $HfO_2$ capping layer effectively delays the permeation of biofluid to the underlying $SiO_2$. Since biofluids contain not only water molecules but alkali metal ions that are known to accelerate the $SiO_2$ dissolution, parametric studies of different ionic concentrations provide additional insights into the underlying chemistry. FIGS. 64A-64E describe the ion effect on the dissolution of $SiO_2$ and its lifetime with/without $HfO_2$ capping layer. The solutions use 10 mM Tris to adjust the pH to a physiological condition, pH 7.4. FIG. 64A summarizes changes in the reflectance of a 320 nm thick single layer of thermal $SiO_2$ on a silicon wafer after soaking in different solutions with different concentrations of sodium chloride (NaCl), indicative of various [Na$^+$], for 14 hours at 96° C. The uniform color distributions are consistent with macroscopically uniform rates of dissolution for all values of [Na$^+$]. The peaks of the reflectance curves in FIG. 64A shift toward shorter wavelengths as the thicknesses decreases. The rates for these shifts increase with concentration, thereby demonstrating the catalyzing effect of Na$^+$ on dissolution. Previous studies show that alkali and alkaline metal ions accelerate the dissolution of quartz and other amorphous silica polymorphs in near-neutral pH solutions.[35-40] As an example for the systems studied here, FIG. 64B shows similar soaking results in solutions containing Ca$^{2+}$. Here, 0.047M and 0.333M calcium chloride (CaCl$_2$)) concentrations yield ionic strengths similar to those of the 0.14M and 1M NaCl solutions in FIG. 64A. The dissolution behavior depends more strongly on [Ca$^{2+}$], than [Na$^+$] at the same ionic strength. FIG. 64C summarizes the dissolution rates of thermal $SiO_2$ in solutions with various values of [Na$^+$] and [Ca$^{2+}$], quantitatively determined from the reflectance data in FIGS. 64A-64B. The results indicate that the presence of Ca$^{2+}$ could determine the lifetime of the $SiO_2$ layer even when its concentration is lower than that of Na$^+$. According to studies in the literature, cations facilitate deprotonation of —OH groups on the surface of $SiO_2$ by shielding negative charges, as supported by empirical rate laws that indicate an increase in dissolution rates with surface charge.[38,39,41] Other experimental and computational evidence suggest that cations can modify the interfacial water structure to promote hydrolysis of Si—O—Si bonds.[37,40]

Figure 64D:
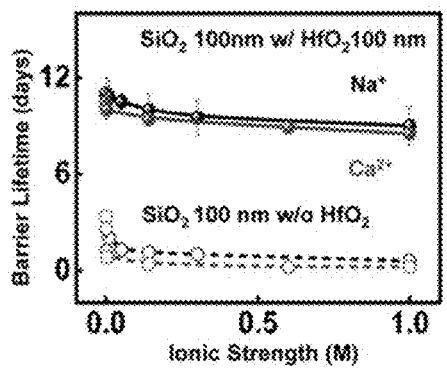
Figure 64E:
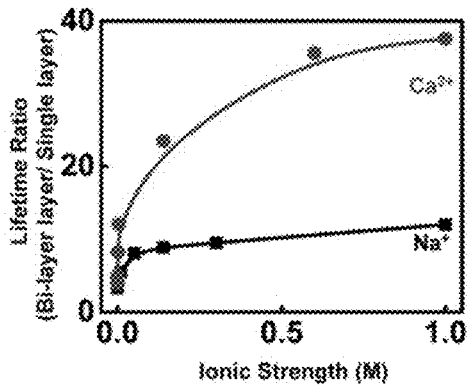

FIG. 64D shows results of experiments on the lifetimes of a 100 nm thick layer of thermal $SiO_2$ with/without an $HfO_2$ capping layer, all in the presence of ions. The two dotted curves correspond to lifetimes in Na$^+$ (black) and Ca$^{2+}$ (red) containing solutions. The results are consistent with the dissolution rates of $SiO_2$ (FIG. 64C). The solid lines show prolonged lifetimes with the addition of the 100 nm thick capping layer of $HfO_2$. As with the single layer of $SiO_2$ barrier, the results for $HfO_2/SiO_2$ barrier show longer lifetimes in Na$^+$ solutions than in Ca$^{2+}$ solutions at the same ionic strength. Compared to 100 nm thick layer of thermal $SiO_2$, the bilayer barrier of $HfO_2/SiO_2$ (100/100 nm thick) enhances the lifetime by a factor of ten. FIG. 64E calculates the lifetime ratios between the bilayer of $HfO_2/SiO_2$ barrier (100/100 nm thick) and single layer of thermal $SiO_2$ barrier (100 nm thick) at each ionic strength. This ratio increases up to a certain level as the ionic strength increases. In the same context, the $HfO_2/SiO_2$ more strongly mitigates the diffusion of Ca$^{2+}$ rather than Na$^+$, possibly due to a larger hydrated ionic radius and higher positive charge of Ca$^{2+}$ compared to Na$^+$.[42]

Figure 65A:
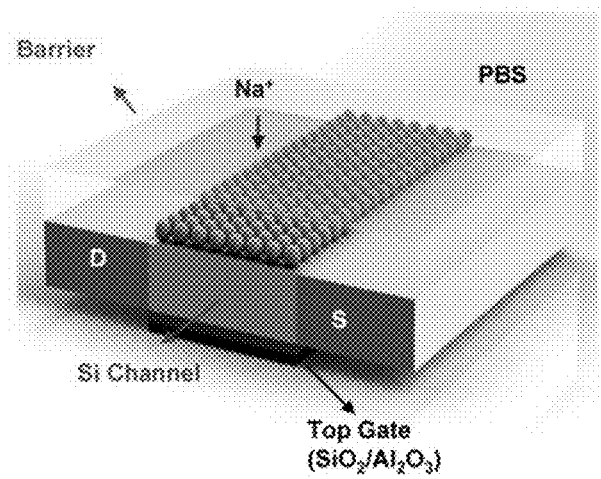
FIGS. 65A-65E. Experimental and simulation results for the behavior of NMOS transistors encapsulated with $SiO_2$ and $HfO_2/SiO_2$ barriers in various tests of immersion in PBS solution at pH 7.4 and 96° C.
Figure 65B:
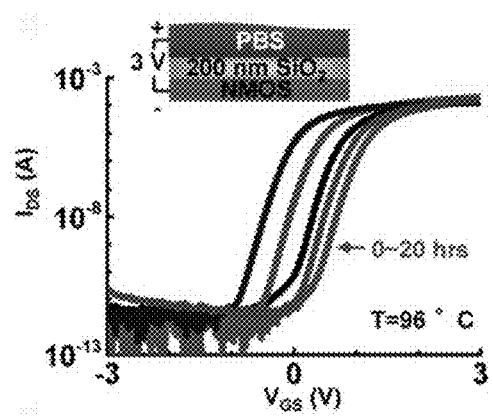
Figure 65C:
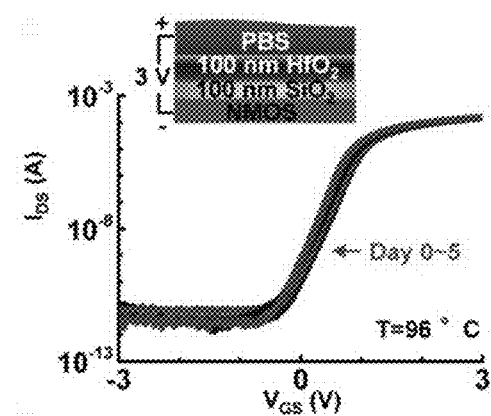

In addition to their effects on dissolution, ions in biofluids (mostly positive species such as Na$^+$) that diffuse through the barriers can adversely affect the performance of underlying transistors, mainly by electrostatically shifting their threshold voltages ($V_T$).[43] Specifically, ion diffusion in PBS can accumulate a layer of positive ions (most Na$^+$) at the transistor channel, as schematically illustrated in FIG. 65A, thus leading to an additional electric field that acts in concert with the gate voltage ($V_G$) at the transistor front gate. These positive ions give rise to a positive enhancement to $V_G$. As a result, the transistor switches on with a more negative $V_G$ at the front gate, corresponding to a negative shift in $V_T$ for an NMOS device. Ion drift-diffusion tests on encapsulated NMOS transistors (layer configuration shown in FIG. 61D) allow comparisons of HfO$_2$/SiO$_2$ and SiO$_2$ as ion barriers. Results of accelerated soak tests of NMOS transistors during application of an external bias while immersed in PBS solution at 96° C. and pH of 7.4 are in FIGS. 65B-65C. The bias (V$_{app}$, 3 V) exists between a platinum probe in the PBS solution and the transistor electrodes (source, drain and gate), as illustrated in the insets. For present purposes, device failure is defined as the point when the shift in the threshold voltage ΔV$_T$ reaches 1 V. The positive V$_{app}$ serves as a driving force to impel positive ion transport through barriers, the result of which shifts V$_T$ of transistors under a 200 nm thick layer of SiO$_2$ barrier by electrostatic interactions with the Si channel, as shown in FIG. 65B. As in FIG. 65C, the key performance characteristics of transistors with bilayer barriers of HfO$_2$/SiO$_2$ (100/100 nm thick) remain constant in accelerated soak tests (in 96° C. PBS solution) over the full duration of the experiments. The results demonstrate that the bilayer of HfO$_2$/SiO$_2$ barriers can effectively retard ion diffusion process compared to the single layer of SiO$_2$ barriers.

Figure 65D:
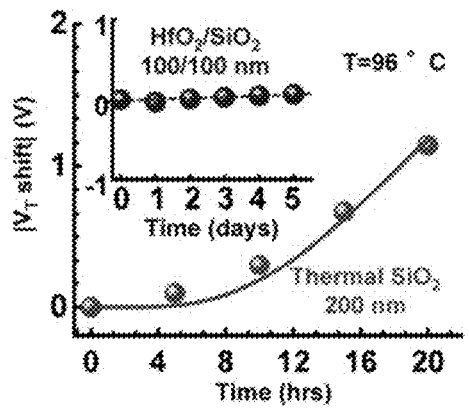
Figure 65E:
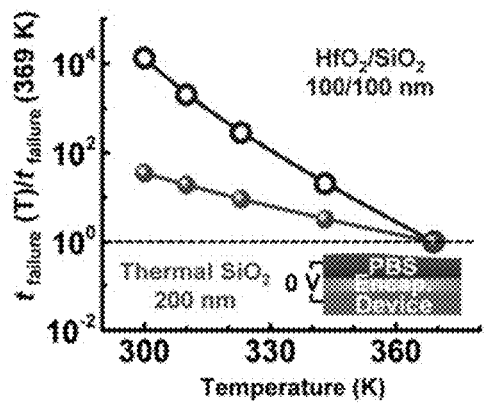
Figure 71:
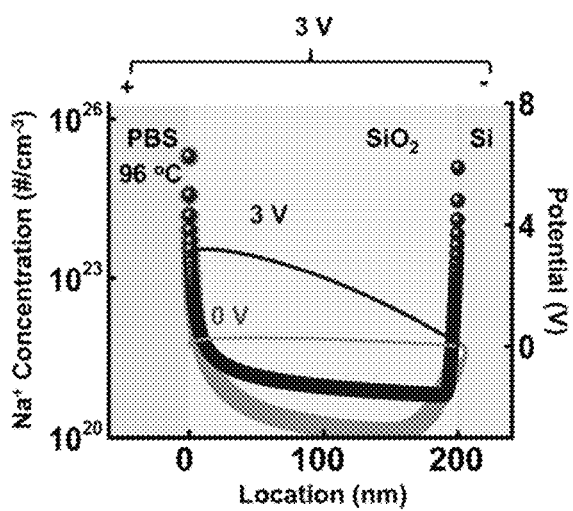
FIG. 71. Computed [$Na^+$] concentration profiles and potential distributions within a layer of thermal $SiO_2$ after 1 days of immersion in PBS at T=96° C. The applied bias is 0 and 3V.

Results of modeling of Na$^+$ transport processes appear in FIGS. 65D-65E. Here, FIG. 65D shows the shift in V$_T$ extracted from FIG. 65B for a 200 nm thick layer of SiO$_2$ within 1 day with V$_{app}$=3 V at T=96° C. The drift-diffusion is closely related to the layer of surface charge density Q$_s$ of Na$^+$ located at the thermal SiO$_2$/substrate Si interface (FIG. 71). To find the relationship between Q$_S$ and ΔV$_T$, we numerically simulate a 2D NMOS transistor with commercial software (Sentaurus Technology Computer Aided Design) using experimentally determined device parameters. The numerical result predicted by this model (red solid lines) fits well with experimental data (red solid dots), as displayed in FIG. 65D. The inset of FIG. 65D presents values of ΔV$_T$ extracted from data in FIG. 65C with a 100/100 nm thick bilayer of HfO$_2$/SiO$_2$ barrier. Here, the shifts in V$_T$ are extraordinarily small (less than ~0.05V) in all cases, which further support the outstanding properties of HfO$_2$/SiO$_2$ as bilayer ion barriers.

Modeling can also capture the competition between dissolution and ion diffusion in SiO$_2$ and HfO$_2$/SiO$_2$. FIG. 65E presents such competition for a 200 nm thick layer of thermal SiO$_2$ and a 100/100 nm thick bilayer of HfO$_2$/SiO$_2$, respectively, both of which form on transistors. The inset of FIG. 65E displays the configuration without V$_{app}$. We consider an acceleration factor (AF) for the failure time as a function of temperature, considering both dissolution and ion diffusion failures together. In all cases, device failure corresponds to the point when the SiO$_2$ disappears due to hydrolysis or when the shift in the threshold voltage ΔV$_T$ reaches 1V. The AF is defined as t$_{failure}$ (T)/t$_{failure}$ (369K), normalized at 369K. The temperature-dependent Na$^+$ diffusion coefficient follows an Arrhenius relationship: D=D$_0$·e$^{-E_A/kT}$, where k is the Boltzmann constant and T is temperature. D$_0$ is the pre-exponential factor and E$_A$ is the activation energy. We extracted D$_0$ and E$_A$ from the data of FIG. 65D. For the single layer of SiO$_2$ barrier, ion penetration dominates the failure time, because the corresponding dissolution failure time is much longer than that of the ion-diffusion process. On the other hand, the bilayer of HfO$_2$/SiO$_2$ barrier offers improved ion-barrier properties. Here, dissolution plays an important role. The AF of HfO$_2$/SiO$_2$ (100/100 nm thick) uses the dissolution failure time from FIG. 63D (369 K) and corresponding simulations for other temperatures in FIG. 70. A bilayer of HfO$_2$/SiO$_2$ barrier offers a projected lifetime of over 40 years at 37° C. PBS (pH of 7.4), leading to a much higher AF (3 orders of magnitude) than that of SiO$_2$, due to the enhanced ion-barrier properties.

In summary, the use of a coating longevity coating, such as HfO$_2$, on top of ultra-thin layers of encapsulation layers, such as SiO$_2$ thermally grown on device-grade silicon wafers, can provide excellent water/ion barrier performance for flexible electronic devices. A comprehensive combination of experiments and simulations highlights the underlying physical and chemical effects associated with this type of bilayer barrier. Implementing these strategies in active flexible electronic and optoelectronic platforms provides a platform for a wide range of chronic studies in animals and for use in advanced bio-electronic implants in humans.

Example 3 References

[1] J.-W. Jeong, J. G. McCall, G. Shin, Y. Zhang, R. Al-Hasani, M. Kim, S. Li, J. Y. Sim, K. I. Jang, Y. Shi, D. Y. Hong, Y. Liu, G. P. Schmitz, L. Xia, Z. He, P. Gamble, W. Z. Ray, Y. Huang, M. R. Bruchas, J. A. Rogers, *Cell,* 2015, 162(3), 662-674.

[2] K. L. Montgomery, A. J. Yeh, J. S. Ho, V. Tsao, S. M. Iyer, L. Grosenick, E. A. Ferenczi, Y. Tanabe, K. Deisseroth, S. L. Delp, A. S Y. Poon, *Nature Methods,* 2015, 12(10), 969-974.

[3] T. Kim, J. G. McCall, Y. H. Jung, X. Huang, E. R. Siuda, Y. Li, J. Song, Y. M. Song, H. A. Pao, R.-H. Kim, C. Lu, S. D. Lee, I.-S. Song, G. Shin, R. Al-Hasani, S. Kim, M. P. Tan, Y. Huang, F. G. Omenetto, J. A. Rogers, M. R. Bruchas, *Science,* 2013, 340(6129), 211-216.

[4] A. Canales, X. Jia, U. P. Froriep, R. A. Koppes, C. M. Tringides, J. Selvidge, C. Lu, C. Hou, L. Wei, Y. Fink, P. Anikeeva, *Nature Biotechnology,* 2015, 33(3), 277-284.

[5] J. Viventi, D.-H. Kim, J. D. Moss, Y.-S. Kim, J. A. Blanco, N. Annetta, A. Hicks, J. L. Xiao, Y. Huang, D. J. Callans, J. A. Rogers, B. Litt, *Science translational medicine,* 2010, 2(24), 24ra22.

[6] D.-H. Kim, N. S. Lu, R. Ghaffari, Y.-S. Kim, S. P. Lee, L. Xu, J. Wu, R.-H. Kim, J. Song, Z. Liu, J. Viventi, B. d. Graff, B. Elolampi, M. Mansour, M. J. Slepian, S. Hwang, J. D. Moss, S.-M. Won, Y. Huang, B. Litt, J. A. Rogers, *Nature Materials,* 2011, 10(4), 316-323.

[7] L. Xu, S. R. Gutbrod, A. P. Bonifas, Y. Su, M. S. Sulkin, N. Lu, H.-J. Chung, K.-I. Jang, Z. Liu, M. Ying, C. Lu, R. C. Webb, J.-S. Kim, J. I. Laughner, H. Cheng, Y. Liu, A. Ameen, J.-W. Jeong, G.-T. Kim, Y. Huang, I. R. Efimov, J. A. Rogers, *Nature Communications* 5, 2014, DOI:10.1038/ncomms4329.

[8] D.-H. Kim, R. Ghaffari, N. Lu, S. Wang, S. P. Lee, H. Keum, R. D'Angelo, L. Klinker, Y. Su, C. Lu, Y.-S. Kim, A. Ameen, Y. Li, Y. Zhang, B. d. Graff, Y.-Y. Hsu, Z. Liu, J. Ruskin, L. Xu, C. Lu, F. G. Omenetto, Y. Huang, M. Mansour, M. J. Slepian, J. A. Rogers, *Proceedings of the National Academy of Sciences,* 2012, 109(49), 19910-19915.

[9] X. Dai, W. Zhou, T. Gao, J. Liu, C. M. Lieber, *Nat. Nanotechnol.,* 2016, 11, 776-782.

[10] B. Tian, T. Cohen-Karni, Q. Qing, X. J. Duan, P. Xie, C. M. Lieber *Science,* 2010, 329(5993), 830-834.

[11] R. Nawrocki, N. Matsuhisa, T. Yokota, T. Someya, *Adv. Electron. Mater.,* 2015, 2(1500452), 1-4.

[12] D.-H. Kim, N. Lu, R. Ma, Y.-S. Kim, R.-H. Kim, S. Wang, J. Wu, S. M. Won, H. Tao, A. Islam, 1 K. J. Yu, T.-i. Kim, R. Chowdhury, M. Ying, L. Xu, M. Li, H.-J. Chung, H. Keum, M. McCormick, P. Liu, Y.-W. Zhang, F. G. Omenetto, Y. Huang, T. Coleman, J. A. Rogers, *Science,* 2011, 333(6044), 838-43

[13] D. J. Lipomi, M. Vosgueritchian, B. C. Tee, S. L. Hellstrom, J. A. Lee, C. H. Fox, Z. Bao, *Nature Nanotechnology*, 2011, 6(12), 788-792.

[14] M. C. McAlpine, H. Ahmad, D. Wang, J. R. Heath, *Nature Materials*, 2007, 6(5), 379-384.

[15] W. Gao, S. Emaminejad, H. Y. Nyein, S. Challa, K. Chen, A. Peck, H. M. Fahad, H. Ota, H. Shiraki, D. Kiriya, D. H. Lien, G. A. Brooks, R. W. Davis, A. Javey, *Nature*, 2016, 529(7587), 509-514.

[16] W. Wu, L. Wang, Y. Li, F. Zhang, L. Lin, S. Niu, D. Chenet, X. Zhang, Y. Hao, T. F. Heinz, J. Hone, Z. L. Wang, *Nature*, 2014, 514(7523), 470-474.

[17] S. Xu, Y. Zhang, L. Jia, K. E. Mathewson, K. I. Jang, J. Kim, H. Fu, X. Huang, P. Chava, R. Wang, S. Bhole, L. Wang, Y. J. Na, Y. Guan, M. Flavin, Z. Han, Y. Huang, J. A. Rogers, *Science*, 2014, 344(6179), 70-4.

[18] M. Kaltenbrunner, T. Sekitani, J. Reeder, T. Yokota, K. Kuribara, T. Tokuhara, M. Drack, R. Schwödiauer, I. Graz, S. Bauer-Gogonea, S. Bauer, T. Someya, *Nature*, 2013, 499(7459), 458-463.

[19] C. M. Lochner, Y. Khan, A. Pierre, A. C. Arias, *Nature Communications*, 2014, 5, 5745.

[20] D. Son, J. Lee, S. Qiao, R. Ghaffari, J. Kim, J. E. Lee, C. Song, S. J. Kim, D. J. Lee, S. W. Jun, S. Yang, M. Park, J. Shin, K. Do, M. Lee, K. Kang, C. S. Hwang, N. Lu, T. Hyeon, D.-H. Kim, *Nature Nanotechnology*, 2014, 9(5), 397-404.

[21] Thejo Kalyani N, Dhoble S J, *Renewable and Sustainable Energy Reviews*, 2015, 44, 319-347.

[22] L. Bowman, J. D. Meindl, *IEEE Transactions on Biomedical Engineering*, 1986, BME-33(2), 248-255.

[23] J.-S. Park, H. Chae, H. K. Chung, S. I. Lee, *Semiconductor Science and Technology*, 2011, 26(3), 034001.

[24] H. S. Mayberg, A. M. Lozano, V. Voon, H. E. McNeely, D. Seminowicz, C. Hamani, J. M. Schwalb, S. H. Kennedy, *Neuron*, 2005, 45(5), 651-660.

[25] B. S. Wilson, C. C. Finley, D. T. Lawson, R. D. Wolford, D. K. Eddington, W. M. Rabinowitz, *Nature*, 1991, 352(6332), 236-238.

[26] R. S. Sanders, M. T. Lee, *Proceedings of the IEEE*, 1996, 84(3), 480-486.

[27] J. Ahmad, K. Bazaka, L. J. Anderson, R. D. White, M. V. Jacob, *Renewable and Sustainable Energy Reviews*, 2013, 27, 104-117.

[28] H. Fang, J. Zhao, K. J. Yu, E. Song, A. B. Farimani, C.-H. Chiange, X. Jin, Y. Xue, D. Xu, W. Dui, K. J. Seo, Y. Zhong, Z. Yang, S. M. Won, G. Fang, S. W. Choi, S. Chaudhuri, Y. Huang, M. A. Alam, J. Viventi, N. R. Aluru, J. A. Rogers, *Proceedings of the National Academy of Sciences*, 2016, 113(42), 11682-11687.

[29] H. Fang, K. J. Yu, C. Gloschat, Z. Yang, E. Song, C.-H. Chiang, J. Zhao, S. M. Won, S. Xu, M. Trumpis, Y. Zhong, S. W. Han, Y. Xue, D. Xu, S. W. Choi, G. Cauwenberghs, M. Kay, Y. Huang, J. Viventi, I. R. Efimov and J. A. Rogers, *Nature Biomedical Engineering*, 2017, 1(3), 0038.

[30] S.-K. Kang, S.-W. Hwang, H. Cheng, S. Yu, B. H. Kim, J.-H. Kim, Y. Huang, J. A. Rogers, *Adv. Funct. Mater.*, 2014, 24, 4427.

[31] R. Li, H. Cheng, Y. Su, S.-W. Hwang, L. Yin, H. Tao, M. A. Brenckle, D.-H. Kim, F. G. Omenetto, J. A. Rogers, Y. Huang, *Advanced Functional Materials*, 2013, 23, 3106.

[32] P. V. Danckwerts, *Transactions of the Faraday Society*, 1950, 46, 300.

[33] K. M. Davis, M. Tomozawa, *Journal of Non-Crystalline Solids*, 1995, 185, 203.

[34] M. Tomozawa, K. M. Davis, *Materials Science and Engineering*, 1999, A272, 114.

[35] J. D. Rimstidt, *Geochim. Cosmochim. Acta*, 2015, 167, 195.

[36] P. M. Dove, N. Han, J. J. De Yoreo, *Proc. Natl. Acad. Sci. U.S.A.*, 2005, 102, 15357-62.

[37] P. M. Dove & D. A. Crerar, *Geochim. Cosmochim. Acta*, 1990, 54, 955.

[38] P. V. Brady, J. V. Walther, *Chem. Geol.*, 1990, 82, 253.

[39] M. Karlsson, C. Craven, P. M. Dove, W. H. Casey, *Aquat. Geochemistry*, 2001, 7, 13.

[40] O. Majérus, T. Gérardin, G. Manolescu, P. Barboux, D. Caurant, *Phys. and Chem. of Glasses—European Journal of Glass Science and Technology B*, 2014, 13, 261.

[41] K. C. Jena, P. A. Covert, D. K. Hore, *J. Phys. Chem. Lett.*, 2011, 2, 1056.

[42] P. M. Dove, P. M., C. J. Nix, *Geochim. Cosmochim. Acta*, 1997, 61, 3329.

[43] S. M. Sze (2008) Semiconductor devices: physics and technology ($2^{nd}$ edition). John Wiley & Sons, p. 183, USA, 2008.

Fabrication Methods for Transistors and Test Structures with Water Barrier: The process started with formations of isolated silicon transistors on an SOI wafer. Solid source doping with phosphorus yielded source and drain contacts at concentration level of p-doping $\sim 10^{19}$ cm$^{-3}$. Thermal oxidation and ALD yielded a dielectric stack of thermal $SiO_2$ (30 nm)/$Al_2O_3$(13 nm) at ~1150° C. and 80° C., respectively. Photolithographicaly patterned metallization (Cr/Au, 10/300 nm) defined source, drain and gate electrodes. A transfer process bonded the front side of this substrate to a thin polymer film (Kapton, DuPont, 13 μm) laminated onto a glass substrate coated with a layer of dimethylsiloxane (PDMS; 10 μm) as a temporary support. This process started with spin casting and curing a coating of polyimide (PI-2545, HD MicroSystems; 3.5 μm) uniformly across the transistors, followed by deposition of a thin layer of $Al_2O_3$ (20 nm). A commercial adhesive (Kwik-Sil, World Precision Instruments) enhanced the adhesion between the $Al_2O_3$ and the PDMS (coated with Ti (5 nm)/$SiO_2$ (50 nm)) on the temporary support. After bonding, inductively coupled plasma reactive ion etching (ICP-RIE, Surface Technology System) with gas flow of $SF_6/O_2$ 40/3 sccm at a pressure of 50 mT removed the silicon wafer. Subsequent RIE dry etching reduced thermal $SiO_2$ thickness with gas flow of $CF4/O_2$ 40/1.2 sccm at a pressure of 50 mT by a rate of 100 nm/5 min. In this manner, thermal $SiO_2$ can be tuned down to a selectable thickness, e.g. 100 nm (see FIG. 66). Selectively, a conformal layer of ALD $HfO_2$ (200° C., Ultratech/Cambridge Nanotech) formed on surface of thermal $SiO_2$ by a rate of 1.07 Å/cycle after an oxide layer cleaning procedure, which included a soaking in piranha solution (Sulfuric acid and hydrogen peroxide, volume ratio 1:1, at room temperature for 3 minutes) and then 5 minutes of Ultraviolet ozone (UVO) treatment. Peeling the device completed the process, yielding a bi-layer barrier of $HfO_2/SiO_2$.

For the transistor encapsulated by single layer of $HfO_2$, the fabrication process in this case began with transfer-printing[1] of Si nanomembranes (derived from the top silicon layer of SOI wafers) onto the $HfO_2$ surface coated with a layer of polyimide as an adhesive (diluted PI 2545, thickness <300 nm). Subsequent fabrication steps followed those described previously for the case of single layer $SiO_2$ encapsulation.

Analysis of Transistor Characteristics: The effective mobility ($\mu_{eff}$) can be extracted using the following equation:

$$\mu_{\text{eff}} = \frac{\partial I_{DS}}{\partial V_{DS}} \cdot \frac{L}{WC_{OX}(V_{GS} - V_T - 0.5V_{DS})} \quad \text{(S1)}$$

where $V_T$ is the threshold voltage and $C_{OX}$ is the specific capacitance of the gate per unit gating area, while the transistor gate area is 20×200 µm (L×W). Here we account for the lateral diffusion of phosphorus during activation. We subtract the total phosphorus diffusion length from the lithography length (L, 20 µm), thus yielding the effective channel length $L_{\text{eff}}$. The dopants diffusion length can be determined by the thermal process of phosphorus after doping, which is dominantly influenced during the thermal oxidation step for the gate oxide (1,150° C. for 37 min). Therefore the estimated value of $L_{\text{eff}}$ yields ~14 µm. As a result, the peak mobility is ~400 cm² (V·s)$^{-1}$, which is consistent with previous reports of Ref. 29.

Water Barrier Demonstrated with Performances of NMOS Transistor: All transistors were under electrical measurements in a series of accelerated soak tests. A well structure made of poly (dimethylsiloxane) (PDMS) confined the PBS solution within the central regions on the barrier layers (~1 cm²), thus eliminating any PBS penetration through the edges of the samples. UVO treatment of the surfaces of these oxide layers and the bottom surfaces of PDMS well structures ensures strong bonding of physical contact in order to yield a waterproof seal in various temperatures.

Figure 67A:
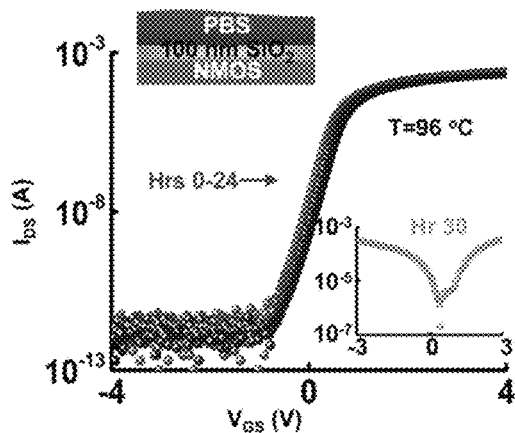
FIGS. 67A-67B. Results of accelerated soak tests of NMOS transistors with different single layer encapsulation in 96° C.
Figure 67B:
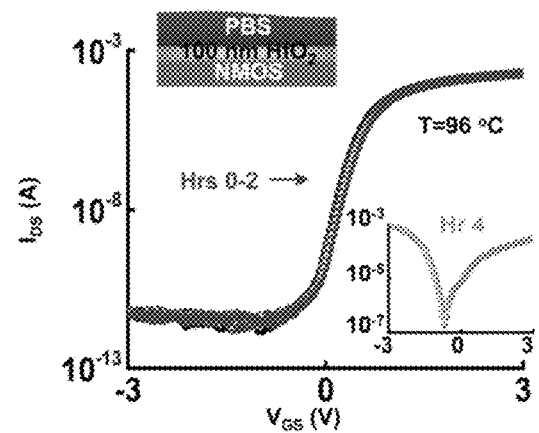

In this test structure, FIGS. 67A-67B establish the collections of transfer characteristics of Si transistor performances during accelerated immersion test in 96° C. PBS solution at pH of 7.4. Here the water barriers are a 100 nm thick layer of single thermal SiO$_2$ (FIG. 67A) and a 100 nm thick layer of single HfO$_2$ (FIG. 67B), respectively. All devices retain functionality, without measurable change from their initial state within each lifetime (24 hours for single thermal SiO$_2$ layers; 2 hours for single HfO$_2$ layers). The electrical performances fail suddenly and catastrophically right after water diffusion leading to a short circuit, as displayed in insets of FIGS. 67A-67B.

Figure 68:
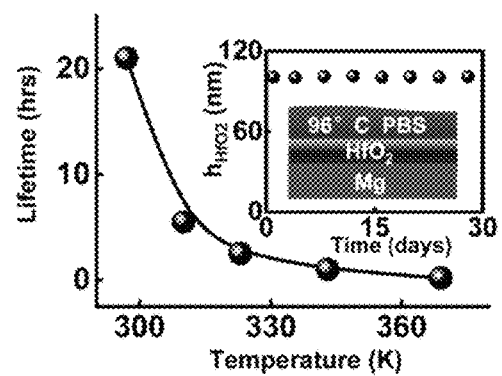
FIG. 68. Temperature-dependent Mg soak test of 100-nm-thick layer of $HfO_2$ in PBS solution. The lifetime decreases as an exponential relationship with increasing temperature. Inset shows the thickness remains unchanged during soaking 96° C. PBS solution at pH of 7.4.

Fabrication of Mg test device with different encapsulation materials: (1) *Mg Test Structures for Evaluation of Single-layer Water Barrier (SiO$_2$ or HfO$_2$)*: Photolithography with a negative photoresist (AZ nLOF 2070, MicroChemicals) formed 200×400 pmt square area on a clean wafer with a thermal SiO$_2$ layer or glass substrate. Subsequent electron-beam evaporation and lift-off yielded layer of Ti/Mg (5 nm/300 nm) in the pre-defined area. For a 100 nm thick layer of single thermal SiO$_2$ barrier, fabrication steps followed those described previously in FIG. 61A. For a 100 nm thick layer of single HfO$_2$ barrier, a superior formation of ALD HfO$_2$ appeared on surface of Mg pads by ALD deposition in 200° C. FIG. 68 exhibits results of temperature-dependent Mg soak tests of 100 nm thick layers of HfO$_2$ in PBS solution at pH of 7.4. The Mg lifetime decreases as an exponential relationship with increasing temperature, which demonstrates a survival of ~1 day in room temperature while <1 hour in 96° C. However, the thickness of HfO$_2$ remains unchanged even in 96° C. PBS solution during one month, as shown in inset of FIG. 68. As a result, the immersion tests indicate that HfO$_2$ layer as a water barrier fails in a pinhole manner and the periods needed of water-diffusion through these pinholes decreases in an exponential relationship with increasing surrounding temperature.

(2) Mg Test Structures for Evaluation of SiO$_2$-Based Bilayer Water Barrier Performance of Various Materials: Photolithography with a negative photoresist (AZ nLOF 2070, MicroChemicals) defined Mg patterns on a clean wafer with a thermal SiO$_2$ layer. Subsequent electron-beam evaporation and lift-off yield 5/300 nm Ti/Mg. Such devices were bound to a glass handling substrate and thermal SiO$_2$ were exposed by the etching back technique as stated above. Different deposition methods for candidates were used to yield various capping materials on the top of SiO$_2$ before or after Mg formation (FIG. 62C; Table 2). Parylene C was chemical-vapor-deposited with various thicknesses (SCS Parylene Deposition System). Ti/Pt was prepared by electron-beam evaporation. Formation of the SiN$_x$ (<250 M Pa compressive stress, ROGUE VALLEY MICRODEVICES) relied on high temperature (1200 K) growth on a layer of thermal SiO$_2$ (100 nm thickness). Other candidate bi-layer barriers were combined with different polymers (Table 2). A photodefinable epoxy (SU-8 2000, MicroChem), polyimide (PI-2545, HD MicroSystems) and Polymethylmethacrylate (PMMA-A2 495, MicroChem) were prepared by spin coating.

Reactive Diffusion Model of Water Barrier Performances: FIG. 62C and Table 2 summarize all of the experimental results. Popular organic passivation materials, for instance, SU-8 and Polyimide, enhance thermal SiO$_2$ limitedly, lifetime of which is lower than that of Parylene C with same thicknesses. As a result, Parylene C is the strongest polymer among all of candidates in Table 2 with ultra-thin structure, possibly due to fabrication methods of Parylene C. For example, 100/100 nm thick bilayer barriers of Parylene C (contact PBS solution)/SiO$_2$ survive for around 5 days in 96° C. PBS solution at pH of 7.4, which is still not as long as HfO$_2$ encapsulation on SiO$_2$.

Both single-layer and bi-layer reactive diffusion models are established to capture the water barrier performances, as shown in the main text. By solving the single-layer model illustrated in FIG. 63A, the water concentration can be analytically solved by applying the method of separation of variables, yielding $$\frac{w(y, t)}{w_0} = \frac{\cosh\left(\sqrt{\frac{k_{SiO_2} h_0^2}{D_{SiO_2}}} \frac{y}{h_0}\right)}{\cosh\sqrt{\frac{k_{SiO_2} h_0^2}{D_{SiO_2}}}} + \quad \text{(S2)}$$

$$2\sum_{n=1}^{\infty} \frac{(-1)^n \left(n - \frac{1}{2}\right)\pi}{\frac{k_{SiO_2} h_0^2}{D_{SiO_2}} + \left(n - \frac{1}{2}\right)^2 \pi^2} e^{-\left[\frac{k_{SiO_2} h_0^2}{D_{SiO_2}} + \left(n - \frac{1}{2}\right)^2 \pi^2\right] \frac{D_{SiO_2} t}{h_0^2}} \cos\left[\left(n - \frac{1}{2}\right)\pi \frac{y}{h_0}\right].$$

The thickness $h_{SiO_2}$ of the thermal SiO$_2$ layer, changing with time, is obtained by subtraction from $h_0$ of the integration of $k_{SiO_2} w M_{SiO_2} h_0/(q\rho_{SiO_2} M_{H_2O})$ over both the thickness direction y and time t (i.e., the thickness of thermal SiO$_2$ dissolved), where q=2 is the number of water molecules that react with each atom of SiO$_2$, $\rho_{SiO_2}$ is the mass density of thermal SiO$_2$ (=2.33 g cm$^{-3}$), $M_{SiO_2}$ (=60 g mol$^{-1}$) and $M_{H_2O}$ (=18 g mol$^{-1}$) are the molar masses of SiO$_2$ and water, respectively. We thus have $$\frac{h_{SiO_2}}{h_0} = 1 - \frac{w_0 M_{SiO_2}}{q\rho_{SiO_2} M_{H_2O}} \frac{k_{SiO_2} h_0^2}{D_{SiO_2}} \left\{ \frac{D_{SiO_2} t}{h_0^2} \cdot \frac{\tanh\sqrt{\frac{k_{SiO_2} h_0^2}{D_{SiO_2}}}}{\sqrt{\frac{k_{SiO_2} h_0^2}{D_{SiO_2}}}} - \right.$$

$$\left. 2\sum_{n=1}^{\infty} \frac{1 - e^{-\left[\frac{k_{SiO_2} h_0^2}{D_{SiO_2}} + \left(n - \frac{1}{2}\right)^2 \pi^2\right] \frac{D_{SiO_2} t}{h_0^2}}}{\left[\frac{k_{SiO_2} h_0^2}{D_{SiO_2}} + \left(n - \frac{1}{2}\right)^2 \pi^2\right]^2} \right\},$$

(S3)

which reveals that the non-dimensional thickness, $h_{SiO_2}/h_0$, depends on the non-dimensional time $D_{SiO_2} t/h_0^2$, non-dimensional parameter $k_{SiO_2} h_0^2/D_{SiO_2}$, and a single combination of water concentration $w_0$ and mass density $\rho_{SiO_2}$ of thermal $SiO_2$, $w_0 M_{SiO_2}/(q\rho_{SiO_2} M_{H_2O})$. For the present study, the summation in Equation (S3) is negligible such that the equation is simplified to Equation (2). By solving the bi-layer model illustrated in FIG. 3c, the analytical water concentration solution is $$w = w_0 \left[ \sum_{n=1}^{\infty} C_n e^{-\lambda_n t} f_n(y) + g(y) \right], \text{ where} \quad (S4)$$

$$f_n(y) = \begin{cases} \sin\left(\sqrt{\frac{\lambda_n}{D_{HfO_2}}} h_{HfO_2}\right) \cos\left(\sqrt{\frac{\lambda_n - k_{SiO_2}}{D_{SiO_2}}} y\right), & 0 \le y \le h_0 \\ \cos\left(\sqrt{\frac{\lambda_n - k_{SiO_2}}{D_{SiO_2}}} h_0\right) \sin\left[\sqrt{\frac{\lambda_n}{D_{HfO_2}}} (h_0 + h_{HfO_2} - y)\right], & h_0 \le y \le h_0 + h_{HfO_2} \end{cases}, \text{ and} \quad (S5)$$

$$g(y) = \begin{cases} G \cosh\left(\sqrt{\frac{k_{SiO_2}}{D_{SiO_2}}} y\right), & 0 \le y \le h_0 \\ 1 - H(h_0 + h_{HfO_2} - y), & h_0 \le y \le h_0 + h_{HfO_2} \end{cases}, \quad (S6)$$

in which $$G = \frac{1}{\sqrt{D_{SiO_2} k_{SiO_2}} \frac{h_{HfO_2}}{D_{HfO_2}} \sinh\sqrt{\frac{k_{SiO_2} h_0^2}{D_{SiO_2}}} + \cosh\sqrt{\frac{k_{SiO_2} h_0^2}{D_{SiO_2}}}} \quad (S7)$$

$$H = \frac{1}{\frac{D_{HfO_2}}{\sqrt{D_{SiO_2} k_{SiO_2}}} \coth\sqrt{\frac{k_{SiO_2} h_0^2}{D_{SiO_2}}} + h_{HfO_2}}.$$

$\lambda_n$ (n=1,2,3,...) are the roots of the eigen equation $\tan\sqrt{(\lambda - k_{SiO_2}) h_0^2/D_{SiO_2}}$ $\tan$ $\sqrt{\lambda h_{HfO_2}^2/D_{HfO_2}} = \sqrt{\lambda D_{HfO_2}/[(\lambda - k_{SiO_2}) D_{SiO_2}]}$, which is obtained from the condition of continuity of concentration and flux of water at the $HfO_2/SiO_2$ interface. The initial condition of zero water concentration requires $$\sum_{n=1}^{\infty} C_n f_n(y) + g(y) = 0.$$

The orthogonality of eigenfunctions $$\int_0^{h_0 + h_{HfO_2}} f_m(y) f_n(y) dy = 0$$

(for m≠n) gives the coefficient $C_n$ as $$C_n = \quad (S8)$$

$$-\frac{\int_0^{h_0 + h_{HfO_2}} f_n(y) g(y) dy}{\int_0^{h_0 + h_{HfO_2}} f_n^2(y) dy} = \frac{-\frac{2}{\lambda_n}\sqrt{\lambda_n D_{HfO_2}} \cos\left(\sqrt{\frac{\lambda_n - k_{SiO_2}}{D_{SiO_2}}} h_0^2\right)}{\left\{ h_0 \sin^2\left(\sqrt{\frac{\lambda_n}{D_{HfO_2}}} h_{HfO_2}^2\right) \left[ 1 + \frac{\sin\left(2\sqrt{\frac{\lambda_n - k_{SiO_2}}{D_{SiO_2}}} h_0^2\right)}{2\sqrt{\frac{\lambda_n - k_{SiO_2}}{D_{SiO_2}}} h_0^2} \right] + h_{HfO_2} \cos^2\left(\sqrt{\frac{\lambda_n - k_{SiO_2}}{D_{SiO_2}}} h_0^2\right) \left[ 1 - \frac{\sin\left(2\sqrt{\frac{\lambda_n}{D_{HfO_2}}} h_{HfO_2}^2\right)}{2\sqrt{\frac{\lambda_n}{D_{HfO_2}}} h_{HfO_2}^2} \right] \right\}}.$$

In the same manner as described in the single-layer model, the non-dimensional thickness of the thermal $SiO_2$ layer is given by $$\frac{h_{SiO_2}}{h_0} = \quad (S9)$$

$$1 - \frac{w_0 M_{SiO_2}}{q\rho_{SiO_2} M_{H_2O}} k_{SiO_2} \left[ Gt \cdot \frac{\sinh\sqrt{\frac{k_{SiO_2} h_0^2}{D_{SiO_2}}}}{\sqrt{\frac{k_{SiO_2} h_0^2}{D_{SiO_2}}}} + \sum_{n=1}^{\infty} \frac{C_n}{\lambda_n} (1 - e^{-\lambda_n t}) \right.$$

$$\left. \frac{\sin\sqrt{\frac{\lambda_n - k_{SiO_2}}{D_{SiO_2}}} h_0^2}{\sqrt{\frac{\lambda_n - k_{SiO_2}}{D_{SiO_2}}}} \cdot \sin\sqrt{\frac{\lambda_n}{D_{HfO_2}} h_{HfO_2}^2} \right].$$

For the present study, the summation in Equation (S9) is negligible such that the equation is simplified to Equation (5).

Figure 69:
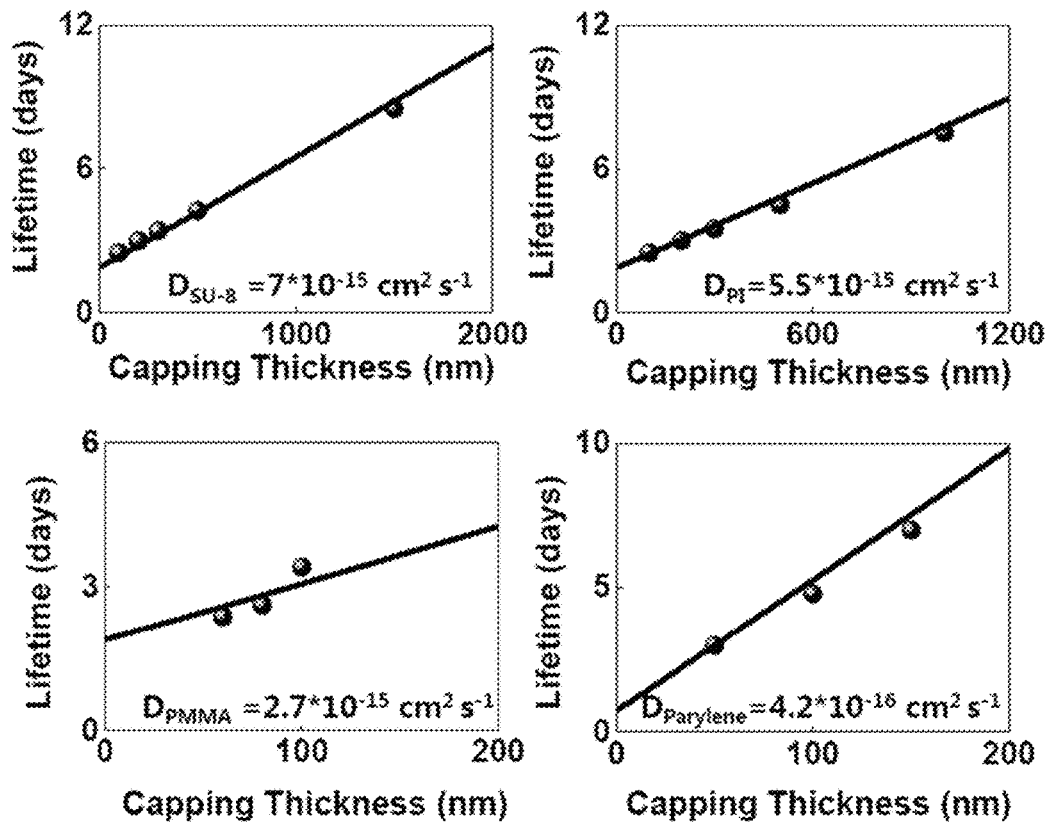
FIG. 69. Barrier lifetime of polymer/$SiO_2$ bi-layers versus thickness of polymer capping layers. Here, $SiO_2$ thickness is a constant of 100 nm.

For the bi-layers with thermal $SiO_2$ capped by different polymers, the diffusivities are determined from the bi-layer reactive diffusion model according to the experimental lifetime tests. For SU-8, polyimide, PMMA, and Parylene C, the diffusivities are $D_{SU-8}=7\times10^{-15}$ cm$^2$ s$^{-1}$, $D_{PI}=5.5\times10^{-15}$ cm$^2$ s$^{-1}$, $D_{PMMA}$=2.7×10$^{-15}$ cm$^2$ s$^{-1}$, and $D_{Parylene}$=4.2×10$^{-16}$ cm$^2$ s$^{-1}$, respectively. It is obvious that the best polymer for water barrier is Parylene C, and the worst one is SU-8. FIG. 69 reveals good agreement of barrier lifetime versus capping layer thickness between the theoretical results (lines) and those from experiments (symbols).

Figure 70:
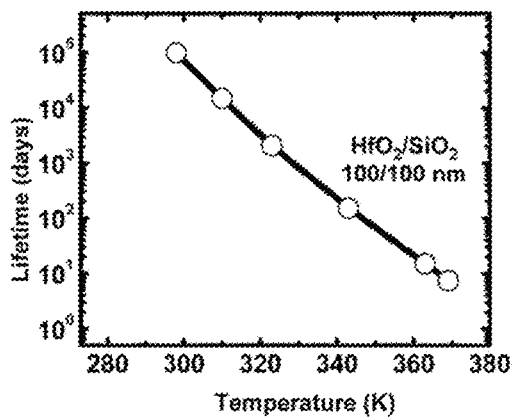
FIG. 70. Simulation of temperature-dependent lifetime of 100 nm/100 nm-thick-$HfO_2/SiO_2$ encapsulation layer.

FIG. 70 plots the temperature-dependent lifetime of 100 nm/100 nm-thick-HfO$_2$/SiO$_2$ encapsulation layer according to the bi-layer model. For thermal SiO$_2$, $k_{SiO_2}$ at different temperatures are obtained from the Arrhenius equation $k_{SiO_2}$=$k_0$ exp(-$E_A$/RT), where $k_0$ is the pre-exponential factor, $E_A$ is the activation energy (=1.32 eV),[2] R is the universal gas constant (=8.314 J K$^{-1}$ mol$^{-1}$), and T is the absolute temperature. Using $k_{SiO_2}$=2×10$^{-4}$ s$^{-1}$ at 96° C., $k_0$ is determined, and $k_{SiO_2}$ is obtained as $k_{SiO_2}$=2.1×10$^{14}$×exp(-15313/T) s$^{-1}$. $D_{SiO_2}$ at different temperatures are obtained from the dissolution rates measured in previous experiments (2) based on the single-layer reactive diffusion model. For example, $D_{SiO_2}$=5.4×10$^{-21}$ cm$^2$ s$^{-1}$ at 25° C., 5.3×10$^{-20}$ cm$^2$ s$^{-1}$ at 37° C., 6×10$^{-19}$ cm$^2$ s$^{-1}$ at 50° C., 9.5×10$^{-18}$ cm$^2$ s$^{-1}$ at 70° C., 4.4×10$^{-17}$ cm$^2$ s$^{-1}$ at 90° C., and 1.5×10$^{-16}$ cm$^2$ s$^{-1}$ at 96° C. $D_{HfO_2}$ at different temperatures are obtained from the lifetime tests of 100 nm/100 nm thick bilayer of HfO$_2$/SiO$_2$ barrier at 90° C. (~15 days) and 96° C. (~8 days) based on the bi-layer reactive diffusion model, which gives $D_{HfO_2}$=10^(1.58-6340/T) cm$^2$ s$^{-1}$ according to Arrhenius scaling.

Preparation for Na$^+$ and Ca$^{2+}$ Solutions and Related SiO$_2$ Thickness Measurement in Various Ionic Strengths: 1M NaCl and CaCl$_2$) (Sigma Aldrich, USA) solutions were diluted in deionized water to make the desired concentrations. Each solution was buffered with 10 mM Tris at pH7.4 at 96° C. with a calibration coefficient -0.025 pH/° C. The reflectance of the thermally grown SiO$_2$ was measured with Mprobe (SemiconSoft, USA) from wavelength of 400 nm to 1000 nm to calculate the thickness before and after the soaking tests.

Sodium Transport Simulations and Numerical Simulation for Induced NMOS $V_T$ Shift: Results of modeling of Na$^+$ transport processes appear in FIG. 71 with the following assumptions. As the area of the barrier layer (y & z planes) is much larger than its thickness (x direction), analysis can exploit a one dimensional (1D) model where x=0 and x=200 nm in FIG. 71 corresponds to the PBS/SiO$_2$ and SiO$_2$/Si interfaces, respectively. At the PBS/SiO$_2$ interface, the [Na$^+$] in PBS solution (137 mmol/L (8.24×10$^{25}$ m$^{-3}$)) is larger than its solubility limit (33 mmol L(2×10$^{25}$ m$^{-3}$)) inside thermal SiO$_2$.[3] Nevertheless, the retardation happens at the Si/SiO$_2$ boundary where Na$^+$ diffusivity $D_{Na^+,SiO_2}$>>$D_{Na^+,Si}$[4-6] The Na$^+$ concentration decreases significantly near x=0 and Na$^+$ accumulates at x=200 nm. The voltage drops primarily across the oxide layer neglecting the PBS solution resistance and the capacitive drop over the SiO$_2$/Si screening ions.

Specifically, modeling of Na$^+$ transport process involves solving for the density profile of Na$^+$ ($n_{Na^+}$) in the barrier layer follows from time-dependent solutions of the coupled equation:

$$\frac{\partial^2 \phi(x\cdot t)}{\partial x^2} = -\frac{q\cdot n_{Na^+}}{\epsilon} \quad (S10)$$

$$\frac{\partial n_{Na^+}}{\partial t} = -\frac{\partial}{\partial x}\left(\mu_{Na^+} n_{Na^+}\frac{\partial \phi(x\cdot t)}{\partial x} - D_{Na^+}\frac{\partial n_{Na^+}}{\partial x}\right) \quad (S11)$$

where $\phi(x\cdot t)$ is the electrical potential, E is the dielectric permittivity. $\mu_{Na^+}$ and $D_{Na^+}$ are the mobility and diffusivity of Na$^+$. Einstein's relation:

$$\frac{D_{Na^+}}{\mu_{Na^+}} = \frac{kT}{q}$$

connects these quantities. These two coupled equations were solved numerically on a one-dimensional domain using COMSOL Multiphysics®. A value of the diffusivity (D) of Na$^+$ in wet thermal SiO$_2$ from previous reports allowed calculation of the corresponding ion migration mobility ($\mu$) using the Nernst-Einstein relation. A constant boundary condition V=V$_{app}$ and V=0 corresponds to an applied bias at the PBS/SiO$_2$ and SiO$_2$/Si interfaces, respectively.

FIG. 71 shows the spatially distributed Na$^+$ concentration and electrostatic potential profile computed after 1 day for the case of h=200 nm thermal SiO$_2$ in 96° C. with V$_{app}$ of 0 and 3 V. Specifically, Na$^+$ migrates through the SiO$_2$ layer and accumulates near the SiO$_2$—Si substrate interface, and form a form a thin layer of accumulated Na$^+$ with surface charge density Q$_s$ (in unit of C/m$^3$). We calculate Q$_s$ from the spatially distributed Na$^+$ density shown in FIG. 71 by integrating Na$^+$ concentration over the thickness of the of the accumulated Na$^+$ layer $\Delta$h:

$$Q_S = q\int_{h-\Delta h}^{h} n_{Na^+}(x,t)dx \quad (S12)$$

where q is the elementary charge, t is the time, h is the thickness of the thermal SiO$_2$ layer. Similar to the inversion charge density calculation in the MOSFET, this $\Delta$h can be expressed as:

$$\Delta h = \frac{kT/q}{V_{app}}\cdot h \quad (S13)$$

The accumulated Na$^+$ surface density Q$_s$ leads to an enhancement on V$_G$ at the front gate. An NMOS model in the Sentaurus simulator allows quantitative calculation of the influence on $\Delta$V$_T$. FIG. 65A demonstrates the cross section of embedded NMOS device underneath the encapsulation layer. The device dimensions are the same as those in experiment: channel length (L=20 um), Si substrate thickness (t$_{Si}$=100 nm) and gate oxide thickness (t$_{ox}$=40 nm). The material for the channel is intrinsic Si and that for the source and drain regions is n-type Si with a doping level of 10$^{19}$ cm$^{-3}$. We apply V$_{ds}$=0.1 V between source and drain, sweep the gate voltage V$_{Gs}$ from -3V to 3V, and plot the I$_{ds}$-V$_{GS}$ curve to obtain the corresponding $\Delta$V$_T$, as shown in FIG. 65D.

Also incorporated by reference herein, is: Song et al. "Transferred, Ultra-thin Oxide Bilayers as Biofluid Barriers for Flexible Electronic Implants" Advanced Functional Materials 1702284 (Jul. 20, 2017).

REFERENCES

[1] Y. Sun, J. A. Rogers, Adv. Mater. 2007, 19, 1897-1916.
[2] H. Fang, J. Zhao, K. J. Yu, E. Song, A. B. Farimani, C.-H. Chiange, X. Jin, Y. Xue, D. Xu, W. Dui, K. J. Seo, Y. Zhong, Z. Yang, S. M. Won, G. Fang, S. W. Choi, S. Chaudhuri, Y. Huang, M. A. Alam, J. Viventi, N. R. Aluru, J. A. Rogers, Proceedings of the National Academy of Sciences, 2016, 113(42), 11682-11687.

[3] E. Yon, W. Ko, A. Kuper, *IEEE Transactions on Electron Devices*, 1966, Ed13, 276-280.
[4] J. Mecha, J. Steinmann, *Journal of the American Ceramic Society*, 1979, 62, 343-346.
[5] V. Korol, *Physica status solidi* (a), 1988, 110, 9-34.
[6] T. Burges, J. C. Baum, F. M. Fowkes, R. Holmstrom, G. A. Shim, *J. Electrochem. Soc.*, 1969, 116(7), 1005-1008.

Example 4: Thin, Transferred Layers of Silicon Dioxide and Silicon Nitride as Water and Ion Barriers for Implantable Flexible Electronic Systems Thin, physically transferred layers of silicon dioxide ($SiO_2$) thermally grown on the surfaces of silicon wafers offer excellent properties as long-lived, hermetic biofluid barriers in flexible electronic implants. This example explores materials and physics aspects of the transport of ions through the $SiO_2$ and the resultant effects on device performance and reliability. Accelerated soak tests of devices under electrical bias stress relative to a surrounding phosphate-buffered saline (PBS) solution at a pH of 7.4 reveal the field dependence of these processes. Similar experimental protocols establish that coatings of $SiN_x$ on the $SiO_2$ can block the passage of ions. Systematic experimental and theoretical investigations reveal the details associated with transport though this bilayer structure, and they serve as the basis for lifetime projections of more than a decade of immersion in PBS solution at 37° C. for the case of 100/200 nm of $SiO_2/SiN_x$. Temperature dependent simulations offer further understanding of two competing failure mechanisms-dissolution and ion diffusion—on device lifetime. These findings establish a basic physical understanding of effects that are essential to the stable operation of flexible electronics as chronic implants.

High performance, flexible integrated electronic/optoelectronic systems offer powerful capabilities in a range of important applications, from devices for neuromodulation and bioelectronic medicines, to advanced surgical diagnostic systems to tools for biomedical research. Some of the most sophisticated systems use ultrathin inorganic active materials (e.g. nanomembranes of silicon, and others) as the basis for flexible transistors capable of supporting amplification and multiplexed addressing in flexible sheets for high resolution electrophysiological mapping on the cortical or epicardial surfaces[1-5] and injectable needles for optical stimulation of targeted neural circuits in the brain.[6-9] These platforms can bend and conform as minimally invasive interfaces to soft, dynamic biological systems, while offering many of the performance characteristics associated with rigid, planar integrated circuits and optoelectronic components built on semiconductor wafers.[10-20] A critical challenge in realizing chronically implantable bio-electronic systems of this type is in the development of broadly useful material coatings that can serve as robust, long-lived barriers to surrounding bio-fluids.

The ideal coating would offer low flexural rigidity in thin film form, and compatibility not only with the surrounding biology but also with a range of materials in the underlying electronics. The essential requirement is for negligible permeability (arising from combined effects of intrinsic as well as extrinsic, i.e. pinholes, grain boundaries, defects, etc., properties) to water and to ions and other species in bio-fluids, with lifetimes measured in decades. Conventional encapsulation strategies, such as bulk metal/ceramic enclosures, thin-film polymers, and organic/inorganic multilayer stacks (deposited in research oriented cleanroom facilities), fail to meet these requirements.[21-27] Recent research establishes that thin, transferred layers of $SiO_2$ thermally grown on silicon wafers offer exceptional characteristics in this context.[28] (see, e.g., Examples 1-2 above). The extremely low water permeability intrinsic to $SiO_2$, taken together with the high levels of perfection that are possible in thermally grown material on silicon wafers, allows layers of $SiO_2$ with thicknesses of only a few hundred nanometers to support, over areas measured in square centimeters, device lifetimes of many decades, as extrapolated from temperature dependent studies of immersion in PBS solution. Alternatives based on conventional coatings deposited or grown in the typical fashion in standard, academic laboratory conditions, offer lifetimes that are many orders of magnitude shorter than those of transferred, thermal $SiO_2$. Nevertheless, despite the superior barrier properties, the possibility of ion penetration through thermal $SiO_2$ while immersed in biofluids is of concern due to the potential of such species to shift and/or degrade the switching properties of the underlying transistors when in proximity to the channel regions. Furthermore, the competing effects of hydrolysis of $SiO_2$ and ion diffusion in bio-fluids demand attention.

The results presented here address these and other key issues. The studies exploit test platforms that consist of thermally grown $SiO_2$ on silicon-on-insulator (SOI) wafers as barriers in flexible silicon devices. Specifically, various voltages (AC, DC) applied between bio-fluids and NMOS transistors reveal essential aspects of ion transport through measurements of electrostatically induced shifts in the properties of the transistors. Temperature dependent drift-diffusion modeling establishes the coupling of dissolution and ion diffusion and their effects on device lifetime. Additional results demonstrate that layers of $SiN_x$ formed by low pressure chemical vapor deposition (LPCVD) can serve as highly effective ion barriers, which in combination with thermal $SiO_2$, yield bilayer (i.e. $SiO_2/SiN_x$) that are simultaneously impermeable to water and ions. A combination of electrical tests, temperature dependent measurements and related simulations indicate that this bilayer structure provides superior capabilities of relevance to use in flexible electronic implants, independent of bias conditions.

Figure 72A:
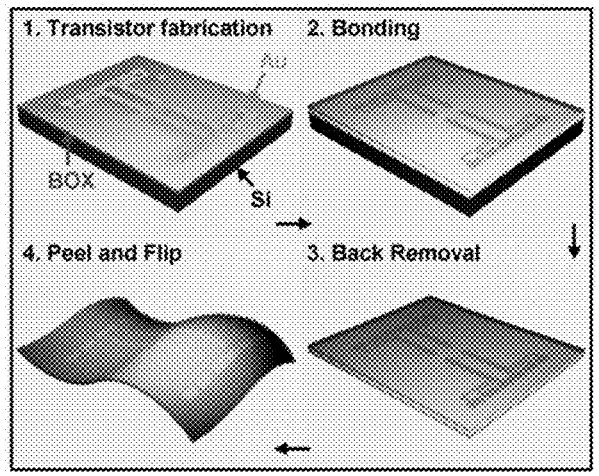
FIGS. 72A-72E. Thin layers of $SiO_2$ thermally grown on device-grade silicon wafers, deployed as barrier layers in flexible electronic implants.
Figure 72B:
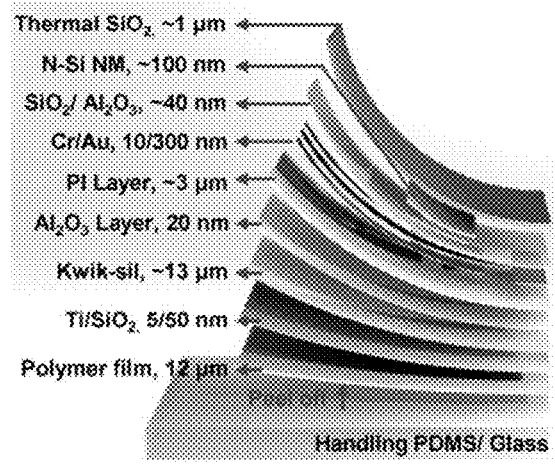
Figure 72C:
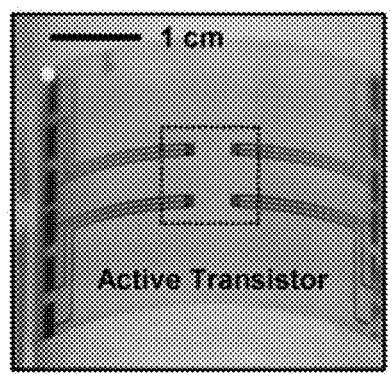
Figure 72D:
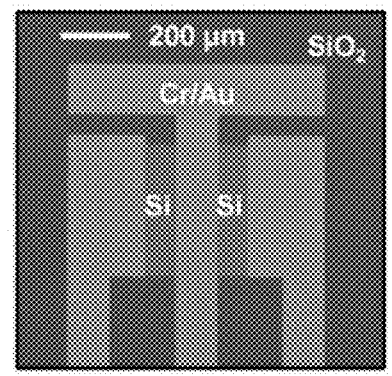
Figure 72E:
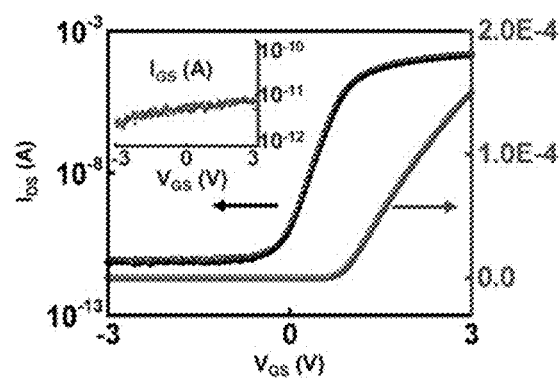

The fabrication process utilizes thermally grown layers of $SiO_2$ transferred onto flexible electronic platforms (FIG. 72A). Unlike conventional processing sequences in which deposition of the encapsulation material occurs last, the scheme here (FIG. 72A) starts with a fully formed barrier layer in which device fabrication occurs in a layer by layer fashion on top. Briefly, the process begins with formation of isolated silicon transistors on an SOI wafer (~100 nm thick device Si and 1 μm thick buried thermal $SiO_2$). Solid source doping with phosphorus forms source and drain contacts at concentrations of ~$10^{19}$ cm$^{-3}$. Thermal oxidation and atomic layer deposition (ALD) at ~1150° C. and 80° C., respectively, yield a dielectric stack of thermal $SiO_2$ (30 nm)/$Al_2O_3$ (13 nm). Photolithographically patterned metallization (Cr/Au, 10/300 nm) defines source, drain and gate electrodes. A transfer process bonds the front side of this substrate to a thin polymer film (Kapton, DuPont, 13 μm) laminated onto a glass substrate coated with a layer of dimethylsiloxane (PDMS; 10 μm) as a temporary support. This process begins with spin casting and curing a coating of polyimide (PI-2545, HD MicroSystems; 3.5 μm) uniformly across the transistors, followed by deposition of a thin layer of $Al_2O_3$ (20 nm). A commercial adhesive (Kwik-Sil, World Precision Instruments) enhances the adhesion between the $Al_2O_3$ and the PDMS (coated with Ti (5 nm)/$SiO_2$ (50 nm)) on the temporary support. After bonding, inductively coupled plasma reactive ion etching (ICP-RIE, Surface Technology System) with a gas flow of $SF_6/O_2$ 40/3 sccm at a pressure of 50 mT removes the silicon wafer. This process leaves the buried thermal $SiO_2$ of the SOI wafer as a bio-fluid barrier. Peeling the material stack from the temporary substrate yields a piece of flexible electronics encapsulated by a layer of thermal $SiO_2$ that has low rigidity and good bendability by virtue of its small thickness. FIG. 72B shows a schematic illustration of the multilayer configuration, as an exploded-view. Recent work demonsrates that $SiO_2$ formed and manipulated in similar fashion can serve as a flexible/bendable dielectric/encapsulation for high resolution, actively multiplexed electrophysiological mapping systems for use on the surfaces of the heart.[29] These results provide strong evidence for broad applications in advanced bio-implants. FIGS. 72C-72D display an optical image and a colorized scanning electron microscope (SEM) image of such a piece of flexible electronics with a set of NMOS transistors (channel width W=300 µm, length L=20 µm). FIG. 72E presents transfer characteristics of a representative transistor (in FIG. 72D) in both linear and semi-log scale at a supply voltage $V_{DS}$=0.1 V. The on and off currents are 0.2 mA and 1 µA, respectively. The inset shows that the leakage current between the gate and source electrodes ($I_{GS}$) is below 10 µA. The transistor exhibits a peak effective electron mobility of ~400 $cm^2/V \cdot s$, which is consistent to transistors by traditional fabrication process.[30]

Figure 73A:
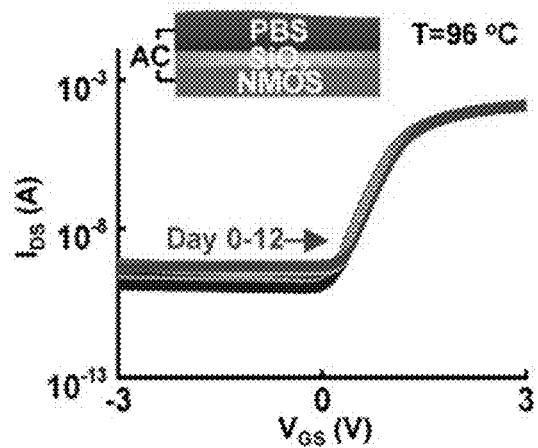
FIGS. 73A-73H. Experimental and simulation results for the behavior of NMOS transistors encapsulated with thermal $SiO_2$ in various tests of immersion in PBS solution at pH 7.4 and 96° C.
Figure 73B:
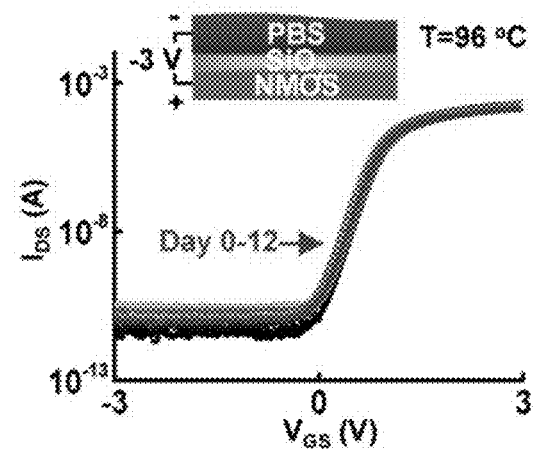
Figure 73C:
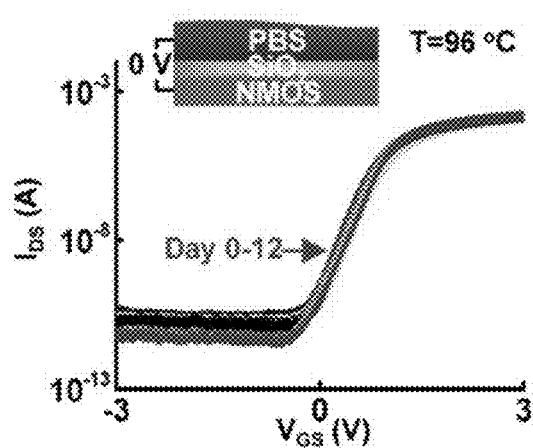

The water permeability through thermal $SiO_2$ is extremely small, and that a slow hydrolysis process is the cause for eventual failure.[28] Examples 1-2, above. In addition to water, ions in bio-fluids (mostly small, positive species such as $Na^+$ and $K^+$) can adversely affect the performance of the transistors, mainly by electrostatically shifting their threshold voltage ($V_T$).[31] Results of accelerated soak tests of NMOS transistors during application of an external bias in an accelerated immersion test (in PBS solution at 96° C. and pH of 7.4) are in FIGS. 73A-73F. Here, the accelerated immersion tests refer to those performed at elevated temperatures to increase the rate of the hydrolysis reaction. A bias ($V_{app}$) exists between a platinum probe in the PBS solution and the transistor electrodes (source, drain and gate), as illustrated in the insets. FIGS. 73A-73C present transfer characteristics measured with $V_{app}$ at AC, negative DC and 0 V conditions. All transistors in such cases exhibit a fixed $V_T$ until sudden failure due to hydrolysis of the $SiO_2$ (corresponding to a dissolution rate of ~80 nm/day in 96° C., consistent with previous reports Ref. 28), $Si+4H_2O \rightarrow Si(OH)_4+H_2$. At 0V, $V_T$ remains nearly constant, consistent with the lack of an electrical field to drive preferential flow of ions through the $SiO_2$. Here results at 0 V also match with reported results.[28] For an AC bias consisting of a square-wave with amplitude of 3 V and frequency of 100 Hz, the period is much shorter than the time for ions to transport through the $SiO_2$ layer. This condition therefore has little effect on net ionic flow, such that again $V_T$ remains constant. The negative DC condition corresponds to a constant potential of −3 V. In this case, positive ions such as $Na^+$ are repelled from the transistor structure, thereby preventing their diffusion through the $SiO_2$. As expected, thermal $SiO_2$ provides an outstanding barrier from negative ions such as $Cl^-$, due to their large size. Here as well, $V_T$ remains constant. These results therefore demonstrate that thermal $SiO_2$ can perform as an outstanding ion barrier under certain bias conditions, i.e., AC, zero or DC at negative voltages.

Figure 73D:
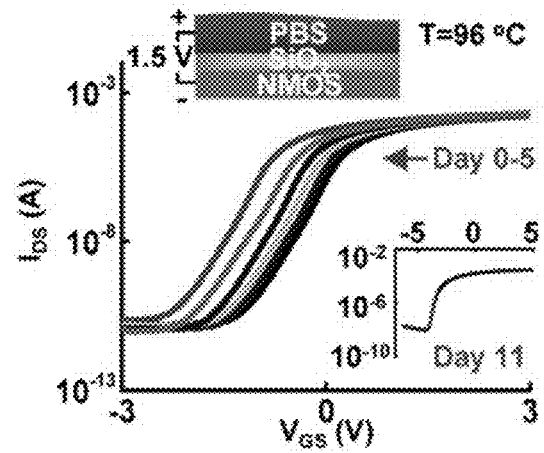
Figure 73E:
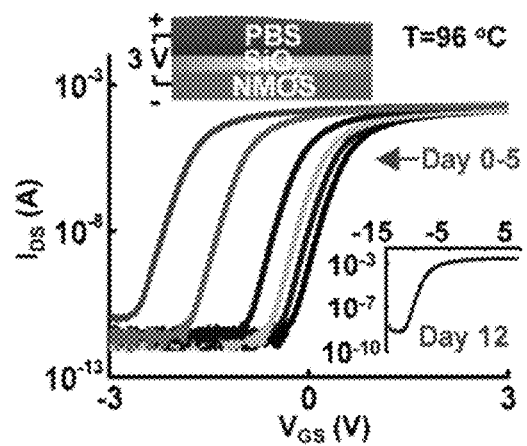
Figure 73F:
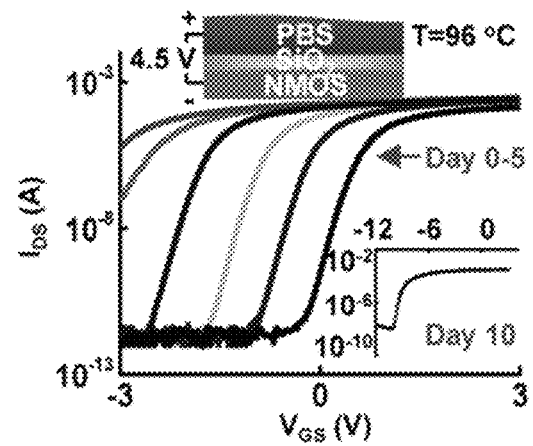

Nevertheless, for positive biases, $V_T$ exhibits time dependent shifts. FIGS. 73D-73F display accelerated test data, similar to that in FIGS. 73A-73C, but with various $V_{app}$ from 1.5 V to 4.5 V at increments of 1.5 V. For present purposes, device failure is defined as the point when the $SiO_2$ disappears due to hydrolysis or at which the shift in the threshold voltage $\Delta V_T$ for a 1 µm equivalent oxide thickness (EOT) reaches 1 V (less than 5 days under these accelerated conditions). The insets show the transfer characteristics just before failure by hydrolysis. The positive $V_{app}$ serves as a driving force for positive ion transport through the $SiO_2$, the result of which shifts $V_T$ through electrostatic interactions with the transistor channel. Specifically, because the thickness of the Si is around 100 nm, the layer of $Na^+$ near the channel can lead to an accumulation of electrons. These positive ions act as a virtual gate, such that the transistor turns on with a more negative $V_G$ at the front gate, corresponding to a negative shift in $V_T$ for an NMOS device. The magnitude of this $\Delta V_T$ increases significantly with $V_{app}$ (for a certain fixed thickness), as shown in FIGS. 73D-73F.

Figure 73G:
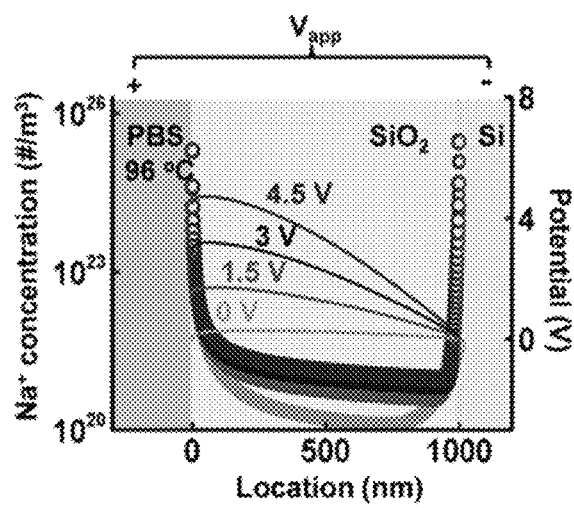
Figure 73H:
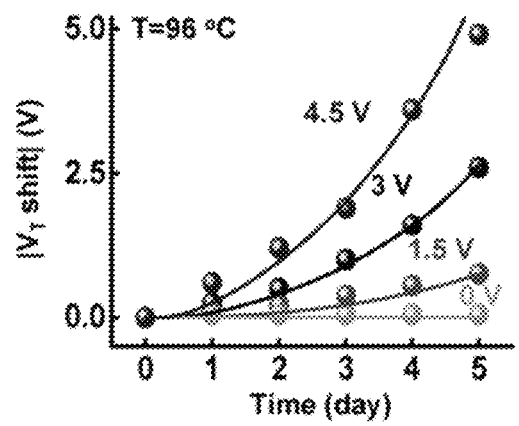
Figure 76:
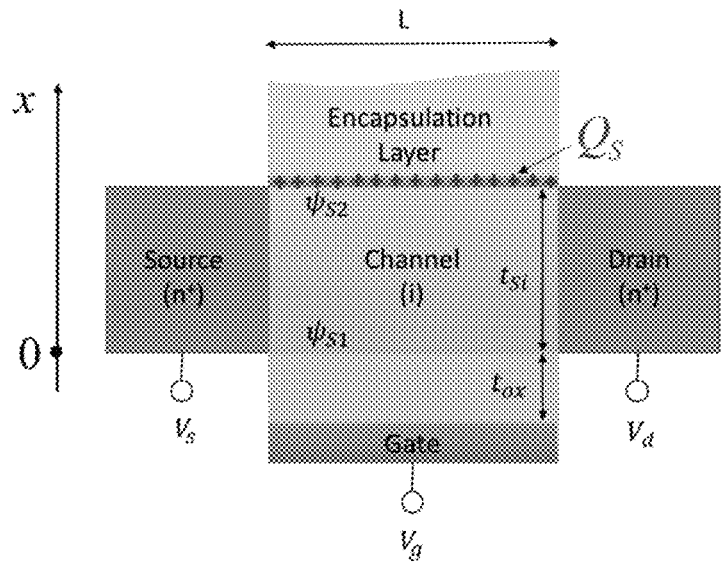
FIG. 76. Cross-section of the embedded MOSFET device with sodium in channel.

Results of modeling of $Na^+$ transport processes appear in FIGS. 73G-73H. As the area of the barrier layer (y & z planes) is much larger than its thickness (x direction), therefore, our analysis can exploit a one dimensional (1D) model[32] where x=0 and x=1 um in FIG. 73G correspond to the $PBS/SiO_2$ and $SiO_2/Si$ interfaces, respectively. At the $PBS/SiO_2$ interface, the $Na^+$ concentration in PBS solution (137 mmol/L ($8.24 \times 10^{25}$ $m^{-3}$)) is larger than its solubility limit (33 mmol/L($2 \times 10^{25}$ $m^{-3}$)) inside thermal $SiO_2$.[33] The $Na^+$ dissolution in thermal $SiO_2$ is sufficiently fast that it does not limit the total drift-diffusion process. Nevertheless, a retardation occurs at the $Si/SiO_2$ boundary where $Na^+$ diffusivity $D_{Na^+,SiO_2} \gg D_{Na^+,Si}$,[34-36] as illustrated in FIG. 76. The concentration of $Na^+$ ($c_{[Na^+]}$) in the barrier layer follows from the time-dependent solutions of the coupled Poisson's equation and continuity equation:

$$\frac{\partial^2 \phi(x \cdot t)}{\partial x^2} = -\frac{q \cdot c_{[Na^+]}}{\epsilon} \quad (1)$$

$$\frac{\partial c_{[Na^+]}}{\partial t} = -\frac{\partial}{\partial x}\left(\mu_{[Na^+]} c_{[Na^+]} \frac{\partial \phi(x \cdot t)}{\partial x} - D_{[Na^+]} \frac{\partial c_{[Na^+]}}{\partial x}\right) \quad (2)$$

where $\phi(x \cdot t)$ is the electrical potential, E is the dielectric permittivity. $\mu_{Na^+}$ and $D_{Na^+}$ are the mobility and diffusivity of $Na^+$. Einstein's relation:

$$\frac{D_{Na^+}}{\mu_{Na^+}} = \frac{kT}{q}$$

connects these quantities. A constant boundary condition (V=$V_{app}$ and V=0) corresponds to the applied bias across the $PBS/SiO_2$ and $SiO_2/Si$ interfaces, respectively. FIG. 73G shows the spatially distributed $Na^+$ concentration and electrostatic potential profile computed after 10 days for the case of h=1 µm thermal $SiO_2$ in 96° C. (without considering hydrolysis). Consistent with the experimental result shown in FIG. 73H, $V_{app}$ varies from 0 V to 4.5 V with increments of 1.5V. The $Na^+$ concentration decreases significantly near x=0 and $Na^+$ accumulates at the other side, namely, at x=1 µm. The voltage drops primarily across the oxide layer because the resistance of the $SiO_2$ is much larger than the PBS solution and the 200 nm Si layer below. The potential barriers due to the charge accumulation near the $PBS/SiO_2$ and $SiO_2/Si$ interfaces delay the $Na^+$ transport process.

FIG. 73H shows the shift in $V_T$ within 5 days for different bias voltages at T=96° C. The drift-diffusion process accelerates with increasing $V_{app}$, leading to an accelerated $V_T$ shift, which is closely related to the layer of surface charge density $Q_s$ of $Na^+$ located at the thermal $SiO_2$/substrate Si interface. We calculate $Q_s$ (in unit of $C/m^3$) from the spatially distributed $Na^+$ density shown in FIG. 73G by integrating $Na^+$ concentration over the thickness of the accumulated $Na^+$ layer $\Delta h$:

$$Q_S = q\int_{h-\Delta h}^{h} \rho_a(x,t)dx \quad (3)$$

where q is the elementary charge and $\rho_a$ is the $Na^+$ bulk density (in unit of $m^{-3}$), which can be obtained with recalibrated $Na^+$ diffusion coefficient. t is the time, h is the thickness of the thermal $SiO_2$ layer. Similar to the inversion charge density calculation in the MOSFET, this $\Delta h$ can be expressed as:[37]

$$\Delta h = \frac{kT/q}{V_{app}} \cdot h \quad (4)$$

Next, to account for the hydrolysis of the $SiO_2$ layer, we shrink the thickness h in our $Na^+$ transport numerical simulation as a time dependent variable:

$$h(t) = h_0 - r_{dis} \cdot t \quad (5)$$

where $h_0$ is the initial thermal $SiO_2$ thickness (1 μm in this particular case), $r_{dis}$ is the $SiO_2$ dissolution rate (~80 nm/day at 96° C. from soaking experiment). To find the relationship between $Q_s$ and $\Delta V_T$, we numerically simulate a 2D NMOS transistor with commercial software (Sentaurus Technology Computer Aided Design; FIG. 76) using experimentally determined device parameters. FIG. 73H shows that the numerical result predicted by this model (solid lines) fits well with experimental data extracted from FIGS. 73C-73F (solid dots) with $V_{app}$ from 0V to 4.5V. Specifically, $\Delta V_T$ increases with time and by larger amounts as the bias increases.

Figure 74A:
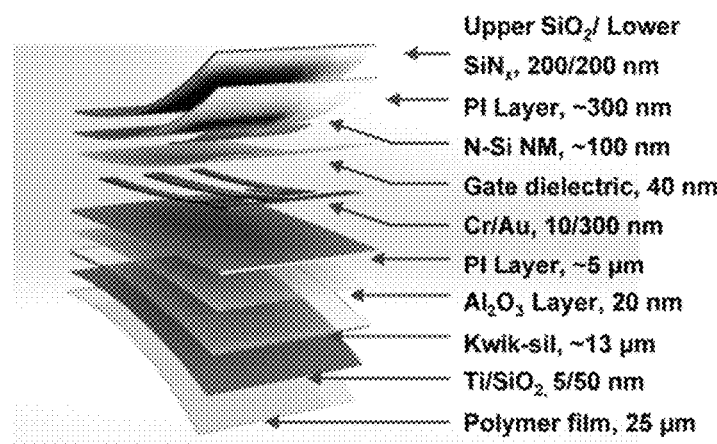
FIGS. 74A-74E. Properties of encapsulation layers that include LPCVD $SiN_x$.

The addition of a layer of silicon nitride, whose ion diffusivity is much lower than that of $SiO_2$, can further suppress ion diffusion. FIG. 74A displays an exploded-view schematic illustration of a system similar to the one in FIGS. 72A-72E, but with an additional coating of LPCVD $SiN_x$ to form a bilayer encapsulation. Thicknesses are indicated. Formation of the $SiN_x$ (200 nm thick, <250 M Pa tensile stress, ROGUE VALLEY MICRODEVICES) relies on high temperature (~1100 K) growth on a layer of thermal $SiO_2$ (200 nm thickness) on a silicon wafer (500 μm thick, 100 mm diameter; UNIVERSITY WAFER). The fabrication scheme begins with transfer-printing[38] of Si nanomembranes (NMs; derived from the top silicon layer of SOI wafers) onto the $SiN_x$ surface coated with a layer of polyimide as an adhesive (diluted PI 2545, thickness <300 nm, which is water-permeable material). Subsequent fabrication steps follow those described previously for the case of single layer $SiO_2$ encapsulation.

Figure 74B:
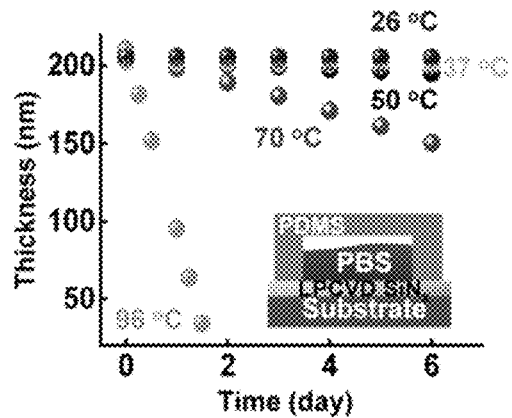
Figure 74C:
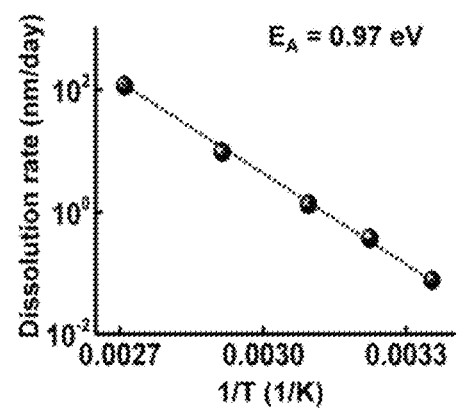

Despite its low ion diffusivity, $SiN_x$ has limitations as a standalone encapsulation layer. First, its dissolution rate is much higher than that of thermal $SiO_2$. FIG. 74B indicates that LPCVD $SiN_x$ dissolves at a rate of ~0.3 nm/day at 37° C. and a pH of 7.4. This value is approximately ten times higher than that of thermal $SiO_2$ (~$4 \times 10^{-2}$ nm/day) under similar conditions.[28] Silicon nitride hydrolyzes in two steps:[39] (1) oxidation into silicon oxide and (2) hydrolysis of silicon oxide, where the overall reaction is $SiN_x + 12H_2O \rightarrow 3Si(OH)_4 + 4NH_3$. Temperature dependent studies of hydrolysis of LPCVD $SiN_x$ in PBS reveal additional insights (FIG. 74B). These experiments involve pieces of $SiO_2$/Si wafers (100 nm thick $SiO_2$, 1 cm×2 cm dies) with 200 nm thick LPCVD $SiN_x$ layers on top. PDMS wells bonded to the $SiN_x$ confine the PBS solution to targeted regions of these wafers, as shown in the inset of FIG. 74B. Ellipsometry defines the thicknesses as a function of immersion time at room temperature (RT), 37° C., 50° C., 70° C. and 96° C., respectively. As expected, the thickness of LPCVD $SiN_x$ decreases linearly with time, to determine the dissolution rate. The rate at a pH of 7.4 and 37° C. is ~0.3 nm/day, consistent with previous reports.[37] The relationship between dissolution rate and temperature (FIG. 74C) is consistent with Arrhenius scaling and an activation energy of $E_A = 0.97$ eV. This value is lower than that of thermal $SiO_2$ (1.32 eV).[28]

Another additional limitation of LPCVD $SiN_x$ as a single layer encapsulation is the tendency to form pinholes and defects during deposition in typical cleanrooms available to academic labs. Experiments that involve magnesium test structures (Mg, 300 nm thick, ~1 $cm^2$ area) in FIG. 77, indicate that the spatial density of visible pinholes in 200 nm thick layers of LPCVD $SiN_x$ is 1-2 per square centimeter for our materials. Although improved deposition conditions offer the potential to reduce this value significantly, most academic cleanrooms do not afford the necessary levels of control.

These considerations motivate the use of a bilayer encapsulation that combines both thermal $SiO_2$ (contacted with PBS) and LPCVD $SiN_x$ (substrate for transistor). Here, the $SiO_2$ layer serves as a pinhole-free water barrier with slow dissolution rates and $SiN_x$ serves as a barrier to ions. Accordingly, any of the methods and devices provided herein comprise an encapsulation layer and an ion-barrier layer, including an ion-barrier layer that is on a surface of the encapsulation layer that is not in direct contact with the surrounding liquid, such as a bioliquid or tissue.

Figure 74D:
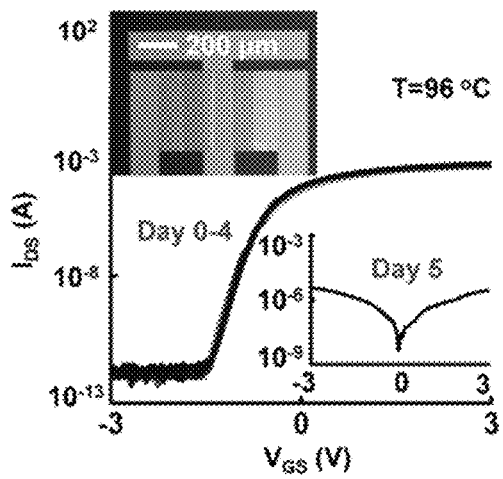

The inset of FIG. 74D displays an optical image of a transistor (channel width W=300 μm, length L=20 μm) that incorporates a frontside encapsulation bilayer of $SiO_2$/$SiN_x$ fabricated using the process described previously. Even with $V_{app}$ of 3V (same as upper inset of FIG. 73E), the key performance characteristics of these transistors remain constant in accelerated soak tests (in 96° C. PBS solution) over the full duration of the experiments, Day 0~4 (FIG. 74D). The devices catastrophically fail at Day 5 (lower inset of FIG. 74D) as a result of hydrolysis of the $SiO_2$ and then the $SiN_x$. The projected lifetime is 16 years at 37° C. considering their dissolution rates (PBS, pH 7.4).[28, 39] The bi-layer also partially balances the opposite stress inside each film (thermal $SiO_2$, compressive stress and LPCVD $SiN_x$, tensile stress). This stress balancing can avoid the cracking in the $SiN_x$ film, and mitigate the curving of the final flexible device.

Figure 74E:
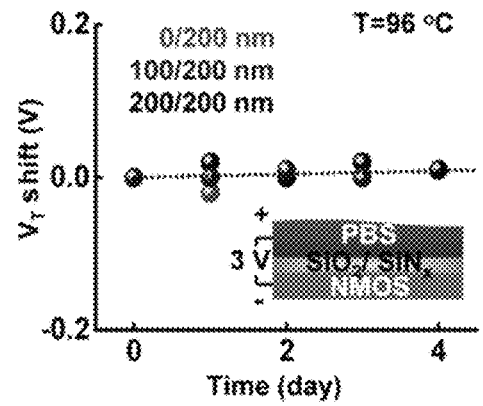

Accelerated soak tests under this same bias condition (3V) with samples that have different thicknesses of $SiO_2$ (0, 100, 200 nm) and a fixed thickness of $SiN_x$ (200 nm) confirm these mechanisms (see FIG. 74D and FIGS. 78A-78B), whereby hydrolysis of the top thermal $SiO_2$ occurs first followed by the bottom $SiN_x$. Values of $\Delta V_T$ extracted from data in FIG. 74D and FIGS. 78A-78B appear in FIG. 74E. The differences in lifetime are consistent with the dissolution rate of thermal $SiO_2$ in 96° C. PBS (~80 nm/day). In all cases, the shifts in $V_T$ are extraordinarily small (less than ~0.05 V). These findings are consistent with simulations of a single layer of $SiN_x$ (200 nm thickness) with 3 V bias (black line in FIG. 74E).

Figure 75A:
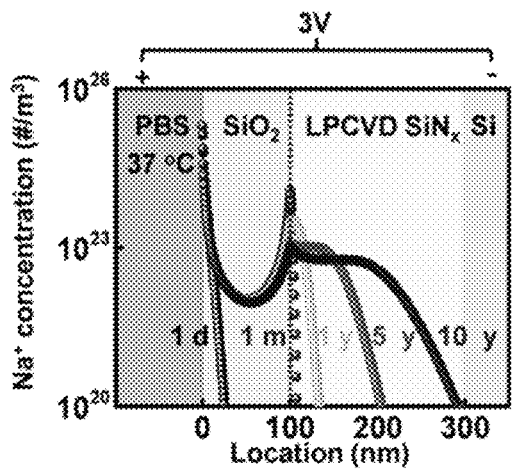
FIGS. 75A-75D. Simulations of ion diffusion through and dissolution of two encapsulation structures.
Figure 75B:
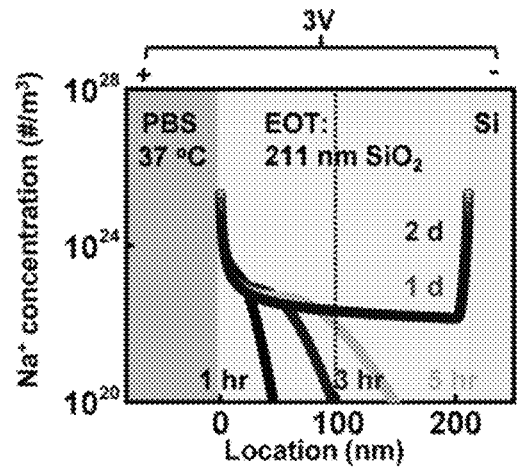

Modeling of the distributions of Na$^+$ allows further comparisons of SiO$_2$/SiN$_x$ and SiO$_2$ (FIGS. 75A-75B). As before, the coupled drift-diffusion equation and Poisson's equation are solved in a 1D domain with V$_{app}$=3 V. As shown in FIG. 75A, the green and yellow regions correspond to SiO$_2$ (100 nm thickness) and SiN$_x$ (200 nm thickness). The values of diffusion coefficients are 6.53×10$^{-21}$ m$^2$/s in thermal SiO$_2$[33] and 4.94×10$^{-25}$ m$^2$/s in LPCVD SiN$_x$ at 37° C.[40] Due to four orders of magnitude differences in diffusivity, Na$^+$ penetrates the top SiO$_2$ layer much faster than the underlying LPCVD SiN$_x$ layer. FIG. 75A shows that within the first month, Na$^+$ builds up inside the SiO$_2$ layer and reaches a short-term saturated concentration profile. At the SiO$_2$/SiN$_x$ interface, Na$^+$ accumulates because the Na$^+$ influx from the SiO$_2$ side is much larger than the outflux into SiN$_x$ side. After this saturation time interval inside SiO$_2$, Na$^+$ begins to slowly transfer into the SiN$_x$ layer. From 1 year up to 10 years, the front end of Na$^+$ concentration spreads out towards the SiN$_x$/Si interface with increasing x (Location axis, from 100~300 nm in FIG. 75A). During this period, the accumulated Na$^+$ peak at the SiO$_2$/SiN$_x$ interface gradually decreases to balance the Na$^+$ that flows into the SiN$_x$ layer. Few Na$^+$ (less than 10$^{20}$/m$^3$) ions can penetrate through SiN$_x$/Si interface within 10 years. The Na+ concentration profile for a corresponding EOT of single layer of thermal SiO$_2$ reveals details (FIG. 75B). Here t, EOT=t$_{high-k}$×(k$_{SiO_2}$/k$_{high-k}$), where t is the thickness and k is the dielectric coefficient (3.9 for SiO$_2$[41] and ~7 for SiN$_x$[31]), which indicates the thickness of a layer of SiO$_2$ that produces the same electrical field effect as the SiN$_x$. Specifically, a SiO$_2$ layer with thickness of ~111 nm offers a capacitance similar to that of a layer of LPCVD SiN$_x$ with 200 nm thickness. As a result, 100/200 nm SiO$_2$/SiN$_x$ corresponds to a total 211 nm thick EOT of SiO$_2$. To make a reasonable comparison, the same boundary conditions and external voltages (3 V) are the same in these two cases, at 37° C. FIG. 75B presents Na$^+$ concentration profiles. The accumulated Na$^+$ at SiO$_2$/Si interface reaches its saturation limit in less than 2 days. The Na$^+$ does not significantly penetrate into the LPCVD SiN$_x$ layer over a period of 10 years.

Figure 75C:
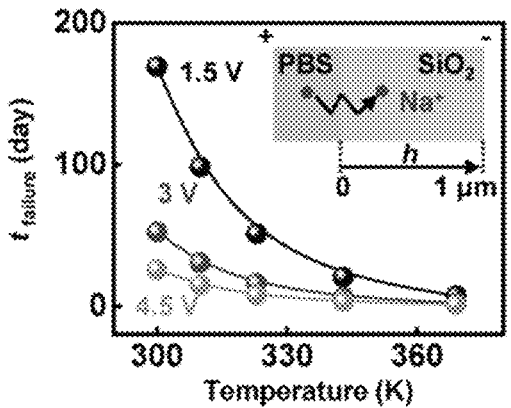

A simulation model based on a 1D domain of a 1 um thick layer of SiO$_2$ (inset of FIG. 75C) using COMSOL Multiphysiscs® reveals the concentration distributions at different V$_{app}$ (1.5, 3, 4.5 V, same in upper insets of FIGS. 73D-73F) with effects of temperature explicitly included. Here, Na$^+$ transports occurs with a constant boundary condition at h=0 and reflective boundary condition at h=1 μm, corresponding to the PBS/SiO$_2$ and SiO$_2$/Si interfaces, and h is the thickness of thermal SiO$_2$. The Na$^+$ penetration rate depends on both applied electrical field and temperature. A failure threshold corresponds to the time at which the Na$^+$ concentration at the SiO$_2$/Si interface reaches 1/40 of its solubility limit: 5×10$^{23}$ m$^{-3}$. The temperature-dependent Na$^+$ diffusion coefficient is: $D=D_0 \cdot e^{-E_A/kT}$, where k is the Boltzmann constant and T is temperature. $D_0$ is the pre-exponential factor and $E_A$ is the activation energy. The diffusion coefficient can be extracted from the data of FIG. 73H, where $D_0$ and $E_A$ are 2.29×10$^{-13}$ m$^2$/s and 0.464 eV, respectively. The calculations yield failure times in various temperature ranges (from 300 to 369K, corresponding from RT to 96° C.) and at various V$_{app}$. In FIG. 75C, together with the consideration of hydrolysis failure, failure time of 1 um thick layer of SiO$_2$ depends exponentially on temperature, and the results at each temperature show a strong dependence on respective V$_{app}$. Specifically, the lifetime at RT under 1.5 V is ~11 times longer than that of 4.5 V, while the difference at 96° C. is ~10 times, which indicates that the lifetime differences respective to various V$_{app}$ is about same at different temperatures.

Figure 75D:
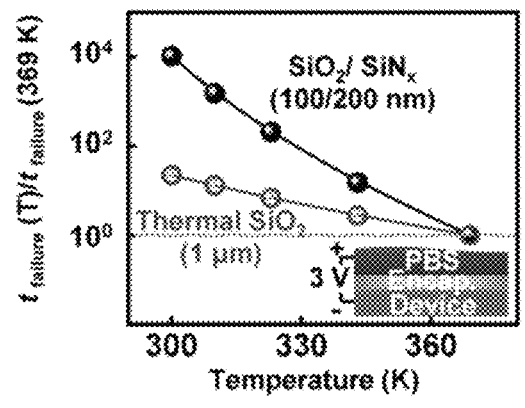

Modeling can also capture the competition between dissolution and ion diffusion in SiO$_2$ and SiO$_2$/SiN$_x$. FIG. 75D presents such competition for single layer of thermal SiO$_2$ and a bi-layer of thermal SiO$_2$/LPCVD SiN$_x$ at thicknesses of 1 μm and 100/200 nm, respectively. The inset of FIG. 75D displays the configuration. We consider an acceleration factor (AF) for the failure time as a function of temperature, considering both dissolution and ion diffusion failures together. The AF is defined as t$_{failure}$ (T)/t$_{failure}$ (369K), normalized at 369 K. In the case of 1 μm thick SiO$_2$, the AF depends on data extracted from FIG. 75C. Here, ion penetration dominates the failure time ratio, because the corresponding dissolution failure time is much longer than ion-diffusion failure time. On the other hand, although SiO$_2$/SiN$_x$ offers improved water/ion barrier properties than single thermal SiO$_2$, the SiN$_x$ has higher dissolution rate than SiO$_2$. As a result, dissolution plays an important role. The AF of SiO$_2$/SiN$_x$ (100/200 nm) uses the dissolution failure time from FIG. 74E. The SiO$_2$ layer dissolves first, followed by the SiN$_x$. As a result, a bi-layer of SiO$_2$/SiN$_x$ offers a lifetime that is ~3 orders of magnitude larger than that of a single layer of SiO$_2$ at 1 μm thickness at 37° C., due to the enhanced ion barrier properties. The bi-layer therefore provides greatly superior performance, even at thicknesses significantly smaller than a corresponding single layer of SiO$_2$.

In summary, the results presented here represent a comprehensive study of ion transport and hydrolysis in ultrathin layers of thermal SiO$_2$ and LPCVD SiN$_x$ in the context of encapsulation strategies for flexible electronic implants. A combination of experiments and simulations demonstrates that bias conditions strongly affect the rate of ion penetration through SiO$_2$, with implications for operational stability of encapsulated transistors. The addition of a layer of LPCVD SiN$_x$ layer can effectively block transport of ions in ways supported by detailed studies of temperature and thickness dependent transistor performance. In these systems, two different failure mechanisms must be considered. For a single layer of thermal SiO$_2$, ion diffusion is dominant due to the low dissolution rate of this material and the comparatively high ion diffusivity. For a bilayer of SiO$_2$/SiN$_x$, dissolution dominates due to excellent ion barrier properties of SiN$_x$. We note that in many practical cases, the ion-barrier layer, including SiN$_x$, can be applied selectively to regions of the system that support transistors or other active semiconductor devices. Accordingly, any of the methods and devices presented herein may have a spatially-varying ion-barrier layer, including with regions of barrier layer corresponding to ion-sensitive electronic devices such as transistors or other semiconductor devices. "Spatially varying" may refer to one or more properties, such as thickness or composition that varies with spatial position along the layer. Other regions without such ion-sensitive materials may not have an ion-barrier layer. In this manner, the overall physical device parameters, including flexibility, bendability, and/or stretchability, may be maintained. Implementing this ion barrier structure in active flexible electronics and optoelectronics provides new possibilities for cardiac and neural and other forms of implants.

Example 4 References

[1] J. Viventi, D.-H. Kim, J. D. Moss, Y.-S. Kim, J. A. Blanco, N. Annetta, A. Hicks, J. L. Xiao, Y. Huang, D. J. Callans, J. A. Rogers, B. Litt, *Science translational medicine*, 2010, 2(24), 24ra22.

[2] D.-H. Kim, N. S. Lu, R. Ghaffari, Y.-S. Kim, S. P. Lee, L. Xu, J. Wu, R.-H. Kim, J. Song, Z. Liu, J. Viventi, B. d. Graff, B. Elolampi, M. Mansour, M. J. Slepian, S. Hwang, J. D. Moss, S.-M. Won, Y. Huang, B. Litt, J. A. Rogers, *Nature Materials*, 2011, 10(4), 316-323.

[3] L. Xu, S. R. Gutbrod, A. P. Bonifas, Y. Su, M. S. Sulkin, N. Lu, H.-J. Chung, K.-I. Jang, Z. Liu, M. Ying, C. Lu, R. C. Webb, J.-S. Kim, J. I. Laughner, H. Cheng, Y. Liu, A. Ameen, J.-W. Jeong, G.-T. Kim, Y. Huang, I. R. Efimov, J. A. Rogers, *Nature Communications* 5, 2014, DOI:10.1038/ncom m s4329.

[4] D.-H. Kim, R. Ghaffari, N. Lu, S. Wang, S. P. Lee, H. Keum, R. D'Angelo, L. Klinker, Y. Su, C. Lu, Y.-S. Kim, A. Ameen, Y. Li, Y. Zhang, B. d. Graff, Y.-Y. Hsu, Z. Liu, J. Ruskin, L. Xu, C. Lu, F. G. Omenetto, Y. Huang, M. Mansour, M. J. Slepian, J. A. Rogers, *Proceedings of the National Academy of Sciences*, 2012, 109(49), 19910-19915.

[5] X. Dai, W. Zhou, T. Gao, J. Liu, C. M. Lieber, *Nat. Nanotechnol.*, 2016, 11, 776-782.

[6] J.-W. Jeong, J. G. McCall, G. Shin, Y. Zhang, R. Al-Hasani, M. Kim, S. Li, J. Y. Sim, K. I. Jang, Y. Shi, D. Y. Hong, Y. Liu, G. P. Schmitz, L. Xia, Z. He, P. Gamble, W. Z. Ray, Y. Huang, M. R. Bruchas, J. A. Rogers, *Cell*, 2015, 162(3), 662-674.

[7] K. L. Montgomery, A. J. Yeh, J. S. Ho, V. Tsao, S. M. Iyer, L. Grosenick, E. A. Ferenczi, Y. Tanabe, K. Deisseroth, S. L. Delp, A. S Y. Poon, *Nature Methods*, 2015, 12(10), 969-974.

[8] T. Kim, J. G. McCall, Y. H. Jung, X. Huang, E. R. Siuda, Y. Li, J. Song, Y. M. Song, H. A. Pao, R.-H. Kim, C. Lu, S. D. Lee, I.-S. Song, G. Shin, R. Al-Hasani, S. Kim, M. P. Tan, Y. Huang, F. G. Omenetto, J. A. Rogers, M. R. Bruchas, *Science*, 2013, 340(6129), 211-216.

[9] A. Canales, X. Jia, U. P. Froriep, R. A. Koppes, C. M. Tringides, J. Selvidge, C. Lu, C. Hou, L. Wei, Y. Fink, P. Anikeeva, *Nature Biotechnology*, 2015, 33(3), 277-284.

[10] R. Nawrocki, N. Matsuhisa, T. Yokota, T. Someya, *Adv. Electron. Mater.*, 2015, 2(1500452), 1-4.

[11] B. Tian, T. Cohen-Karni, Q. Qing, X. J. Duan, P. Xie, C. M. Lieber *Science*, 2010, 329(5993), 830-834.

[12] D.-H. Kim, N. Lu, R. Ma, Y.-S. Kim, R.-H. Kim, S. Wang, J. Wu, S. M. Won, H. Tao, A. Islam, 1 K. J. Yu, T.-i. Kim, R. Chowdhury, M. Ying, L. Xu, M. Li, H.-J. Chung, H. Keum, M. McCormick, P. Liu, Y.-W. Zhang, F. G. Omenetto, Y. Huang, T. Coleman, J. A. Rogers, *Science*, 2011, 333(6044), 838-43

[13] D. J. Lipomi, M. Vosgueritchian, B. C. Tee, S. L. Hellstrom, J. A. Lee, C. H. Fox, Z. Bao, *Nature Nanotechnology*, 2011, 6(12), 788-792.

[14] S. Xu, Y. Zhang, L. Jia, K. E. Mathewson, K. I. Jang, J. Kim, H. Fu, X. Huang, P. Chava, R. Wang, S. Bhole, L. Wang, Y. J. Na, Y. Guan, M. Flavin, Z. Han, Y. Huang, J. A. Rogers, *Science*, 2014, 344(6179), 70-4.

[15] W. Gao, S. Emaminejad, H. Y. Nyein, S. Challa, K. Chen, A. Peck, H. M. Fahad, H. Ota, H. Shiraki, D. Kiriya, D. H. Lien, G. A. Brooks, R. W. Davis, A. Javey, *Nature*, 2016, 529(7587), 509-514.

[16] W. Wu, L. Wang, Y. Li, F. Zhang, L. Lin, S. Niu, D. Chenet, X. Zhang, Y. Hao, T. F. Heinz, J. Hone, Z. L. Wang, *Nature*, 2014, 514(7523), 470-474.

[17] M. C. McAlpine, H. Ahmad, D. Wang, J. R. Heath, *Nature Materials*, 2007, 6(5), 379-384.

[18] M. Kaltenbrunner, T. Sekitani, J. Reeder, T. Yokota, K. Kuribara, T. Tokuhara, M. Drack, R. Schwödiauer, I. Graz, S. Bauer-Gogonea, S. Bauer, T. Someya, *Nature*, 2013, 499(7459), 458-463.

[19] C. M. Lochner, Y. Khan, A. Pierre, A. C. Arias, *Nature Communications*, 2014, 5, 5745.

[20] D. Son, J. Lee, S. Qiao, R. Ghaffari, J. Kim, J. E. Lee, C. Song, S. J. Kim, D. J. Lee, S. W. Jun, S. Yang, M. Park, J. Shin, K. Do, M. Lee, K. Kang, C. S. Hwang, N. Lu, T. Hyeon, D.-H. Kim, *Nature Nanotechnology*, 2014, 9(5), 397-404.

[21] B. S. Wilson, C. C. Finley, D. T. Lawson, R. D. Wolford, D. K. Eddington, W. M. Rabinowitz, *Nature*, 1991, 352(6332), 236-238.

[22] L. Bowman, J. D. Meindl, *IEEE Transactions on Biomedical Engineering*, 1986, BME-33(2), 248-255.

[23] R. S. Sanders, M. T. Lee, *Proceedings of the IEEE*, 1996, 84(3), 480-486.

[24] H. S. Mayberg, A. M. Lozano, V. Voon, H. E. McNeely, D. Seminowicz, C. Hamani, J. M. Schwalb, S. H. Kennedy, *Neuron*, 2005, 45(5), 651-660.

[25] Thejo Kalyani N, Dhoble S J, *Renewable and Sustainable Energy Reviews*, 2015, 44, 319-347.

[26] J.-S. Park, H. Chae, H. K. Chung, S. I. Lee, *Semiconductor Science and Technology*, 2011, 26(3), 034001.

[27] J. Ahmad, K. Bazaka, L. J. Anderson, R. D. White, M. V. Jacob, *Renewable and Sustainable Energy Reviews*, 2013, 27, 104-117.

[28] H. Fang, J. Zhao, K. J. Yu, E. Song, A. B. Farimani, C.-H. Chiange, X. Jin, Y. Xue, D. Xu, W. Dui, K. J. Seo, Y. Zhong, Z. Yang, S. M. Won, G. Fang, S. W. Choi, S. Chaudhuri, Y. Huang, M. A. Alam, J. Viventi, N. R. Aluru, J. A. Rogers, *Proceedings of the National Academy of Sciences*, 2016, 113(42), 11682-11687.

[29] H. Fang, K. J. Yu, C. Gloschat, Z. Yang, E. Song, C.-H. Chiang, J. Zhao, S. M. Won, S. Xu, M. Trumpis, Y. Zhong, S. W. Han, Y. Xue, D. Xu, S. W. Choi, G. Cauwenberghs, M. Kay, Y. Huang, J. Viventi, I. R. Efimov and J. A. Rogers, *Nature Biomedical Engineering*, 2017, 1(3), 0038.

[30] K. J. Yu, D. Kuzum, S.-W. Hwang, B. H. Kim, H. Juul, N. H. Kim, S. M. Won, K. Chiang, M. Trumpis, A. G. Richardson, H. Cheng, H. Fang, M. Thompson, H. Bink, D. Talos, K. J. Seo, H. N. Lee, S.-K. Kang, J.-H. Kim, J. Y. Lee, Y. Huang, F. E. Jensen, M. A. Dichter, T. H. Lucas, J. Viventi, B. Litt and J. A. Rogers, *Nature Materials*, 2016, 15, 782.

[31] S. M. Sze, Semiconductor devices: physics and technology ($2^{nd}$ edition). John Wiley & Sons, USA 2008.

[32] P. Dak, M. A. Alam, *IEEE Transactions on Electron Devices*, 2016, 63(6), 2524-2530.

[33] E. Yon, W. Ko, A. Kuper, *IEEE Transactions on Electron Devices*, 1966, Ed13, 276-280.

[34] J. Mecha, J. Steinmann, *Journal of the American Ceramic Society*, 1979, 62, 343-346.

[35] V. Korol, *Physica status solidi* (a), 1988, 110, 9-34.

[36] T. Burges, J. C. Baum, F. M. Fowkes, R. Holmstrom, G. A. Shirn, *J. Electrochem. Soc.*, 1969, 116(7), 1005-1008.

[37] Y. Taur, T. H. Ning, *Fundamentals of Modern VLSI Devices*. Cambridge University Press, USA 2009.

[38] Y. Sun, J. A. Rogers, *Adv. Mater.* 2007, 19, 1897-1916.

[39] S.-K. Kang, S.-W. Hwang, H. Cheng, S. Yu, B. H. Kim, J.-H. Kim, Y. Huang, J. A. Rogers, *Adv. Funct. Mater.*, 2014, 24, 4427-4434.

[40] J. Osenbach, S. Voris, *Journal of applied physics*, 1988, 63, 4494-4500.

[41] P. R. Gray, P. J. Hurst, S. H. Lewis, R. G. Meyer, Analysis and Design of Analog Integrated Circuits ($5^{th}$ edition). John Wiley & Sons, USA 2009.

Analysis of Transistor Characteristics: The effective mobility ($\mu_{eff}$) can be extracted using the following equation:

$$\mu_{\text{eff}} = \frac{\partial I_{DS}}{\partial V_{DS}} \cdot \frac{L}{W C_{OX}(V_{GS} - V_T - 0.5 V_S)} \quad (S1)$$

where $V_T$ is the threshold voltage and $C_{ox}$ is the specific capacitance of the gate per unit gating area, while the transistor gate area is 20×300 μm (L×W). We subtract the total phosphorus diffusion length from the lithography length (L, 20 μm), thus yielding the effective channel length $L_{\text{eff}}$. The dopants diffusion length can be determined by the activation of phosphorus after doping, which is dominantly influenced by the thermal oxidation step for the gate oxide (1,150° C. for 37 min). Therefore the estimated value of $L_{\text{eff}}$ yields ~14 μm. As a result, the peak mobility is ~400 cm$^2$ (V·s)$^{-1}$.

Numerical Simulation for NMOS $V_T$ Shift: Na$^+$ migrates through the SiO$_2$ layer and accumulates near the SiO$_2$—Si substrate interface, leading to an enhancement on Vat the front gate. An NMOS model in the Sentaurus simulator allows quantitative calculation of the influence on $\Delta V_T$.

FIG. 76 shows the 2D cross section of embedded NMOS device underneath the encapsulation layer. The device dimensions are the same as those in experiment—channel length (L=20 um), Si substrate thickness ($t_{Si}$=100 nm) and gate oxide thickness ($t_{ox}$=400 nm). The material for the channel is intrinsic Si and that for the source and drain regions is n-type Si with a doping level of 10$^{19}$ cm$^{-3}$. We apply $V_{ds}$=0.1V between source and drain, sweep the gate voltage $V_{GS}$ from −3V to 3V, and plot the $I_{ds}$-$V_{GS}$ curve. A thin layer of accumulated Na$^+$ with surface charge density $Q_s$ is located at the interface between the encapsulation layer and Si channel. We change this $Q_S$ and calculate the corresponding $\Delta V_T$ from each $I_{ds}$-$V_{GS}$ curve.

Figure 77:
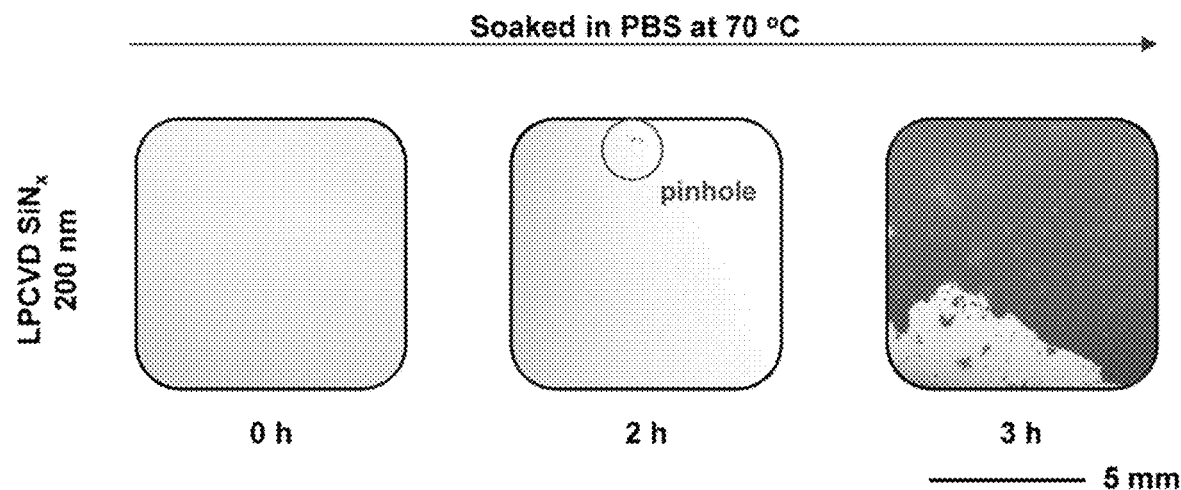
FIG. 77. Mg soak test of 200 nm thick layer of LPCVD $SiN_x$ in 70° C. PBS solution throughout 3 hours.

Mg Test Structures for Evaluation of Water Barrier Performance of LPCVD SiN$_x$: Photolithography with a negative photoresist (AZ nLOF 2070, MicroChemicals) forms ~1 cm$^2$ square area on the clean surface of wafer (ROGUE VALLEY MICRODEVICES) with a 200 nm thick coating of LPCVD SiN$_x$. Subsequent electron-beam evaporation and lift-off yielded a layer of Ti/Mg (5/300 nm) in the predefined area. Spin-coating, soft-baking and curing yields an overcoat of polyimide (PI-2545, HD MicroSystems) with a thickness of 3.5 μm. ALD produces a layer of Al$_2$O$_3$ on the polyimide, to facilitate bonding to a handle glass substrate. The bonding involves the application of a commercial adhesive (Kwik-Sil, World Precision Instruments), which is cured at room temperature. Dry etching by inductively coupled plasma RIE (ICP-RIE, Surface Technology System) with a gas flow of SF$_6$/O$_2$ 40/3 sccm in 50 mT removes the back silicon, thus leaving a scalable and pristine surface of LPCVD SiN$_x$ as a water barrier. Here, the Mg pad serves as a sensor for water penetration in examining the barrier properties of LPCVD SiN$_x$. Specifically, the strong reactivity of Mg with water (Mg+2H$_2$O→Mg(OH)$_2$+H$_2$) quickly produces defects that can be visualized easily by standard microscopy techniques. As shown in FIG. 77, a 200 nm thick layer of LPCVD SiN$_x$ can survive for 3 hours of complete, continuous immersion in 70° C. PBS solution. Isolated, 'pinhole' defects start to appear on Mg pad after 2 hours and then expand significantly, causing complete failure after 3 hours. Therefore, Mg test results indicate that LPCVD SiN$_x$ formed in our academic cleanroom facilities have pinholes at a density of ~1/cm$^2$.

Figure 78A:
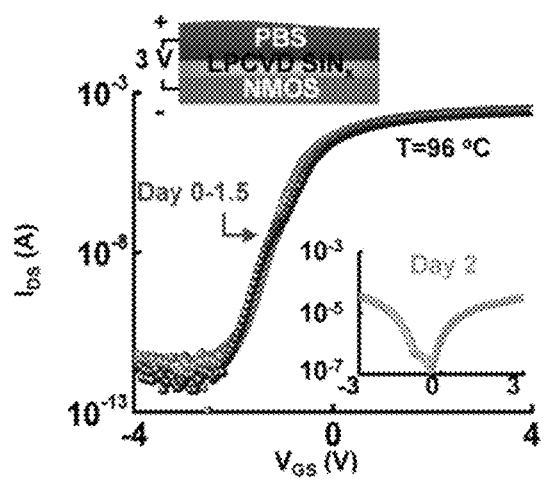
FIGS. 78A-78B. Results of accelerated soak tests of NMOS transistors with external electrical field (3 V) in 96° C.
Figure 78B:
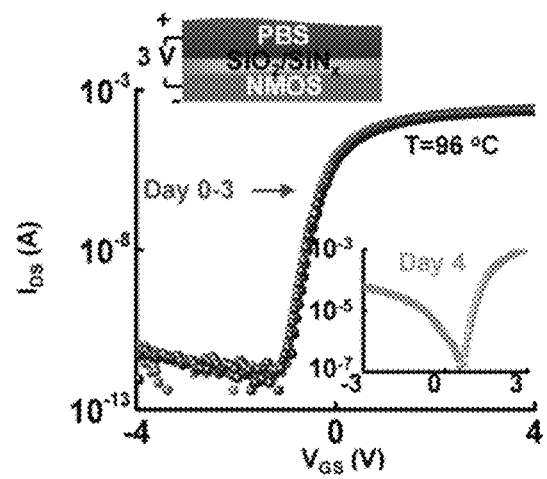

Thickness Ratio Influence of thermal SiO$_2$/LPCVD SiN$_x$ on Transistor Performances: We fabricated transistors encapsulated with different thicknesses of thermal SiO$_2$/LPCVD SiN$_x$ (0/200, 100/200, 200/200 nm). FIGS. 78A-78B demonstrate the transistor performance with a single 200 nm thick layer of LPCVD SiN$_x$ and a bilayer of 100/200 nm SiO$_2$/SiN$_x$ within each lifetime at 96° C., respectively. Upper Insets of FIGS. 78A-78B illustrate the scheme for accelerated soak tests (same as upper inset of FIG. 73E). For the case of a single SiN$_x$ layer, we measured the performances over 2 days at an interval of 0.5 days. The SiN$_x$ dissolves after 2 days, corresponding to a catastrophic failure, as in the lower inset of FIG. 78A; for the bilayer case, measurements occur over 4 days at an interval of 1 day. Here, catastrophic failure occurs at Day 4, as in the lower inset of FIG. 78B, indicating that the bilayer has fully or substantially dissolved. The results here are consistent with hydrolysis rates for thermal SiO$_2$ and LPCVD SiN$_x$ (shown in FIG. 74C) at 96° C.

Also incorporated by reference herein, is: Song et al. "Thin, Transferred Layers of Silicon Dioxide and Silicon Nitride as Water and Ion Barriers for Implantable Flexible Electronic Systems" *Adv. Electron. Mater.* 3 (Jun. 6, 2017).

Example 5: Bioresorbable Pressure Sensors Encapsulated with Thermally Grown Silicon Dioxide for the Monitoring of Chronic Diseases and Healing Processes Pressures in the intracranial, intraocular and intravascular spaces are clinically useful for the diagnosis and management of traumatic brain injury, glaucoma and hypertension, respectively. Conventional devices for measuring these pressures require surgical extraction after a relevant operational timeframe. Bioresorbable sensors, by contrast, eliminate this requirement, thereby minimizing the risk of infection, decreasing the costs of care, and reducing distress and pain for the patient. However, the operational lifetimes of current bioresorbable pressure sensors fall short of many clinical needs. Here, we present materials, device structures and fabrication procedures for bioresorbable pressure sensors with lifetimes exceeding those of previous reports by at least ten-fold. By monitoring intracranial pressures in rats for 25 days, we demonstrate measurement accuracies that compare favorably to those of the most sophisticated clinical standards for non-resorbable devices. Assessments of biodistribution of the constituent materials, complete blood count, blood chemistry and MRI compatibility confirm device biodegradability and clinical utility. Our findings establish routes for the design and fabrication of bioresorbable pressure monitors that meet requirements for clinical use.

Measurements of pressure in organ systems such as the brain, eyes, bladder, and blood vessels form an essential diagnostic basis for assessment of patient health and progression of diseases such as traumatic brain injury, hydrocephalus (intracranial pressure), glaucoma (intraocular pressure), and hypertension (blood pressure). Capabilities in precise, continuous monitoring of pressure can, therefore, be critically important in defining treatment protocols that decrease the rate of morbidity and increase the pace of recovery[1-3]. Conventional sensor technologies designed for this purpose are available in the form of accurate, implantable devices that must be surgically extracted following clinical use. These procedures are costly and expose the patient to additional risks for complications[4]. Additionally, the devices can serve as a nidus for infection[5,6] and immune-mediated inflammatory responses[7]. Emerging classes of bioresorbable electronic sensor systems have the potential to address these disadvantages. Here, all of the constituent materials dissolve in biofluids over well-defined periods of time, with biologically benign end products. This process naturally eliminates the devices after a useful functional period, thereby bypassing surgical extraction. Examples of bioresorbable devices in the recent literature include biophysical sensors of pressure, temperature, flow rate, and motion[8,9] along with several types of biochemical sensors[8,10]. Additional components range from thermal actuators[8] to neural electrodes[11,12], power supplies[13], and controlled drug-delivery vehicles[14,15]. Published animal model studies include deployments in the intracranial, intra-abdominal and leg cavities[8], on cortical surfaces[11,12], and in subdermal regions[15,16].

Although recently reported bioresorbable pressure sensors have sensitivity and accuracy comparable to those of conventional, non-resorbable analogs, they offer stable operation over a period of only several days, which is insufficient for many applications[8,9]. Extending this operational lifetime to several weeks demands solutions to daunting challenges in materials science and device design that follow directly from the requirement that the systems must ultimately dissolve completely, at a molecular level, without adverse effect. This difficulty is inherent to all classes of implantable, bioresorbable systems because immersion in biofluids immediately initiates processes of bioresorption. The most effective method to prolong the lifetime relies on passive encapsulating layers that delay the time required for biofluids to come into contact with the active materials. Bioresorbable polymers such as silk fibroin[15,16], poly(L-lactide) (PLLA)[9], and poly(lactic-co-glycolic acid) (PLGA)[13] are attractive for such purposes, partly because they can be formed easily by spin-coating or molding. The hydrophilic nature of these materials, however, leads to swelling and water permeation, thereby causing premature fracture, buckling and/or dissolution of the underlying materials. Inorganic alternatives such as silicon dioxide[17,18], silicon nitride[18], and various metal oxides[19] formed by chemical or physical vapor deposition offer exceptionally slow rates of dissolution without these other adverse behaviors. Nevertheless, such materials are of limited practical utility due to extreme difficulties in forming coatings without micro/nanocracks, pinholes or other defects that can allow water to pass.

Recent work demonstrates that layers of silicon dioxide thermally grown on device-grade silicon wafers (t-SiO$_2$) can serve as biofluid barriers with defect-free, material-level perfection over large areas[20,21]. Systematic studies show that the eventual failure follows from hydrolysis reactions, as opposed to water permeation through the material or through defects in the films. Specifically, t-SiO$_2$ dissolves in simulated biofluids at physiological temperatures with rates of several hundredths of a nanometer per day, to yield silicic acid as a bioresorbable end product[18,20,21]. These observations suggest the use of ultrathin films of t-SiO$_2$ as bioresorbable encapsulation layers may enable stable operating periods of weeks or longer. This materials strategy has the potential to yield devices that can address lifetime requirements for many envisioned clinical applications, such as monitoring of pressure for traumatic brain injury (up to one week)[22] and glaucoma (several months), as examples. The principal design approach includes: (1) t-SiO$_2$ barriers that prevent interactions with biofluids throughout the desired monitoring period, but with thicknesses sufficiently small enough to allow complete bioresorption within a reasonable timeframe, typically less than a year; (2) structural components that dissolve in a manner that does not affect the measurement accuracy; and (3) interlayer bonding techniques that prevent interfacial water penetration from the periphery.

Here, we demonstrate materials, device structures, and fabrication methods that adhere to this strategy. The overall scheme relies on bonding of a pair of silicon-on-insulator wafers using adhesion layers of amorphous silica formed by calcination of poly(dimethylsiloxane) (PDMS). Eliminating the handle wafers after bonding yields ultrathin, inorganic bioresorbable electronic devices with robust biofluid barriers that allow stable operation over extended periods of time. Data on the biodistribution of dissolved silicon in mice at five weeks following implantation of intracranial sensors formed in this manner, together with assessments of the hematology (complete blood count, CBC), blood chemistry, and MRI compatibility, confirm their biodegradability and clinical utility. Measurements of intracranial pressures in rats over 25 days illustrate high accuracy and low drift, with overall performance that compares favorably to that of non-resorbable clinical standards. The results not only establish routes to bioresorbable pressure monitoring technologies that meet requirements for clinical use, but they also serve as a generalizable platform for broad classes of bioresorbable electronic devices that can offer stable operating characteristics over long periods of time.

Materials, Designs, and Fabrication Procedures.

FIG. 79A shows a schematic illustration of an inorganic bioresorbable pressure sensor based on four silicon nanomembrane (Si NM, 200 nm) sensors (length ~300 μm, width ~8 μm), two of which serve as strain gauges (SGs) and two as temperature gauges (TGs). Partial extension of the SGs over an air filled cavity (200 μm×200 μm×10 μm) yields a floating, pressure-sensitive diaphragm with a piezoresistive response in the SG that depends on the mechanical equilibrium between the pressures of the surroundings and that of the air trapped inside the cavity. The TGs, which are not located on the diaphragm and are therefore unresponsive to changes in pressure, respond to changes in surrounding temperature via their temperature-dependent resistance. The red and blue insets illustrate the layer composition in regions of the diaphragm with (red) and without (blue) the SG. The diaphragm consists of a tri-layer of thermal SiO$_2$ (t-SiO$_2$, ~10 nm), monocrystalline Si (~200 nm), and electron-beam evaporated SiO$_2$ (eb-SiO$_2$, ~600 nm; cross-sectional SEM images are obtained). The t-SiO$_2$ layer insulates the Si devices from exposure to biofluids, thereby extending their functional lifetime. The eb-SiO$_2$ layer constitutes the thickest part of the diaphragm, and serves to increase the vertical separation between the neutral mechanical planes of the SGs and the bulk membrane, thereby improving the response of the SGs to pressure. Four exposed regions of Si NM serve as openings for electrical contact pads (200 μm×200 μm) to allow electrical connection with data acquisition system, while the rest of the device surface is protected by t-SiO$_2$ layer.

A photograph and optical micrograph of a representative device, with size and weight of 1.3 mm×1.3 mm×16 μm and ~60 μg, respectively, appear in FIGS. 79B-79C. FIG. 79D shows a circuit diagram of the pressure sensor, in which four gauges combine to form a Wheatstone bridge to compensate temperature effects on the piezoresistive response of the SGs[23]. A magnified view of the diaphragm in FIG. 79E demonstrates isolation of the SGs (pink) by two gray lines, which represent regions where the Si NM (width ~5 μm) are removed. The diaphragm has an area of 200 μm×200 μm, defined by lateral dimensions (boundary lines) of the trench.

Figure 79F:
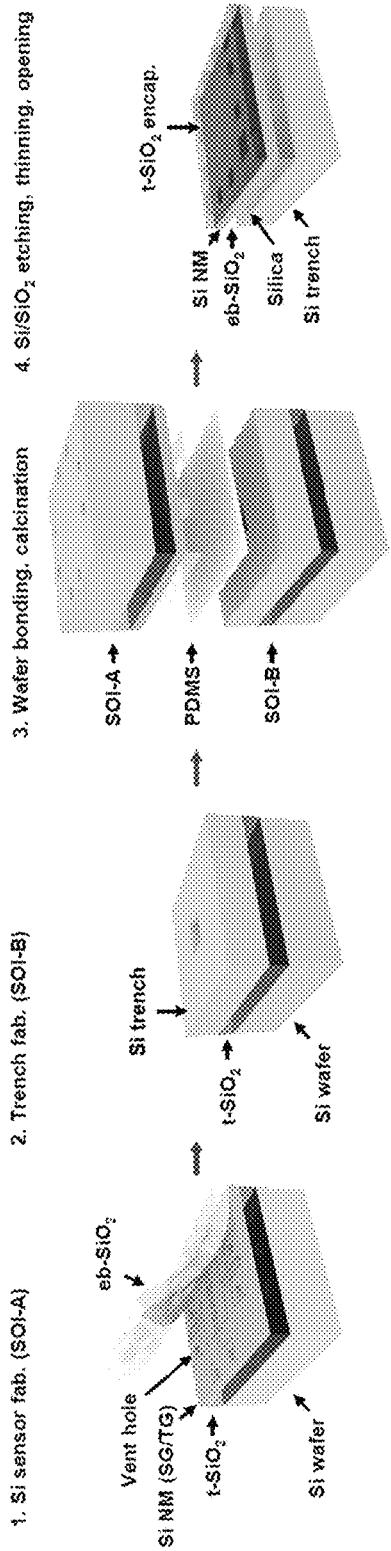

FIG. 79F illustrates the device fabrication steps, beginning with formation of Si NM sensors on a silicon-on-insulator wafer (SOI-A, top Si ~200 nm, buried $SiO_2$ ~1 µm, Si wafer ~100 µm) via solid-state diffusion of phosphorus at 950° C., photolithography and reactive ion etching (Plasma-Therm RIE) to define SGs and TGs from the top Si, and evaporation of eb-$SiO_2$. Photolithography and deep reactive ion etching (STS Pegasus ICP-DRIE) then create an array of holes (100 µm×100 µm) through the thickness of the wafer to release gaseous products of the calcination process described subsequently (step 1). Patterning and etching the top Si layer of a second SOI wafer (SOI-B, top Si ~15 µm, buried $SiO_2$ ~600 nm, Si wafer ~85 µm) creates a trench (step 2). Spin-coating a thin layer of poly(dimethylsiloxane) (PDMS) on SOI-B allows bonding to SOI-A via thermal curing while applying pressure with a steel vise (analysis of errors associated with PDMS coating on the inner surfaces of the trench are obtained).

Heating the vise in a furnace at 550° C. for 2 hours calcines the PDMS adhesion interlayer to yield an amorphous silica material (~200 nm) via a thermal oxidative degradation process[24]. Gaseous by-products such as carbon dioxide and water escape the bonding interface via the vent holes, leaving behind a smooth film of silica. SEM and AFM images of the silica layer are obtained. A single broad peak near −110 ppm in the $^{29}Si$ NMR spectrum of the silica confirms full conversion of PDMS (no peak around −21 ppm, where $SiO_2(CH_3)_2$ would appear) into amorphous $SiO_2$ (Si—(O—Si)$_4$, $Q_4$ site). Electron dispersive spectroscopy (EDS) also confirms the absence of carbon. A series of ICP-DRIE and wet etching (in buffered oxide etchant) processes removes handle wafers, reduces the thickness of t-$SiO_2$ layer to a desired value (~10 nm), and exposes the Si NM for electrical contact (step 4).

Device Characterization.

Figure 79G:
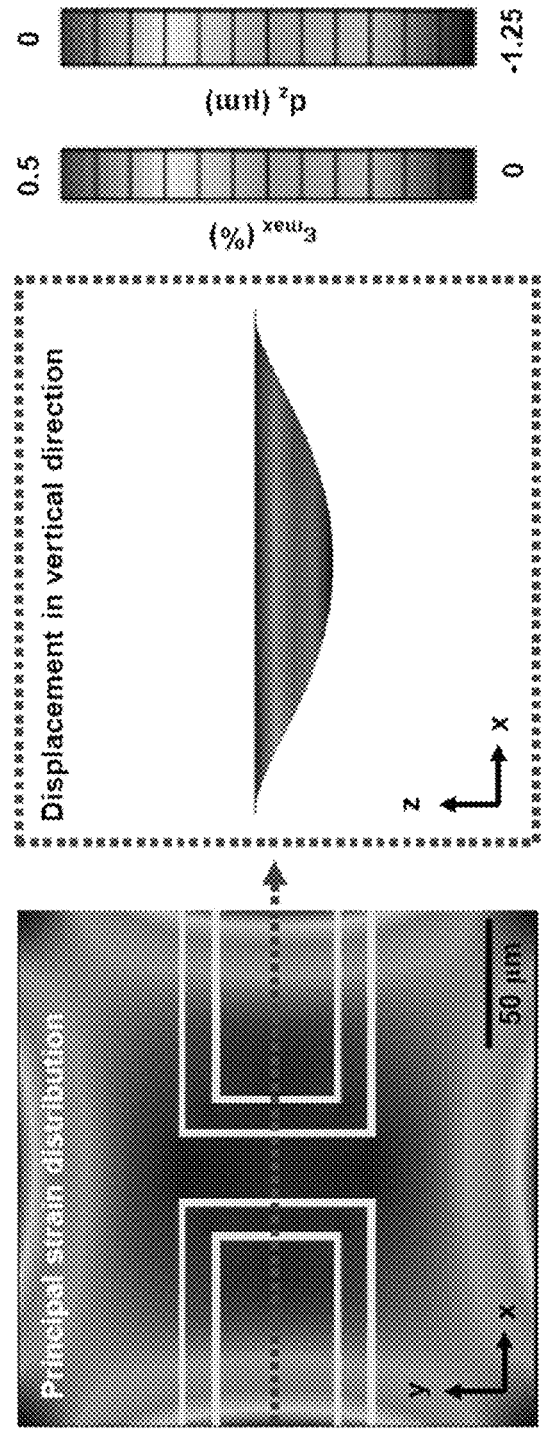

Three-dimensional finite element analysis (3D-FEA) provides insights into the mechanics of pressure sensing using these constructs. Distributions of principal strain and vertical displacements associated with the diaphragm under an external pressure of 40 mmHg above atmospheric appear in FIG. 79G. The maximum strain for any applied pressure over the range of interest occurs along the edge of the trench, where the SGs are located. The relationship between the resistance of a SG and pressure is linear with a slope of −0.13 Ω/mmHg, which corresponds to a gauge factor of ~−20.9, consistent with theory. The modest value of the gauge factor follows from the heavy doping of the top Si needed to allow phosphorus atoms to diffuse through its thickness to the base, at the location of electrical contact pads formed as a result of wafer bonding and etching[25,26]. Reducing the thickness of the Si NM, increasing the area of the diaphragm, and introducing serpentine designs in the SGs can improve the pressure sensitivity. Measurements of the resistance of the TG as a function of temperature reveal a linear response with a temperature coefficient of resistance (TCR) of 0.0012/° C., which lies within a range of expected values for monocrystalline silicon[26,27]. Changes in pressure sensitivity due to changes in temperature within the relevant ranges for the intracranial space (34-40° C.) induce errors that are less than ±0.4 mmHg.

Figure 79H:
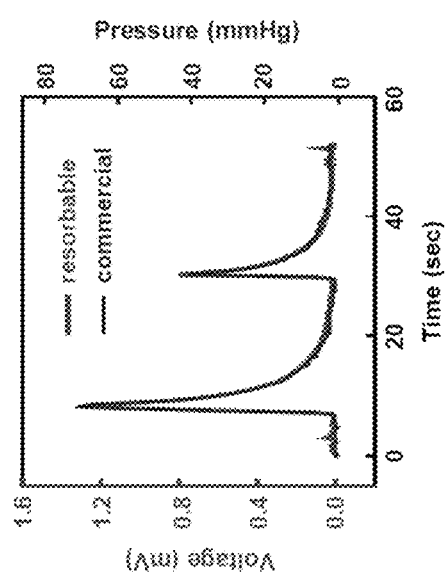

In vitro evaluations that mimic thermodynamic conditions inside the intracranial space illustrate the functional capabilities. An airtight plastic chamber filled with artificial cerebrospinal fluid (ACSF, pH 7.4) at physiological temperature (37° C.) and connected via tubes to a commercial pressure sensor (Neulog, USA) and a syringe allows measurement and control of pressure, respectively. Comparing voltage responses of the sensor (red, $V_s$=2.5 V) with the measured pressures (blue) for values over a range relevant to intracranial monitoring reveals a linear correspondence (FIG. 79H). The level of noise in the response of the bioresorbable sensor, evaluated as the difference between the pressures measured by bioresorbable and commercial sensors (noise floor less than ±0.8 mmHg), lies within ±1 mmHg in the range of 0-30 mmHg and within ±3 mmHg in measured values that exceed this range. These numbers meet the intracranial pressure (ICP) monitoring standards defined by the Association for the Advancement of Medical Instrumentation (AAMI) (that is, a functional range of 0-100 mmHg, accuracy of ±2 mmHg in the range of 0-20 mmHg, and maximum error less than ±10% in the range of 20-100 mmHg)[28]. Comprehensive results from continuous in vitro operation over a period of 22 days reveal variations in pressure sensitivity and baseline within ±1.5% and ±2.5 mmHg, respectively. The observed baseline drift is within the range specified for clinical ICP monitors (that is, ±2 mmHg maximum in the first 24 hours and ±1 mmHg per day thereafter)[29].

Figure 80A:
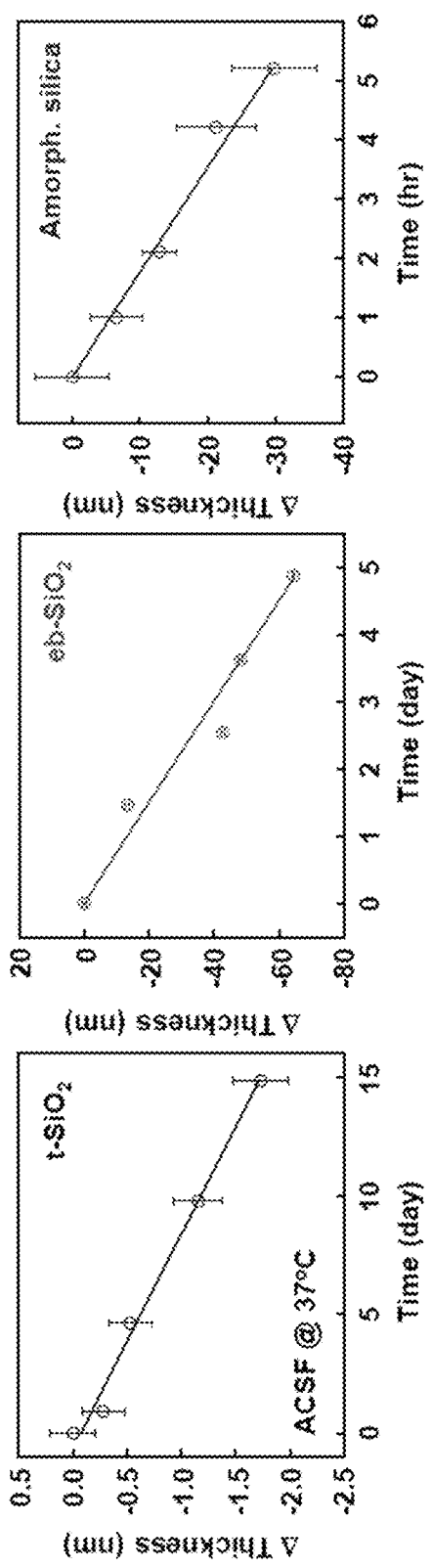
FIGS. 80A-80E. Kinetics of dissolution of a Bioresorbable pressure sensor.

Kinetics of dissolution. The key feature of this system is that the constituent materials are water soluble, with biocompatible end products. Dissolution of Si and $SiO_2$ yields silicic acid $Si(OH)_4$ via hydrolysis, according to $Si+4H_2O \rightarrow Si(OH)_4+2H_2$ and $SiO_2+2H_2O \rightarrow Si(OH)_4$, respectively. FIG. 80A shows the kinetics, evaluated as changes in thicknesses of films of silicon oxides obtained by thermal oxidation, electron beam evaporation, and PDMS calcination in ACSF at T=37° C. The thicknesses of the t-$SiO_2$ and eb-$SiO_2$ layers can be quantified by spectroscopic reflectometry (MProbe), while those of the silica adhesion layer can be assessed most effectively by profilometry (Alpha Step) due to non-uniformities in film thickness that follow from calcination. The layers of t-$SiO_2$, eb-$SiO_2$ and silica dissolve at rates of 0.11±0.01, 13.6±1.6, and 129±9 nm/day, respectively. The rates of dissolution of single-crystalline silicon and bioresorbable metals (Mo, Mg) appear elsewhere.[8,11] These rates, taken together with the overall structures of the devices, yield estimated times for full dissolution of ~400 days. By decreasing the thickness of the trench (~10 µm), this time can be reduced to approximately 290 days without significantly compromising the sensor response.

Figure 80B:
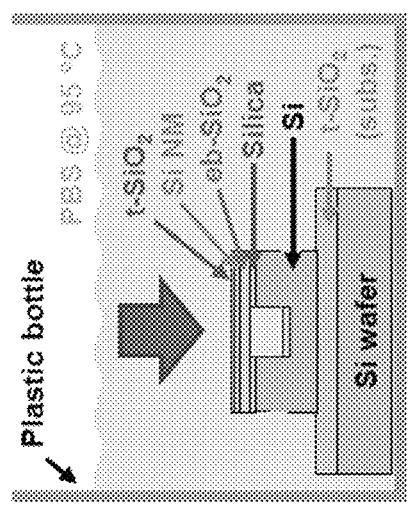
Figure 80C:
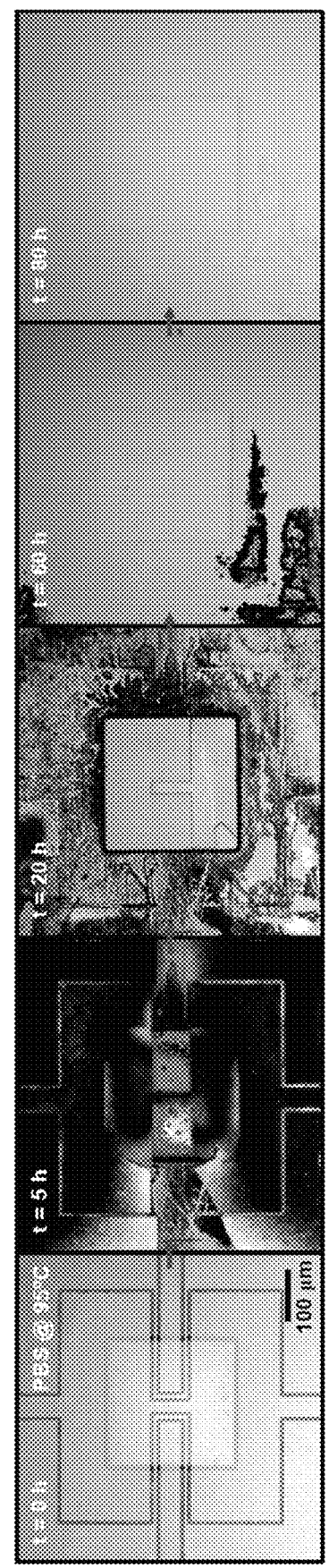

FIG. 80B shows a schematic illustration of a set-up designed to dissolve bioresorbable sensors at accelerated rates by immersion in phosphate-buffered saline (PBS, pH 7.4) at T=95° C. in a plastic bottle. Employing a test design in which the sensor uses a t-$SiO_2$ substrate allows unidirectional thinning of component layers in sequence from top to bottom. FIG. 80C presents optical micrographs collected at various stages of dissolution. Complete hydrolysis of the t-$SiO_2$ layer leads to exposure of the Si NM within 5 hours; fast and non-uniform dissolution of the silicon creates a rough surface profile, which appears as dark shades under the microscope. The eb-$SiO_2$ and silica adhesion layers disappear within 20 hours, followed by the Si trench (outer gray region) in 80 hours. Complete disintegration leaves only the surface of the t-$SiO_2$ substrate with a shallow feature of surface relief (pink).

Figure 80D:
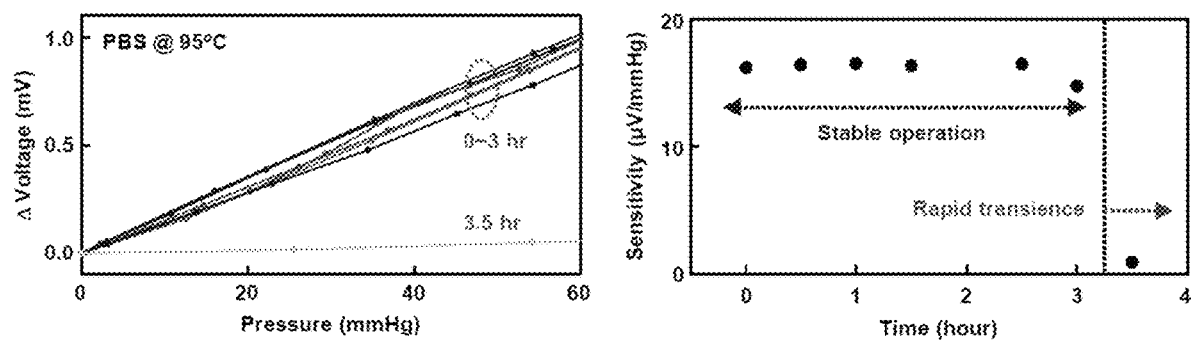
Figure 80E:
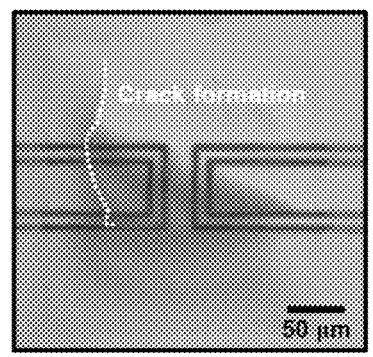

The use of t-$SiO_2$ as a defect-free barrier to prevent biofluid penetration to the Si device layer is critically important to the robust, long-lived operation. The functional lifetime is proportional to the thickness of the t-$SiO_2$ (FIG. 80D)[20]. Calibration curves of a bioresorbable pressure sensor (~10 nm t-$SiO_2$) collected at constant time intervals after immersion of the device in PBS at T=95° C. indicate highly uniform pressure responsivity in the first 3 hours followed by rapid transience. After dissolution of the t-SiO$_2$, the device undergoes premature failure due to pin-point penetration of water through eb-SiO$_2$ regions (along SG boundary lines) of the diaphragm, which leads to formation of cracks, rather than gradual resorption of the Si NMs (FIG. 80E).

In Vivo Biodistribution and Biocompatibility.

Evaluating the biodistribution of dissolved silicon, the hematology (complete blood count, CBC), and the blood chemistry of mice implanted with bioresorbable intracranial sensors provides insights into the physiological reactions to these devices as bioresorbable implants. Use of miniaturized devices (750 µm×750 µm×11 µm; weight ~12 µg) without t-SiO$_2$ encapsulation accelerates the dissolution, thereby facilitating assessments over a five-week period of study. The surgical procedure includes opening a craniectomy defect penetrating through the dura, implanting the sensor, and sealing the intracranial cavity using a drop of bioresorbable tissue adhesive.

Figure 81A:
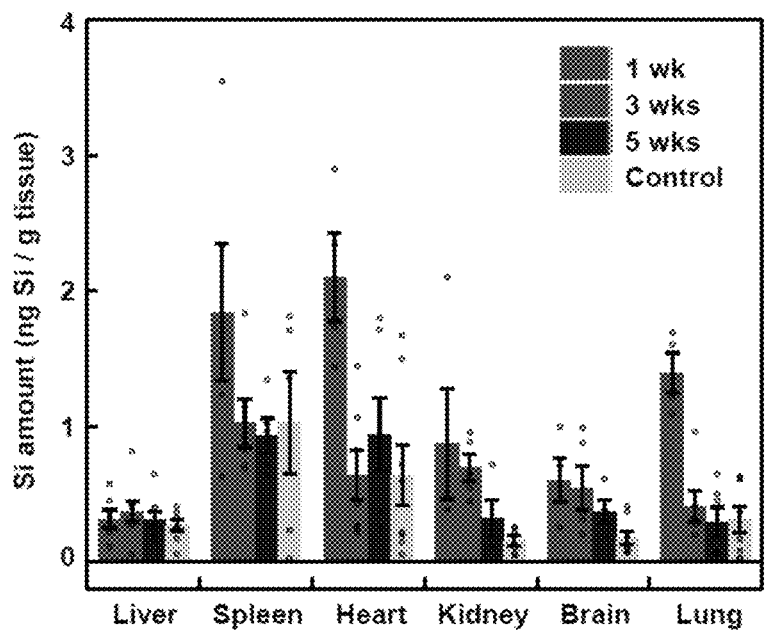
Figure 81B:
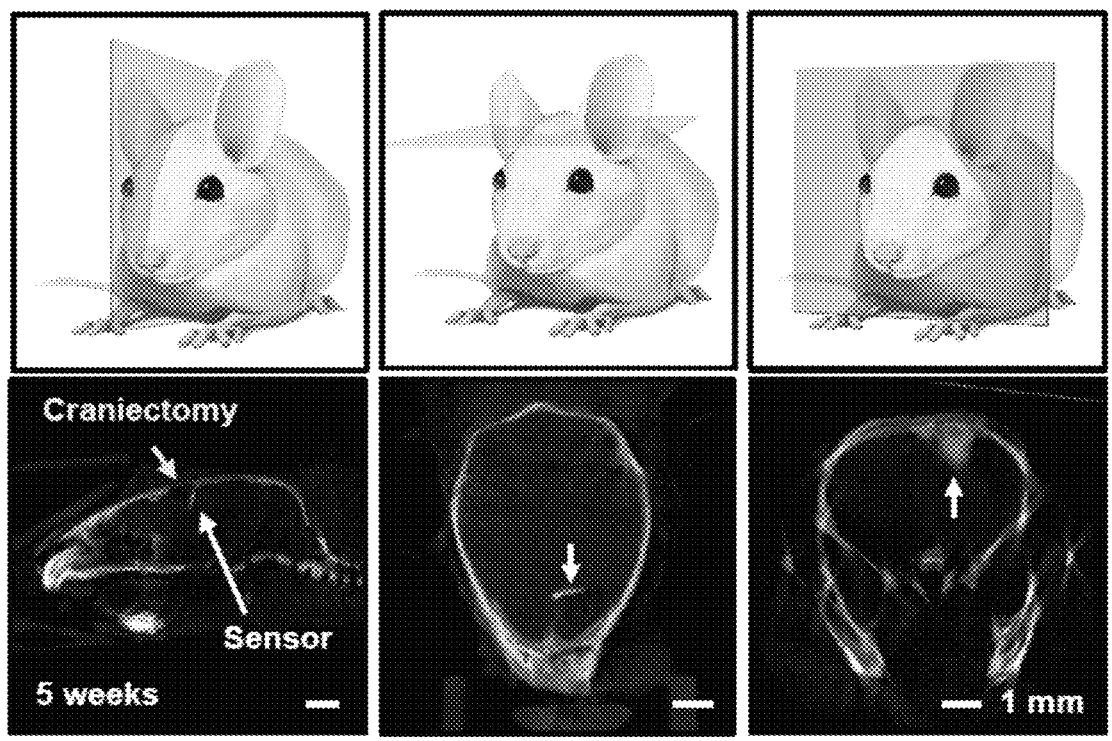

FIG. 81A shows concentrations of silicon in liver, spleen, heart, kidney, brain, and lung tissues explanted from mice at 1, 3, and 5 weeks after implantation, measured by inductively coupled plasma optical emission spectrometry (ICP-OES; see Methods for sample preparation steps). The results indicate deposition of silicon at higher concentrations in spleen, heart, and lung tissues than in the brain, where the device is located, 1 week after implantation. This observation can be attributed to fast turnover of CSF volumes in mice (12-13 times per day in mice; 3-4 times in humans)[30]. The CSF circulates through the brain, then joins the bloodstream by bulk reabsorption via arachnoid villi, transporting dissolved silicic acids to other organs. In particular, mononuclear phagocyte system-related organs such as liver, spleen, and lung have phagocytic cells that uptake nanomaterials in the blood, leading to deposition of silicon in these organs[31]. Clearance of silicic acid from the body via excretion through the kidneys leads to a gradual decrease and nearly complete removal from most organs after 5 weeks. Abnormal levels of silicon in the kidney and brain at week 5, however, suggest presence of residual device silicon in the brain, as verified by computed tomography (CT) images in FIG. 81B. Scans of the mouse brain along the sagittal, coronal, and axial planes reveal the locations of the craniectomy defect and a sensor implanted near the top surface of the brain, fixed in a tilted angle, 5 weeks post implantation.

Figure 81C:
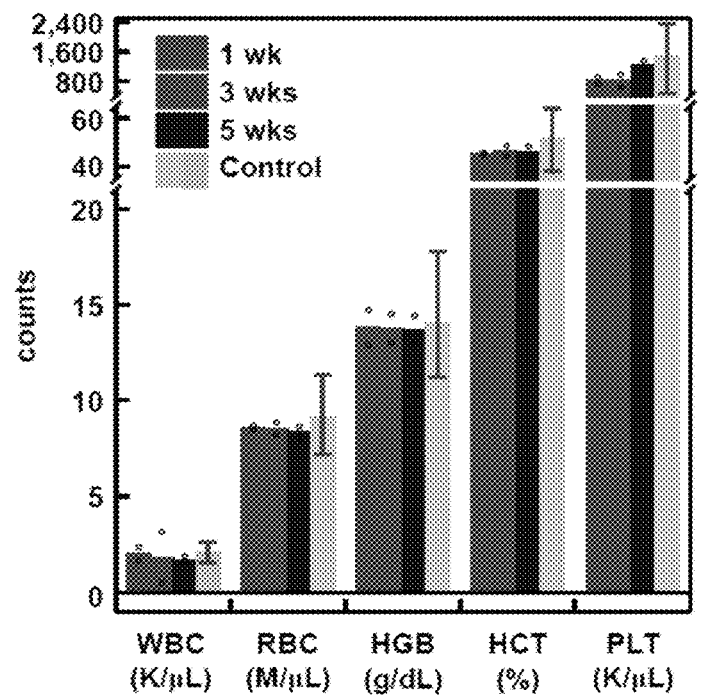
Figure 81D:
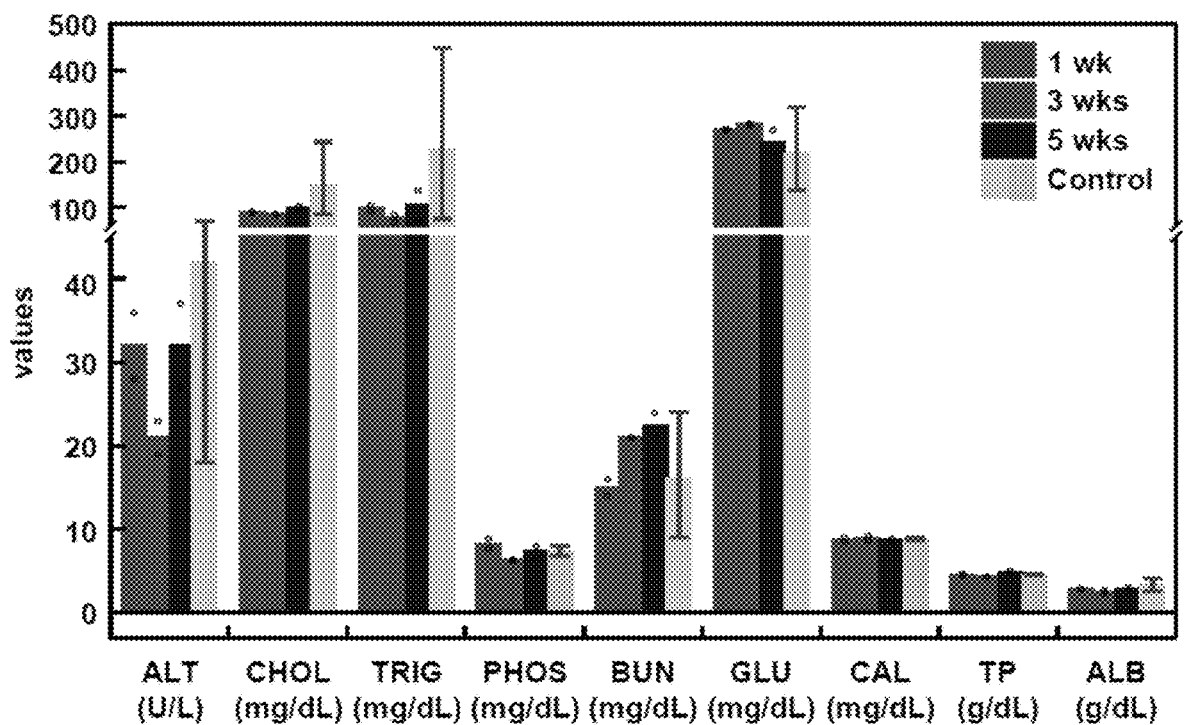

Results of CBC and blood chemistry tests provide a comprehensive understanding of the health of the mice (FIGS. 81C-81D). Average counts of white blood cells (WBC), red blood cells (RBC), platelets (PLT) and levels of hemoglobin (HGB) and hematocrit (HCT, the percentage of red blood cells in blood) show no significant differences between implanted mice from those of control animals throughout the five-week period of the studies. Blood levels of enzymes and electrolytes, which serve as indicators of organ-specific diseases, also fall within confidence intervals of control values. For example, normal levels of alanine aminotransferase (ALT), cholesterol (CHOL) and triglyceride (TRIG), phosphorus (PHOS) and urea nitrogen (BUN), calcium (CAL), and albumin (ALB) and total proteins (TP) indicate absence of disorders in the liver, heart, kidney, bone and nerve, and good overall health, respectively.

The changes in the body weight of mice implanted with intracranial sensors to those of control animals are compared. The differences are minimal, indicating continued maturation without significant toxic effects. Histopathologic evaluation of tissues obtained from a control mouse and a mouse implanted with a sensor for 5 weeks reveals absence of inflammation, ischemic/tissue necrosis, and other architectural/histologic abnormalities in the major organs (brain, spleen, heart, kidney, lung, and liver) for both mice, either grossly or by microscopic examination (see FIG. 81E).

In Vivo Monitoring of ICP.

Figure 82C:
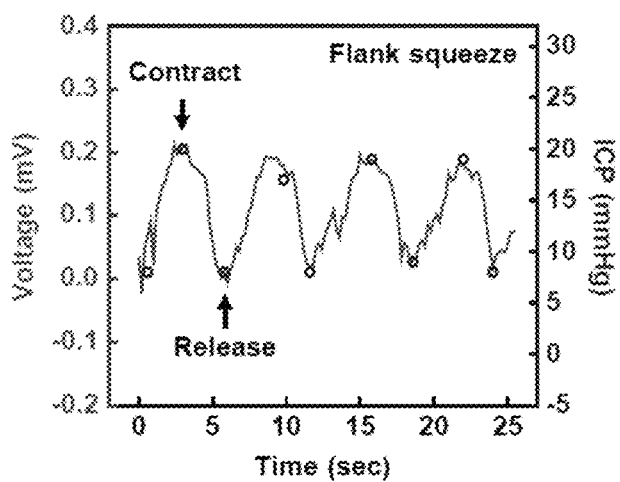

Acute and chronic tracking of ICT and ICP in rats demonstrate the accuracy and long operating lifetimes of the bioresorbable sensors. FIG. 82A illustrates the procedures for implantation, which involve opening a craniotomy defect, placing the sensor mounted on a thin film of poly (lactide-co-glycolide) (PLGA, ~10 µm thick; inset) inside, and applying bioresorbable glue to bond the PLGA film with the surrounding skull, thereby sealing the cavity. Inserting the probe of a standard clinical ICP monitor (Integra LifeSciences, USA) through a separate defect yields reference data for comparison testing. A plastic protector hat, secured on the rat's skull by transcranial screws and dental cement, stores all device components throughout the monitoring period to enable long-term, repeated measurements. All in vivo data in FIGS. 82A-82F rely on direct wire connections to an external digital multimeter (National Instruments, USA) for recording of voltage. Wireless data acquisition is also possible by using a miniaturized wireless potentiostat (Pinnacle Technology, USA) that can wirelessly transmit resistance data to a computer-based base station[8].

Figure 82D:
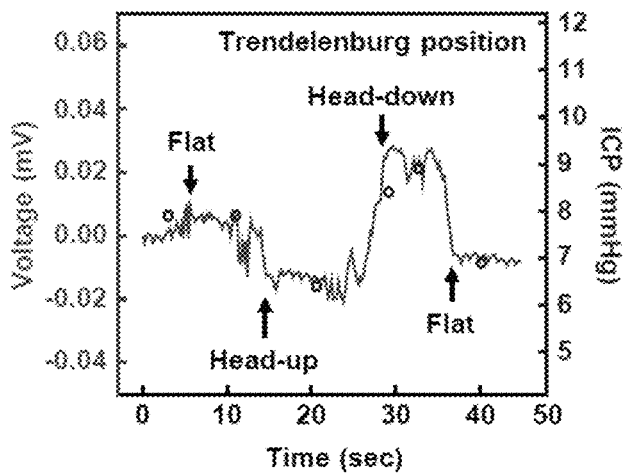
Figure 82E:
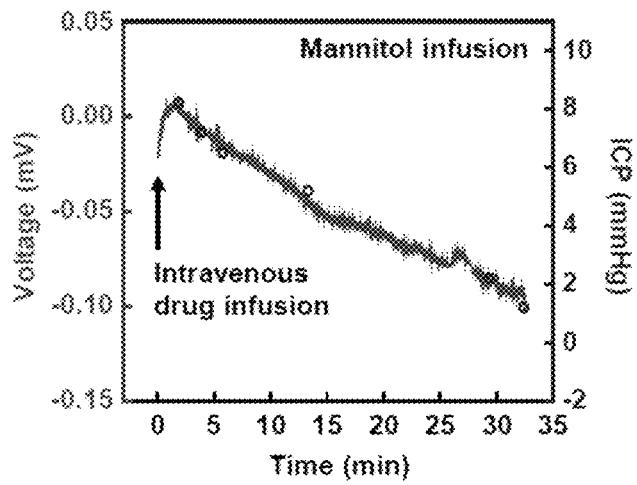

FIG. 82B shows acute recordings of the intracranial temperature (ICT) by both a bioresorbable device (red) and a commercial thermistor (blue) during gradual heating, using an electrical heating blanket, and cooling, using an ice pack, of the animal, indicating similar levels of accuracy. FIGS. 82C-82E demonstrate recordings of acute variation in ICP induced by contracting and releasing the rat's flank (FIG. 82C), laying the rat in Trendelenburg (30° head-down) and reverse Trendelenburg (30° head-up) positions (FIG. 82D), and intravenously infusing Mannitol (dose: 2 g per kg weight) via the saphenous vein (decreases by 2-5 mmHg starting ~10 minutes after infusion; FIG. 82E) using bioresorbable (red) and commercial (blue) ICP sensors. FIG. 82F summarizes ICP signals collected while contracting and releasing the flank on days 1, 8, 18, and 25. Responses of the sensor from days 1 through 18 display absolute accuracy within ±2 mmHg and baseline drift within ±1 mmHg. Recordings on day 25 show ~4 mmHg negative drift, in a range consistent with that of clinical ICP monitors after several days of implantation without re-calibration[29,32-34]. Signals from the device disappear after day 25, possibly due to the dissolution of the bioresorbable metal pads following penetration of water into the sensor-wire interface.

MRI Compatibility.

Figure 83C:
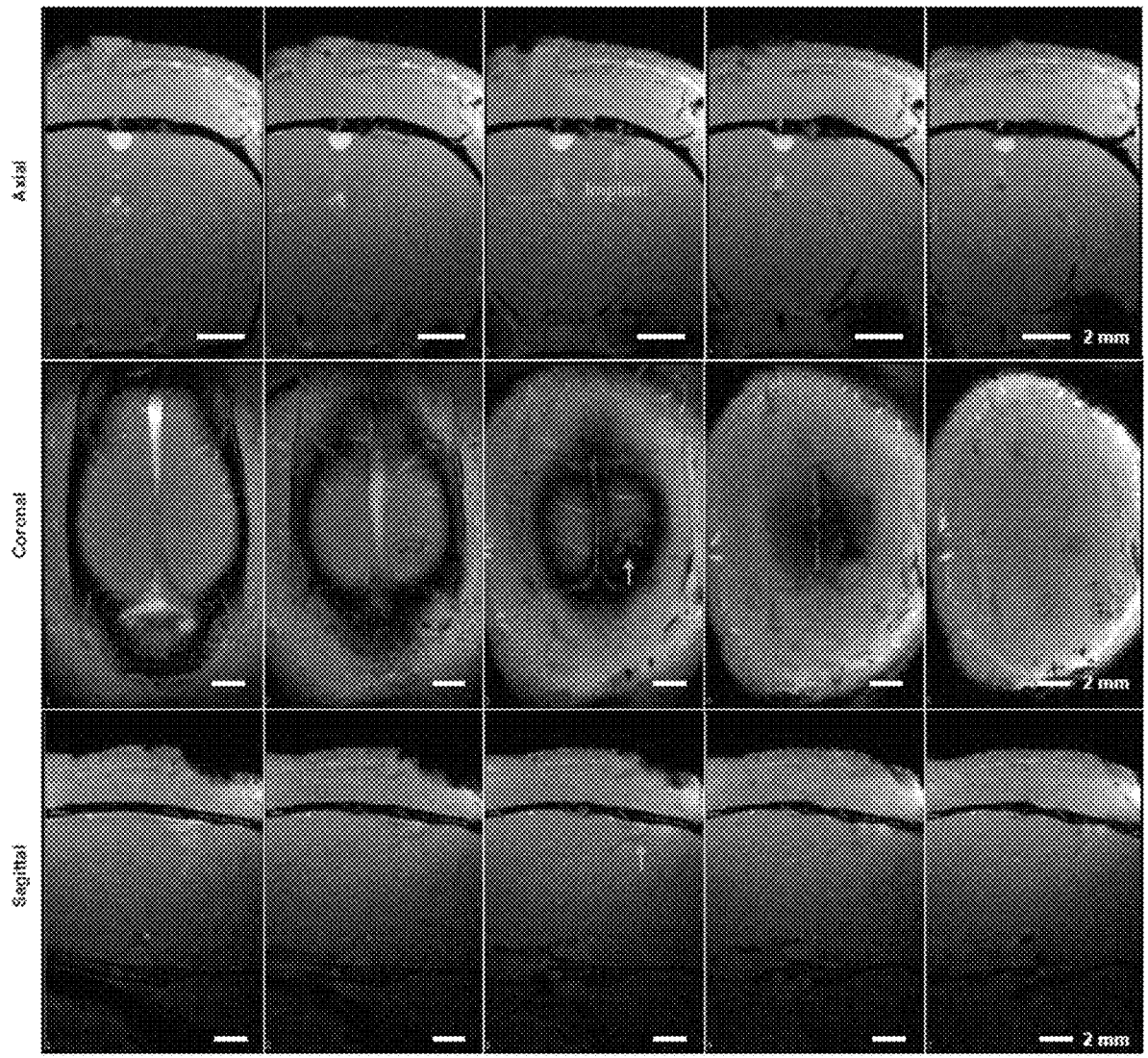

In many clinical scenarios, patients require magnetic resonance imaging (MRI) at various stages of recovery. Biomedical implants made of conductive materials and containing a loop in an electrical circuit can interact with various magnetic and electromagnetic fields of the MRI to cause problems such as device heating and image distortion (due to magnetic susceptibility artifacts). FIGS. 83A-83C illustrate in vitro and in vivo studies that verify the MRI compatibility of bioresorbable Si-based sensors[35,36].

FIG. 83A illustrates in vitro device heating test set-up consisting of a bioresorbable sensor and two fiber-optic temperature probes, one near the sensor and the other distant, embedded in between two 2 cm-thick slabs of gel phantoms that are designed to imitate the conductivity and dielectric constant of the brain. Recordings of the difference in temperatures measured by the two probes throughout a continuous 20-minute, high-specific adsorption rate (SAR)

MRI scan suggest that there is no significant heating associated with the presence of the device (FIG. 83B), possibly due to the small size (~500 μm diameter) of the loop that makes up the Wheatstone bridge circuit. Series of representative in vivo MRI images (0.5 mm slice thickness) of a rat with an implanted sensor confirm the absence of image distortion (FIG. 83C), possibly due to the low magnetic susceptibility of silicon.

The materials, device structures, and fabrication strategies introduced here serve as the foundations for bioresorbable implants capable of accurate, stable monitoring of pressure and temperature for extended periods of operation, previously attainable only through the use of non-resorbable technologies. In vivo experiments to track the elemental biodistribution of silicon, the hematology, and the blood chemistry during and after the processes of bioresorption reveal a lack of any measurable toxic effects or immune reactions. In vivo monitoring of intracranial pressures in rats over 25 days demonstrates the high level of accuracy that can be obtained, with extremely low baseline drifts due to intrinsic (materials biodegradation) and extrinsic (temperature fluctuation) effects. These same device concepts and materials constructs will enable robust, long-term operation across a broad range of bioresorbable implants, including sensors of motion, flow, and various chemical species, and of other components such as stimulators, power supplies, and thermal actuators.

Fabrication of Bioresorbable Pressure and Temperature Sensors with Thermal $SiO_2$ Layers as Biofluid Barriers.

Mechanical back-grinding (Syagrus Systems, USA) reduced the total thickness of a silicon-on-insulator wafer (SOI-A, top Si ~200 nm, buried $SiO_2$ ~1 μm, Si wafer ~100 μm; SOITEC, France) prior to device fabrication. Solid-state diffusion of phosphorus at 950° C. followed by photolithography and reactive ion etching (Plasma-Therm RIE) defined silicon nanomembrane strain gauges (Si NM SGs) and temperature gauges (TGs) in the top Si of the SOI-A wafer. Electron-beam (e-beam) evaporation of $SiO_2$ pellets (99.99%; Kurt J. Lesker Company, USA) formed a layer of $SiO_2$ (~600 nm) on top. Photolithography and deep reactive ion etching (STS Pegasus ICP-DRIE) defined an array of vent holes (area: 100 μm×100 μm) through the thickness of SOI-A. Photolithography and ICP-DRIE formed a square trench with dimensions of 200 μm×200 μm×10 μm on a separate SOI wafer (SOI-B, top Si ~15 μm, buried $SiO_2$ ~600 nm, Si wafer ~85 μm after mechanical grinding; University Wafer, USA). Spin-coating a layer of diluted poly(dimethylsiloxane) (PDMS, part A/part B/hexane=10:1:100, Sylgard 184; Dow Corning, USA) at a speed of 3000 rpm for 30 seconds on SOI-B, partially curing the PDMS by heating the wafer at 110° C. for 1 minute, transferring SOI-A on top of SOI-B in a manner that aligned the SGs of SOI-A directly above the trench of SOI-B, pressing the wafers together in a steel vise (Toomaker's vise; Tormach, Inc., USA), and fully curing the PDMS by placing the vise in a 70° C. convection oven for 2 hours bonded the wafers. Heating the vise in a furnace, by raising the temperature to 550° C. over 2 hours and keeping there for 2 more hours, converted the PDMS adhesion layer to amorphous silica. Next, ICP-DRIE removed the top Si wafer (SOI-A) of the bonded sample to expose the buried oxide. Wet etching in a buffered oxide etchant (BOE, 6:1; Transene Company Inc., USA) reduced the thickness of this oxide to the desired value (~10 nm). Patterned wet etching exposed square areas (~100 μm×100 μm) of Si NM in the four corners. Profiometer (Alpha Step D-500; KLA Tencor, USA) measurements confirmed the thickness of the buried oxide, with additional wet etching as needed to reach the desired value. Sputtering a layer of molybdenum (~100 nm) followed by patterning and wet etching formed metal contact pads (area: 150 μm×150 μm) on top of the four exposed areas of the Si NM. Spin-coating a layer of photoresist on the top surface, etching the handle wafer and buried oxide of SOI-B by ICP-DRIE and wet etching in BOE, and removing the photoresist by RIE (March RIE) completed the fabrication.

Connections to Data Acquisition Systems.

Silver conductive epoxy (MG Chemicals, USA) formed electrical connections between the molybdenum metal pads of the bioresorbable sensor and ultrathin enameled copper wires (~80 um diameter; Remington Industries, USA). A ~100 μm-thick layer of bioresorbable polyanhydride[8] encapsulated the sensor-wire interface to prevent direct exposure to biofluid. Soldering then connected the wires to printed circuit boards (PCBs) with gold pins (DigiKey, USA). Contacting the test hook probes of a digital multimeter (DMM, USB-4065; National Instruments, USA) with the gold pins enabled data acquisition from the sensor with minimal contact resistance. Use of 6.5-digit resolution setting in commercially available LabVIEW SignalExpress for DMM software enabled measurement of small voltage changes of the sensor during all in vitro and in vivo experiments; a lower resolution setting induced noise levels sufficiently large to obscure the actual pressure signal.

Calibration of the Pressure Response.

Absolute pressure calibration of the bioresorbable sensor relied on a custom set-up consisting of an airtight container (Nuovoware, USA) connected by two plastic tubes to a commercial pressure sensor (NUL-210; Neulog, USA) and a syringe for pressure measurement and control, respectively. Placing the bioresorbable sensor inside the container, partially filled with artificial cerebrospinal fluid (ACSF, pH 7.4; Ecocyte BioSciences, USA), followed by connnecting the wires to a power supply ($V_s$=2.5 V) and a digital multimeter prepared the system for testing. Collecting the voltage response of the bioresorbable device and pressures from the commercial device simultaneously, while varying the fluid pressure by moving the plunger of the syringe in and out, yielded a calibration curve over the range of pressures relevant to intracranial monitoring (0-70 mmHg).

Evaluation of the Hydrolysis Kinetics.

Measurements by spectroscopic reflectometry (MProbe; Semiconsoft, Inc., USA) defined changes in thicknesses of films of thermal and e-beam $SiO_2$ (t-$SiO_2$ and eb-$SiO_2$). Profilometry (Alpha Step) revealed the thicknesses of square dots (50 um×50 um) of amorphous silica adhesion interlayer formed on t-$SiO_2$ wafers. Each sample had a lateral size of ~1 cm×1 cm, with coatings of t-$SiO_2$ on the side and bottom surfaces formed by thermal oxidation. The experiments involved placing the sample in a screw cap plastic bottle filled with ~50 mL of ACSF solution, storing the bottle in an oven (Fisher Scientific, USA) to maintain the solution temperature near 37° C., and monitoring the temperature throughout the experiment using a digital thermometer probe (DTP482; CDN, USA) penetrating through the plastic cap. Rinsing the sample with deionized water, drying, measuring the thickness, and placing back in the solution (renewed every 4 days), repeatedly, yielded the dissolution rates.

Accelerated Soaking Tests.

Soaking the device in phosphate buffered saline (PBS, pH 7.4; Sigma-Aldrich, USA) at 95° C. for some time, rinsing with deionized water, drying, and analyzing under an optical microscope yielded images of a bioresorbable sensor through various stages of accelerated dissolution. Similarly, evaluation of the change in the pressure sensitivity of the device throughout a process of thinning of the t-SiO$_2$ encapsulation layer involved soaking the device in PBS at 95° C. for 30 minutes, rinsing with deionized water, drying, calibrating against the commercial pressure sensor, and placing back in the PBS. The dissolution chamber comprised of a screw cap plastic bottle, installed with a penetrating thermometer probe and kept in a heated oven.

Evaluation of the Biodistribution, Hematology, and Blood Chemistry of Mice.

Overnight ultraviolet radiation sterilized miniaturized bioresorbable sensors (size: 750 μm×750 μm×11 μm; weight ~12 μg) without t-SiO$_2$ encapsulation prior to device implantation. The procedures involved anaesthetizing a female CD-1 mouse (Charles River, USA) with isoflurane gas, fixing the head in a stereotaxic frame, forming a craniectomy defect using a drill, implanting the sensor into the intracranial cavity, sealing the defect with a drop of bioresorbable tissue adhesive (TissueSeal, USA), and suturing the scalp. The procedures have been approved by The Institutional Animal Care and Use Committee (IACUC) of Northwestern University. Daily monitoring and weighing of the mice ensured their normal stress and moribund conditions. Computed tomography scans carried out every week tracked the size and location of the implanted device. Euthanization of 1-2 mice at weeks 1, 3, and 5 after device implantation enabled extraction of blood and explantation of organs including liver, spleen, heart, kidney, brain, and lung. Charles River Laboratory (Boston, Mass.) conducted complete blood count and blood chemistry tests on the blood samples collected in K-EDTA tubes and gel tubes, respectively. Weighing, splitting the explanted organs in half, and storing the halves in pre-weighed 15 mL conical metal-free tubes in −20° C. fridge and in 10% buffered formalin in 50 mL conical tubes prepared tissue samples for biodistribution and histology studies, respectively. Dissolving the tissues by adding 1.5 mL nitric acid and 0.35 mL hydrogen peroxide to each tube, keeping the tubes in 65° C. water bath for 5 hours, diluting the dissolved tissue solutions 1:20 by adding Milli-Q water (MilliporeSigma, USA), and analyzing by inductively coupled plasma optical emission spectrometry (ICP-OES) yielded the concentrations of Si in the tissues 1, 3, and 5 weeks after implantation to demonstrate biodistribution and biodegradability of dissolved silicon.

Evaluation in Animal Models.

All procedures of the animal study followed the recommendations in the Guide for the Care and Use of Laboratory Animals of the National Institutes of Health. The Institutional Animal Care and Use Committee (IACUC) of Washington University in St Louis (protocol number 20170189) approved the protocol. Male Lewis rats weighing 250-350 g (Charles River, Wilmington, Mass.) received subcutaneous injections of buprenorphine hydrochloride (0.05 mg kg$^{-1}$; Reckitt Benckiser Healthcare Ltd, USA) for pain management, and of ampicillin (50 mg kg$^{-1}$; Sage Pharmaceuticals, USA) to prevent infection at the implantation site before the surgical process. The surgical procedures involved anaesthetizing the rat with isoflurane gas, holding the head in a stereotaxic frame, opening a craniectomy and dura, implanting the bioresorbable sensor on the cortical surface, and sealing the craniectomy with a PLGA sheet (~10 μm thick) and bioresorbable glue (TissueSeal, USA). A clinical intracranial pressure monitor (Camino System, Model MPM-1; Integra LifeSciences, USA) or a commercial thermistor (Digi-Key, USA) implanted in a nearby craniectomy enabled comparison testing to demonstrate the accuracy of the pressure and temperature measurements by the bioresorbable sensor, respectively. Bioresorbable glue sealed the opening for commercial sensor after testing.

Previous section described the set-up for wired data acquisition from bioresorbable sensor. Soldering the wires to plug connectors (Digi-Key) and plugging formed electrical connection between the bioresorbable sensor and a miniaturized wireless potentiostat (Pinnacle Technology, USA) to enable wireless data acquisition[8]. Pinnacle Acquisition Laboratory (PAL) v.1.6.7 software allowed data collection on a computer. A plastic protector hat, secured on the rat's skull by transcranial screws (#0-80, ⅛" stainless steel screws; Component Supply, USA) and dental cement (Fusio Liquid Dentin; Pentron, USA), stored device components for both wired and wireless modes throughout the monitoring period.

Evaluation of the MRI Compatibility.

The experimental set-up in FIG. 83A consisted of a bioresorbable sensor and two fiber optic temperature probes (Luxtron 812 Fluoroptic Thermometer; LumaSense Technologies, USA), one placed near the sensor and the other distant, sandwiched between two slabs of brain phantom (True Phantom Solutions, Inc., Canada). A 3 Tesla Siemens Magnetom Prisma MRI scanner performed a high-SAR (Specific Adsorption Rate, or RF deposition) turbo spin echo (TSE) scan (repetition time (TR)=6290.0 ms, echo time (TE)=99 ms, 14 slices, thickness=4 mm, flip angle=180°, field of view=230×230 mm) continuously for 20 minutes. To assess the in vivo images for magnetic-susceptibility-related artifacts, a 4.7 Tesla Agilent Small-Animal MRI system captured gradient-echo images of a rat brain implanted with a bioresorbable sensor (with copper wire connections that terminate outside the sutures) in FIG. 83C, using the following acquisition parameters: TR=50 ms, TE=4.56 ms, 5 slices, thickness=0.5 mm (no gap), flip angle=20°, with 117 μm in-plane resolution (30 mm×30 mm, 256×256 field of view), six signal averages, and a total acquisition time of 1 minute 17 seconds. Three independent experiments confirmed this trend.

REFERENCES FOR EXAMPLE 5

1 Jiang, G. Design challenges of implantable pressure monitoring system. Frontiers in Neuroscience 4 (2010).
2 Yu, L., Kim, B. & Meng, E. Chronically Implanted Pressure Sensors: Challenges and State of the Field. Sensors 14, 20620 (2014).
3 Sit, A. J. Continuous Monitoring of Intraocular Pressure: Rationale and Progress Toward A Clinical Device. Journal of Glaucoma 18, 272-279 (2009).
4 Boutry, C. M. et al. Towards biodegradable wireless implants. Philosophical Transactions of the Royal Society A: Mathematical, Physical and Engineering Sciences 370, 2418-2432 (2012).
5 Chamis, A. L. et al. *Staphylococcus aureus* Bacteremia in Patients With Permanent Pacemakers or Implantable Cardioverter-Defibrillators. Circulation 104, 1029-1033 (2001).
6 Hall-Stoodley, L., Costerton, J. W. & Stoodley, P. Bacterial biofilms: from the Natural environment to infectious diseases. Nature Reviews Microbiology 2, 95 (2004).
7 Polikov, V. S., Tresco, P. A. & Reichert, W. M. Response of brain tissue to chronically implanted neural electrodes. Journal of Neuroscience Methods 148, 1-18 (2005).
8 Kang, S.-K. et al. Bioresorbable silicon electronic sensors for the brain. Nature 530, 71 (2016).
9 Luo, M., Martinez, A. W., Song, C., Herrault, F. & Allen, M. G. A Microfabricated Wireless RF Pressure Sensor Made Completely of Biodegradable Materials. Journal of Microelectromechanical Systems 23, 4-13 (2014).

10 Hwang, S.-W. et al. Biodegradable Elastomers and Silicon Nanomembranes/Nanoribbons for Stretchable, Transient Electronics, and Biosensors. Nano Letters 15, 2801-2808 (2015).

11 Yu, K. J. et al. Bioresorbable silicon electronics for transient spatiotemporal mapping of electrical activity from the cerebral cortex. Nature Materials 15, 782 (2016).

12 Lee, Y. K. et al. Dissolution of Monocrystalline Silicon Nanomembranes and Their Use as Encapsulation Layers and Electrical Interfaces in Water-Soluble Electronics. ACS Nano 11, 12562-12572 (2017).

13 Lee, G. et al. Fully Biodegradable Microsupercapacitor for Power Storage in Transient Electronics. Advanced Energy Materials 7, 1700157 (2017).

14 Lee, C. H. et al. Wireless Microfluidic Systems for Programmed, Functional Transformation of Transient Electronic Devices. Advanced Functional Materials 25, 5100-5106 (2015).

15 Tao, H. et al. Silk-based resorbable electronic devices for remotely controlled therapy and in vivo infection abatement. Proceedings of the National Academy of Sciences 111, 17385-17389 (2014).

16 Hwang, S.-W. et al. A Physically Transient Form of Silicon Electronics. Science 337, 1640-1644 (2012).

17 Hwang, S.-W. et al. High-Performance Biodegradable/Transient Electronics on Biodegradable Polymers. Advanced Materials 26, 3905-3911, doi:10.1002/adma.201306050 (2014).

18 Kang, S.-K. et al. Dissolution Behaviors and Applications of Silicon Oxides and Nitrides in Transient Electronics. Advanced Functional Materials 24, 4427-4434 (2014).

19 Kang, S.-K. et al. Biodegradable Thin Metal Foils and Spin-On Glass Materials for Transient Electronics. Advanced Functional Materials 25, 1789-1797 (2015).

20 Fang, H. et al. Ultrathin, transferred layers of thermally grown silicon dioxide as biofluid barriers for biointegrated flexible electronic systems. Proceedings of the National Academy of Sciences 113, 11682-11687 (2016).

21 Lee, Y. K. et al. Kinetics and Chemistry of Hydrolysis of Ultrathin, Thermally Grown Layers of Silicon Oxide as Biofluid Barriers in Flexible Electronic Systems. ACS Applied Materials & Interfaces 9, 42633-42638 (2017).

22 Haddad, S. H. & Arabi, Y. M. Critical care management of severe traumatic brain injury in adults. Scandinavian Journal of Trauma, Resuscitation and Emergency Medicine 20, 12 (2012).

23 Wang, Q., Ding, J. & Wang, W. Fabrication and temperature coefficient compensation technology of low cost high temperature pressure sensor. Sensors and Actuators A: Physical 120, 468-473 (2005).

24 Camino, G., Lomakin, S. M. & Lazzari, M. Polydimethylsiloxane thermal degradation Part 1. Kinetic aspects. Polymer 42, 2395-2402 (2001).

25 Kanda, Y. A graphical representation of the piezoresistance coefficients in silicon. IEEE Transactions on Electron Devices 29, 64-70 (1982).

26 Lund, E. & Finstad, T. G. Temperature and Doping Dependency of Piezoresistivity in p-type Silicon. MRS Proceedings 657 (2000).

27 Norton, P. & Brandt, J. Temperature coefficient of resistance for p- and n-type silicon. Solid-State Electronics 21, 969-974 (1978).

28 Brain Trauma, F. et al. Guidelines for the management of severe traumatic brain injury. VI. Indications for intracranial pressure monitoring. J Neurotrauma 24 Suppl 1, S37-44 (2007).

29 Post craniotomy subdural pressure monitoring kit. Model 110-4G, in San Diego, Calif.: Integra NeuroSciences (2010).

30 Johanson, C. E. et al. Multiplicity of cerebrospinal fluid functions: New challenges in health and disease. Cerebrospinal Fluid Research 5, 10 (2008).

31 Moghimi, S. M. & Patel, H. M. Serum-mediated recognition of liposomes by phagocytic cells of the reticuloendothelial system—The concept of tissue specificity. Advanced Drug Delivery Reviews 32, 45-60 (1998).

32 Gelabert-Gonzalez, M. et al. The Camino intracranial pressure device in clinical practice. Assessment in a 1000 cases. Acta Neurochirurgica 148, 435-441 (2006).

33 Martinez-Manas, R. M., Santamarta, D., de Campos, J. M. & Ferrer, E. Camino® intracranial pressure monitor: prospective study of accuracy and complications. Journal of Neurology, Neurosurgery & amp; amp; Psychiatry 69, 82 (2000).

34 Zacchetti, L., Magnoni, S., Di Corte, F., Zanier, E. R. & Stocchetti, N. Accuracy of intracranial pressure monitoring: systematic review and meta-analysis. Critical Care 19, 420 (2015).

35 Dunn, J. F. et al. Functional mapping at 9.4 T using a new MRI compatible electrode chronically implanted in rats. Magnetic resonance in medicine 61, 222-228 (2009).

36 M., S. G. A. & G., S. F. Pre-MRI Procedure Screening: Recommendations and Safety Considerations for Biomedical Implants and Devices. Journal of Magnetic Resonance Imaging 12, 92-106 (2000).

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLES

TABLE 1

| Category | # | Material | Deposition method | Thickness for Mg test | Barrier lifetime (at 37° C.) | Leakage mode |
|---|---|---|---|---|---|---|
| Organic | 1 | SU-8 | Spin coating | 1 μm | <1 day | Bulk |
|  | 2 | Polyimide (PI) | Spin coating | 1 μm | <1 day | Bulk |
|  | 3 | Parylene C | CVD | 1 μm | <1 day | Bulk |
|  | 4 | PDMS | Spin coating | 1 μm | <1 day | Bulk |
|  | 5 | LCP | — | 25 μm | 147-309 day* | Bulk |
| Inorganic | 6 | $SiO_x$ | PECVD | 1 μm | <1 day | Bulk |
|  | 7 | $SiN_x$ | PECVD | 1 μm | <1 day | Bulk |
|  | 8 | $Al_2O_3$ | ALD | 100 nm | <1 day | Pinhole |
|  | 9 | $HfO_2$ | ALD | 100 nm | <1 day | Pinhole |
| Inorganic Multilayer | 10 | $SiO_x/SiN_x \times 3$ | PECVD | 16.6/16.6 nm × 3 | <1 day | Pinhole |
|  | 11 | $Al_2/HfO_2 \times 3$ | ALD | 16.6/16.6 nm × 3 | <1 day | Pinhole |
| Inorganic/organic Multilayer | 12 | $Al_2O_3$/Parylene C | ALD/CVD | 50/950 nm | 3-7 day* | Pinhole |
|  | 13 | $Al_2O_3$/Parrlene C | ALD/CVD | 50/6000 nm | 5-11 day | Pinhole |
|  | 14 | $Al_2O_3$/Parylene C × 3 | ALD/CVD | 50/283.3 nm × 3 | <1 day | Pinhole |
|  | 15 | $Al_2O_3$/PI | ALD/Spin coating | 50/950 nm | <1 day | Pinhole |
|  | 16 | $Al_2O_3$/PI × 3 | ALD/Spin coating | 50/283.3 nm × 3 | <1 day | Pinhole |
|  | 17 | $HfO_2$/Parylene C | ALD/CVD | 50/950 nm | 102-214 day* | Pinhole |
|  | 18 | $HfO_2$/Parylene C × 3 | ALD/CVD | 50/283.3 nm × 3 | 22-39 day | Pinhole |
|  | 19 | $HfO_2$/PI | ALD/Spin coating | 50/950 nm | <1 day | Pinhole |
|  | 20 | $HfO_2$/PI × 3 | ALD/Spin coating | 50/283.3 nm × 3 | <1 day | Pinhole |
|  | 21 | $SiN_x/Al_2O_3$/Parylene C | PECVD/ALD/CVD | 50/50/900 nm | 2-3 day | Pinhole |
| Thermal Oxide | 22 | $SiO_2$ | Thermally grown | 100 nm | 6-7 years** | Slow dissolution |

Permeability measured at 37° C., 90% Relative Humidity

*Indicates data from accelerated soak test. Reaction Rate Factor Q10 = 2-2.5.

**Barrier lifetime defined as the soaking time period before any defect area on Mg pad reach 30 $mm^2$.

TABLE 2

Summary of Mg soak test for different candidate bi-layer barrier with SiO2-polymer-based materials

| Category | SiO$_2$ Material Inform. | Deposition method | Polymer Thickness [nm] | Barrier lifetime (at 96° C.)[a] | Leakage mode [b] |
|---|---|---|---|---|---|
| SU-8 | 200 nm thick SiO$_2$ | Spin coating | 100 | <2.5 day | Bulk |
| | | Spin coating | 200 | <3 day | Bulk |
| | | Spin coating | 300 | <3 day 10 hrs | Bulk |
| | | Spin coating | 500 | <5 day | Bulk |
| | | Spin Coating | 1500 | <8 day 12 hrs | Bulk |
| PI2545 | 200 nm thick SiO$_2$ | Spin coating | 100 | <2.5 day | Bulk |
| | | Spin coating | 200 | <3 day | Bulk |
| | | Spin coating | 300 | <4 day | Bulk |
| | | Spin Coating | 500 | <5 day | Bulk |
| | | Spin Coating | 1000 | <7 day 10 hrs | Bulk |
| PMMA A2 495 | 200 nm thick SiO$_2$ | Spin coating | 60 | <2 day 15 hrs | Bulk |
| | | Spin coating | 80 | <2 day 18 hrs | Bulk |
| | | Spin coating | 100 | <3 day | Bulk |
| Parylene C | 100 nm thick SiO$_2$ | CVD | 50 | <3 day | Bulk |
| | 100 nm thick SiO$_2$ | CVD | 100 | <4.8 day | Bulk |
| | 100 nm thick SiO$_2$ | CVD | 150 | <7 day | Bulk |
| | 200 nm thick SiO$_2$ | CVD | 100 | <8 day 10 hrs | Bulk |
| | 300 nm thick SiO$_2$ | CVD | 100 | <10 day | Bulk |

[a] Barrier lifetime defined as the soaking time period before any defect area on Mg pad observed by microscope;
[b] Leakage mode is defined with water-permeability measured at 96° C., which refers to isolated pinhole defects on Mg pad (pinhole mode) or uniform dissolution of the entire Mg pad (bulk mode).

We claim:

1. A method of making a long-term implantable electronic device, the method comprising:
   providing a substrate having a first encapsulation layer that covers at least a portion of the substrate, the first encapsulation layer having a receiving surface;
   providing one or more electronic devices on the first encapsulation layer receiving surface;
   removing at least a portion of the substrate from the first encapsulation layer, wherein each of the one or more electronic devices and the first encapsulation layer has an exposed surface;
   depositing a barrier layer over the exposed surfaces of the one or more electronic devices and the first encapsulation layer;
   adhering to the barrier layer a top substrate having a second encapsulation layer, wherein the second encapsulation layer faces the barrier layer; and
   removing at least a portion of the top substrate from the second encapsulation layer,
   thereby making the long-term implantable electronic device.

2. The method of claim 1, wherein said providing the substrate having the first encapsulation layer comprises:
   forming the first encapsulation layer on the substrate by depositing, growing, or transfer printing the first encapsulation layer on the substrate.

3. The method of claim 1, wherein said providing the substrate having the first encapsulation layer comprise:
   forming the first encapsulation layer by thermally oxidizing a portion of the substrate.

4. The method of claim 1, wherein the long-term implantable electronic device is formed to be flexible, elastic, or flexible and elastic.

5. The method of claim 1, wherein the substrate comprises a silicon wafer.

6. The method of claim 1, wherein the top substrate comprises a silicon wafer.

7. The method of claim 1, wherein at least one of the first and/or second encapsulation layers comprises an oxide of silicon.

8. The method of claim 1, wherein each of the first and second encapsulation layers has a thickness that is greater than 10 nm and less than 100 μm.

9. The method of claim 1, wherein the first and second encapsulation layers are flexible and configured to facilitate compliance of the one or more electronic devices with a surface tissue during implantation process.

10. The method of claim 1, wherein the first encapsulation layer has an encapsulation layer thickness and composition that are adapted to provide a functional encapsulating lifetime that ranges between 1 hour and 70 years.

11. The method of claim 1, wherein the substrate has a large surface area, wherein the large surface area greater than or equal to 100 mm$^2$.

12. The method of claim 1, wherein the first encapsulation layer comprises SiO$_2$, diamond, SiC, Al$_2$O$_3$, HfO$_2$, or a polymer including a poly(p-xylylene) polymer.

13. The method of claim 1, wherein the first encapsulation layer has an encapsulation layer thickness adapted to achieve a medical device lifetime that is greater than 20 years.

14. The method of claim 1, further comprising sealing and bonding exposed edges of the first and second encapsulation layers to fully encapsulate the one or more electronic devices.

15. The method of claim 1, wherein one of the first and second encapsulation layers is a biofluid barrier and the other of the first and second encapsulation layer is part of a bio-interface configured to couple between the one or more electronic devices and an adjacent tissue.

16. The method of claim 1, wherein the first encapsulation layer comprises:
   SiO$_2$;
   a transferred or bonded thin layer of SiC;
   an oxide material deposited by atomic layer deposition, chemical vapor deposition, or physical vapor deposition; or
   SiO$_2$ and spin-coated polymer layers.

17. The method of claim 1, wherein said providing the one or more electronic devices comprises one or more of:

transfer printing;
epitaxially growing;
depositing;
patterning; and
etching.

18. The method of claim 1, wherein said providing the substrate having the first encapsulation layer comprise:
forming the first encapsulation layer by thermal oxidation at a thermal oxidation temperature that is greater than a maximum electronic device temperature at which an electronic device defect occurs, and the thermal oxidation is remotely separated from the one or more electronic devices, wherein the thermal oxidation temperature is greater than 800° C.

19. The method of claim 1, wherein the one or more electronic devices further comprise a water barrier and adhesion promoting layer formed of $Al_2O_3$, or $HfO_2$ connected to the first encapsulation layer.

20. The method of claim 1, wherein said removing the at least a portion of the substrate from the first encapsulation layer comprises removing a sufficient amount of the substrate so that the substrate and the first encapsulation layer have a flexibility and bendability compatible with the one or more electronic devices so that the one or more electronic devices are capable of achieving and maintaining conformability to a biological tissue during use.

21. The method of claim 1, wherein said removing the at least a portion of the substrate from the first encapsulation layer comprises removing at least 80% of the substrate original mass.

22. The method of claim 1, wherein said removing the at least a portion of the substrate from the first encapsulation layer comprises reactive ion etching, chemical etching, chemical planarization and/or mechanical planarization.

23. The method of claim 1, wherein after said removing the at least a portion of the substrate from the first encapsulation layer, a pristine encapsulation surface remains for electronic device back surface and top bio-interface surface, wherein the pristine encapsulation surface has a defect density less than $1/mm^2$, including for a layer of $SiO_2$.

24. The method of claim 1, wherein the one or more electronic devices are configured to detect and/or actuate one or more of:
an optical property;
an electrical property;
a magnetic property;
a thermal property;
a chemical property; and
a physical property.

25. The method of claim 1, wherein the substrates comprise silicon wafers, the first and second encapsulation layers comprise $SiO_2$, and the first and second encapsulation layers have a large surface area that is substantially defect free with respect to liquid or liquid vapor penetration.

26. The method of claim 1, wherein the one or more electronic devices comprise an array of passively addressed or actively addressed electrodes.

27. The method of claim 1, further comprising coating the exposed surface of the first encapsulation layer with a longevity-extending layer.

28. The method of claim 27, wherein said coating comprises depositing the longevity-extending layer on the encapsulation layer by atomic layer deposition (ALD).

29. The method of claim 27, wherein said coating comprises forming the longevity-extending layer with a material selected from the group consisting of one or more of:
$HfO_2$;
$Al_2O_3$;
$Al_2O_3/TiO_2$;
$SiN_x$; and
Parylene, PDMS, PI, SU-8, PMMA.

30. The method of claim 27, wherein the longevity-extending layer has a thickness less than 500 nm.

31. The method of claim 1, further comprising coating the exposed surface of the first encapsulation layer with an ion-barrier layer.

32. The method of claim 31, wherein said coating comprises depositing the ion-barrier layer on the first encapsulation layer by chemical vapor deposition.

33. The method of claim 31, wherein the ion-barrier layer comprises $SiN_x$.

34. The method of claim 31, wherein each of the first encapsulation layer and the ion-barrier layer has a thickness less than 500 nm.

35. The method of claim 31, wherein the ion-barrier is spatially varying.

36. The method of claim 1, further comprising providing a longevity-extending layer and an ion-barrier layer over at least one of the first and second encapsulation layers to increase device lifetime and decrease ion permeability.

37. The method of claim 1, wherein the one or more electronic devices comprise capacitive sensors.

38. The method of claim 1, wherein the barrier layer comprises a polymer, an adhesive, or both a polymer and an adhesive.

39. A method of making a long-term implantable electronic device, comprising:
providing a substrate having a first encapsulation layer that covers at least a portion of the substrate, the first encapsulation layer having a receiving surface;
providing one or more electronic devices on the first encapsulation layer receiving surface; and
removing at least a portion of the substrate from the first encapsulation layer; thereby making the long-term implantable electronic device,
wherein said providing the substrate having the first encapsulation layer comprises:
forming the first encapsulation layer from the substrate by thermal oxidation, wherein the thermal oxidation comprises heating a silicon substrate to a temperature that is greater than 800° C., and the silicon substrate is a pristine silicon wafer, having a defect density less than or equal to $1/mm^2$ or a leakage current that is less than 1 µA, so that the first encapsulation layer formed from the pristine silicon wafer prevents biofluid migration across the first encapsulation layer.

40. A method of making a long-term implantable electronic device, comprising:
providing a first substrate having a first encapsulation layer supported by at least a portion of the first substrate;
providing one or more electronic devices on the first encapsulation layer;
providing a second substrate having a second encapsulating layer supported by at least a portion of the second substrate; and
covering an exposed surface of the one or more electronic devices provided on the first encapsulation layer with the second encapsulating layer,
thereby making the long-term implantable electronic device, wherein said one or more electronic device comprise an electrical sensor, an optical sensor, a mechanical sensor, a thermal sensor, a capacitive sensor, or a combination thereof.

41. The method of claim 40, wherein the capacitive sensors comprise an array of at least 50 multiplexed capacitive sensors, each capacitive sensor having a footprint of between 0.1 mm$^2$ and 1 mm$^2$.

42. The method of claim 40, wherein each of the capacitive sensors is operably connected to an amplifier to compensate for high impedance from the encapsulation layer at a biological interface and each capacitive sensor is further operably connected to an electronic circuit comprising a multiplexer and/or analog filter.

43. The method of claim 40, wherein each capacitive sensor comprises two silicon nanomembrane transistors.

44. The method of claim 40, wherein at least one of the first and second encapsulation layers is configured to couple the capacitive sensors to an adjacent tissue.

* * * * *